(12) United States Patent
Hahn et al.

(10) Patent No.: US 7,998,989 B2
(45) Date of Patent: Aug. 16, 2011

(54) 2-IMINO-1,3-THIAZOLINE-BASED COMPOUNDS AND T-TYPE CALCIUM CHANNEL INHIBITORS CONTAINING THE SAME

(75) Inventors: Hoh-Gyu Hahn, Seoul (KR); Dong-Yun Shin, Seoul (KR); Kee-Dal Nam, Seoul (KR); Hye-Whon Rhim, Seoul (KR)

(73) Assignee: Korea Institute of Science and Technology, Hawolgok-Dong, Seongbuk-Gu Seoul (KR)

( * ) Notice: Subject to any disclaimer, the term of this patent is extended or adjusted under 35 U.S.C. 154(b) by 126 days.

(21) Appl. No.: 12/124,737

(22) Filed: May 21, 2008

(65) Prior Publication Data
US 2008/0293786 A1 Nov. 27, 2008

(30) Foreign Application Priority Data
May 23, 2007 (KR) ........................ 10-2007-0050185

(51) Int. Cl.
*A61K 31/426* (2006.01)
*C07D 277/42* (2006.01)

(52) U.S. Cl. ........................................ 514/370; 548/194
(58) Field of Classification Search .................. None
See application file for complete search history.

(56) References Cited

U.S. PATENT DOCUMENTS
2006/0111366 A1* 5/2006 Andersen et al. ........ 514/253.01

FOREIGN PATENT DOCUMENTS
| WO | WO 01 07424 | 2/2001 |
| WO | WO 02 02542 | 1/2002 |
| WO | WO 02 13611 | 2/2002 |
| WO | WO 02 055510 | 7/2002 |

OTHER PUBLICATIONS

S. Naik, G. Bhattacharjya, B. Talukdar, B. K. Patel, Eur. J. Org. Chem., 2004, 1254-1260.*
Hahn et al. Journal of the Korean Chemical Society (2001), vol. 45, No. 6.*
"Pain," Merck Manuals Online Medical Library: Home Edition. Accessed Mar. 24, 2009. <http://www.merck.com/mmhe/sec06/ch078/ch078a.html>.*
Stillman, Mark. "Clinical approach to patients with neuropathic pain." Cleveland Clinic Journal of Medicine, 73 (8), pp. 726- 730, 733-739.*

* cited by examiner

*Primary Examiner* — Rebecca Anderson
*Assistant Examiner* — Alicia L Otton
(74) *Attorney, Agent, or Firm* — Lexyoume IP Group, PLLC.

(57) ABSTRACT

Novel 2-imino-1,3-thiazoline based compounds represented by Chemical Formula I, and T-type calcium channel inhibitors containing the compound are provided. The T-type calcium channel inhibitors according to the present invention are useful as a treating agent of diseases associated with overexpression of the T-type calcium channel.

(Chemical Formula I)

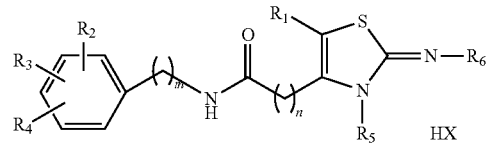

10 Claims, No Drawings

2-IMINO-1,3-THIAZOLINE-BASED COMPOUNDS AND T-TYPE CALCIUM CHANNEL INHIBITORS CONTAINING THE SAME

CROSS REFERENCE TO RELATED APPLICATION

This application claims priority to and the benefit of Korean Patent Application No. 10-2007-0050185 filed on May 23, 2007, which is hereby incorporated by reference for all purposes as if fully set forth herein.

BACKGROUND OF THE INVENTION (a) Field of the Invention

2-Imino-1,3-thiazoline-based compounds represented by the following Chemical Formula I, and T-type calcium channel inhibitors containing the compound are provided. The T-type calcium channel inhibitors according to the present invention are useful as a treating agent of diseases associated with over-expression of T-type calcium channel.

(Chemical Formula I)

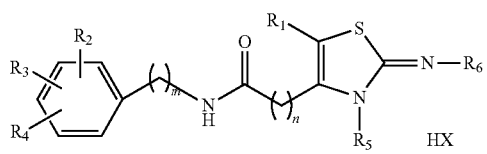

(b) Description of the Related Art

The T-type calcium channel is a kind of voltage-dependent calcium channel, and plays an important role in regulating the intracellular calcium level at depolarization. As coding genes for the voltage-dependent calcium channels, ten (10) genes have been found, which may be classified into two (2) families of a high voltage activated (HVA) family and a low voltage activated (LVA) family according to the intensity of the activating voltage. The voltage-dependent calcium channels may be classified into three (3) families of L-type channels (Cav1), P/Q-type and N-type (nervous unit) channels (Cav2), and T-type channels, wherein the L-type channels and the P/Q-type and N-type channels belong to the high voltage activated family, and the T-type channels belong to the low voltage activated family (Ertel et al., 2000).

The T-type calcium channel is characterized by a low-voltage activated calcium current, rapid activation, and slow inactivation. Thus far, as coding genes for the T-type calcium channel, three (3) genes have been identified, and they are called α1G (Cav3.1), α1H (Cav3.2), and α1I (Cav3.3), respectively (Cribbs et al., 1998; Perez-Reyes et al., 1998; Klugbauer et al., 1999; Lee et al., 1999; Monteil et al., 2000). The T-type calcium channels may be expressed in the whole body, such as in nervous tissue, the heart, the kidney, smooth muscles, and endocrine organs. The T-type calcium channels have been found to have functions of regulating burst-firing of nervous cells (Huguenard, J. R. et al., Annu. Rev. Physiol. 1996, 58, 329-348), heart pacemaker activity (Zhou, Z. et al., J. Mol. Cell. Cardiol. 1994, 26, 1211-1219), secretion of the hormone aldosterone (Rossier, M. E et al., Endocrinology 1996, 137, 4817-4826), and fertilization (Amoult, C. et al., Proc. Natl. Acad. Sci. 1996, 93, 13004-13009). Recently, it has been revealed that the T-type calcium channels are also associated with pain signaling (Ikeda, H. et al., Science, 2003, 299, 1237-1240).

A relationship between the expression of the T-type calcium channel and various diseases has been found. The expression of the T-type calcium channel in the brain has been found to be associated with nociception and repetitive low threshold firing. Particularly, a recent study has reported a direct relationship between the expression of the T-type calcium channel and pain using a knock-out mouse wherein the T-type calcium channel was deleted (Bourinet E. et al., EMBO, 2005, 24, 315-324; Shin, H. S. et al., Science, 2003, 302, 117-119). In addition, the T-type calcium channel is associated with epilepsy. Absence seizure, which is a type of epilepsy, is caused by over-activation of the T-type calcium channel in the brain (Tsakiridou E. et al., J. Neurosci. 1995, 15, 3110-3117). Ethosuccimide is an inhibitor against the T-type calcium channel, and has been used in treatment of absence seizure. The T-type calcium channel is commonly expressed in the heart and smooth muscles, and thus the inhibitors thereof can also be useful in treatment of hypertension, angina pectoris, and arrhythmia. Recently, it has been found that the T-type calcium channel is associated with the invasion and metastasis of cancer cells, and thus inhibitors thereof may be useful as anticancer drugs (Petty, H. R. et al., US 20060003020A1; McCalmont, W. F. et al, Bioorg. Med. Chem. Lett. 2004, 14, 3691-3695).

The exemplary inhibitor against the T-type calcium channel is miberfradil (Posicor®), developed by Roche. Mibefradil, which is a non-dihydropyridine calcium channel inhibitor, obtained FDA approval as a treatment drug against hypertension and angina pectoris in 1997. However, Mibefradil has been voluntarily removed since 1999 because of its side effect caused by drug-drug interaction by CYP 3A4 enzyme inhibition.

Therefore, efficient T-type calcium channel inhibitors have not yet been developed. In view of the effects of the T-type calcium channel on nerves, pain, epilepsy, hypertension, angina pectoris, heart muscle diseases, blood vessels, cancer metastasis, and the like, it has been required to develop efficient T-type calcium channel inhibitors that are capable of preventing and treating various T-type calcium channel associated diseases by inhibiting the over-expression and over-activation of the T-type calcium channel.

SUMMARY OF THE INVENTION

To satisfy the above request, an embodiment of the present invention provides novel 2-imino-1,3-thiazoline-based compounds having T-type calcium channel inhibiting activity, and T-type calcium channel inhibitors containing the compound.

DETAILED DESCRIPTION OF THE PREFERRED EMBODIMENTS

A more complete appreciation of the invention, and many of the attendant advantages thereof, will be readily apparent as the same becomes better understood by reference to the following detailed description.

2-imino-1,3-thiazoline-based compounds represented by the following Chemical Formula I, and T-type calcium channel inhibitors containing the compound are provided. The T-type calcium channel inhibitors according to the present invention are useful as a treating agent of diseases associated with over-expression of the T-type calcium channel.

An embodiment of the present invention provides 2-imino-1,3-thiazoline-based compounds represented by the following Chemical Formula I:

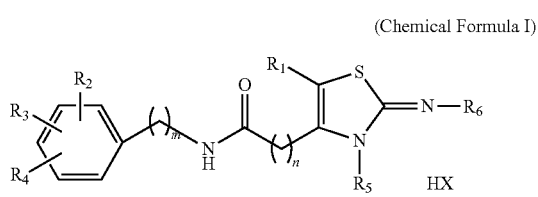

(Chemical Formula I)

wherein $R_1$ may be a hydrogen atom, or a C1-C5 linear or branched alkyl group, $R_2$, $R_3$, and $R_4$ may be the same or different from one another, and independently selected from the group consisting of a hydrogen atom, a halogen atom, a C1-C5 linear or branched alkyl group, a C1-C5 alkyloxy group, a trifluoromethyl group, a trifluoromethoxy group, a phenyloxy group, an amino group, a methanesulfoneamino group, a paratoluenesulfoneamino group, a nitro group, a C1-C5 cyanoalkyl group, a cyano group, a C1-C6 alkoxycarbonyl group, and a C3-C12 cycloalkyl group, $R_5$ may be selected from the group consisting of a C1-C5 linear or branched alkyl group, a C3-C6 cycloalkyl group, and a benzyl group, $R_6$ may be selected from the group consisting of a C3-C12 cycloalkyl group, a C4-C17 alkylcycloalkyl group, an adamantly group, a benzyl group, and a C8-C13 benzylalkyl group, n and m may be independently 0 or 1, HX may be present or absent, and when HX is present, X may be a halogen atom.

Another embodiment of the present invention provides a method of preparing the 2-imino-1,3-thiazoline based compound.

In a preferable embodiment, the method may include the steps of:

heating/reflowing the compounds represented by Chemical Formulas II and III in a solution of a C1 to C5 alcohol, preferably ethanol, for 5 to 20 hours, preferably 8 to 12 hours, at 20 to 130° C., preferably 50 to 90° C., to prepare the a compound represented by Chemical Formula IV; adding a basic aqueous solution, preferably a caustic soda solution, heating/reflowing for 30 minutes to 5 hours, preferably 1 to 3 hours, at 20 to 120° C., preferably 80 to 100° C., and then adjusting the pH to 1 to 4, preferably 2 to 3, by adding a hydrogen halide, to prepare the compound represented by Chemical Formula V; and adding the compound represented by Chemical Formula VI and an amide condensation binder to the obtained compound represented by Chemical Formula V, and allowing them to react, to prepare the compound represented by Chemical Formula I.

The amide condensation binder may be any agent that is capable of allowing condensation binding of an amino group and a carboxylic acid group, for example one or more selected from the group consisting of diisopropylcarbodiimide, dicyclohexylcarbodiimide, diethylcarbodiimide, and the like.

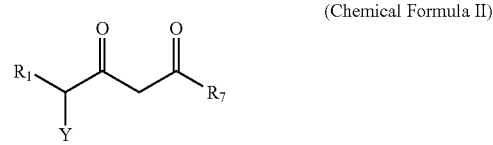

(Chemical Formula II)

(Chemical Formula III)

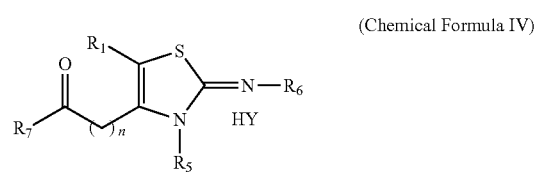

(Chemical Formula IV)

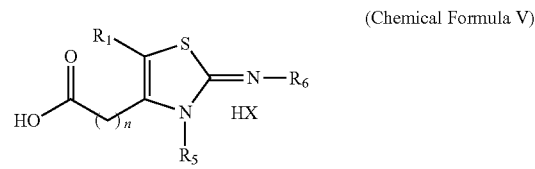

(Chemical Formula V)

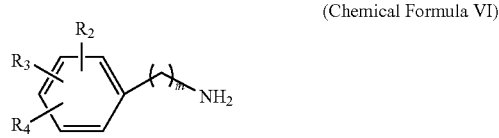

(Chemical Formula VI)

In Chemical Formula II, $R_7$ may be an alkoxy having 1 to 6 carbon atoms, preferably methoxy or ethoxy.

The preparation method may be illustrated by Reaction Scheme 1.

(Reaction Scheme 1)

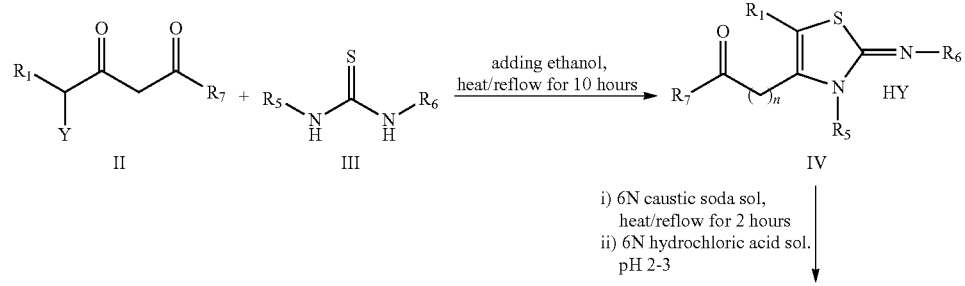

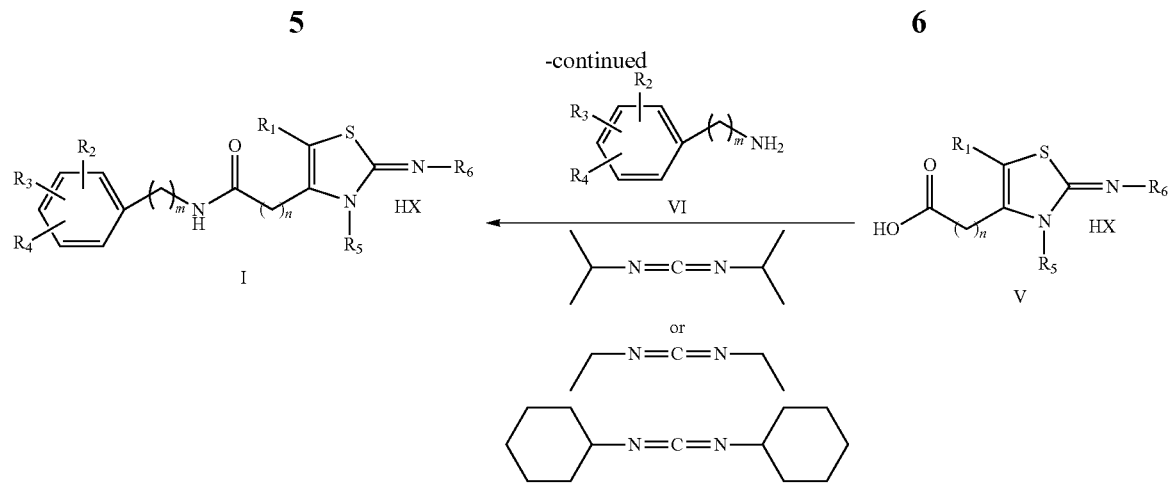

The HX and HY may be independently selected from the group consisting of hydrofluoric acid, hydrochloric acid, hydrobromic acid, and hydroiodic acid, X and Y may be the same or different from each other, and may be a halogen atom independently selected from the group consisting of fluorine, chlorine, bromine, and iodine, $R_1$ to $R_6$ are the same as defined above, and $R_7$ may be an alkoxy having 1 to 6 carbon atoms, preferably methoxy or ethoxy.

For example, the preparation method of the compound of Chemical Formula I where $R_1$ is hydrogen, any one of $R_2$, $R_3$, and $R_4$ is phenyloxy, $R_5$ is methyl, $R_6$ is cycloheptyl, and the other substituents are hydrogen, may be illustrated by Reaction Scheme 1-1.

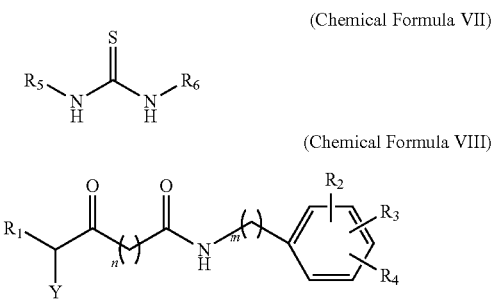

(Chemical Formula VII)

(Chemical Formula VIII)

(Reaction Scheme 1-1)

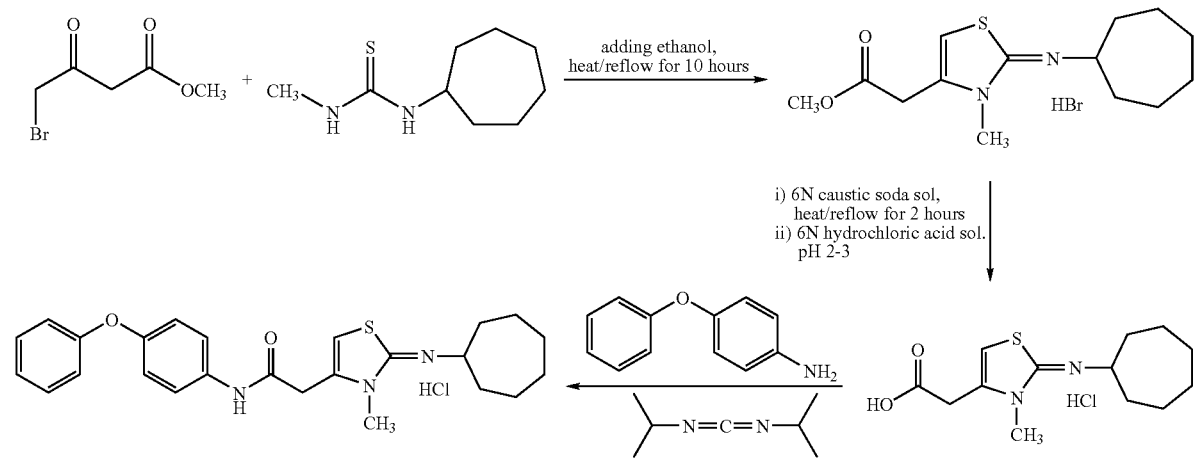

In another embodiment, the method of preparing the compound represented by Chemical Formula I may include the step of heating/reflowing the compounds represented by Chemical Formulas VII and VIII in a solution of a C1 to C5 alcohol, preferably ethanol, for 5 to 25 hours, preferably 10 to 20 hours, at 20 to 130° C., preferably 50 to 80° C., and allowing them to directly react, to prepare the compound represented by Chemical Formula I.

The preparation method may be illustrated by Reaction Scheme 2.

(Reaction Scheme 2)

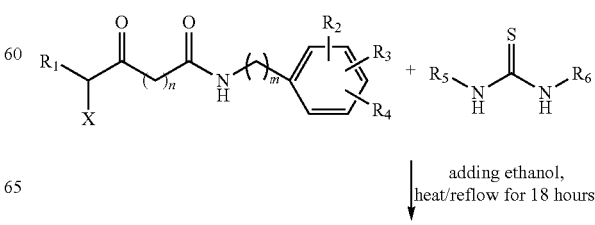

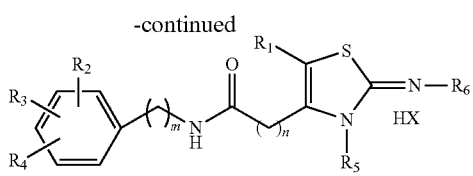

wherein $R_1$ to $R_6$ and X are the same as defined above.

For example, the preparation method of the compound represented by Chemical Formula I where $R_1$ is hydrogen, any one of $R_2$, $R_3$, and $R_4$ is phenyloxy, $R_5$ is methyl, $R_6$ is cycloheptyl, and the other substituents are hydrogen, may be illustrated by Reaction Scheme 2-1.

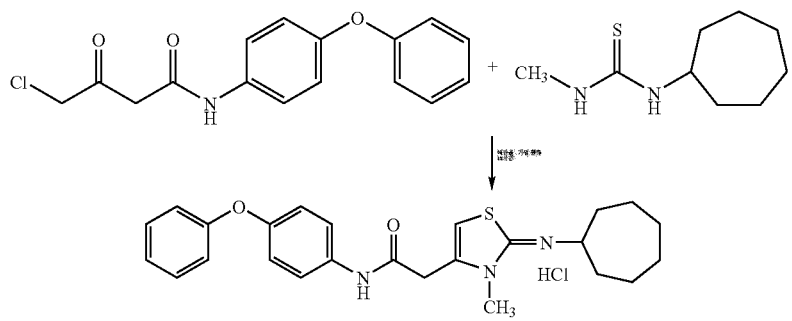

The compound represented by Chemical Formula I may be prepared by any one of Reaction Schemes 1 and 2, and any other conventional method known to the relevant field. Among the methods of Reaction Schemes 1 and 2, the method of Reaction Scheme 2 is simpler and excellent in terms of yield, but in other aspects, the method requires a high degree of technology to directly prepare the starting material, the compound of Chemical Formula VII. The method of Reaction Scheme 1 is convenient in obtaining the starting material, but the processes thereof are complicated. Any one of the two methods may be appropriately selected according to the availability of the starting material.

The 2-imino-1,3-thiazoline-based compounds of the present invention have excellent T-type calcium channel inhibiting activities, as shown in the experimental examples below. As described above, since the over-expression or over-activation of the T-type calcium channel may cause nerve diseases, pain, epilepsy, hypertension, angina pectoris, heart muscle disease, vascular disorder, cancer metastasis, and the like, the 2-imino-1,3-thiazoline-based compounds of the present invention can be used in preventing or treating such diseases.

Therefore, another embodiment of the present invention provides a composition for inhibiting T-type calcium channel, and a composition for preventing or treating a disease selected from the group consisting of nerve disease, pain, epilepsy, hypertension, angina pectoris, heart muscle disease, vascular disorder, and cancer, which contains the 2-imino-1, 3-thiazoline based compound represented by Chemical Formula I, or pharmaceutically acceptable salt thereof, as an active ingredient.

The amount of the 2-imino-1,3-thiazoline-based compound contained in the composition according to the present invention may be approximately 0.1 to 99 wt %, but is more preferably appropriately controlled according to its usage. Further, the administration dosage may be determined considering age, sex, and condition of the patient, absorption and inactivation rates in the body of the active ingredient, and co-administered drugs. For example, the dosage of the composition may be 1 mg/kg (body weight)/day to 500 mg/kg/day, preferably 1 mg/kg/day to 100 mg/kg/day, based on the active ingredient.

The composition according to the present invention may contain the 2-imino-1,3-thiazoline-based compound with or without other pharmaceutically acceptable drugs, carriers, or excipients. The carriers and excipients used in the present invention may be appropriately selected depending on the intended formulation type of the composition, for example, one or more selected from the group consisting of conventional diluents, fillers, expanders, wetting agents, disintegrants, and/or surfactants. Representative diluents or excipients may include water, dextrin, calcium carbonate, lactose, propylene glycol, liquid paraffin, talc, isomerized sugar, sodium metabisulfite, methylparaben, propylparaben, magnesium stearate, milk sugar, normal saline, flavorings, and colorants.

The composition may be administered by oral or parenteral pathway. The formulation type of the composition may vary depending on its usage. For example, the composition may be formulated in the form of plasters, granules, lotions, powders, syrups, liquids, solutions, aerosols, ointments, fluidextracts, emulsions, suspensions, infusions, tablets, injections, capsules, pills, and the like.

Another embodiment of the present invention provides foods, health supplement foods, or food additives containing the compounds of the present invention. The foods, health supplement foods, or food additives have no special limitations, and for example include foods for special diets (e.g., formula milks, foods for infants or toddlers, and the like), processed meat products, processed fish products, bean curd, acorn curd, noodles (e.g., instant noodles, noodles, and the like), breads, functional foods, seasoning foods (e.g., soy sauces, soybean pastes, Korean hot pepper pastes, mixed sauces, and the like), sauces, confectionery (e.g., snacks), processed milk products (e.g., fermented milk, cheeses, and the like), other processed foods, kimchi, pickled foods (e.g., various kimchies, Korean pickles, and the like), beverages (e.g., fruit or vegetables drinks, soybean milk, fermented drinks, and the like), and seasonings (e.g., instant noodle seasoning and the like), and may be prepared by any conventional method.

The present invention is further explained in more detail with reference to the following examples. These examples, however, should not be interpreted as limiting the scope of the present invention in any manner.

EXAMPLE 1

EXAMPLE 1

Preparation According to Reaction Scheme 1

EXAMPLE 1-1

Synthesis of KHG24123 (2-cycloheptylimino-3-methyl-1,3-thiazolidine-4-yl)-N-(4-phenoxyphenyl)-acetamide hydrochloride [$R_1$=H, $R_2$=4-$OC_6H_5$, $R_3$=$R_4$=H, $R_5$=$CH_3$, $R_6$=$C_7H_{13}$, n=1, m=0, X=Cl]

4-bromo-3-oxopentanoic acid methyl ester (14.6 g 75 mmol) and cycloheptylmethylthiourea (13.04 g, 70 mmol) were added to ethanol (150 mL), and subjected to heat/reflux for 10 hours. The reaction mixture was cooled to room temperature, and left for 3 hours at room temperature and for a further 12 hours at −20° C. The produced precipitate was filtrated to obtain a light yellow solid (17.6 g). The obtained solid was dissolved in methanol (35 mL), 6N caustic soda solution (22 mL) was added thereto, and the reaction mixture was subjected to heat/reflux for 2.5 hours.

The reaction mixture was cooled to room temperature and washed once with methylenechloride. To the reaction mixture, 6N hydrochloric acid solution was slowly added until the pH reached 2-3. The produced precipitate was filtrated and dried in the atmosphere to obtain a white solid (9.6 g). (2-cycloheptylimino-3-methyl-1,3-thiazolidine-4-yl)-acetic acid hydrochloride (305 mg, 1 mmol) and 4-phenoxyaniline (185 mg, 1 mmol) were dissolved in methylenechloride (10 mL), and cooled to 0° C. by ice bath. To the reaction mixture, diisopropylcarbodiimide (126 mg) was slowly added over 10 minutes.

The obtained reaction mixture was stirred at the same temperature for 3 hours, washed three times with water, once with dilute hydrochloric acid, once with a solution of bicarbonate of soda, and once with water, in turn, and then dried with anhydrous magnesium sulfate. The solvent was removed by reduced pressure evaporation. The remained reaction mixture was crystallized in ethylacetate and n-hexane to obtain (2-cycloheptylimino-3-methyl-1,3-thiazolidine-4-yl)-N-(4-phenoxyphenyl)-acetamide hydrochloride [$R_1$=H, $R_2$=4-$OC_6H_5$, $R_3$=R=H, $R_5$=$CH_3$, $R_6$=$C_7H_{13}$, n=1, m=0, X=Cl] (212 mg).

yield: 45%; melting point: 229-230° C.
$^1$H NMR (300 MHz, DMSO-$d_6$) δ 10.60 (s, 1H, HCl), 9.68 (s, 1H, NH), 7.51 (d, 2H, J=7.8 $H_z$, Ar—H), 7.17 (d, 2H, J=7.9 $H_z$, Ar—H), 7.04 (s, 1H, vinyl-H), 3.96 (s, 2H, 4-$CH_2$), 3.58 (s, 3H, N—$CH_3$), 3.23 (s, 1H, cyclohexyl-$C_1$H), 2.81 (m, 1H, J=6.6 $H_z$, Ar—CH($CH_3$)$_2$), 1.99-1.16 (m, 10H, cyclohexyl-H), 1.16 (d, 6H, J=6.8 $H_z$, Ar—CH($CH_3$)$_2$).

EXAMPLE 1-2

Synthesis of KHG24816 (2-adamantylimino-3-propyl-1,3-thiazolidine-4-yl)-N-(4-chloro-2-fluorophenyl)-acetamide hydrochloride [$R_1$=H, $R_2$=2-F, $R_3$=4-Cl, $R_4$=H, $R_5$=n-Pr, $R_6$=1-adamantyl, n=1, m=0, X=Cl]

Ethyl 4-chloro acetoacetate (13.1 g 80 mmol) and 1-adamantyl-n-propylthiourea (20.1 g, 80 mmol) were added to ethanol (150 ml), and subjected to heat/reflux for 10 hours. The reaction mixture was cooled to room temperature, and left for 3 hours at room temperature and for a further 12 hours at −20° C. The produced precipitate was filtrated to obtain a white solid (23.2 g). The obtained solid was dissolved in methanol (50 mL), 6N caustic soda solution (25 mL) was added thereto, and the reaction mixture was subject to heat/reflux for 2.5 hours.

The reaction mixture was cooled to room temperature, and washed once with methylenechloride. To the reaction mixture, 6N hydrochloric acid solution was slowly added until the pH reached 2-3. The produced precipitate was filtrated and dried in the atmosphere to obtain a white solid (14.1 g).

(2-adamantylimino-3-propyl-1,3-thiazolidine-4-yl)-acetic acid hydrochloride (370 mg, 1 mmol) and 4-chloro-2-fluoroaniline (145 mg, 1 mmol) were dissolved in methylenechloride (5 ml), and cooled to 0° C. by ice bath. To the reaction mixture, diisopropylcarbodiimide (126 mg) was slowly added over 10 minutes.

The obtained reaction mixture was stirred at the same temperature for 3 hours, washed three times with water, once with dilute hydrochloric acid, once with a solution of bicarbonate of soda, and once with water, in turn, and then dried with anhydrous magnesium sulfate. The solvent was removed by reduced pressure evaporation. The remaining reaction mixture was crystallized in ethylacetate and n-hexane to obtain (2-adamantylimino-3-propyl-1,3-thiazolidine-4-yl)-N-(4-chloro-2-fluorophenyl)-acetamide hydrochloride (331 mg).

yield: 66.4%; melting point: 131° C.
$^1$H NMR (300 MHz, DMSO-$d_6$) δ 10.52 (s, 1H, HCl), 8.64 (s, 1H, NH), 7.90-7.27 (m, 3H, ArH), 7.13 (s, 1H, vinyl-H), 4.24 (m, 2H, $CH_2CH_2$), 4.06 (s, 2H, $CH_2$), 2.16-1.61 (m, 15H, adamantyl H), 1.58 (m, 2H, $CH_2CH_2CH_3$), 0.86 (t, J=7.3 Hz, 3H, $CH_3$)

EXAMPLE 2

Preparation According to Reaction Scheme 2

EXAMPLE 2-1

Synthesis of KHG24123 (2-cycloheptylimino-3-methyl-1,3-thiazolidine-4-yl)-N-(4-phenoxyphenyl)-acetamide hydrochloride [$R_1$=H, $R_2$=4-$OC_6H_5$, $R_3$=$R_4$=H, $R_5$=$CH_3$, $R_6$=$C_7H_{13}$, n=1, m=0, X=Cl]

4-chloro-3-oxo-N-(4-phenoxyphenyl) butaneamide (152 mg, 0.5 mmol) and cycloheptylmethylurea (93 mg, 0.5 mmol) were added to ethanol (5 mL), and subjected to heat/reflux for 18 hours. The obtained reaction mixture was cooled to room temperature, diethylether (15 mL) was added thereto, and the reaction mixture was left overnight at −20°. The produced white solid was filtrated (166 mg).

yield: 70.6%; melting point: 229-230° C.
$^1$H NMR (300 MHz, DMSO-d6) δ 10.60 (s, 1H, HCl), 9.68 (s, 1H, NH), 7.51 (d, 2H, J=7.8 Hz, Ar—H), 7.17 (d, 2H, J=7.9 Hz, Ar—H), 7.04 (s, 1H, vinyl-H), 3.96 (s, 2H, 4-CH2), 3.58 (s, 3H, N—CH3), 3.23 (s, 1H, cyclohexyl-C1H), 2.81 (m, 1H, J=6.6 Hz, Ar—CH(CH3)2), 1.99-1.16 (m, 10H, cyclohexyl-H), 1.16 (d, 6H, J=6.8 Hz, Ar—CH(CH3)2).

EXAMPLE 2-2

Synthesis of KHG24237 [2-(1-adamantyl)imino-3-methyl-1,3-thiazolidine-4-yl]-N-(4-fluorophenyl)-acetamide hydrochloride [$R_1$=H, $R_2$=4-F, $R_3$=$R_4$=H, $R_5$=$CH_3$, $R_6$=1-adamantyl, n=1, m=0, X=Cl]

4-chloro-3-oxo-N-(4-fluorophenyl) butaneamide (115 mg, 0.5 mmol) and 1-adamantylmethylurea (112 mg, 0.5 mmol) were added to ethanol (5 mL), and subjected to heat/reflow for 15 hours. The obtained reaction mixture was cooled to room temperature, diethylether (15 mL) was added thereto, and the reaction mixture was left overnight at −20° C. The produced white solid was filtrated (211 mg).

yield: 96.8%; melting point: 201.9° C.

$^1$H NMR (300 MHz, $CD_3OD$) δ 7.58 (dd, 2H, J=9.06, 4.84 Hz, ArH-3' and ArH-5'), 7.08 (dd, 2H, J=8.78, 8.77 Hz, ArH-2' and ArH-6'), 6.99 (s, 1H, vinyl-H), 3.99 (s, 2H, $COCH_2$), 3.63 (s, 3H, $NCH_3$), 2.20-2.24 (m, 9H, adamantyl), 1.81 (br s, 6H, adamantyl).

EXAMPLE 2-3

Synthesis of KHG24847 [2-(1-adamantylimino)-3-ethyl-1,3-thiazolidine-4-yl]-N-(4-ethylphenyl)-acetamide hydrochloride [$R_1$=H, $R_2$=4-$C_2H_5$, $R_3$=$R_4$=H, $R_5$=$C_2H_5$, $R_6$=1-adamantyl, n=1, m=0, X=Cl]

4-chloro-3-oxo-N-(4-ethylphenyl) butaneamide (120 mg, 0.5 mmol) and 1-adamantylethylurea (119 mg, 0.5 mmol) was added to ethanol (5 mL), and subjected to heat/reflow for 15 hours. The obtained reaction mixture was cooled to room temperature, diethylether (15 mL) was added thereto, and the reaction mixture was left overnight at −20° C. The produced white solid was filtrated (43.5 mg).

yield: 18.9%; melting point: 144-145° C.

$^1$H NMR (300 MHz, DMSO-$d_6$) δ 10.63 (s, 1H, HCl), 8.40 (s, 1H, NH), 7.50 (d, 2H, J=8.4 Hz, ArH), 7.14 (d, 2H, J=8.4 Hz, ArH), 7.11 (s, 1H, vinyl H), 4.32-4.25 (m, 2H, 3-$CH_2CH_3$), 3.96 (s, 2H, $CH_2$), 2.55 (m, 2H, $CH_2CH_3$) 2.49-1.67 (m, 15H, adamantyl), 1.21-1.12 (m, 6H, 2ㅅ$CH_3$)

The compounds shown in Table 1 were prepared as illustrated in Example 1-1 to 2-3. As described above, the compounds of Table 1 may prepared by any method according to Reaction Scheme 1 or 2, and one skilled in the art may easily select an appropriate method of the two methods to prepare the compounds.

TABLE 1

| Compound code | $R_1$ | n | m | $R_2, R_3, R_4$ | $R_5$ | $R_6$ | salt(O, HBr, HCl) |
|---|---|---|---|---|---|---|---|
| KHG23210 | H | 1 | 0 | 4-F | CH3 | cy-6 | HCl |
| KHG23354 | H | 1 | 0 | 4-Br | CH3 | cy-6 | HCl |
| KHG23355 | H | 1 | 0 | 4-OPh | CH3 | cy-6 | HCl |
| KHG23356 | H | 1 | 0 | 3-Cl, 5-Cl | CH3 | cy-6 | HCl |
| KHG23360 | H | 1 | 0 | 2-F, 5-NO2 | CH3 | cy-6 | HCl |
| KHG23361 | H | 1 | 0 | 2-F, 4-Cl | CH3 | cy-6 | HCl |
| KHG23362 | H | 1 | 0 | 4-Cl | CH3 | cy-6 | HCl |
| KHG23364 | H | 1 | 0 | 4-isoPr | CH3 | cy-6 | HCl |
| KHG23365 | H | 1 | 0 | 4-n-Bu | CH3 | cy-6 | HCl |
| KHG24070 | H | 1 | 0 | 3-Cl, 4-OCH3 | CH3 | cy-6 | HCl |
| KHG24071 | H | 1 | 0 | 2-Cl, 4-CH3, 5-Cl | CH3 | cy-6 | HCl |
| KHG24072 | H | 1 | 0 | 3-Cl, 4-CH3 | CH3 | cy-6 | HCl |
| KHG24073 | H | 1 | 0 | 4-tBu | CH3 | cy-6 | HCl |
| KHG24074 | H | 1 | 0 | 4-CF3 | CH3 | cy-6 | HCl |
| KHG24075 | H | 1 | 0 | 3-CF3, 5-CF3 | CH3 | cy-6 | HCl |
| KHG24076 | H | 1 | 0 | 3-OCH3 | CH3 | cy-6 | HCl |
| KHG24077 | H | 1 | 0 | 4-CH3 | CH3 | cy-6 | HCl |
| KHG24080 | H | 1 | 0 | 2-F, 5-F | CH3 | cy-6 | HCl |
| KHG24081 | H | 1 | 0 | 2-F, 4-F | CH3 | cy-6 | HCl |
| KHG24082 | H | 1 | 1 | 2-CH3 | CH3 | cy-6 | HCl |
| KHG24083 | H | 1 | 1 | 2-CF3 | CH3 | cy-6 | HCl |
| KHG24084 | H | 1 | 1 | 3-CF3 | CH3 | cy-6 | HCl |
| KHG24085 | H | 1 | 0 | 3-CO2Et | CH3 | cy-6 | HCl |
| KHG24086 | H | 1 | 1 | 3,4-OCH2O | CH3 | cy-6 | HCl |
| KHG24087 | H | 1 | 0 | 2-F, 5-F | CH3 | cy-6 | HCl |
| KHG24088 | H | 1 | 0 | 3-Cl, 4-Cl | CH3 | cy-6 | HCl |
| KHG24089 | H | 1 | 1 | H | CH3 | cy-6 | HCl |
| KHG24090 | H | 1 | 0 | 3-OCH3, 4-OCH3 | CH3 | cy-6 | HCl |
| KHG24091 | H | 1 | 0 | 3-F, 4-CH3 | CH3 | cy-6 | HCl |
| KHG24092 | H | 1 | 0 | 4-C2H5 | CH3 | cy-5 | HCl |
| KHG24093 | H | 1 | 0 | 4-F | CH3 | cy-5 | HCl |
| KHG24094 | H | 1 | 0 | 4-OCH3 | CH3 | cy-5 | HCl |
| KHG24095 | H | 1 | 0 | 2-Cl, 4-F | CH3 | cy-5 | HCl |
| KHG24096 | H | 1 | 0 | 4-CH2CN | CH3 | cy-5 | HCl |
| KHG24097 | H | 1 | 0 | 2-Cl, 4-CH3 | CH3 | cy-5 | HCl |
| KHG24098 | H | 1 | 0 | 4-Br | CH3 | cy-5 | HCl |
| KHG24099 | H | 1 | 0 | 4-OPh | CH3 | cy-5 | HCl |
| KHG24100 | H | 1 | 0 | 3-Cl, 5-Cl | CH3 | cy-5 | HCl |
| KHG24101 | H | 1 | 0 | 2-F, 4-CH3 | CH3 | cy-5 | HCl |
| KHG24102 | H | 1 | 0 | 2-F, 4-F | CH3 | cy-5 | HCl |
| KHG24103 | H | 1 | 0 | 2-F, 5-Cl | CH3 | cy-5 | HCl |
| KHG24104 | H | 1 | 0 | 2-F, 5-N02 | CH3 | cy-5 | HCl |
| KHG24105 | H | 1 | 0 | 2-F, 4-Cl | CH3 | cy-5 | HCl |
| KHG24106 | H | 1 | 0 | 4-Cl | CH3 | cy-5 | HCl |
| KHG24107 | H | 1 | 0 | H | CH3 | cy-5 | HCl |

TABLE 1-continued

| Compound code | $R_1$ | n | m | $R_2, R_3, R_4$ | $R_5$ | $R_6$ | salt(O, HBr, HCl) |
|---|---|---|---|---|---|---|---|
| KHG24108 | H | 1 | 0 | 3-NO2 | CH3 | cy-6 | HCl |
| KHG24109 | H | 1 | 0 | 3-F | CH3 | cy-6 | HCl |
| KHG24110 | H | 1 | 0 | 4-isoPr | CH3 | cy-6 | HCl |
| KHG24111 | H | 1 | 0 | 3-CH3, 4-Br | CH3 | cy-6 | HCl |
| KHG24112 | H | 1 | 1 | 4-F | CH3 | cy-6 | HCl |
| KHG24113 | H | 1 | 1 | 4-Cl | CH3 | cy-6 | HCl |
| KHG24114 | H | 1 | 1 | 4-OCH3 | CH3 | cy-6 | HCl |
| KHG24115 | H | 1 | 0 | 4-isoPr | CH3 | cy-5 | HCl |
| KHG24116 | H | 1 | 0 | 4-n-Bu | CH3 | cy-5 | HCl |
| KHG24117 | H | 1 | 0 | 4-C2H5 | CH3 | cy-7 | HCl |
| KHG24118 | H | 1 | 0 | 4-F | CH3 | cy-7 | HCl |
| KHG24119 | H | 1 | 0 | 4-OCH3 | CH3 | cy-7 | HCl |
| KHG24120 | H | 1 | 0 | 2-Cl, 4-F | CH3 | cy-7 | HCl |
| KHG24121 | H | 1 | 0 | 4-CH2CN | CH3 | cy-7 | HCl |
| KHG24122 | H | 1 | 0 | 4-Br | CH3 | cy-7 | HCl |
| KHG24123 | H | 1 | 0 | 4-OPh | CH3 | cy-7 | HCl |
| KHG24124 | H | 1 | 0 | 2-Cl, 4-CH3 | CH3 | cy-7 | HCl |
| KHG24125 | H | 1 | 0 | 3-Cl, 5-Cl | CH3 | cy-7 | HCl |
| KHG24126 | H | 1 | 0 | 2-F, 4-CH3 | CH3 | cy-7 | HCl |
| KHG24127 | H | 1 | 0 | 2-F, 4-F | CH3 | cy-7 | HCl |
| KHG24128 | H | 1 | 0 | 2-F, 5-Cl | CH3 | cy-7 | HCl |
| KHG24129 | H | 1 | 0 | 2-F, 5-NO2 | CH3 | cy-7 | HCl |
| KHG24130 | H | 1 | 0 | 2-F, 4-Cl | CH3 | cy-7 | HCl |
| KHG24131 | H | 1 | 0 | 4-Cl | CH3 | cy-7 | HCl |
| KHG24132 | H | 1 | 0 | H | CH3 | cy-7 | HCl |
| KHG24133 | H | 1 | 0 | 4-isoPr | CH3 | cy-7 | HCl |
| KHG24134 | H | 1 | 0 | 4-n-Bu | CH3 | cy-7 | HCl |
| KHG24135 | H | 1 | 0 | 4-Et | CH3 | cy-3 | HCl |
| KHG24136 | H | 1 | 0 | 4-F | CH3 | cy-3 | HCl |
| KHG24137 | H | 1 | 0 | 4-OCH3 | CH3 | cy-3 | HCl |
| KHG24138 | H | 1 | 0 | 2-Cl, 4-F | CH3 | cy-3 | HCl |
| KHG24139 | H | 1 | 0 | 4-CH2CN | CH3 | cy-3 | HCl |
| KHG24140 | H | 1 | 0 | 4-Br | CH3 | cy-3 | HCl |
| KHG24141 | H | 1 | 0 | 4-OPh | CH3 | cy-3 | HCl |
| KHG24142 | H | 1 | 0 | 2-Cl, 4-Me | CH3 | cy-3 | HCl |
| KHG24144 | H | 1 | 0 | 2-F, 4-CH3 | CH3 | cy-3 | HCl |
| KHG24145 | H | 1 | 0 | 2-F, 4-F | CH3 | cy-3 | HCl |
| KHG24146 | H | 1 | 0 | 2-F, 5-Cl | CH3 | cy-3 | HCl |
| KHG24147 | H | 1 | 0 | 2-F, 5-NO2 | CH3 | cy-3 | HCl |
| KHG24148 | H | 1 | 0 | 2-F, 4-Cl | CH3 | cy-3 | HCl |
| KHG24149 | H | 1 | 0 | 4-Cl | CH3 | cy-3 | HCl |
| KHG24150 | H | 1 | 0 | H | CH3 | cy-3 | HCl |
| KHG24151 | H | 1 | 0 | 4-isoPr | CH3 | cy-3 | HCl |
| KHG24152 | H | 1 | 0 | 4-n-Bu | CH3 | cy-3 | HCl |
| KHG24153 | H | 1 | 1 | 4-F | CH3 | cy-3 | HCl |
| KHG24154 | H | 1 | 1 | 4-Cl | CH3 | cy-3 | HCl |
| KHG24155 | H | 1 | 1 | 4-OCH3 | CH3 | cy-3 | HCl |
| KHG24156 | H | 1 | 1 | 4-F | CH3 | cy-5 | HCl |
| KHG24157 | H | 1 | 1 | 4-Cl | CH3 | cy-5 | HCl |
| KHG24158 | H | 1 | 1 | 4-OCH3 | CH3 | cy-5 | HCl |
| KHG24159 | H | 1 | 1 | 4-F | CH3 | cy-7 | HCl |
| KHG24160 | H | 1 | 1 | 4-Cl | CH3 | cy-7 | HCl |
| KHG24161 | H | 1 | 1 | 4-OCH3 | CH3 | cy-7 | HCl |
| KHG24216 | H | 1 | 0 | 3-CF3, 5-CF3 | CH3 | CH2CH2Ph | HCl |
| KHG24218 | H | 1 | 0 | 3-CF3, 5-CF3 | CH3 | CH2-cy-6 | HCl |
| KHG24220 | H | 1 | 0 | 4-isoPr | CH3 | CH2CH2Ph | HCl |
| KHG24222 | H | 1 | 0 | 4-isoPr | CH3 | CH2-cy-6 | HCl |
| KHG24224 | H | 1 | 0 | 4-OPh | CH3 | CH2CH2Ph | HCl |
| KHG24226 | H | 1 | 0 | 4-OPh | CH3 | CH2-cy-6 | HCl |
| KHG24228 | H | 1 | 0 | 4-Cl | CH3 | CH2CH2Ph | HCl |
| KHG24230 | H | 1 | 0 | 4-Cl | CH3 | CH2-cy-6 | HCl |
| KHG24232 | H | 1 | 0 | 2-F, 5-NO2 | CH3 | CH2CH2Ph | HCl |
| KHG24234 | H | 1 | 0 | 2-F, 5-NO2 | CH3 | CH2-cy-6 | HCl |
| KHG24235 | H | 1 | 0 | 4-CH3 | CH3 | 1-Ad | HCl |
| KHG24236 | H | 1 | 0 | 4-CH2CH3 | CH3 | 1-Ad | HCl |
| KHG24237 | H | 1 | 0 | 4-F | CH3 | 1-Ad | HCl |
| KHG24238 | H | 1 | 0 | 4-Cl | CH3 | 1-Ad | HCl |
| KHG24239 | H | 1 | 0 | 4-Br | CH3 | 1-Ad | HCl |
| KHG24240 | H | 1 | 0 | 4-CF3 | CH3 | 1-Ad | HCl |
| KHG24241 | H | 1 | 0 | 3-CF3, 5-CF3 | CH3 | 1-Ad | HCl |
| KHG24242 | H | 1 | 0 | 2-F, 5-Cl | CH3 | 1-Ad | HCl |
| KHG24243 | H | 1 | 0 | 4-isoPr | CH3 | 1-Ad | HCl |
| KHG24244 | H | 1 | 0 | 4-OC6H5 | CH3 | 1-Ad | HCl |
| KHG24261 | H | 1 | 0 | 3-CF3, 5-CF3 | CH2CH3 | cy-6 | HCl |
| KHG24262 | H | 1 | 0 | 4-Cl | n-Bu | cy-6 | HCl |
| KHG24263 | H | 1 | 0 | 4-Br | n-Bu | cy-6 | HCl |
| KHG24264 | H | 1 | 0 | 3-CF3, 5-CF3 | n-Bu | cy-6 | HCl |

TABLE 1-continued

| Compound code | $R_1$ | n | m | $R_2, R_3, R_4$ | $R_5$ | $R_6$ | salt(O, HBr, HCl) |
|---|---|---|---|---|---|---|---|
| KHG24265 | H | 1 | 0 | 4-Br | cy-6 | cy-6 | HCl |
| KHG24266 | H | 1 | 0 | 4-Cl | cy-6 | cy-6 | HCl |
| KHG24267 | H | 1 | 0 | 3-CF3, 5-CF3 | cy-3 | cy-6 | HCl |
| KHG24268 | H | 1 | 0 | 4-CF3 | cy-3 | cy-6 | HCl |
| KHG24270 | H | 1 | 0 | 4-n-Bu | cy-3 | cy-6 | HCl |
| KHG24271 | H | 1 | 0 | 2-F, 5-Cl | cy-3 | cy-6 | HCl |
| KHG24272 | H | 1 | 0 | 4-CH2CH3 | cy-3 | cy-6 | HCl |
| KHG24273 | H | 1 | 0 | 4-Br | cy-3 | cy-6 | HCl |
| KHG24274 | H | 1 | 0 | 4-CH3 | cy-3 | cy-6 | HCl |
| KHG24275 | H | 1 | 0 | 4-Cl | CH2CH3 | cy-6 | HCl |
| KHG24276 | H | 1 | 0 | 4-0Ph | CH2CH3 | cy-6 | HCl |
| KHG24277 | H | 1 | 0 | 4-n-Bu | CH2CH3 | cy-6 | HCl |
| KHG24278 | H | 1 | 0 | 2-F, 5-N02 | CH2CH3 | cy-6 | HCl |
| KHG24279 | H | 1 | 0 | 4-CH3 | CH2CH3 | cy-6 | HCl |
| KHG24280 | H | 1 | 0 | 4-CF3 | CH2CH3 | cy-6 | HCl |
| KHG24281 | H | 1 | 0 | 4-0Ph | n-Bu | cy-6 | HCl |
| KHG24282 | H | 1 | 0 | 4-n-Bu | n-Bu | cy-6 | HCl |
| KHG24283 | H | 1 | 0 | 4-isoPr | n-Bu | cy-6 | HCl |
| KHG24284 | H | 1 | 0 | 4-F | n-Bu | cy-6 | HCl |
| KHG24285 | H | 1 | 0 | 4-CH3 | n-Bu | cy-6 | HCl |
| KHG24286 | H | 1 | 0 | 4-CH2CH3 | n-Bu | cy-6 | HCl |
| KHG24287 | H | 1 | 0 | 4-Cl | n-Pr | cy-6 | HCl |
| KHG24288 | H | 1 | 0 | 4-Br | n-Pr | cy-6 | HCl |
| KHG24289 | H | 1 | 0 | 3-CF3, 5-CF3 | n-Pr | cy-6 | HCl |
| KHG24290 | H | 1 | 0 | 4-0Ph | n-Pr | cy-6 | HCl |
| KHG24291 | H | 1 | 0 | 4-n-Bu | n-Pr | cy-6 | HCl |
| KHG24292 | H | 1 | 1 | 4-CH3 | CH2CH3 | cy-6 | HCl |
| KHG24293 | H | 1 | 1 | 4-CH3 | n-Bu | cy-6 | HCl |
| KHG24294 | H | 1 | 0 | 4-isoPr | n-Pr | cy-6 | HCl |
| KHG24295 | H | 1 | 0 | 2-F, 5-N02 | n-Pr | cy-6 | HCl |
| KHG24296 | H | 1 | 0 | 4-F | n-Pr | cy-6 | HCl |
| KHG24297 | H | 1 | 0 | 4-CH3 | n-Pr | cy-6 | HCl |
| KHG24298 | H | 1 | 0 | 4-CH2CH3 | n-Pr | cy-6 | HCl |
| KHG24299 | H | 1 | 0 | 4-Cl | benzyl | cy-6 | HCl |
| KHG24300 | H | 1 | 0 | 4-Br | benzyl | cy-6 | HCl |
| KHG24301 | H | 1 | 0 | 3-CF3, 5-CF3 | benzyl | cy-6 | HCl |
| KHG24302 | H | 1 | 0 | 4-0Ph | benzyl | cy-6 | HCl |
| KHG24303 | H | 1 | 0 | 4-isoPr | benzyl | cy-6 | HCl |
| KHG24304 | H | 1 | 0 | 2-F, 5-N02 | benzyl | cy-6 | HCl |
| KHG24305 | H | 1 | 0 | 4-F | benzyl | cy-6 | HCl |
| KHG24306 | H | 1 | 0 | 4-CH2CH3 | benzyl | cy-6 | HCl |
| KHG24307 | H | 1 | 0 | 3-CF3, 5-CF3 | cy-6 | cy-6 | HCl |
| KHG24308 | H | 1 | 0 | 4-isoPr | cy-6 | cy-6 | HCl |
| KHG24309 | H | 1 | 0 | 4-0Ph | cy-6 | cy-6 | HCl |
| KHG24310 | H | 1 | 0 | 4-CF3 | cy-6 | cy-6 | HCl |
| KHG24311 | H | 1 | 0 | 4-n-Bu | cy-6 | cy-6 | HCl |
| KHG24312 | H | 1 | 0 | 4-F | cy-6 | cy-6 | HCl |
| KHG24313 | H | 1 | 0 | 4-CH3 | cy-6 | cy-6 | HCl |
| KHG24314 | H | 1 | 0 | 4-CH2CH3 | cy-6 | cy-6 | HCl |
| KHG24315 | H | 1 | 0 | 4-0Ph | cy-3 | cy-6 | HCl |
| KHG24336 | H | 0 | 1 | 3-Cl | CH3 | cy-7 | HCl |
| KHG24337 | H | 0 | 1 | 4-Cl | CH3 | cy-7 | HCl |
| KHG24338 | H | 0 | 1 | 3-Cl, 4-Cl | CH3 | cy-7 | HCl |
| KHG24339 | H | 0 | 1 | 4-0CH3 | CH3 | cy-7 | HCl |
| KHG24403 | H | 1 | 0 | 4-F | CH2CH3 | cy-6 | HCl |
| KHG24404 | H | 1 | 0 | 4-CF3 | n-Pr | cy-6 | HCl |
| KHG24405 | H | 1 | 0 | 3-Cl, 4-CH3 | n-Pr | cy-6 | HCl |
| KHG24406 | H | 1 | 0 | 4-n-Bu | benzyl | cy-6 | HCl |
| KHG24407 | H | 1 | 0 | 4-CF3 | benzyl | cy-6 | HCl |
| KHG24408 | H | 1 | 0 | 2-F, 5-Cl | benzyl | cy-6 | HCl |
| KHG24409 | H | 1 | 0 | 4-n-Bu | CH3 | 1-Ad | HCl |
| KHG24410 | H | 1 | 0 | 3-Cl, 5-Cl | CH3 | 1-Ad | HCl |
| KHG24411 | H | 1 | 0 | 2-F, 4-Cl | CH3 | 1-Ad | HCl |
| KHG24412 | H | 1 | 0 | H | CH3 | 1-Ad | HCl |
| KHG24413 | H | 1 | 0 | 2-Cl, 4-CH3 | CH3 | 1-Ad | HCl |
| KHG24414 | H | 1 | 0 | 3-Cl, 5-Cl | CH2CH3 | cy-6 | HCl |
| KHG24415 | H | 1 | 0 | 3-Cl, 5-Cl | n-Pr | cy-6 | HCl |
| KHG24416 | H | 1 | 0 | 3-Cl, 5-Cl | n-Bu | cy-6 | HCl |
| KHG24417 | H | 1 | 0 | 3-Cl, 5-Cl | CH3 | 1-Ad | HCl |
| KHG24418 | H | 1 | 0 | 2-Cl, 4-CH3 | CH3 | 1-Ad | HCl |
| KHG24419 | H | 1 | 0 | 4-0CH3 | CH3 | 1-Ad | HCl |
| KHG24420 | H | 1 | 0 | 2-Cl, 4-CH3 | CH2CH3 | cy-6 | HCl |
| KHG24421 | H | 1 | 0 | 2-Cl, 4-CH3 | n-Bu | cy-6 | HCl |
| KHG24422 | H | 1 | 0 | 3-Cl, 5-Cl | benzyl | cy-6 | HCl |
| KHG24445 | H | 1 | 0 | 4-N02 | CH3 | cy-7 | HCl |
| KHG24446 | H | 1 | 0 | 4-NH2 | CH3 | cy-7 | HCl |
| KHG24447 | H | 1 | 0 | 4-NHMs | CH3 | cy-7 | HCl |

TABLE 1-continued

| Compound code | R₁ | n | m | R₂, R₃, R₄ | R₅ | R₆ | salt(O, HBr, HCl) |
|---|---|---|---|---|---|---|---|
| KHG24448 | H | 1 | 0 | 4-NHTs | CH3 | cy-7 | HCl |
| KHG24449 | H | 1 | 1 | 4-NHTs | CH3 | cy-7 | HCl |
| KHG24450 | H | 1 | 1 | 4-NHMs | CH3 | cy-7 | HCl |
| KHG24478 | H | 1 | 0 | 3-Cl, 5-Cl | H | H | HCl |
| KHG24479 | H | 1 | 0 | 4-Cl | H | H | HCl |
| KHG24480 | CH3 | 1 | 0 | 4-Cl | CH3 | cy-6 | O |
| KHG24481 | CH3 | 1 | 0 | 4-OCH3 | CH3 | cy-6 | O |
| KHG24482 | CH3 | 1 | 0 | 4-Br | CH3 | cy-6 | O |
| KHG24483 | CH3 | 1 | 0 | 3-Cl, 5-Cl | CH3 | cy-6 | O |
| KHG24484 | CH3 | 1 | 0 | 2-F, 5-NO2 | CH3 | cy-6 | O |
| KHG24485 | CH3 | 1 | 0 | 4-OCH3 | CH3 | cy-7 | O |
| KHG24486 | CH3 | 1 | 0 | 4-Br | CH3 | cy-7 | O |
| KHG24516 | CH3 | 1 | 0 | 4-n-Bu | CH3 | cy-7 | HCl |
| KHG24517 | CH3 | 1 | 0 | 4-CH2CH3 | CH3 | cy-7 | HCl |
| KHG24518 | CH3 | 1 | 0 | 4-F | CH3 | cy-7 | HCl |
| KHG24519 | CH3 | 1 | 0 | 4-isoPr | CH3 | cy-7 | HCl |
| KHG24520 | CH3 | 1 | 0 | 4-CF3 | CH3 | cy-7 | HCl |
| KHG24521 | CH3 | 1 | 0 | 4-t-Bu | CH3 | cy-7 | HCl |
| KHG24522 | CH3 | 1 | 0 | 3-CF3, 5-CF3 | CH3 | cy-6 | HCl |
| KHG24523 | CH3 | 1 | 0 | 4-CH2CH3 | CH3 | cy-6 | HCl |
| KHG24524 | CH3 | 1 | 0 | 4-OCF3 | CH3 | cy-6 | HCl |
| KHG24525 | CH3 | 1 | 0 | 4-F | CH3 | cy-6 | HCl |
| KHG24526 | CH3 | 1 | 0 | 4-isoPr | CH3 | cy-6 | HCl |
| KHG24527 | CH3 | 1 | 0 | 4-CF3 | CH3 | cy-6 | HCl |
| KHG24528 | H | 1 | 0 | 3-isoPr | CH3 | cy-6 | HCl |
| KHG24529 | H | 1 | 0 | 3-CF3, 5-CF3 | CH3 | cy-6 | HCl |
| KHG24530 | H | 1 | 0 | 2-Cl, 3-Cl | CH3 | cy-6 | HCl |
| KHG24531 | H | 1 | 0 | 3-Cl, 4-Cl | CH3 | cy-6 | HCl |
| KHG24532 | H | 1 | 0 | 2-Cl, 5-Cl | CH3 | cy-6 | HCl |
| KHG24533 | H | 1 | 0 | 2-Cl, 4-Cl, 5-Cl | CH3 | cy-6 | HCl |
| KHG24534 | H | 1 | 0 | 3-F, 5-F | CH3 | cy-6 | HCl |
| KHG24535 | H | 1 | 0 | 4-CH3 | cy-6 | cy-6 | HCl |
| KHG24536 | H | 1 | 0 | 4-F | cy-6 | cy-6 | HCl |
| KHG24537 | H | 1 | 0 | 3-Cl, 4-CH3 | cy-6 | cy-6 | HCl |
| KHG24538 | H | 1 | 0 | 4-CH2CH3 | cy-6 | cy-6 | HCl |
| KHG24539 | H | 1 | 0 | 4-Cl | cy-6 | cy-6 | HCl |
| KHG24540 | H | 1 | 0 | 2-F, 5-Cl | cy-6 | cy-6 | HCl |
| KHG24541 | H | 1 | 0 | 4-n-Pr | cy-6 | cy-6 | HCl |
| KHG24542 | H | 1 | 0 | 4-Br | cy-6 | cy-6 | HCl |
| KHG24543 | H | 1 | 0 | 4-CF3 | cy-6 | cy-6 | HCl |
| KHG24544 | H | 1 | 1 | 4-Cl | cy-6 | cy-6 | HCl |
| KHG24545 | H | 1 | 0 | 4-t-Bu | cy-6 | cy-6 | HCl |
| KHG24546 | H | 1 | 0 | 3-CF3, 5-CF3 | cy-6 | cy-6 | HCl |
| KHG24547 | H | 1 | 1 | 2-CF3 | cy-6 | cy-6 | HCl |
| KHG24548 | H | 1 | 0 | 4-OPh | cy-6 | cy-6 | HCl |
| KHG24549 | H | 1 | 0 | 3-Cl, 5-Cl | cy-6 | cy-6 | HCl |
| KHG24550 | H | 1 | 0 | cy-7 | CH3 | Ph(2-Cl) | HCl |
| KHG24622 | H | 0 | 1 | H | CH3 | cy-7 | O |
| KHG24623 | H | 0 | 1 | H | CH3 | cy-7 | HCl |
| KHG24624 | H | 0 | 1 | 2-Cl | CH3 | cy-7 | O |
| KHG24625 | H | 0 | 1 | 2-F, 5-F | CH3 | cy-7 | O |
| KHG24626 | H | 0 | 1 | 2-F, 5-F | CH3 | cy-7 | HCl |
| KHG24627 | H | 0 | 1 | 3-F, 4-F | CH3 | cy-7 | O |
| KHG24628 | H | 0 | 1 | 4-CH3 | CH3 | cy-7 | O |
| KHG24629 | H | 0 | 1 | 4-CH3 | CH3 | cy-7 | HCl |
| KHG24630 | H | 0 | 1 | 3-CF3, 5-CF3 | CH3 | cy-7 | O |
| KHG24631 | H | 0 | 0 | 4-F | CH3 | cy-7 | O |
| KHG24632 | H | 0 | 1 | 3-CF3, 5-CF3 | CH3 | cy-7 | HCl |
| KHG24633 | H | 0 | 1 | 2-Br | CH3 | cy-7 | O |
| KHG24634 | H | 0 | 1 | 2-Br | CH3 | cy-7 | HCl |
| KHG24635 | CH3 | 1 | 0 | H | CH3 | cy-6 | HCl |
| KHG24636 | CH3 | 1 | 0 | 3-F | CH3 | cy-6 | HCl |
| KHG24637 | CH3 | 1 | 0 | 4-t-Bu | CH3 | cy-6 | HCl |
| KHG24638 | CH3 | 1 | 0 | H | CH3 | cy-7 | HCl |
| KHG24639 | CH3 | 1 | 0 | 4-CH3 | CH3 | cy-7 | HCl |
| KHG24640 | CH3 | 1 | 0 | 2-F | CH3 | cy-7 | HCl |
| KHG24641 | CH3 | 1 | 0 | 3-F | CH3 | cy-7 | HCl |
| KHG24642 | CH3 | 1 | 0 | 4-NO2 | CH3 | cy-7 | HCl |
| KHG24643 | CH3 | 1 | 0 | 4-Cl | CH3 | cy-7 | HCl |
| KHG24644 | CH3 | 1 | 0 | 3-Cl, 5-Cl | CH3 | cy-7 | HCl |
| KHG24645 | CH3 | 1 | 0 | 2-F, 5-NO2 | CH3 | cy-7 | HCl |
| KHG24646 | CH3 | 1 | 0 | 3-CF3, 5-CF3 | CH3 | cy-7 | HCl |
| KHG24647 | CH3 | 1 | 0 | 4-OCF3 | CH3 | cy-7 | HCl |
| KHG24653 | CH3 | 1 | 0 | H | CH3 | cy-5 | HCl |
| KHG24654 | CH3 | 1 | 0 | 4-CH3 | CH3 | cy-5 | HCl |
| KHG24655 | CH3 | 1 | 0 | 3-F | CH3 | cy-5 | HCl |
| KHG24656 | CH3 | 1 | 0 | 4-t-Bu | CH3 | cy-5 | HCl |

TABLE 1-continued

| Compound code | $R_1$ | n | m | $R_2, R_3, R_4$ | $R_5$ | $R_6$ | salt(O, HBr, HCl) |
|---|---|---|---|---|---|---|---|
| KHG24657 | CH3 | 1 | 0 | 4-Cl | CH3 | cy-5 | HCl |
| KHG24658 | CH3 | 1 | 0 | 4-N02 | CH3 | cy-6 | HCl |
| KHG24659 | CH3 | 1 | 0 | 2-F | CH3 | cy-5 | HCl |
| KHG24660 | H | 0 | 0 | 2-F, 5-N02 | CH3 | cy-7 | HBr |
| KHG24661 | H | 0 | 0 | 2-F, 5-N02 | CH3 | cy-7 | 0 |
| KHG24662 | H | 0 | 0 | 4-F | CH3 | cy-7 | HCl |
| KHG24663 | H | 0 | 0 | 4-CH2CH3 | CH3 | cy-7 | HBr |
| KHG24664 | H | 0 | 0 | 4-CH2CH3 | CH3 | cy-7 | 0 |
| KHG24666 | H | 0 | 1 | 3-F | CH3 | cy-7 | HCl |
| KHG24667 | H | 0 | 1 | 3-F | CH3 | cy-7 | 0 |
| KHG24668 | H | 0 | 1 | 3-Br | CH3 | cy-7 | HBr |
| KHG24669 | H | 0 | 1 | 3-Br | CH3 | cy-7 | 0 |
| KHG24670 | H | 0 | 1 | 2-CF3 | CH3 | cy-7 | HBr |
| KHG24671 | H | 0 | 1 | 2-CF3 | CH3 | cy-7 | 0 |
| KHG24672 | H | 0 | 0 | 4-CH3 | CH3 | cy-7 | HBr |
| KHG24673 | H | 0 | 0 | 4-CH3 | CH3 | cy-7 | 0 |
| KHG24674 | H | 0 | 0 | 3-Cl, 5-Cl | CH3 | cy-7 | 0 |
| KHG24675 | H | 0 | 0 | 3-Cl, 5-Cl | CH3 | cy-7 | HBr |
| KHG24676 | H | 0 | 0 | 4-Cl | CH3 | cy-7 | HBr |
| KHG24677 | H | 0 | 0 | 4-Cl | CH3 | cy-7 | 0 |
| KHG24678 | H | 0 | 0 | 4-n-Bu | CH3 | cy-7 | HBr |
| KHG24679 | H | 0 | 0 | 4-isoPr | CH3 | cy-7 | HBr |
| KHG24680 | H | 0 | 0 | 4-isoPr | CH3 | cy-7 | 0 |
| KHG24681 | H | 0 | 0 | 4-0Ph | CH3 | cy-7 | HBr |
| KHG24682 | H | 0 | 0 | 4-0Ph | CH3 | cy-7 | 0 |
| KHG24683 | H | 0 | 0 | 4-t-Bu | CH3 | cy-7 | HBr |
| KHG24684 | H | 0 | 0 | 4-t-Bu | CH3 | cy-7 | 0 |
| KHG24685 | H | 0 | 0 | 2-F, 5-Cl | CH3 | cy-7 | HBr |
| KHG24686 | H | 0 | 0 | 2-F, 5-Cl | CH3 | cy-7 | 0 |
| KHG24687 | H | 0 | 0 | 3-CF3, 5-CF3 | CH3 | cy-7 | HBr |
| KHG24688 | H | 0 | 0 | 3-CF3, 5-CF3 | CH3 | cy-7 | 0 |
| KHG24689 | H | 0 | 0 | 4-n-Bu | CH3 | cy-7 | 0 |
| KHG24775 | H | 1 | 0 | 4-Cl | n-Bu | 1-Ad | HCl |
| KHG24776 | H | 1 | 0 | 4-n-Bu | n-Bu | 1-Ad | HCl |
| KHG24777 | H | 1 | 0 | 4-CF3 | n-Bu | 1-Ad | HCl |
| KHG24778 | H | 1 | 0 | 3-Cl, 5-Cl | n-Bu | 1-Ad | HCl |
| KHG24779 | H | 1 | 0 | 3-CF3, 5-CF3 | n-Bu | 1-Ad | HCl |
| KHG24780 | H | 1 | 0 | 4-F | n-Bu | 1-Ad | HCl |
| KHG24781 | H | 1 | 0 | 4-CH3 | n-Bu | 1-Ad | HCl |
| KHG24782 | H | 1 | 0 | 4-CH2CH3 | n-Bu | 1-Ad | HCl |
| KHG24783 | H | 1 | 0 | 2-F, 4-Cl | n-Bu | 1-Ad | HCl |
| KHG24784 | H | 1 | 0 | 4-Br | n-Bu | 1-Ad | HCl |
| KHG24785 | H | 1 | 0 | 2-F, 5-Cl | n-Bu | 1-Ad | HCl |
| KHG24788 | H | 1 | 0 | 4-isoPr | cy-3 | 1-Ad | HCl |
| KHG24789 | H | 1 | 0 | 4-n-Bu | cy-3 | 1-Ad | HCl |
| KHG24790 | H | 1 | 0 | 4-CF3 | cy-3 | 1-Ad | HCl |
| KHG24792 | H | 1 | 0 | 3-CF3, 5-CF3 | cy-3 | 1-Ad | HCl |
| KHG24795 | H | 1 | 0 | 4-isoPr | n-Bu | 1-Ad | HCl |
| KHG24796 | H | 1 | 0 | 4-0Ph | n-Bu | 1-Ad | HCl |
| KHG24799 | H | 1 | 0 | 4-CH2CH3 | cy-3 | 1-Ad | HCl |
| KHG24800 | H | 1 | 0 | 4-0Ph | cy-3 | 1-Ad | HCl |
| KHG24801 | H | 1 | 0 | 2-F, 4-Cl | cy-3 | 1-Ad | HCl |
| KHG24802 | H | 1 | 0 | 2-F, 5-Cl | cy-3 | 1-Ad | HCl |
| KHG24803 | H | 1 | 0 | 3-0CH20-4 | n-Bu | 1-Ad | HCl |
| KHG24804 | H | 1 | 0 | 3-0CH20-4 | cy-3 | 1-Ad | HCl |
| KHG24805 | H | 1 | 0 | 3-Cl, 5-Cl | n-Pr | 1-Ad | HCl |
| KHG24807 | H | 1 | 0 | 4-isoPr | n-Pr | 1-Ad | HCl |
| KHG24808 | H | 1 | 0 | 4-n-Bu | n-Pr | 1-Ad | HCl |
| KHG24809 | H | 1 | 0 | 4-CF3 | n-Pr | 1-Ad | HCl |
| KHG24811 | H | 1 | 0 | 4-F | n-Pr | 1-Ad | HCl |
| KHG24812 | H | 1 | 0 | 4-Br | n-Pr | 1-Ad | HCl |
| KHG24813 | H | 1 | 0 | 4-CH3 | n-Pr | 1-Ad | HCl |
| KHG24814 | H | 1 | 0 | 4-CH2CH3 | n-Pr | 1-Ad | HCl |
| KHG24815 | H | 1 | 0 | 4-0Ph | n-Pr | 1-Ad | HCl |
| KHG24816 | H | 1 | 0 | 2-F, 4-Cl | n-Pr | 1-Ad | HCl |
| KHG24817 | H | 1 | 0 | 2-F, 5-Cl | n-Pr | 1-Ad | HCl |
| KHG24818 | H | 1 | 0 | 2-Cl, 4-CH3 | n-Pr | 1-Ad | HCl |
| KHG24819 | H | 1 | 0 | 4-isoPr | CH2CH3 | 1-Ad | HCl |
| KHG24820 | H | 1 | 0 | 4-n-Bu | CH2CH3 | 1-Ad | HCl |
| KHG24821 | H | 1 | 0 | 4-CF3 | CH2CH3 | 1-Ad | HCl |
| KHG24823 | H | 1 | 0 | 4-Cl | isoPr | 1-Ad | HCl |
| KHG24825 | H | 1 | 0 | 4-n-Bu | isoPr | 1-Ad | HCl |
| KHG24826 | H | 1 | 0 | 4-CF3 | isoPr | 1-Ad | HCl |
| KHG24828 | H | 1 | 0 | 3-CF3, 5-CF3 | isoPr | 1-Ad | HCl |
| KHG24829 | H | 1 | 0 | 4-F | isoPr | 1-Ad | HCl |
| KHG24831 | H | 1 | 0 | 4-CH3 | isoPr | 1-Ad | HCl |
| KHG24832 | H | 1 | 0 | 4-CH2CH3 | isoPr | 1-Ad | HCl |

TABLE 1-continued

| Compound code | $R_1$ | n | m | $R_2, R_3, R_4$ | $R_5$ | $R_6$ | salt(O, HBr, HCl) |
|---|---|---|---|---|---|---|---|
| KHG24833 | H | 1 | 0 | 4-OPh | isoPr | 1-Ad | HCl |
| KHG24834 | H | 1 | 0 | 2-F, 4-Cl | isoPr | 1-Ad | HCl |
| KHG24835 | H | 1 | 0 | 2-F, 5-Cl | isoPr | 1-Ad | HCl |
| KHG24836 | H | 1 | 0 | 2-Cl, 4-CH3 | isoPr | 1-Ad | HCl |
| KHG24837 | H | 1 | 0 | 3-OCH20-4 | n-Pr | 1-Ad | HCl |
| KHG24838 | H | 1 | 0 | 3-OCH20-4 | isoPr | 1-Ad | HCl |
| KHG24839 | H | 1 | 0 | 2-F, 5-N02 | n-Pr | 1-Ad | HCl |
| KHG24840 | H | 1 | 0 | 2-F, 5-N02 | isoPr | 1-Ad | HCl |
| KHG24841 | H | 1 | 0 | 4-n-Bu | CH3 | 2-Ad | HCl |
| KHG24842 | H | 1 | 0 | 4-F | CH3 | 2-Ad | HCl |
| KHG24844 | H | 1 | 0 | 4-isoPr | CH3 | 2-Ad | HCl |
| KHG24847 | H | 1 | 0 | 4-CH2CH3 | CH2CH3 | 1-Ad | HCl | wherein
NHMs indicates

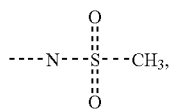

NHTs indicates

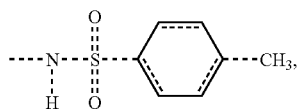

cy-3 indicates cyclopropyl, cy-5 indicates cyclopentyl, cy-6 indicates cyclohexyl, cy-7 indicates cycloheptyl, Pr indicates propyl, Bu indicates butyl, Ph indicates phenyl, 1-Ad indicates 1-adamantyl, and 2-Ad indicates 2-adamantyl.

$R_2$, $R_3$, and $R_4$ represent substituents at the phenyl group, and when the substituent is hydrogen, it is not indicated.

COMPARATIVE EXAMPLE

Preparation of Compounds where $R_6$ is a Phenyl Group

The compounds where $R_6$ is a phenyl group were prepared by the same method of Example 1 or Example 2. The prepared compounds are shown in Table 3 below.

EXPERIMENTAL EXAMPLE

Test for T-type Calcium Channel Inhibiting Activity

In the present invention, in order to examine an efficient inhibitor against the T-type calcium channel, a primary assay for T-type calcium channel inhibiting activity was conducted by a high-efficient assay using FDSS6000, wherein mammal HEK293 cell lines (originated from human kidney carcinoma cells) that specifically express α1G of the T-type calcium channel was used for primary assay. Through the primary assay, compounds that show meaningful inhibition effects were selected. The selected compounds were used in a second assay for T-type calcium channel inhibiting activity using an electrophysiological whole cell patch clamp method, wherein mammal HEK293 cell lines (originated from human kidney carcinoma cells) that specifically express $\alpha_{1G}$ of the T-type calcium channel was used for the second assay. Mibefradil, which had been developed as a T-type calcium channel inhibitor, was used as a reference.

EXPERIMENTAL EXAMPLE 1

Method of Assay for % Inhibiting Activity Against T-Type Calcium Channel Using FDSS6000

At 12-24 hours before being used for this assay, cells of HEK293 cell line ($\alpha_{1G}$ cell line: KCTC 10519BP, Korean Collection for Type Cultures), which stably express $\alpha_{1G}$ T-type calcium channel and Kir2.1, were sub-cultured in a poly-L-lysine treated 96-well plate with the density of $4\times10^4$ per well using a 96-well cell dispenser (Titertek). On the day of assay, the 96-well plate to which the cells were attached was washed three times with HEPES buffer solution (150 mM of NaCl, 5 mM of KCl, 1 mM of $MgCl_2$, 2 mM of $CaCl_2$, 10 mM of HEPES, 10 mM of glucose; pH 7.4) using a 96-well plate automatic washing device (Bio Tek), then reacted with HEPES buffer solution containing 5 μM fluo-3/AM and 0.001% Pluronic F-127 at room temperature for 1 hour, to label with fluorescent dye, and then further washed two times with HEPES buffer solution.

Thereafter, at 10 minutes before the measurement using device FDSS6000, washing with HEPES buffer solution containing 10 mM $CaCl_2$ was conducted once more, and the final volume was adjusted to 81 μl. Besides the above 96-well plate containing the cells, two additional drug 96-well plates were provided, wherein the 96-well plates contained an inhibiting drug and KCl (final concentration: 75 mM) for activating the T-type calcium channel, respectively. Since most of cell-based HTS devices are equipped with a liquid application system for injection of drug, but have no liquid sucking system, the inhibiting drug to be tested and KCl were respectively provided at a five-times higher concentration in 10 mM $CaCl_2$ HEPES buffer solution at the amount of 27 μl, diluted by five-times at the final cell plate volume of 135 μl, and then used in this test. The concrete method of measurement using FDSS6000 was as follows. After recording the reference value of 20 seconds, the change of intracellular $Ca^{2+}$ concentration that was induced by treatment of the inhibiting drug to be tested for 75 seconds followed by administration of KCl was measured, wherein the percentage (%) inhibition effect of the test drug, through estimating the area of ratio value of 340/380 in the control without treatment of the test drug, was 100%. As a reference drug, 10 μM mibefradil was used.

For accurate calcium imaging, the light source of 4 xenon lamps in FDSS6000 were radiated to selectively expose the cells to the excitation wavelength (340 nm and 380 nm) by a computer-controlled filter wheel. Data was obtained at intervals of 1.23 seconds. The emitter fluorescence light inflowed through a long-pass filter was obtained as an average 340/380 ratio value for each well in the 96-wells by using a CCD camera and a digital fluorescence analyzer in FDSS6000. All image data and analyses were obtained by using a FDSS6000-exclusive program from Hamamatsu Photonics.

The obtained results are shown in Table 2 (the results from the compounds according to the examples of the present invention) and Table 3 (the results from the compounds according to the comparative example where $R_6$ is a phenyl group) [FDSS (% inhibition) 10 μM].

TABLE 2

FDSS values of the compounds according to the examples of the present invention (concentration: 10 μM)

| Compound Code | FDSS (% inhibition)/10uM |
|---|---|
| KHG23210 | 46.69 |
| KHG23354 | 54.26 |
| KHG23355 | 58.95 |
| KHG23356 | 60.46 |
| KHG23360 | 66.64 |
| KHG23361 | 62.4 |
| KHG23362 | 66.17 |
| KHG23364 | 53 |
| KHG23365 | 60.16 |
| KHG24070 | 52.96 |
| KHG24071 | 52.13 |
| KHG24072 | 63.5 |
| KHG24073 | 57.30 |
| KHG24074 | 65.2 |
| KHG24075 | 73.72 |
| KHG24076 | 39.94 |
| KHG24077 | 46.41 |
| KHG24081 | 38.27 |
| KHG24082 | 37.39 |
| KHG24083 | 47.92 |
| KHG24084 | 58.61 |
| KHG24085 | 52.60 |
| KHG24086 | 30.49 |
| KHG24087 | 35.35 |
| KHG24088 | 43.19 |
| KHG24090 | 32.09 |
| KHG24091 | 30.27 |
| KHG24092 | 43.13 |
| KHG24093 | 34.77 |
| KHG24095 | 30.53 |
| KHG24098 | 50.54 |
| KHG24099 | 58.17 |
| KHG24100 | 60.81 |
| KHG24103 | 45.01 |
| KHG24104 | 34.30 |
| KHG24105 | 40.42 |
| KHG24106 | 49.44 |
| KHG24108 | 44.42 |
| KHG24109 | 48.39 |
| KHG24110 | 53.56 |
| KHG24111 | 67.74 |
| KHG24112 | 30.27 |
| KHG24113 | 54.13 |
| KHG24115 | 49.91 |
| KHG24116 | 65.43 |
| KHG24117 | 67.09 |
| KHG24118 | 66 |
| KHG24119 | 52.85 |
| KHG24120 | 60.08 |
| KHG24121 | 41.02 |
| KHG24122 | 71.12 |
| KHG24123 | 76.6 |
| KHG24124 | 59.49 |
| KHG24125 | 71.79 |
| KHG24126 | 53.79 |
| KHG24127 | 49.69 |
| KHG24128 | 62.56 |
| KHG24129 | 61.39 |
| KHG24130 | 70.4 |

TABLE 2-continued

FDSS values of the compounds according to the examples of the present invention (concentration: 10 μM)

| Compound Code | FDSS (% inhibition)/10uM |
|---|---|
| KHG24131 | 72.86 |
| KHG24132 | 50.94 |
| KHG24133 | 69.18 |
| KHG24134 | 75.92 |
| KHG24141 | 35.67 |
| KHG24152 | 33.88 |
| KHG24157 | 36.68 |
| KHG24159 | 48.52 |
| KHG24160 | 61.93 |
| KHG24161 | 31.29 |
| KHG24216 | 35.96 |
| KHG24218 | 52.8 |
| KHG24220 | 40.77 |
| KHG24222 | 34.75 |
| KHG24224 | 31.98 |
| KHG24228 | 48.58 |
| KHG24230 | 32.97 |
| KHG24232 | 33.68 |
| KHG24234 | 45.44 |
| KHG24235 | 61.65 |
| KHG24236 | 69.55 |
| KHG24237 | 74.81 |
| KHG24238 | 73.31 |
| KHG24239 | 69.55 |
| KHG24240 | 70.68 |
| KHG24241 | 70.68 |
| KHG24242 | 53.38 |
| KHG24243 | 60.9 |
| KHG24244 | 53.67 |
| KHG24261 | 65.03 |
| KHG24262 | 52.95 |
| KHG24263 | 52.11 |
| KHG24266 | 33.58 |
| KHG24267 | 70.98 |
| KHG24268 | 58.73 |
| KHG24270 | 62.65 |
| KHG24271 | 37.76 |
| KHG24272 | 37.64 |
| KHG24273 | 48.47 |
| KHG24276 | 42.79 |
| KHG24277 | 61.14 |
| KHG24278 | 53.77 |
| KHG24279 | 44.11 |
| KHG24280 | 54.04 |
| KHG24281 | 31.39 |
| KHG24282 | 43.59 |
| KHG24283 | 51.17 |
| KHG24284 | 44.56 |
| KHG24285 | 46.01 |
| KHG24286 | 55.16 |
| KHG24287 | 58.52 |
| KHG24288 | 54.96 |
| KHG24290 | 62.21 |
| KHG24291 | 63.16 |
| KHG24292 | 43.85 |
| KHG24293 | 55.83 |
| KHG24294 | 65.74 |
| KHG24295 | 36.18 |
| KHG24296 | 53.09 |
| KHG24297 | 51.03 |
| KHG24298 | 60.39 |
| KHG24299 | 45.63 |
| KHG24300 | 36.73 |
| KHG24303 | 31.1 |
| KHG24305 | 58.88 |
| KHG24306 | 53.2 |
| KHG24307 | 43.88 |
| KHG24313 | 31.04 |
| KHG24315 | 60.8 |
| KHG24336 | 60.11 |
| KHG24337 | 56.62 |
| KHG24338 | 70.79 |
| KHG24339 | 44.19 |
| KHG24403 | 49.12 |
| KHG24404 | 64.67 |

TABLE 2-continued

FDSS values of the compounds according to the examples of the present invention (concentration: 10 μM)

| Compound Code | FDSS (% inhibition)/10uM |
|---|---|
| KHG24405 | 68.39 |
| KHG24406 | 34.44 |
| KHG24407 | 48.66 |
| KHG24408 | 32.62 |
| KHG24409 | 57.43 |
| KHG24410 | 64.09 |
| KHG24411 | 62.67 |
| KHG24412 | 56.4 |
| KHG24413 | 62.08 |
| KHG24414 | 60.98 |
| KHG24415 | 64.16 |
| KHG24416 | 59.78 |
| KHG24417 | 59.08 |
| KHG24418 | 56.94 |
| KHG24419 | 46.7 |
| KHG24420 | 58.51 |
| KHG24421 | 65.75 |
| KHG24422 | 46.27 |
| KHG24445 | 50.8 |
| KHG24448 | 47.4 |
| KHG24449 | 40.5 |
| KHG24480 | 51.65 |
| KHG24482 | 52.39 |
| KHG24483 | 52.53 |
| KHG24484 | 32.82 |
| KHG24486 | 55.82 |
| KHG24516 | 54.57 |
| KHG24517 | 49.61 |
| KHG24518 | 50.74 |
| KHG24519 | 55.73 |
| KHG24520 | 64.82 |
| KHG24521 | 54.29 |
| KHG24522 | 47.91 |
| KHG24523 | 46.3 |
| KHG24524 | 41.33 |
| KHG24525 | 31.51 |
| KHG24526 | 42.32 |
| KHG24527 | 46.97 |
| KHG24528 | 54.17 |
| KHG24529 | 58.22 |
| KHG24530 | 38.5 |
| KHG24531 | 48.42 |
| KHG24532 | 52.54 |
| KHG24533 | 48.89 |
| KHG24534 | 45.69 |
| KHG24535 | 40.31 |
| KHG24547 | 51.06 |
| KHG24626 | 42.6 |
| KHG24627 | 48.51 |
| KHG24628 | 42.63 |
| KHG24629 | 47.03 |
| KHG24630 | 56.77 |
| KHG24632 | 57.06 |
| KHG24633 | 40.39 |
| KHG24634 | 46.88 |
| KHG24636 | 35.24 |
| KHG24638 | 40.77 |
| KHG24639 | 48.46 |
| KHG24640 | 39.61 |
| KHG24641 | 63.52 |
| KHG24642 | 66.74 |
| KHG24643 | 65.38 |
| KHG24644 | 53.37 |
| KHG24645 | 48.38 |
| KHG24646 | 58.12 |
| KHG24647 | 62.36 |
| KHG24656 | 46.14 |
| KHG24657 | 47.95 |
| KHG24666 | 46.2 |
| KHG24667 | 45.99 |
| KHG24668 | 50.71 |
| KHG24669 | 36.57 |
| KHG24670 | 46.74 |
| KHG24671 | 47.2 |
| KHG24775 | 62.91 |
| KHG24776 | 33.76 |
| KHG24777 | 49.23 |
| KHG24780 | 55.28 |
| KHG24781 | 47.18 |
| KHG24782 | 30.6 |
| KHG24783 | 54.43 |
| KHG24784 | 36.63 |
| KHG24785 | 47.09 |
| KHG24788 | 72.88 |
| KHG24789 | 78.21 |
| KHG24790 | 73.05 |
| KHG24792 | 67.05 |
| KHG24795 | 33.71 |
| KHG24799 | 63.41 |
| KHG24800 | 83.5 |
| KHG24801 | 63.76 |
| KHG24802 | 62.39 |
| KHG24803 | 66.47 |
| KHG24804 | 44.67 |
| KHG24805 | 32.24 |
| KHG24807 | 59.69 |
| KHG24808 | 37.57 |
| KHG24809 | 57.27 |
| KHG24811 | 71.82 |
| KHG24812 | 53.84 |
| KHG24813 | 61.56 |
| KHG24814 | 76.32 |
| KHG24815 | 32.7 |
| KHG24816 | 80.83 |
| KHG24817 | 60.49 |
| KHG24818 | 68.24 |
| KHG24819 | 69.25 |
| KHG24820 | 58.02 |
| KHG24821 | 73.69 |
| KHG24823 | 54.1 |
| KHG24826 | 46.49 |
| KHG24828 | 35.38 |
| KHG24829 | 68.99 |
| KHG24831 | 57 |
| KHG24832 | 46.52 |
| KHG24833 | 37.05 |
| KHG24834 | 65.73 |
| KHG24835 | 55.17 |
| KHG24836 | 48.91 |
| KHG24837 | 68.43 |
| KHG24838 | 53.33 |
| KHG24839 | 59.7 |
| KHG24840 | 49.43 |
| KHG24842 | 59.82 |
| KHG24847 | 72.23 |

TABLE 3

FDSS values of the compounds where $R_6$ is a phenyl group
(concentration: 10 μM)

| Compond Code | $R_1$ | n | m | $R_2, R_3, R_4$ | $R_5$ | $R_6$ | HX(O, HCl, HBr) | FDSS |
|---|---|---|---|---|---|---|---|---|
| KHG21648 | H | 1 | 0 | 4-Cl | $CH_3$ | Ph(4-$OCH_3$) | HCl | 26.19 |
| KHG21649 | H | 1 | 0 | 4-Cl | $CH_3$ | Ph(3-$OCH_3$) | HCl | 27.79 |
| KHG21650 | H | 1 | 0 | 4-Cl | $CH_3$ | Ph(4-OPh) | HCl | 2.59 |
| KHG21651 | H | 1 | 0 | 4-Cl | $CH_3$ | Ph(4-$OCF_3$) | HCl | −0.56 |
| KHG21652 | H | 1 | 0 | 4-Cl | $CH_3$ | Ph(4-Cl) | HCl | −7.70 |
| KHG21653 | H | 1 | 0 | 4-Cl | $CH_3$ | Ph(3-$OCH(CH_3)_2$) | HCl | −2.17 |
| KHG21654 | H | 1 | 0 | 4-Cl | $CH_3$ | Ph(4-n-Bu) | HCl | −1.13 |
| KHG21655 | H | 1 | 0 | 4-Cl | $CH_3$ | Ph(3-$NO_3$) | HCl | 4.68 |
| KHG21943 | H | 1 | 0 | 4-$CH(CH_3)_2$ | $CH_3$ | Ph(4-$CF_3$) | HCl | −2.56 |
| KHG21944 | H | 1 | 0 | 4-$CH(CH_3)_2$ | $CH_3$ | Ph(2-F, 4-Cl, 5-$OCH(CH_3)_2$) | HCl | 5.89 |
| KHG21945 | H | 1 | 0 | 4-$CH(CH_3)_2$ | $CH_3$ | Ph(4-CN) | HCl | 7.71 |
| KHG21947 | H | 1 | 0 | 4-$CH(CH_3)_2$ | $CH_3$ | Ph(3-Cl, 4-F) | HCl | 23.90 |
| KHG21949 | H | 1 | 0 | 4-$(CH_3)_2$ | $CH_3$ | Ph(3-Br) | HCl | 5.41 |
| KHG23064 | H | 1 | 0 | 2-F, 4-Cl | $CH_3$ | Ph(4-Cl) | HCl | 7.37 |
| KHG23065 | H | 1 | 0 | 2-F, 4-Cl | $CH_3$ | Ph(4-Br) | HCl | 3.57 |
| KHG23066 | H | 1 | 0 | 2-F, 4-Cl | $CH_3$ | Ph(4-n-Bu) | HCl | 1.30 |
| KHG23067 | H | 1 | 0 | 2-F, 4-Cl | $CH_3$ | Ph(4-CN) | HCl | −2.73 |
| KHG23068 | H | 1 | 0 | 2-F, 4-Cl | $CH_3$ | Ph(4-$CF_3$) | HCl | 5.76 |
| KHG23069 | H | 1 | 0 | 2-F, 4-Cl | $CH_3$ | Ph(4-$CH_3$) | HCl | 4.33 |
| KHG23070 | H | 1 | 0 | 2-F, 4-Cl | $CH_3$ | Ph(4-$OCF_3$) | HCl | 7.44 |
| KHG23071 | H | 1 | 0 | 2-F, 4-Cl | $CH_3$ | Ph(4-$CH(CH_3)_2$) | HCl | 15.51 |
| KHG23072 | H | 1 | 0 | 2-F, 4-Cl | $CH_3$ | Ph(2-$CH_2CH_3$) | HCl | 29.45 |
| KHG23073 | H | 1 | 0 | 2-F, 4-Cl | $CH_3$ | Ph(4-Ph) | HCl | 28.31 |
| KHG32076 | H | 1 | 0 | 2-F, 4-Cl | $CH_3$ | Ph(3-F) | HCl | 20.50 |

As shown in Tables 2 and 3, the compounds according to the examples of the present invention have excellent FDSS values compared to the compounds where $R_6$ is a phenyl group.

The compounds where R6 of Chemical Formula I is a phenyl have already been published (Korean Patent No. 247729, Korean Patent No. 387583, WO 02/13611, U.S. Pat. No. 6,921,770, EP 1311160, Korean Patent No. 0559367). However, as shown in Tables 1 and 2, the compounds where R6 is a phenyl has a lower effect of inhibiting T-type calcium channel activity than the compounds according to the present invention. Therefore, the substituents used at $R_6$ in the present invention exhibit different activities from those of the phenyl that has been known, and thus the compounds according to the present invention are distinguished from the known compounds in effects as well as structure.

EXPERIMENTAL EXAMPLE 2

Measurement of IC50 for T-type Calcium Channel Activity in HEK293 Cells Using an Electrophysiological Method 10% Fetal bovine serum (FBS) and 1% penicillin/streptomycin (v/v) were added to Dulbecco's modified Eagle's medium (DMEM), to be used as a media solution. The cells were cultured in an incubator under a wet condition of 95% air/5% $CO_2$ and a temperature of 36.5° C. The media solution was refreshed every 3 or 4 days, and the cells were sub-cultured every week. Only the cells that expressed $\alpha_{1G}$ T-type calcium channel were cultured using a G-418 (0.5 mg/ml) solution. The recording of the cells used in the T-type calcium channel activity analysis was conducted at 2-7 days after the cells were culturing on a cover slip coated with poly-L-lysine (0.5 mg/ml) when conducting every sub-culture. For analysis at a single cell level, the T-type calcium channel current was measured by an electrophysiological whole cell patch clamp method using EPC-9 amplifier (HEKA, German).

As solutions for analyzing T-type calcium channel activity, a solution including NaCl 140 mM, $CaCl_2$ 2 mM, and HEPES10 mM (pH 7.4, Sigma; 4-(2-hydroxyethyl)piperazine-1-ethanesulfonic acid) was used as an extracellular solution, and a solution including KCl 130 mM, HEPES 10 mM (Sigma), EGTA 11 mM (ethylene glycol-bis(2-aminoethylether)-N,N,N',N'-tetraacetic acid, Sigma), and MgATP 5 mM (pH 7.4, Sigma) was used as an intracellular solution. The protocol for T-type calcium channel activity that is activated at low voltage is as follows. A micro-glass electrode with resistance of 3-4 MΩ wherein the above-prepared intracellular solution was filled was pricked into a single cell, to make a whole-cell recording mode. Thereafter, the cell membrane potential was fixed to −100 mV, and then the inward current due to the T-type calcium channel activity when hypopolarizing to −30 mV (50 ms duration) was measured every 10 seconds.

Each compound to be tested was dissolved in 100% dimethylsulfoxide (DMSO) to make a 10 mM stock solution. The effect of the compound on the T-type calcium channel current compound was initially examined in the stock solution with the 1000-times diluted concentration of 10 μM (containing 0.1% DMSO) and then examined in the solution with the concentration for IC50 measurement (mostly 0.1 to 100 μM), to obtain an $IC_{50}$ value. More specifically, the cells were treated in each compound together with the extracellular solution for 30 to 60 seconds, and the inhibition level of peak current induced by the compound was calculated as a percentage, to obtain the % inhibition value as shown in Table 4.

TABLE 4

| Compound Code | HEK293cell (% Inhibition) 10 μM | IC50 (a1G) |
|---|---|---|
| KHG22344 | 53.9 ± 2.8 | 0.07 ± 0.02 |
| KHG22671 | 66.4 ± 3.6 | 1.11 ± 0.24 |
| KHG23185 | 88.2 ± 1.4 | 1.31 ± 0.22 |
| KHG23210 | 59.6 ± 1.5 | 6.50 ± 0.50 |

TABLE 4-continued

| Compound Code | HEK293cell (% Inhibition) 10 μM | IC50 (a1G) |
|---|---|---|
| KHG23354 | 83.0 ± 1.4 | 2.47 ± 0.18 |
| KHG23355 | 88.1 ± 2.0 | 1.51 ± 0.17 |
| KHG23356 | 97.0 ± 0.7 | 0.23 ± 0.01 |
| KHG23360 | 87.8 ± 2.2 | 0.78 ± 0.08 |
| KHG23361 | 71.4 ± 3.4 | 4.09 ± 0.70 |
| KHG23362 | 89.3 ± 0.9 | 0.53 ± 0.03 |
| KHG23364 | 97.0 ± 0.7 | 0.87 ± 0.18 |
| KHG23365 | 97.6 ± 0.5 | 0.60 ± 0.06 |
| KHG23394 | 95.9 ± 1.1 | 1.28 ± 0.20 |
| KHG24072 | 91.2 ± 1.6 | 0.99 ± 0.03 |
| KHG24074 | 94.7 ± 0.5 | 0.66 ± 0.06 |
| KHG24075 | 94.1 ± 1.5 | 0.32 ± 0.02 |
| KHG24077 | 57.0 ± 1.5 | 7.22 ± 0.36 |
| KHG24083 | 76.5 ± 2.3 | 3.63 ± 0.54 |
| KHG24084 | 82.2 ± 1.4 | 2.79 ± 0.11 |
| KHG24113 | 64.8 ± 1.4 | 5.40 ± 0.41 |
| KHG24117 | 93.0 ± 2.5 | 0.57 ± 0.07 |
| KHG24118 | 80.3 ± 1.1 | 1.88 ± 0.22 |
| KHG24119 | 72.9 ± 1.0 | 4.44 ± 0.28 |
| KHG24120 | 82.7 ± 0.9 | 2.75 ± 0.25 |
| KHG24121 | 58.1 ± 4.9 | 8.53 ± 1.72 |
| KHG24122 | 94.6 ± 0.5 | 0.39 ± 0.03 |
| KHG24123 | 94.2 ± 2.0 | 1.09 ± 0.20 |
| KHG24124 | 87.1 ± 1.2 | 1.77 ± 0.10 |
| KHG24125 | 95.6 ± 1.2 | 0.08 ± 0.01 |
| KHG24126 | 87.7 ± 0.6 | 1.20 ± 0.08 |
| KHG24127 | 80.8 ± 0.6 | 2.66 ± 0.33 |
| KHG24128 | 88.1 ± 1.9 | 0.55 ± 0.01 |
| KHG24129 | 90.0 ± 0.4 | 1.57 ± 0.11 |
| KHG24130 | 90.0 ± 0.9 | 0.81 ± 0.08 |
| KHG24131 | 86.2 ± 0.3 | 0.52 ± 0.02 |
| KHG24132 | 76.8 ± 1.0 | 5.00 ± 1.97 |
| KHG24133 | 96.0 ± 1.9 | 0.42 ± 0.01 |
| KHG24134 | 95.1 ± 2.0 | 0.34 ± 0.03 |
| KHG24159 | 76.8 ± 1.4 | 3.57 ± 0.29 |
| KHG24160 | 92.9 ± 0.7 | 1.33 ± 0.03 |
| KHG24161 | 81.2 ± 1.3 | 1.67 ± 0.51 |
| KHG24235 | 93.2 ± 1.9 | 1.17 ± 0.08 |
| KHG24236 | 94.4 ± 0.6 | 0.23 ± 0.02 |
| KHG24237 | 91.2 ± 3.1 | 0.77 ± 0.03 |
| KHG24238 | 95.9 ± 1.8 | 0.53 ± 0.02 |
| KHG24239 | 96.5 ± 1.3 | 0.61 ± 0.07 |
| KHG24240 | 96.2 ± 1.1 | 0.23 ± 0.02 |
| KHG24241 | 92.2 ± 0.5 | 0.17 ± 0.02 |
| KHG24242 | 85.2 ± 1.3 | 0.97 ± 0.14 |
| KHG24243 | 97.0 ± 1.1 | 0.05 ± 0.01 |
| KHG24244 | 90.6 ± 3.6 | 0.92 ± 0.08 |
| KHG24788 | 95.3 ± 0.4 | 0.31 ± 0.02 |
| KHG24789 | 95.1 ± 0.7 | 0.19 ± 0.02 |
| KHG24790 | 94.8 ± 0.9 | 0.24 ± 0.01 |
| KHG24800 | 95.4 ± 0.5 | 0.43 ± 0.07 |
| KHG24811 | 94.8 ± 0.7 | 0.60 ± 0.04 |
| KHG24814 | 96.9 ± 1.8 | 0.30 ± 0.01 |
| KHG24816 | 95.6 ± 0.8 | 0.51 ± 0.01 |
| KHG24821 | 92.3 ± 1.8 | 0.36 ± 0.02 |
| KHG24847 | 95.5 ± 2.7 | 0.35 ± 0.01 |

As shown in Table 4, the 2-imino-1,3-thiazoline based compounds according to the present invention have excellent T-type calcium channel inhibiting activities.

Identification Data

The identification data of the compounds shown in Tables 1 and 2 are as follows.

KHG21648 [2-(4-methoxyphenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (4-$OCH_3$), n=1, m=0, X=Cl]

yield: 46%; melting point: 250-253° C.

$^1$H NMR (300 MHz, DMSO-$d_6$) δ 3.75 (s, 3H, 3-$CH_3$), 3.80 (s, 3H, $OCH_3$), 4.05 (s, 2H, 4-$CH_2$), 7.01 (s, 1H, 5-vinyl H), 7.08-7.70 (m, 8H, ArH), 11.01 (s, 1H, NH).

KHG21649 [2-(3-methoxyphenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (3-$OCH_3$), n=1, m=0, X=Cl]

yield: 74%; melting point: 228-231° C.

$^1$H NMR (300 MHz, DMSO-$d_6$) δ 3.77 (s, 3H, 3-$CH_3$), 3.78 (s, 3H, $OCH_3$), 4.07 (s, 2H, 4-$CH_2$), 6.96 (s, 1H, 5-vinyl H), 7.07-7.70 (m, 8H, ArH), 11.04 (s, 1H, NH).

KHG21650 [2-(4-phenoxyphenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (4-$OC_6H_5$), n=1, m=0, X=Cl]

yield: 38%; melting point: 238-242° C.

$^1$H NMR (300 MHz, DMSO-$d_6$) δ 3.76 (s, 3H, 3-$CH_3$), 4.05 (s, 2H, 4-$CH_2$), 7.03 (s, 1H, 5-vinyl H), 7.10-7.70 (m, 8H, ArH), 10.96 (s, 1H, NH).

KHG21652 [2-(4-chlorophenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (4-Cl), n=1, m=0, X=Cl]

yield: 90%; melting point: 239-242° C.

$^1$H NMR (300 MHz, DMSO-$d_6$) δ 3.76 (s, 3H, 3-$CH_3$), 4.07 (s, 2H, 4-$CH_2$), 7.05 (s, 1H, 5-vinyl H), 7.36-7.70 (m, 8H, ArH), 10.30 (s, 1H, NH).

KHG21653 [2-(3-isopropoxyphenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (4-$OCH(CH_3)_2$), n=1, m=0, X=Cl]

yield: 65%; melting point: 201-203° C.

$^1$H NMR (300 MHz, DMSO-$d_6$) δ 1.28 (d, 6H, J=6.0 Hz, isopropoxy ($CH_3)_2$), 3.78 (s, 3H, 3-$CH_3$), 4.06 (s, 2H, 4-$CH_2$), 4.61 (m, 1H, J=6.0 Hz, isopropoxy CH), 6.93 (s, 1H, 5-vinyl H), 7.01-7.70 (m, 8H, ArH), 10.30 (s, 1H, NH).

KHG21654 [2-(4-n-butylphenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (4-n-$C_4H_9$), n=1, m=0, X=Cl]

yield: 59%; melting point: 239-241° C.

$^1$H NMR (300 MHz, DMSO-$d_6$) δ 0.90 (t, 3H, J=7.2 Hz, n-butyl $CH_3$), 1.32 (m, 2H, $CH_2$), 1.57 (m, 2H, $CH_2$), 2.62 (t, 2H, J=7.2 Hz, $CH_2$), 3.78 (s, 3H, 3-$CH_3$), 4.06 (s, 2H, 4-$CH_2$), 7.03 (s, 1H, 5-vinyl H), 7.33-7.70 (m, 8H, ArH), 10.99 (s, 1H, NH).

KHG21655 [2-(3-nitrophenylimino)-3-methyl-1,3-thiazolidine-4-yl]-N-(4-chlorophenyl)-acetamide hydrochloride [$R_1$=H, $R_2$=4-Cl, $R_3$H, $R_5$=$CH_3$, $R_6$=Ph (3-$NO_2$), n=1, m=0, X=Cl]

yield: 26%; melting point: 228° C.

$^1$H NMR (300 MHz, DMSO-$d_6$) δ 3.79 (s, 3H, 3-$CH_3$), 4.04 (s, 2H, 4-$CH_2$), 6.96 (s, 1H, 5-vinyl H), 7.36-8.28 (m, 8H, ArH), 10.83 (s, 1H, NH).

KHG21943 [2-(4-trifluoromethylphenylimino)-3-methyl-1,3-thiazolidine-4-yl]-N-(4-isopropylphenyl)-acetamide hydrochloride [$R_1$=H, $R_2$=4-$CH(CH_3)_2$, $R_3$H, $R_4$=H, $R_5$=$CH_3$, $R_6$=Ph (4-$CF_3$), n=1, m=0, X=Cl]

yield: 56%; melting point: 238-242.8° C.

$^1$H NMR (300 MHz, DMSO-$d_6$) δ 1.16-1.18 (d, 6H, J=6.9 Hz, $CH(CH_3)_2$), 2.80-2.88 (m, 1H, J=6.9 Hz, $CH(CH_3)_2$), 3.79 (s, 3H, 3-$CH_3$), 4.03 (s, 2H, 4-$CH_2$), 7.04 (s, 1H, 5-vinyl H), 7.17-7.88 (m, 8H, ArH), 10.65 (s, 1H, NH).

KHG21944 [2-(4-chloro-5-isopropoxy-2-fluorophenylimino)-3-methyl-1,3-thiazolidine-4-yl]-N-(4-isopropylphenyl)-acetamide hydrochloride [$R_1$=H, $R_2$=4-$CH(CH_3)_2$, $R_3$=$R_4$=H, $R_5$=$CH_3$, $R_6$=Ph (2-F, 4-Cl, 5-$OCH(CH_3)_2$, n=1, m=0, X=Cl]

yield: 46%; melting point: 190-194° C.

¹H NMR (300 MHz, DMSO-d₆) δ 1.16-1.18 (d, 6H, J=6.9 Hz, CH(CH₃)₂), 1.28-1.30 (d, 6H, J=6.0 Hz, OCH(CH₃)₂), 2.80-2.88 (m, 1H, J=6.9 Hz, CH(CH₃)₂), 3.68 (s, 3H, 3-CH₃), 3.97 (s, 2H, 4-CH₂), 4.53-4.62 (m, 1H, J=6.0 Hz, OCH(CH₃)₂), 6.86 (s, 1H, 5-vinyl H), 7.17-7.67 (m, 6H, ArH), 10.61 (s, 1H, NH).

KHG21945 [2-(4-cyanophenylimino)-3-methyl-1,3-thiazolidine-4-yl]-N-(4-isopropylphenyl)-acetamide hydrochloride [R₁=H, R₂=4-CH(CH₃)₂, R₃=H, R₅=CH₃, R₆=Ph (4-CN), n=1, m=0, X=Cl]

yield: 39%; melting point: 234-235° C.

¹H NMR (300 MHz, DMSO-d₆) δ 1.16-1.18 (d, 6H, J=6.8 Hz, CH(CH₃)₂), 2.80-2.88 (m, 1H, J=6.8 Hz, CH(CH₃)₂), 3.72 (s, 3H, 3-CH₃), 3.99 (s, 2H, 4-CH₂), 6.95 (s, 1H, 5-vinyl H), 7.17-7.93 (m, 8H, ArH), 10.56 (s, 1H, NH).

KHG21947 [2-(3-chloro-4-fluorophenylimino)-3-methyl-1,3-thiazolidine-4-yl]-N-(4-isopropylphenyl)-acetamide hydrochloride [R₁=H, R₂=4-CH(CH₃)₂, R₃=R₄=H, R₅=CH₃, R₆=Ph (3-Cl, 4-F), n=1, m=0, X=Cl]

yield: 77%; melting point: 239-241° C.

¹H NMR (300 MHz, DMSO-d₆) δ 1.16-1.19 (d, 6H, J=6.8 Hz, CH(CH₃)₂), 2.80-2.88 (m, 1H, J=6.8 Hz, CH(CH₃)₂), 3.78 (s, 3H, 3-CH₃), 4.03 (s, 2H, 4-CH₂), 7.02 (s, 1H, 5-vinyl H), 7.17-7.81 (m, 8H, ArH), 10.67 (s, 1H, NH).

KHG21949 [2-(3-bromophenylimino)-3-methyl-1,3-thiazolidine-4-yl]-N-(4-isopropylphenyl)-acetamide hydrochloride [R₁=H, R₂=4-CH(CH₃)₂, R₃=R₄=H, R₅=CH₃, R₆=Ph (3-Br), n=1, m=0, X=Cl]

yield: 74%; melting point: 198-201° C.

¹H NMR (300 MHz, DMSO-d₆) δ 1.16-1.19 (d, 6H, J=7.3 Hz, CH(CH₃)₂), 2.80-2.88 (m, 1H, J=7.3 Hz, CH(CH₃)₂), 3.78 (s, 3H, 3-CH₃), 4.02 (s, 2H, 4-CH₂), 7.02 (s, 1H, 5-vinyl H), 7.17-7.75 (m, 8H, ArH), 10.65 (s, 1H, NH).

KHG23064 [2-(4-chlorophenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-Cl), n=1, m=0, X=Cl]

yield: 64%; melting point: 239-240° C.

¹H NMR (300 MHz, DMSO-d₆) δ 3.81 (s, 3H, N—CH₃), 4.14 (s, 2H, 4-CH₂), 7.07 (s, 1H, vinyl H), 7.29-7.93 (m, 7H, Ar—H), 10.51 (s, 1H, NH).

KHG23065 [2-(4-bromophenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-Br), n=1, m=0, X=Cl]

yield: 84%; melting point: 239-240° C.

¹H NMR (300 MHz, DMSO-d₆) δ 3.79 (s, 3H, N—CH₃), 4.12 (s, 2H, 4-CH2), 7.04 (s, 1H, vinyl H), 7.29-7.94 (m, 7H, Ar—H), 10.47 (s, 1H, NH).

KHG23066 [2-(4-n-butylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-n-C₄H₉), n=1, m=0, X=Cl]

yield: 70%; melting point: 223-224° C.

¹H NMR (300 MHz, DMSO-d₆) δ 0.91-0.96 (t, 3H, CH₂CH₂CH₂CH₃), 1.30-1.38 (m, 2H, CH₂CH₂CH₂CH₃), 1.55-1.63 (m, 2H, CH₂CH₂CH₂CH₃), 2.63-2.68 (t, 2H, CH₂CH₂CH₂CH₃), 3.76 (s, 3H, N—CH₃), 4.11 (s, 2H, 4-CH₂), 7.02 (s, 1H, vinyl H), 7.30-7.95 (m, 7H, Ar—H), 10.43 (s, 1H, NH).

KHG23067 [2-(4-cyanophenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-CN), n=1, m=0, X=Cl]

yield: 74%; melting point: 136-137° C.

¹H NMR (300 MHz, DMSO-d₆) δ 3.67 (s, 3H, N—CH₃), 4.06 (s, 2H, 4-CH₂), 6.86 (s, 1H, vinyl H), 7.29-7.95 (m, 7H, Ar—H), 10.39 (s, 1H, NH).

KHG23068 [2-(4-trifluoromethylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-CF₃), n=1, m=0, X=Cl]

yield: 67%; melting point: 222-223° C.

¹H NMR (300 MHz, DMSO-d₆) δ 3.67 (s, 3H, N—CH₃), 4.06 (s, 2H, 4-CH₂), 6.86 (s, 1H, vinyl H), 7.29-7.95 (m, 7H, Ar—H), 10.39 (s, 1H, NH).

KHG23069 [2-(4-methylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-CH₃), n=1, m=0, X=Cl]

yield: 74%; melting point: 243-245° C.

¹H NMR (300 MHz, DMSO-d₆) δ 2.37 (s, 3H, Ar—CH₃), 3.81 (s, 3H, N—CH₃), 4.13 (s, 2H, 4-CH₂), 7.05 (s, 1H, vinyl H), 7.29-7.93 (m, 7H, Ar—H), 10.51 (s, 1H, NH).

KHG23070 [2-(4-trifluoromethoxyphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-OCF₃), n=1, m=0, X=Cl]

yield: 66%; melting point: 236-237° C.

¹H NMR (300 MHz, DMSO-d₆) δ 3.74 (s, 3H, N—CH₃), 4.09 (s, 2H, 4-CH₂), 6.97 (s, 1H, vinyl H), 7.26-7.97 (m, 7H, Ar—H), 10.39 (s, 1H, NH).

KHG23071 [2-(4-isopropylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-CH(CH₃)₂, n=1, m=0, X=Cl]

yield: 72%; melting point: 237-238° C.

¹H NMR (300 MHz, DMSO-d₆) δ 1.24-1.26 (d, 6H, CH(CH₃)₂), 2.93-3.02 (m, 1H, CH(CH₃)₂), 3.77 (s, 3H, N—CH₃), 4.11 (s, 2H, 4-CH₂), 7.02 (s, 1H, vinyl H), 7.30-7.95 (m, 7H, Ar—H), 10.42 (s, 1H, NH).

KHG23072 [2-(4-ethylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-C₂H₅), n=1, m=0, X=Cl]

yield: 87%; melting point: 242° C.

¹H NMR (300 MHz, DMSO-d₆) δ 1.20-1.25 (t, 3H, CH₂CH₃), 2.64-2.72 (q, 2H, CH₂CH₃), 3.79 (s, 3H, N—CH₃), 4.12 (s, 2H, 4-CH₂), 7.04 (s, 1H, vinyl H), 7.29-7.94 (m, 7H, Ar—H), 10.47 (s, 1H, NH).

KHG23073 [2-(4-phenylphenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (4-C₆H₅), n=1, m=0, X=Cl]

yield: 65%; melting point: 222-223° C.

¹H NMR (300 MHz, $_{DMSO}$-d₆) δ 3.77 (s, 3H, N—CH₃), 4.11 (s, 2H, 4-CH₂), 7.02 (s, 1H, vinyl H), 7.10-7.95 (m, 12H, Ar—H), 10.43 (s, 1H, NH).

KHG23076 [2-(3-fluorophenylimino)-3-methyl-1,3-thiazolidine-4-yl]-N-(4-chloro-2-fluorophenyl)-acetamide hydrochloride [R₁=H, R₂=2-F, R₃=4-Cl, R₄=H, R₅=CH₃, R₆=Ph (3-CF₃), n=1, m=0, X=Cl]

yield: 74%; melting point: 229-231° C.

¹H NMR (300 MHz, DMSO-d₆) δ 3.77 (s, 3H, N—CH₃), 4.11 (s, 2H, 4-CH₂), 7.02 (s, 1H, vinyl H), 7.19-7.94 (m, 7H, Ar—H), 10.43 (s, 1H, NH).

KHG23210 (2-cyclohexylimino-3-methyl-1,3-thiazolidine-4-yl)-N-(4-fluorophenyl)-acetamide hydrochloride [R₁=H, R₂=4-F, R₃=R₄=H, R₅=CH₃, R₆=C₆H₁₁, n=1, m=0, X=Cl]

yield: 75%; melting point: 265-266° C.

¹H NMR (300 MHz, DMSO-d₆) δ 11.80 (s, 1H, HCl), 9.64 (br. s, 1H, NH), 7.66-7.14 (m, 4H, Ar—H), 7.05 (s, 1H, vinyl-H), 3.98 (s, 2H, 4-CH₂), 3.58 (s, 3H, N—CH₃), 3.34 (br. s, 1H, cyclohexyl-C₁H), 1.99-1.10 (m, 10H, cyclohexyl-H).

KHG23354 (2-cyclohexylimino-3-methyl-1,3-thiazolidine-4-yl)-N-(4-bromophenyl)-acetamide hydrochloride [R₁=H, R₂=4-Br, R₃=R₄=H, R₅=CH₃, R₆=C₆H₁₁, n=1, m=0, X=Cl]

yield: 94%; melting point: 261-263° C.

¹H NMR (300 MHz, DMSO-d₆) δ 11.03 (s, 1H, HCl), 9.75 (d, 1H, J=4.6 H$_z$, NH), 7.62-7.47 (m, 4H, Ar—H), 7.05 (s, 1H, vinyl-H), 4.00 (s, 2H, 4-CH₂), 3.59 (s, 3H, N—CH₃), 3.22 (br. s, 1H, cyclohexyl-C₁H), 1.97-1.11 (m, 10H, cyclohexyl-H).

KHG23355 (2-cyclohexylimino-3-methyl-1,3-thiazolidine-4-yl)-N-(4-phenoxyphenyl)-acetamide hydrochloride [R₁=H, R₂=4-OPh, R₃=R₄=H, R₅=CH₃, R₆=C₆H₁₁, n=1, m=0, X=Cl]

yield: 98%; melting point: 255-257° C.

¹H NMR (300 MHz, DMSO-d₆) δ 11.80 (s, 1H, HCl), 9.71 (d, 1H, J=3.7 H$_z$, NH), 7.65-6.94 (m, 4H, Ar—H), 7.05 (s, 1H, vinyl-H), 3.98 (s, 2H, 4-CH₂), 3.60 (s, 3H, N—CH₃), 3.23 (br. s, 1H, cyclohexyl-C₁H), 1.98-1.08 (m, 10H, cyclohexyl-H).

KHG23356 (2-cyclohexylimino-3-methyl-1,3-thiazolidine-4-yl)-N-(3,5-dichlorophenyl)-acetamide hydrochloride [R₁=H, R₂=3-Cl, R₃=4-Cl, R₄=H, R₅=CH₃, R₆=C₆H₁₁, n=1, m=0, X=Cl]

yield: 62%; melting point: 255-257° C.

¹H NMR (300 MHz, DMSO-d₆) δ 11.37 (s, 1H, HCl), 9.61 (d, 1H, J=5.5 H$_z$, NH), 7.73 (s, 2H, o-ArH), 7.29 (s, 1H, p-ArH), 7.07 (s, 1H, vinyl-H), 4.02 (s, 2H, 4-CH₂), 3.56 (s, 3H, N—CH₃), 3.22 (br. s, 1H, cyclohexyl-C₁H), 1.98-1.08 (m, 10H, cyclohexyl-H).

KHG23360 (2-cyclohexylimino-3-methyl-1,3-thiazolidine-4-yl)-N-(2-fluoro-5-nitrophenyl)-acetamide hydrochloride [R₁=H, R₂=2-F, R₃=5-NO₂, R₄=H, R₅=CH₃, R₆=C₆H₁₁, n=1, m=0, X=Cl]

yield: 96%; melting point: 219-221° C.

¹H NMR (300 MHz, DMSO-d₆) δ 10.77 (s, 1H, HCl), 9.71 (br. s, 1H, NH), 8.92-7.57 (m, 3H, ArH), 7.06 (s, 1H, vinyl-H), 4.10 (s, 2H, 4-CH₂), 3.58 (s, 3H, N—CH₃), 3.24 (br. s, 1H, cyclohexyl-C₁H), 1.98-1.09 (m, 10H, cyclohexyl-H).

KHG23361 (2-cyclohexylimino-3-methyl-1,3-thiazolidine-4-yl)-N-(4-chloro-2-fluorophenyl)-acetamide hydrochloride [R₁=H, R₂=2-F, R₃=4-Cl, R₃=CH₃, R₄=H, R₅=CH₃, R₆=C₆H₁₁, n=1, m=0, X=Cl]

yield: 90%; melting point: 255-257° C.

¹H NMR (300 MHz, DMSO-d₆) δ 10.38 (s, 1H, HCl), 9.67 (br. s, 1H, NH), 7.88-7.25 (m, 3H, ArH), 7.03 (s, 1H, vinyl-H), 4.02 (s, 2H, 4-CH₂), 3.56 (s, 3H, N—CH₃), 3.23 (br. s, 1H, cyclohexyl-C₁H), 1.98-1.08 (m, 10H, cyclohexyl-H).

KHG23362 (2-cyclohexylimino-3-methyl-1,3-thiazolidine-4-yl)-N-(4-chlorophenyl)-acetamide hydrochloride [R₁=H, R₂=4-Cl, R₃=R₄=H, R₅=CH₃, R₆=C₆H₁₁, n=1, m=0, X=Cl]

yield: 72%; melting point: 266.8-267.3° C.

¹H NMR (300 MHz, DMSO-d₆) δ 11.1 (s, 1H, HCl), 9.82 (br. s, 1H, NH), 7.69-7.34 (m, 4H, ArH), 7.07 (s, 1H, vinyl-H), 4.01 (s, 2H, 4-CH₂), 3.65 (s, 3H, N—CH₃), 3.21 (br. s, 1H, cyclohexyl-C₁H), 1.97-1.10 (m, 10H, cyclohexyl-H).

KHG23364 (2-cyclohexylimino-3-methyl-1,3-thiazolidine-4-yl)-N-(4-isopropylphenyl)-acetamide hydrochloride [R₁=H, R₂=4-CH(CH₃)₂, R₃=R₄=H, R₅=CH₃, R₆=C₆H₁₁, n=1, m=0, X=Cl]

yield: 94%; melting point: 244° C.

¹H NMR (300 MHz, DMSO-d₆) δ 10.48 (s, 1H, HCl), 9.55 (br. s, 1H, NH), 7.50-7.16 (m, 4H, ArH), 7.02 (s, 1H, vinyl-H), 3.93 (s, 2H, 4-CH₂), 3.55 (s, 3H, N—CH₃), 3.24 (br. s, 1H, cyclohexyl-C₁H), 2.85-2.97 (m, 1H, isopropyl-CH), 1.98-1.22 (m, 10H, cyclohexyl-H), 1.16 (d, 6H, J=5.1 Hz, isopropyl-(CH₃)₂).

KHG23365 (2-cyclohexylimino-3-methyl-1,3-thiazolidine-4-yl)-N-(4-n-butylphenyl)-acetamide hydrochloride [R₁=H, R₂=4-n-C₄H₉, R₃=R₄=H, R₅=CH₃, R₆=C₆H₁₁, n=1, m=0, X=Cl]

yield: 79%; melting point: 242-244° C.

¹H NMR (300 MHz, DMSO-d₆) δ 10.42 (s, 1H, HCl), 9.47 (d, J=4.1 Hz, 1H, NH), 7.48-7.10 (m, 4H, ArH), 7.02 (s, 1H, vinyl-H), 3.92 (s, 2H, 4-CH₂), 3.53 (s, 3H, N—CH₃), 3.23 (br. s, 1H, cyclohexyl-C₁H), 2.50 (t, 2H, J=5.5 Hz, CH₂CH₂CH₂CH₃), 1.98-1.12 (m, 14H, cyclohexyl-H and CH₂CH₂CH₂CH₃), 0.87 (t, 3H, J=5.5 Hz, CH₂CH₂CH₂CH₃).

KHG24070 (2-cyclohexylimino-3-methyl-1,3-thiazolidine-4-yl)-N-(3-chloro-4-methoxyphenyl)-acetamide hydrochloride [R₁=H, R₂=3-Cl, R₃=4-OCH₃, R₅=CH₃, R₆=C₆H₁₁, n=1, m=0, X=Cl]

yield: 75.6%; melting point: 233.5-235° C.

¹H NMR (300 MH$_z$, DMSO-d₆) δ 10.90 (s, 1H, HCl), 9.71 (d, 1H, J=6.3 H$_z$, NH), 7.81 (d, 1H, J=2.4 Hz, Ar—H), 7.49 (dd, 1H, J=8.7 H$_z$, J=2.4 H$_z$, Ar—H), 7.11 (d, 1H, J=8.9 Hz, Ar—H), 7.06 (s, 1H, vinyl-H), 3.97 (s, 2H, 4-CH₂), 3.81 (s, 3H, Ar—OCH₃), 3.60 (s, 3H, N—CH₃), 3.24 (s, 1H, cyclohexyl-C₁H), 1.93-1.11 (m, 10H, cyclohexyl-H).

KHG24071 (2-cyclohexylimino-3-methyl-1,3-thiazolidine-4-yl)-N-(2,5-dichloro-4-methylphenyl)-acetamide hydrochloride [R₁=H, R₂=2-Cl, R₃=4-CH₃, R₄=5-Cl, R₅=CH₃, R₆=C₆H₁₁, n=1, m=0, X=Cl]

yield: 66.9%; melting point: 146° C.

¹H NMR (300 MH$_z$, DMSO-d₆) δ 10.86 (s, 1H, HCl), 9.79 (d, 1H, NH), 8.05 (s, 2H, Ar—H), 7.10 (s, 1H, vinyl-H), 4.08 (s, 2H, 4-CH₂), 3.61 (s, 3H, N—CH₃), 3.25 (s, 1H, cyclohexyl-C₁H), 1.98-1.11 (m, 10H, cyclohexyl-H).

KHG24072 (2-cyclohexylimino-3-methyl-1,3-thiazolidine-4-yl)-N-(3-chloro-4-methylphenyl)-acetamide hydrochloride [R₁=H, R₂=2-Cl, R₃=4-CH₃, R₄=H, R₃=CH₃, R₆=C₆H₁₁, n=1, m=0, X=Cl]

yield: 72.1%; melting point: 224-224.5° C.

¹H NMR (300 MHz, DMSO-d₆) δ 11.06 (s, 1H, HCl), 9.77 (d, 1H, J=5.5 H$_z$, NH), 7.83 (d, 1H, J=1.8 H$_z$, Ar—H), 7.41 (q, 1H, J=8.3 H$_z$, J=1.8 H$_z$, Ar—H), 7.27 (d, 1H, J=8.3 H$_z$, Ar—H), 7.07 (s, 1H, vinyl-H), 4.01 (s, 2H, 4-CH₂), 3.61 (s, 3H, N—CH₃), 3.23 (s, 1H, cyclohexyl-C₁H), 2.26 (s, 3H, Ar—CH₃), 1.93-1.11 (m, 10H, cyclohexyl-H).

KHG24073 (2-cyclohexylimino-3-methyl-1,3-thiazolidine-4-yl)-N-(4-t-butylphenyl)-acetamide hydrochloride [R₁=H, R₂=4-t-C₄H₉, R₃=R₄=H, R₅=CH₃, R₆=C₆H₁₁, n=1, m=0, X=Cl]

yield: 59.2%; melting point: 234-235.5° C.

¹H NMR (300 MH$_z$, DMSO-d₆) δ 10.56 (s, 1H, HCl), 9.64 (d, 1H, J=5.4 H$_z$, NH), 7.51 (d, 2H, J=8.6 H$_z$, Ar—H), 7.32 (d, 2H, J=8.6 H$_z$, Ar—H), 7.04 (s, 1H, vinyl-H), 3.95 (s, 2H, 4-CH₂), 3.57 (s, 3H, N—CH₃), 3.25 (s, 1H, cyclohexyl-C₁H), 1.99-1.16 (m, 10H, cyclohexyl-H), 1.25 (s, 9H, Ar—C(CH₃)₃).

KHG24074 (2-cyclohexylimino-3-methyl-1,3-thiazolidine-4-yl)-N-(4-trifluoromethylphenyl)-acetamide hydrochloride [R₁=H, R₂=4-CF₃, R₃=R₄=H, R₅=CH₃, R₆=C₆H₁₁, n=1, m=0, X=Cl]

yield: 61.6%; melting point: 241-242° C.

¹H NMR (300 MHz, DMSO-d₆) δ 11.23 (s, 1H, HCl), 9.69 (d, 1H, J=6.7 H$_z$, NH), 7.86 (d, 1H, J=8.5 H$_z$, Ar—H), 7.69 (d, 1H, J=8.6 H$_z$, Ar—H), 7.08 (s, 1H, vinyl-H), 4.06 (s, 2H, 4-CH₂), 3.59 (s, 3H, N—CH₃), 3.26 (s, 1H, cyclohexyl-C₁H), 1.99-1.12 (m, 10H, cyclohexyl-H).

KHG24075 (2-cyclohexylimino-3-methyl-1,3-thiazolidine-4-yl)-N-(3,5-ditrifluoromethylphenyl)-acetamide hydrochloride [$R_1$=H, $R_2$=3-$CF_3$, $R_3$=5-$CF_3$, $R_4$=H, $R_5$=$CH_3$, $R_6$=$C_6H_{11}$, n=1, m=0, X=Cl]

yield: 80.1%; melting point: 208-209° C.

$^1$H NMR (300 MHz, DMSO-$d_6$) δ 11.76 (s, 1H, HCl), 9.62 (d, 1H, J=7.3 $H_z$, NH), 8.35 (s, 2H, Ar—H), 7.78 (s, 1H, Ar—H), 7.10 (s, 1H, vinyl-H), 4.08 (s, 2H, 4-$CH_2$), 3.58 (s, 3H, N—$CH_3$), 3.25 (s, 1H, cyclohexyl-$C_1$H), 1.99-1.16 (m, 10H, cyclohexyl-H).

KHG24076 (2-cyclohexylimino-3-methyl-1,3-thiazolidine-4-yl)-N-(3-methoxyphenyl)-acetamide hydrochloride [$R_1$=H, $R_2$=3-$OCH_3$, $R_3$=$R_4$=H, $R_5$=$CH_3$, $R_6$=$C_6H_{11}$, n=1, m=0, X=Cl]

yield: 78.2%; melting point: 156-158° C.

$^1$H NMR (300 $MH_z$, DMSO-$d_6$) δ 10.73 (s, 1H, HCl), 9.70 (d, 1H, J=6.4 $H_z$, NH), 7.34 (s, 1H, Ar—H), 7.24-7.10 (m, 2H, Ar—H), 7.05 (s, 1H, vinyl-H), 6.66-6.63 (m, 1H, J=7.8 Hz, Ar—H), 3.98 (s, 2H, 4-$CH_2$), 3.71 (s, 3H, Ar—$OCH_3$), 3.58 (s, 3H, N—$CH_3$), 3.25 (s, 1H, cyclohexyl-$C_1$H), 1.99-1.15 (m, 10H, cyclohexyl-H).

KHG24077 (2-cyclohexylimino-3-methyl-1,3-thiazolidine-4-yl)-N-(4-methylphenyl)-acetamide hydrochloride [$R_1$=H, $R_2$=4-$CH_3$, $R_3$=$R_4$=H, $R_5$=$CH_3$, $R_6$=$C_6H_{11}$, n=1, m=0, X=Cl]

yield: 57.2%; melting point: 238-240° C.

$^1$H NMR (300 MHz, DMSO-$d_6$) δ 10.59 (s, 1H, HCl), 9.67 (d, 1H, J=5.7 $H_z$, NH), 7.49 (d, 2H, J=8.3 $H_z$, Ar—H), 7.11 (d, 2H, J=8.3 $H_z$, Ar—H), 7.04 (s, 1H, vinyl-H), 3.96 (s, 2H, 4-$CH_2$), 3.59 (s, 3H, N—$CH_3$), 3.25 (s, 1H, cyclohexyl-$C_1$H), 2.25 (s, 3H, Ar—$CH_3$), 1.93-1.11 (m, 10H, cyclohexyl-H).

KHG24080 (2-cyclohexylimino-3-methyl-1,3-thiazolidine-4-yl)-N-(2,5-difluorophenyl)-acetamide hydrochloride [$R_1$=H, $R_2$=2-F, $R_3$=5-F, $R_4$=H, $R_5$=$CH_3$, $R_6$=$C_6H_{11}$, n=1, m=0, X=Cl]

yield: 47.1%; melting point: 216-218° C.

$^1$H NMR (300 $MH_z$, DMSO-$d_z$) δ 9.67 (d, 1H, J=5.0 $H_z$, HCl), 8.98 (t, 1H, J=5.6 $H_z$, NH), 7.28-7.12 (m, 3H, Ar—H), 6.97 (s, 1H, vinyl-H), 4.31 (d, 2H, J=5.6 $H_z$, N—CH2), 3.80 (s, 2H, 4-$CH_2$), 3.52 (s, 3H, N—$CH_3$), 3.23 (s, 1H, cyclohexyl-$C_1$H), 1.97-1.11 (m, 10H, cyclohexyl-H).

KHG24081 (2-cyclohexylimino-3-methyl-1,3-thiazolidine-4-yl)-N-(2,4-difluorophenyl)-acetamide hydrochloride [$R_1$=H, $R_2$=2-F, $R_3$=4-F, $R_4$=H, $R_5$=$CH_3$, $R_6$=$C_6H_{11}$, n=1, m=0, X=Cl]

yield: 19.7%; melting point: 206-208° C.

$^1$H NMR (300 $MH_z$, DMSO-$d_6$) δ 9.60 (d, 1H, J=5.7 $H_z$, HCl), 8.95 (t, 1H, J=5.8 $H_z$, NH), 7.44-7.30 (m, 2H, Ar—H), 7.13 (s, 1H, Ar—H), 6.97 (s, 1H, vinyl-H), 4.27 (d, 2H, J=5.8 $H_z$, N—$CH_2$), 3.78 (s, 2H, 4-$CH_2$), 3.50 (s, 3H, N—$CH_3$), 3.25 (s, 1H, cyclohexyl-$C_1$H), 1.98-1.11 (m, 10H, cyclohexyl-H).

KHG24082 (2-cyclohexylimino-3-methyl-1,3-thiazolidine-4-yl)-N-(2-methylbenzyl)-acetamide hydrochloride [$R_1$=H, $R_2$=2-$CH_3$, $R_3$=$R_4$=H, $R_5$=$CH_3$, $R_6$=$C_6H_{11}$, n=1, m=1, X=Cl]

yield: 64.2%; melting point: 220-221° C.

$^1$H NMR (300 $MH_z$, DMSO-$d_z$) δ 9.70 (d, 1H, J=4.6 $H_z$, HCl), 8.75 (t, 1H, J=5.2 $H_z$, NH), 7.23-7.17 (m, 4H, Ar—H), 6.96 (s, 1H, vinyl-H), 4.26 (d, 2H, J=5.5 $H_z$, N—$CH_2$), 3.77 (s, 2H, 4-$CH_2$), 0.54 (s, 3H, N—$CH_3$), 3.23 (s, 1H, cyclohexyl-H), 2.27 (s, 3H, Ar—$CH_3$), 1.97-1.15 (m, 10H, cyclohexyl-H).

KHG24083 (2-cyclohexylimino-3-methyl-1,3-thiazolidine-4-yl)-N-(2-trifluoromethylphenyl)-acetamide hydrochloride [$R_1$=H, $R_2$=2-$CF_3$, $R_3$=$R_4$=H, $R_5$=$CH_3$, $R_6$=$C_6H_{11}$, n=1, m=0, X=Cl]

yield: 54.2%; melting point: 189-190° C.

$^1$H NMR (300 MHz, DMSO-$d_6$) δ 9.82 (s, 1H, HCl), 9.07 (t, 1H, J=5.6 $H_z$, NH), 7.73-7.46 (m, 4H, Ar—H), 7.00 (s, 1H, vinyl-H), 4.47 (d, 2H, J=5.4 $H_z$, N—$CH_2$), 3.85 (s, 2H, 4-$CH_2$), 3.57 (s, 3H, N—$CH_3$), 3.22 (s, 1H, cyclohexyl-$C_1$H), 1.97-1.11 (m, 10H, cyclohexyl-H).

KHG24084 (2-cyclohexylimino-3-methyl-1,3-thiazolidine-4-yl)-N-(3-trifluoromethylphenyl)-acetamide hydrochloride [$R_1$=H, $R_2$=3-$CF_3$, $R_3$=$R_4$=H, $R_5$=$CH_3$, $R_6$=$C_6H_{11}$, n=1, m=0, X=Cl]

yield: 19.7%; melting point: 189-191° C.

$^1$H NMR (300 MHz, DMSO-$d_6$) δ 9.75 (s, 1H, HCl), 9.08 (t, 1H, J=57 $H_z$, NH), 7.61-7.56 (m, 4H, Ar—H), 6.97 (s, 1H, vinyl-H), 4.38 (d, 2H, J=5.8 Hz, N—$CH_2$), 3.81 (s, 2H, 4-$CH_2$), 3.52 (s, 3H, N—$CH_3$), 3.21 (s, 1H, cyclohexyl-$C_1$H), 1.96-1.15 (m, 10H, cyclohexyl-H).

KHG24085 (2-cyclohexylimino-3-methyl-1,3-thiazolidine-4-yl)-N-(3-ethoxycarbonylethoxyphenyl)-acetamide hydrochloride [$R_1$=H, $R_2$=3-$COOC_2H_5$, $R_3$=$R_4$=H, $R_5$=$CH_3$, $R_6$=$C_6H_{11}$, n=1, m=0, X=Cl]

yield: 70.8%; melting point: 241-242° C.

$^1$H NMR (300 MHz, DMSO-$d_6$) δ 11.20 (s, 1H, HCl), 9.72 (d, 1H, J=6.9 $H_z$, NH), 7.92 (d, 2H, J=8.7 $H_z$, Ar—H), 7.78 (d, 2H, J=8.7 $H_z$, Ar—H), 7.07 (s, 1H, vinyl-H), 4.27 (q, 2H, J=7.0 $H_z$, Ar—$CO_2CH_2CH_3$), 4.05 (s, 2H, 4-$CH_2$), 3.60 (s, 3H, N—$CH_3$), 3.25 (s, 1H, cyclohexyl-$C_1$H), 1.99-1.11 (m, 10H, cyclohexyl-H), 1.30 (t, 3H, J=7.0 Hz, Ar—$CO_2CH_2CH_3$).

KHG24086 (2-cyclohexylimino-3-methyl-1,3-thiazolidine-4-yl)-N-(3,4-methylenedioxyphenyl)-acetamide hydrochloride [$R_1$=H, $R_2$, $R_3$=3,4-$OCH_2O$—, $R_4$=H, $R_5$=$CH_3$, $R_6$=$C_6H$, n=1, m=1, X=Cl]

yield: 35.2%; melting point: 146-147° C.

$^1$H NMR (300 $MH_z$, DMSO-$d_6$) δ 9.68 (d, 1H, J=5.2 Hz, HCl), 8.82 (t, 1H, J=5.8 $H_z$, NH), 6.96 (s, 1H, Ar—H), 6.86-6.73 (m, 2H, Ar—H), 6.84 (s, 1H, vinyl-H), 5.98 (s, 2H, $OCH_2$), 4.18 (d, 2H, J=5.8 $H_z$, N—$CH_2$), 3.75 (s, 2H, 4-$CH_2$), 3.52 (s, 3H, N—$CH_3$), 3.25 (s, 1H, cyclohexyl-$C_1$H), 1.97-1.30 (m, 10H, cyclohexyl-H).

KHG24087 (2-cyclohexylimino-3-methyl-1,3-thiazolidine-4-yl)-N-(2,5-difluorophenyl)-acetamide hydrochloride [$R_1$=H, $R_2$=2-F, $R_3$=5-F, $R_4$=H, $R_5$=$CH_3$, $R_6$=$C_6H_{11}$, n=1, m=0, X=Cl]

yield: 68.3%; melting point: 196.5-198° C.

$^1$H NMR (300 MHz, DMSO-$d_6$) δ 10.49 (s, 1H, HCl), 9.77 (d, 1H, J=6.3 $H_z$, NH), 7.85-7.00 (m, 3H, Ar—H), 7.05 (s, 1H, vinyl-H), 4.06 (s, 2H, 4-$CH_2$), 3.58 (s, 3H, N—$CH_3$), 3.25 (s, 1H, cyclohexyl-$C_1$H), 1.98-1.15 (m, 10H, cyclohexyl-H).

KHG24088 (2-cyclohexylimino-3-methyl-1,3-thiazolidine-4-yl)-N-(3,4-dichlorobenzyl)-acetamide hydrochloride [$R_1$=H, $R_2$=3-Cl, $R_3$=4-Cl, $R_4$=H, $R_5$=$CH_3$, $R_6$=$C_6H_{11}$, n=1, m=1, X=Cl]

yield: 51.3%; melting point: 215-216° C.

$^1$H NMR (300 $MH_z$, DMSO-$d_6$) δ 9.79 (d, 1H, J=4.7 Hz, HCl), 8.97 (t, 1H, J=5.6 $H_z$, NH), 7.46-7.30 (m, 3H, Ar—H), 6.98 (s, 1H, vinyl-H), 4.36 (d, 2H, J=5.6 $H_z$, N—$CH_2$), 3.82 (s, 2H, 4-$CH_2$), 3.56 (s, 3H, N—$CH_3$), 3.22 (s, 1H, cyclohexyl-$C_1$H), 1.97-1.30 (m, 10H, cyclohexyl-H).

KHG24089 (2-cyclohexylimino-3-methyl-1,3-thiazolidine-4-yl)-N-benzyl-acetamide hydrochloride [$R_1$=H, $R_2$=$R_3R_4$=H, $R_5$=$CH_3$, $R_6$=$C_6H_{11}$, n=1, m=0, X=Cl]

yield: 44.6%; melting point: 206-206.5° C.

¹H NMR (300 MH$_z$, DMSO-d$_6$) δ 9.77 (d, 1H, J=5.5 Hz, HCl), 8.93 (t, 1H, J=5.7 H$_z$, NH), 7.35-7.22 (m, 5H, Ar—H), 6.97 (s, 1H, vinyl-H), 4.28 (d, 2H, J=5.7 H$_z$, N—CH$_2$), 3.77 (s, 2H, 4-CH$_2$), 3.54 (s, 3H, N—CH$_3$), 3.23 (s, 1H, cyclohexyl-C$_1$H), 1.97-1.11 (m, 10H, cyclohexyl-H).

KHG24090 (2-cyclohexylimino-3-methyl-1,3-thiazolidine-4-yl)-N-(3,4-dimethoxyphenyl)-acetamide hydrochloride [R$_1$=H, R$_2$=3-OCH$_3$, R$_3$=4-OCH$_3$, R$_4$=H, R$_5$=CH$_3$, R$_6$=C$_6$H$_{11}$, n=1, m=0, X=Cl]

yield: 86.9%; melting point: 233-234° C.

¹H NMR (300 MH$_z$, DMSO-d$_6$) δ 10.90 (s, 1H, HCl), 9.71 (d, 1H, J=6.3 H$_z$, NH), 7.81 (d, 1H, J=2.4 H$_z$, Ar—H), 7.49 (dd, 1H, J=8.7 H$_z$, J=2.4 H$_z$, Ar—H), 7.11 (d, 1H, J=8.9 H$_z$, Ar—H), 7.06 (s, 1H, vinyl-H), 3.97 (s, 2H, 4-CH$_2$), 3.81 (s, 3H, Ar—OCH$_3$), 3.60 (s, 3H, N—CH$_3$), 3.24 (s, 1H, cyclohexyl-C$_1$H), 1.93-1.11 (m, 10H, cyclohexyl-H).

KHG24091 (2-cyclohexylimino-3-methyl-1,3-thiazolidine-4-yl)-N-(3-fluoro-4-methylphenyl)-acetamide hydrochloride [R$_1$=H, R$_2$=3-F, R$_3$=4-CH$_3$, R$_4$=H, R$_5$=CH$_3$, R$_6$=C$_6$H$_{11}$, n=1, m=0, X=Cl]

yield: 51.1%; melting point: 210-212° C.

¹H NMR (300 MH$_z$, DMSO-d$_6$) δ 10.26 (s, 1H, HCl), 9.85 (d, 1H, J=6.0 H$_z$, N—(H), 7.63-6.95 (m, 3H, Ar—H), 6.97 (s, 1H, vinyl-H), 4.02 (s, 2H, 4-CH$_2$), 3.60 (s, 3H, N—CH$_3$), 3.24 (s, 1H, cyclohexyl-C$_1$H), 2.25 (s, 3H, Ar—CH$_3$), 1.98-1.09 (m, 10H, cyclohexyl-H).

KHG24092 (2-cyclopentylimino-3-methyl-1,3-thiazolidine-4-yl)-N-(4-ethylphenyl)-acetamide hydrochloride [R$_1$=H, R$_2$=4-C$_2$H$_5$, R$_3$R$_4$=H, R$_5$=CH$_3$, R$_6$=C$_5$H$_9$, n=1, m=0, X=Cl]

yield: 87.5%; melting point: 213-214.5° C.

¹H NMR (300 MHz, DMSO-d$_6$) δ 1.14-1.18 (t, J=7.5 Hz, 3H, CH$_2$CH$_3$), 9.67 (s, 1H, NH—Ar), 7.12-7.52 (m, 4H, Ar—H), 7.05 (s, 1H, vinyl-H), 3.95 (s, 2H, COCH$_2$), 3.59 (s, 3H, N—CH$_3$), 2.53-2.60 (q, J=7.5 Hz, 2H, CH$_2$CH$_3$), 1.58-3.80 (m, 9H, NH-cyclopentyl-H), 1.14-1.18 (t, J=7.5 Hz, 3H, CH$_2$CH$_3$).

KHG24093 (2-cyclopentylimino-3-methyl-1,3-thiazolidine-4-yl)-N-(4-ethylphenyl)-acetamide hydrochloride [R$_1$=H, R$_2$=2-C$_2$H$_5$, R$_3$=R$_4$=H, R$_5$=CH$_3$, R$_6$=C$_5$H$_9$, n=1, m=0, X=Cl]

yield: 78.9%; melting point: 242-242.5° C.

¹H NMR (300 MHz, DMSO-d$_6$) δ 9.72 (d, 1H, J=4.5 Hz NH—Ar), 7.12-7.67 (m, 4H, ArH), 7.05 (s, 1H, vinyl-H), 3.98 (s, 2H, COCH$_2$), 3.60 (s, 3H, N—CH$_3$), 1.45-3.85 (m, 9H, NH-cyclopentyl-H).

KHG24094 (2-cyclopentylimino-3-methyl-1,3-thiazolidine-4-yl)-N-(4-methoxyphenyl)-acetamide hydrochloride [R$_1$=H, R$_2$=4-OCH$_3$, R$_3$=R$_4$=H, R$_5$=CH$_3$, R$_6$=C$_5$H$_9$, n=1, m=0, X=Cl]

yield: 46.2%; melting point: 210-211° C.

¹H NMR (300 MHz, DMSO-d$_6$) δ 9.68 (s, 1H, NH—Ar), 6.86-7.67 (m, 4H, Ar—H), 7.05 (s, 1H, vinyl-H), 3.93 (s, 2H, COCH$_2$), 3.70 (s, 3H, OCH$_3$), 3.60 (s, 3H, N—CH$_3$), 1.58-3.8 (m, 9H, NH-cyclopentyl-H).

KHG24095 (2-cyclopentylimino-3-methyl-1,3-thiazolidine-4-yl)-N-(2-chloro-4-fluorophenyl)-acetamide hydrochloride [R$_1$=H, R$_2$=2-Cl, R$_3$=4-F), R$_4$=H, R$_5$=CH$_3$, R$_6$=C$_5$H$_9$, n=1, m=0, X=Cl]

yield: 93.4%; melting point: 209-210.5° C.

¹H NMR (300 MHz, DMSO-d$_6$) δ 9.77 (s, 1H, NH—Ar), 7.20-7.64 (m, 3H, Ar—H), 7.05 (s, 1H, vinyl-H), 4.01 (s, 2H, COCH$_2$), 3.61 (s, 3H, N—CH$_3$), 1.58-3.80 (m, 9H, NH-cyclopentyl-H).

KHG24096 (2-cyclopentylimino-3-methyl-1,3-thiazolidine-4-yl)-N-(4-cyanomethylphenyl)-acetamide hydrochloride [R$_1$=H, R$_2$=4-CH$_2$CN, R$_3$=R$_4$=H, R$_5$=CH$_3$, R$_6$=C$_5$H$_9$, n=1, m=0, X=Cl]R$_3$=R$_4$=H, yield: 18.5%; melting point: 199.5-200° C.

¹H NMR (300 MHz, DMSO-d$_6$) δ 9.46 (s, 1H, NH—Ar), 7.28-7.62 (m, 4H, Ar—H), 7.04 (s, 1H, vinyl-H), 3.97 (s, 2H, COCH$_2$), 3.55 (d, J=4.0 Hz, 2H, CN—CH$_2$), 3.32 (s, 3H, N—CH$_3$), 1.59-3.80 (m, 9H, NH-cyclopentyl-H).

KHG24097 (2-cyclopentylimino-3-methyl-1,3-thiazolidine-4-yl)-N-(2-chloro-4-methylphenyl)-acetamide hydrochloride [R$_1$=H, R$_2$=2-Cl, R$_3$=4-CH$_3$, R$_4$=H, R$_5$=CH$_3$, R$_6$=C$_5$H$_9$, n=1, m=0, X=Cl]

yield: 82.7%; melting point: 185-186.5° C.

¹H NMR (300 MHz, DMSO-d$_6$) δ 9.84 (d, 1H, J=4.0 Hz NH—Ar), 7.12-7.49 (m, 3H, Ar—H), 7.05 (s, 1H, vinyl-H), 4.00 (s, 2H, COCH$_2$), 3.63 (s, 3H, N—CH$_3$), 2.28 (s, 3H, Ar—CH$_3$), 1.56-3.80 (m, 9H, NH-cyclopentyl-H).

KHG24098 (2-cyclopentylimino-3-methyl-1,3-thiazolidine-4-yl)-N-(4-bromophenyl)-acetamide hydrochloride [R$_1$=H, R$_2$=4-Br, R$_3$=R$_4$=H, R$_5$=CH$_3$, R$_6$=C$_5$H$_9$, n=1, m=0, X=Cl]

yield: 30.0%; melting point: 228-228.5° C.

¹H NMR (300 MHz, DMSO-d$_6$) δ 9.68 (d, 1H, J=4.7 Hz NH—Ar), 7.47-7.62 (m, 4H, Ar—H), 7.05 (s, 1H, vinyl-H), 3.99 (s, 2H, COCH$_2$), 3.59 (s, 3H, N—CH$_3$), 1.58-3.79 (m, 9H, NH-cyclopentyl-H).

KHG24099 (2-cyclopentylimino-3-methyl-1,3-thiazolidine-4-yl)-N-(4-phenoxyphenyl)-acetamide hydrochloride [R$_1$=H, R$_2$=4-OPh, R$_3$=R$_4$=H, R$_5$=CH$_3$, R$_6$=C$_5$H$_9$, n=1, m=0, X=Cl]

yield: 74.1%; melting point: 230-230.5° C.

¹H NMR (300 MHz, DMSO-d$_6$) δ 9.68 (d, 1H, J=4.7 Hz NH—Ar), 7.07-7.64 (m, 5H, O—Ar—H), 7.05 (s, 1H, vinyl-H), 6.94-7.01 (m, 4H, N—Ar—H), 3.97 (s, 2H, COCH$_2$), 3.60 (s, 3H, N—CH$_3$), 1.58-3.79 (m, 9H, NH-cyclopentyl-H).

KHG24100 (2-cyclopentylimino-3-methyl-1,3-thiazolidine-4-yl)-N-(3,5-dichlorophenyl)-acetamide hydrochloride [R$_1$=H, R$_2$=3-Cl, R$_3$=5-Cl, R$_4$=H, R$_5$=CH$_3$, R$_6$=C$_5$H$_9$, n=1, m=0, X=Cl]

yield: 87.6%; melting point: 231-232.5° C.

¹H NMR (300 MHz, DMSO-d$_6$) δ 9.64 (d, 1H, J=4.7 Hz NH—Ar), 7.28-7.74 (m, 3H, Ar—H), 7.07 (s, 1H, vinyl-H), 4.03 (s, 2H, COCH$_2$), 3.58 (s, 3H, N—CH$_3$), 1.58-3.79 (m, 9H, NH-cyclopentyl-H).

KHG24101 (2-cyclopentylimino-3-methyl-1,3-thiazolidine-4-yl)-N-(2-fluoro-4-methylphenyl)-acetamide hydrochloride [R$_1$=H, R$_2$=2-F, R$_3$=4-CH$_3$, R$_4$=H, R$_5$=CH$_3$, R$_6$=C$_5$H$_9$, n=1, m=0, X=Cl]

yield: 43.9%; melting point: 189-190° C.

¹H NMR (300 MHz, DMSO-d$_6$) δ 9.84 (d, 1H, J=4.0 Hz NH—Ar), 6.95-7.65 (m, 3H, Ar—H), 7.07 (s, 1H, vinyl-H), 3.99 (s, 2H, COCH$_2$), 3.60 (s, 3H, N—CH$_3$), 2.28 (s, 3H, Ar—CH$_3$), 1.58-3.80 (m, 9H, NH-cyclopentyl-H).

KHG24102 (2-cyclopentylimino-3-methyl-1,3-thiazolidine-4-yl)-N-(2,4-difluorophenyl)-acetamide hydrochloride [R$_1$=H, R$_2$=2-F, R$_3$=4-F, R$_4$=H, R$_5$=CH$_3$, R$_6$=C$_5$H$_9$, n=1, m=0, X=Cl]

yield: 13.6%; melting point: 240-242.5° C.

¹H NMR (300 MHz, DMSO-d$_6$) δ 9.78 (d, 1H, J=4.7 Hz NH—Ar), 7.04-7.79 (m, 3H, Ar—H), 7.07 (s, 1H, vinyl-H), 4.01 (s, 2H, COCH$_2$), 3.60 (s, 3H, N—CH$_3$), 1.58-3.79 (m, 9H, NH-cyclopentyl-H).

KHG24103 (2-cyclopentylimino-3-methyl-1,3-thiazolidine-4-yl)-N-(5-chloro-2-fluorophenyl)-acetamide hydrochloride [$R_1$=H, $R_2$=2-F, $R_3$=5-Cl, =H, $R_5$=$CH_3$, $R_6$=$C_5H_9$, n=1, m=0, X=Cl]

yield: 54.3%; melting point: 214-216° C.

$^1$H NMR (300 MHz, DMSO-$d_6$) δ 9.86 (s, 1H, NH—Ar), 7.20-8.01 (m, 3H, Ar—H), 7.06 (s, 1H, vinyl-H), 4.06 (s, 2H, $COCH_2$), 3.62 (s, 3H, N—$CH_3$), 1.56-3.79 (m, 9H, NH-cyclopentyl-H).

KHG24104 (2-cyclopentylimino-3-methyl-1,3-thiazolidine-4-yl)-N-(2-fluoro-5-nitrophenyl)-acetamide hydrochloride [$R_1$=H, $R_2$=2-F, $R_3$=5-$NO_2$, $R_4$=H, $R_5$=$CH_3$, $R_6$=$C_5H_9$, n=1, m=0, X=Cl]

yield: 55.4%; melting point: 234.5-236° C.

$^1$H NMR (300 MHz, DMSO-$d_6$) δ 9.83 (d, 1H, J=4.7 Hz NH—Ar), 7.56-8.93 (m, 3H, Ar—H), 7.08 (s, 1H, vinyl-H), 4.12 (s, 2H, COCH2), 3.62 (s, 3H, N—$CH_3$), 1.56-3.79 (m, 9H, NH-cyclopentyl-H).

KHG24105 (2-cyclopentylimino-3-methyl-1,3-thiazolidine-4-yl)-N-(4-chloro-2-fluorophenyl)-acetamide hydrochloride [$R_1$=H, $R_2$=2-F, $R_3$=4-Cl, =H, $R_5$=$CH_3$, $R_6$=$C_5H_9$, n=1, m=0, X=Cl]

yield: 54.2%; melting point: 228-230.5° C.

$^1$H NMR (300 MHz, DMSO-$d_6$) δ 9.76 (s, 1H, NH—Ar), 7.25-7.89 (m, 3H, Ar—H), 7.04 (s, 1H, vinyl-H), 4.03 (s, 2H, $COCH_2$), 3.59 (s, 3H, N—$CH_3$), 1.58-3.79 (m, 9H, NH-cyclopentyl-H).

KHG24106 (2-cyclopentylimino-3-methyl-1,3-thiazolidine-4-yl)-N-(4-chlorophenyl)-acetamide hydrochloride [$R_1$=H, $R_2$=4-Cl, $R_3$=$R_4$=H, $R_5$=$CH_3$, $R_6$=$C_5H_9$, n=1, m=0, X=Cl]

yield: 81.5%; melting point: 215-216° C.

$^1$H NMR (300 MHz, DMSO-$d_6$) δ 9.65 (d, 1H, NH—Ar), 7.36-7.66 (m, 4H, Ar—H), 7.05 (s, 1H, vinyl-H), 3.98 (s, 2H, $COCH_2$), 3.58 (s, 3H, N—$CH_3$), 1.58-3.80 (m, 9H, NH-cyclopentyl-H).

KHG24107 (2-cyclopentylimino-3-methyl-1,3-thiazolidine-4-yl)-N-phenyl-acetamide hydrochloride [$R_1$=H, $R_2$=$R_3$=$R_4$=H, $R_5$=$CH_3$, $R_6$=$C_5H_9$, n=1, m=0, X=Cl]

yield: 65.6%; melting point: 231.5-233° C.

$^1$H NMR (300 MHz, DMSO-$d_6$) δ 9.77 (s, 1H, NH—Ar), 7.06-7.63 (m, 5H, Ar—H), 7.03 (s, 1H, vinyl-H), 3.99 (s, 2H, $COCH_2$), 3.62 (s, 3H, N—$CH_3$), 1.56-3.79 (m, 9H, NH-cyclopentyl-H).

KHG24108 (2-cyclohexylimino-3-methyl-1,3-thiazolidine-4-yl)-N-(3-nitrophenyl)-acetamide hydrochloride [$R_1$=H, $R_2$=3-$NO_2$, $R_3$=$R_4$=H, $R_5$=$CH_3$, $R_6$=$C_6H_{11}$, n=1, m=0, X=Cl]

yield: 34%; melting point: 207° C.

$^1$H NMR (300 MHz, DMSO-$d_6$) δ 10.41 (s, 1H, HCl), 9.54 (br. s, 1H, NH), 7.83-6.98 (m, 4H, ArH), 7.01 (s, 1H, vinyl-H), 4.03 (s, 2H, 4-$CH_2$), 3.54 (s, 3H, N—$CH_3$), 3.23 (br. s, 1H, cyclohexyl-$C_1$H), 1.98-1.12 (m, 10H, cyclohexyl-H).

KHG24109 (2-cyclohexylimino-3-methyl-1,3-thiazolidine-4-yl)-N-(3-fluorophenyl)-acetamide hydrochloride [$R_1$=H, $R_2$=3-F, $R_3$=$R_4$=H, $R_5$=$CH_3$, $R_6$=$C_6H_{11}$, n=1, m=0, X=Cl]

yield: 78.3%; melting point: 238-239.5° C.

$^1$H NMR (300 MH$_z$, DMSO-$d_6$) δ 11.06 (s, 1H, HCl), 9.68 (d, 1H, J=4.8H$_z$, NH), 7.63-6.87 (m, 4H, Ar—H), 6.93 (s, 1H, vinyl-H), 4.01 (s, 2H, 4-$CH_2$), 3.59 (s, 3H, N—$CH_3$), 3.29 (s, 1H, cyclohexyl-$C_1$H), 1.99-1.11 (m, 10H, cyclohexyl-H).

KHG24110 (2-cyclohexylimino-3-methyl-1,3-thiazolidine-4-yl)-N-(4-isopropylphenyl)-acetamide hydrochloride [$R_1$=H, $R_2$=$C_6H_4$(4-CH($CH_3$)$_2$, $R_3$=$CH_3$, $R_4$=$C_6H_{11}$, n=1, m=0, X=Cl]

yield: 70.6%; melting point: 229-230° C.

$^1$H NMR (300 MH$_z$, DMSO-$d_6$) δ 10.60 (s, 1H, HCl), 9.68 (s, 1H, NH), 7.51 (d, 2H, J=7.8 H$_z$, Ar—H), 7.17 (d, 2H, J=7.9 H$_z$, Ar—H), 7.04 (s, 1H, vinyl-H), 3.96 (s, 2H, 4-$CH_2$), 3.58 (s, 3H, N—$CH_3$), 3.23 (s, 1H, cyclohexyl-$C_1$H), 2.81 (m, 1H, J=6.6 H$_z$, Ar—CH($CH_3$)$_2$), 1.99-1.16 (m, 10H, cyclohexyl-H), 1.16 (d, 6H, J=6.8 Hz, Ar—CH($CH_3$)$_2$).

KHG24111 (2-cyclohexylimino-3-methyl-1,3-thiazolidine-4-yl)-N-(4-bromo-3-methylphenyl)-acetamide hydrochloride [$R_1$=H, $R_2$=3-$CH_3$, $R_3$=4-Br, $R_4$=H, $R_5$=$CH_3$, $R_6$=$C_6H_{11}$, n=1, m=0, X=Cl]

yield: 79.6%; melting point: 237-238° C.

$^1$H NMR (300 MH$_z$, DMSO-$d_6$) δ 10.86 (s, 1H, HCl), 9.67 (d, 1H, J=6.3 H$_z$, NH), 7.65-7.38 (m, 3H, Ar—H), 7.05 (s, 1H, vinyl-H), 3.99 (s, 2H, 4-$CH_2$), 3.58 (s, 3H, N—$CH_3$), 3.25 (s, 1H, cyclohexyl-$C_1$H), 1.98-1.11 (m, 10H, cyclohexyl-H).

KHG24112 (2-cyclohexylimino-3-methyl-1,3-thiazolidine-4-yl)-N-(4-fluorobenzyl)-acetamide hydrochloride [$R_1$=H, $R_2$=4-F, $R_3$=$R_4$=H, $R_5$=$CH_3$, $R_6$=$C_6H_{11}$, n=1, m=1, X=Cl]

yield: 63.4%; melting point: 200-201° C.

$^1$H NMR (300 MH$_z$, DMSO-$d_6$) δ 9.68 (s, 1H, HCl), 8.93 (t, 1H, J=5.7 H$_z$, NH), 7.34-7.12 (m, 4H, Ar—H), 6.96 (s, 1H, vinyl-H), 4.26 (d, 2H, J=5.6 H$_z$, N—$CH_2$), 3.76 (d, 2H, 4-$CH_2$), 3.53 (s, 3H, N—$CH_3$), 3.22 (s, 1H, cyclohexyl-$C_1$H), 1.98-1.15 (m, 10H, cyclohexyl-H).

KHG24113 (2-cyclohexylimino-3-methyl-1,3-thiazolidine-4-yl)-N-(4-chlorobenzyl)-acetamide hydrochloride [$R_1$=H, $R_2$=4-Cl, $R_3$=$R_4$=H, $R_5$=$CH_3$, $R_6$=$C_6H_{11}$, n=1, m=1, X=Cl]

yield: 77.0%; melting point: 204° C.

$^1$H NMR (300 MHz, DMSO-$d_6$) δ 9.79 (d, 1H, J=5.0 H$_z$, HCl), 9.01 (t, 1H, J=5.7 H$_z$, NH), 7.38 (d, 2H, J=8.4 H$_z$, Ar—H), 7.29 (d, 2H, J=8.4 H$_z$, Ar—H), 6.97 (s, 1H, vinyl-H), 4.27 (d, 2H, J=5.8 H$_z$, N—$CH_2$), 3.78 (s, 2H, 4-$CH_2$), 3.54 (s, 3H, N—$CH_3$), 3.21 (s, 1H, cyclohexyl-$C_1$H), 1.97-1.11 (m, 10H, cyclohexyl-H).

KHG24114 (2-cyclohexylimino-3-methyl-1,3-thiazolidine-4-yl)-N-(4-methoxybenzyl)-acetamide hydrochloride [$R_1$=H, $R_2$=4-$OCH_3$, $R_3$=$R_4$=H, $R_5$=$CH_3$, $R_6$=$C_6H_{11}$, n=1, m=1, X=Cl]

yield: 64.8%; melting point: 193-195° C.

$^1$H NMR (300 MH$_z$, DMSO-$d_6$) δ 9.67 (s, 1H, J=6.2 Hz, HCl), 8.80 (t, 1H, J=5.6 H$_z$, NH), 7.19 (d, 2H, J=8.5 H$_z$, Ar—H), 6.95 (s, 1H, vinyl-H), 3.97 (s, 2H, 4-$CH_2$), 6.98 (d, 2H, J=8.5 Hz, Ar—H), 4.21 (d, 2H, J=5.7 Hz, N—$CH_2$), 3.73 (s, 2H, 4-$CH_2$), 3.72 (s, 3H, Ar—$OCH_3$), 3.52 (s, 3H, N—$CH_3$), 3.21 (s, 1H, cyclohexyl-$C_1$H), 1.97-1.11 (m, 10H, cyclohexyl-H).

KHG24115 (2-cyclopentylimino-3-methyl-1,3-thiazolidine-4-yl)-N-(4-isopropylphenyl)-acetamide hydrochloride [$R_1$=H, $R_2$=4-CH($CH_3$)$_2$, $R_3$=$R_4$=H, $R_5$=$CH_3$, $R_6$=$C_5H_9$, n=1, m=0, X=Cl]

yield: 75.9%; melting point: 213-215.5° C.

$^1$H NMR (300 MHz, DMSO-$d_6$) δ 9.77 (s, 1H, NH—Ar), 7.15-7.53 (m, 4H, Ar—H), 7.05 (s, 1H, vinyl-H), 3.96 (s, 2H, $COCH_2$), 3.61 (s, 3H, N—$CH_3$), 2.78-2.85 (q, 1H, J=6.8 Hz Ar—CH($CH_3$)$_2$), 1.56-3.79 (m, 9H, NH-cycloheptyl-H), 1.15-1.17 (d, 6H, J=6.9 Hz Ar—CH($CH_3$)$_2$.

KHG24116 (2-cyclopentylimino-3-methyl-1,3-thiazolidine-4-yl)-N-(4-n-butylphenyl)-acetamide hydrochloride [$R_1$=H, $R_2$=4-n-$C_4H_9$, $R_3$=$R_4$=H, $R_5$=$CH_3$, $R_6$=$C_5H_9$, n=1, m=0, X=Cl]

yield: 36.9%; melting point: 216-217.5° C.

$^1$H NMR (300 MHz, DMSO-$d_6$) δ 9.70 (s, 1H, NH—Ar), 7.10-7.51 (m, 4H, Ar—H), 7.04 (s, 1H, vinyl-H), 3.95 (s, 2H, COCH$_2$), 3.60 (s, 3H, N—CH$_3$), 1.23-3.79 (m, 15H, NH-cycloheptyl-H, Ar—(CH$_2$)$_3$(CH$_3$)), 0.85-0.89 (t, 3H, J=7.2 Hz Ar—(CH$_2$)$_3$(CH$_3$)).

KHG24117 (2-cycloheptylimino-3-methyl-1,3-thiazolidine-4-yl)-N-(4-ethylphenyl)-acetamide hydrochloride [R$_1$=H, R$_2$=4-C$_2$H$_5$, R$_3$=R$_4$=H, R$_5$=CH$_3$, R$_6$=C$_7$H$_{13}$, n=1, m=0, X=Cl]

yield: 93.8%; melting point: 217-218° C.

$^1$H NMR (300 MHz, DMSO-d$_6$) δ 9.61-9.63 (d, J=6.0 Hz 1H, NH—Ar), 7.12-7.52 (m, 4H, Ar—H), 7.03 (s, 1H, vinyl-H), 3.95 (s, 2H, COCH$_2$), 3.57 (s, 3H, N—CH$_3$), 2.53-2.58 (q, J=7.5 Hz, 2H, CH$_2$CH$_3$), 1.46-3.42 (m, 13H, NH-cycloheptyl-H), 1.11 (t, J=7.5 Hz, 3H, CH$_2$CH$_3$).

KHG24118 (2-cycloheptylimino-3-methyl-1,3-thiazolidine-4-yl)-N-(4-fluorophenyl)-acetamide hydrochloride [R$_1$=H, R$_2$=4-F, R$_3$=R$_4$=H, R$_5$=CH$_3$, R$_6$=C$_7$H$_{13}$, n=1, m=0, X=Cl]

yield: 70.7%; melting point: 219-220.5° C.

$^1$H NMR (300 MHz, DMSO-d$_6$) δ 9.59-9.61 (d, J=5.9 Hz 1H, NH—Ar), 7.13-7.65 (m, 4H, Ar—H), 7.04 (s, 1H, vinyl-H), 3.96 (s, 2H, COCH$_2$), 3.57 (s, 3H, N—CH$_3$), 1.47-3.41 (m, 13H, NH-cycloheptyl-H).

KHG24119 (2-cycloheptylimino-3-methyl-1,3-thiazolidine-4-yl)-N-(4-methoxyphenyl)-acetamide hydrochloride [R$_1$=H, R$_2$=4-OCH$_3$, R$_3$=R$_4$=H, R$_5$=CH$_3$, R$_6$=C$_7$H$_{13}$, n=1, m=0, X=Cl]

yield: 63.6%; melting point: 230-232° C.

$^1$H NMR (300 MHz, DMSO-d$_6$) δ 9.68-9.70 (d, J=6.5 Hz, NH—Ar), 6.86-7.54 (m, 4H, Ar—H), 7.03 (s, 1H, vinyl-H), 3.94 (s, 2H, COCH$_2$), 3.71 (s, 3H, OCH$_3$), 3.59 (s, 3H, N—CH$_3$), 1.45-3.43 (m, 13H, NH-cycloheptyl-H).

KHG24120 (2-cycloheptylimino-3-methyl-1,3-thiazolidine-4-yl)-N-(2-chloro-4-fluorophenyl)-acetamide hydrochloride [R$_1$=H, R$_2$=2-Cl, R$_3$=4-F, R$_4$=H, R$_5$=CH$_3$, R$_6$=C$_7$H$_{13}$, n=1, m=0, X=Cl]

yield: 84.6%; melting point: 172-173.5° C.

$^1$H NMR (300 MHz, DMSO-d$_6$) δ 9.68-9.71 (d, J=6.9 Hz, NH—Ar), 7.23-7.64 (m, 3H, Ar—H), 7.05 (s, 1H, vinyl-H), 4.01 (s, 2H, COCH$_2$), 3.59 (s, 3H, N—CH$_3$), 1.46-3.42 (m, 13H, NH-cycloheptyl-H).

KHG24121 (2-cycloheptylimino-3-methyl-1,3-thiazolidine-4-yl)-N-(4-cyanomethylphenyl)-acetamide hydrochloride [R$_1$=H, R$_2$=4-CH$_2$CN, R$_3$=R$_4$=H, R$_5$=CH$_3$, R$_6$=C$_7$H$_{13}$, n=1, m=0, X=Cl]

yield: 91.4%; melting point: 216-218.5° C.

$^1$H NMR (300 MHz, DMSO-d$_6$) δ 9.61-9.63 (d, J=6.8 Hz, NH—Ar), 7.27-7.64 (m, 4H, Ar—H), 7.04 (s, 1H, vinyl-H), 3.97-3.98 (d, J=2.50 Hz, 4H, CNCH$_2$, COCH$_2$), 3.57 (s, 3H, N—CH$_3$), 1.46-3.57 (m, 13H, NH-cycloheptyl-H).

KHG24122 (2-cycloheptylimino-3-methyl-1,3-thiazolidine-4-yl)-N-(4-bromophenyl)-acetamide hydrochloride [R$_1$=H, R$_2$=4-Br, R$_3$=R$_4$=H, R$_5$=CH$_3$, R$_6$=C$_7$H$_{13}$, n=1, m=0, X=Cl]

yield: 49.5%; melting point: 224-224.5° C.

$^1$H NMR (300 MHz, DMSO-d$_6$) δ 9.60-9.62 (d, 1H, J=6.7 Hz, NH—Ar), 7.48-7.61 (m, 4H, Ar—H), 7.04 (s, 1H, vinyl-H), 3.98 (s, 2H, COCH$_2$), 3.56 (s, 3H, N—CH$_3$), 1.46-3.41 (m, 13H, NH-cycloheptyl-H).

KHG24123 (2-cycloheptylimino-3-methyl-1,3-thiazolidine-4-yl)-N-(4-phenoxyphenyl)-acetamide hydrochloride [R$_1$=H, R$_2$=4-OC$_6$H$_5$, R$_3$=R$_4$=H, R$_5$=CH$_3$, R$_6$=C$_7$H$_{13}$, n=1, m=0, X=Cl]

yield: 85.8%; melting point: 229.5-232° C.

$^1$H NMR (300 MHz, DMSO-d$_6$) δ 9.72-9.74 (d, 1H, J=6.4 Hz, NH—Ar), 6.93-7.66 (m, 10H, O—Ar—H, Ar—H, vinyl-H), 3.98 (s, 2H, COCH$_2$), 3.60 (s, 3H, N—CH$_3$), 1.45-3.41 (m, 13H, NH-cycloheptyl-H).

KHG24124 (2-cycloheptylimino-3-methyl-1,3-thiazolidine-4-yl)-N-(4-methyl-2-chlorophenyl)-acetamide hydrochloride [R$_1$=H, R$_2$=2-Cl, R$_3$=4-CH$_3$, R$_4$=H, R$_5$=CH$_3$, R$_6$=C$_7$H$_{13}$, n=1, m=0, X=Cl]

yield: 68.4%; melting point: 153-155° C.

$^1$H NMR (300 MHz, DMSO-d$_6$) δ 9.64 (s, 1H, NH—Ar), 7.12-7.50 (m, 3H, Ar—H), 7.03 (s, 1H, vinyl-H), 3.99 (s, 2H, COCH$_2$), 3.58 (s, 3H, N—CH$_3$), 2.28 (s, 3H, Ar—CH$_3$), 1.46-3.41 (m, 13H, NH-cycloheptyl-H).

KHG24125 (2-cycloheptylimino-3-methyl-1,3-thiazolidine-4-yl)-N-(3,5-chlorophenyl)-acetamide hydrochloride [R$_1$=H, R$_2$=3-Cl, R$_3$=5-Cl, R$_4$=H, R$_5$=CH$_3$, R$_6$=C$_7$H$_{13}$, n=1, m=0, X=Cl]

yield: 72.9%; melting point: 215-217.5° C.

$^1$H NMR (300 MHz, DMSO-d$_6$) δ 9.58-9.60 (d, 1H, J=7.0 Hz, NH—Ar), 7.28-7.73 (m, 3H, Ar—H), 7.06 (s, 1H, vinyl-H), 4.02 (s, 2H, COCH$_2$), 3.56 (s, 3H, N—CH$_3$), 1.46-3.42 (m, 13H, NH-cycloheptyl-H).

KHG24126 (2-cycloheptylimino-3-methyl-1,3-thiazolidine-4-yl)-N-(2-fluoro-4-methylphenyl)-acetamide hydrochloride [R$_1$=H, R$_2$=2-F, R$_3$=4-CH$_3$, R$_4$=H, R$_5$=CH$_3$, R$_6$=C$_7$H$_{13}$, n=1, m=0, X=Cl]

yield: 54.5%; melting point: 183-185° C.

$^1$H NMR (300 MHz, DMSO-d$_6$) δ 9.68-9.70 (d, 1H, J=7.1 Hz, NH—Ar), 6.95-7.65 (m, 3H, Ar—H), 7.02 (s, 1H, vinyl-H), 3.98 (s, 2H, COCH$_2$), 3.57 (s, 3H, N—CH$_3$), 2.28 (s, 3H, Ar—CH$_3$), 1.46-3.43 (m, 13H, NH-cycloheptyl-H).

KHG24127 (2-cycloheptylimino-3-methyl-1,3-thiazolidine-4-yl)-N-(2,4-difluorophenyl)-acetamide hydrochloride [R$_1$=H, R$_2$=2-F, R$_3$=4-F, R$_4$=H, R$_5$=CH$_3$, R$_6$=C$_7$H$_{13}$, n=1, m=0, X=Cl]

yield: 57.1%; melting point: 196.5-198.5° C.

$^1$H NMR (300 MHz, DMSO-d$_6$) δ 9.78-9.81 (d, 1H, J=7.1 Hz NH—Ar), 7.07-7.76 (m, 3H, Ar—H), 7.04 (s, 1H, vinyl-H), 4.01 (s, 2H, COCH$_2$), 3.59 (s, 3H, N—CH$_3$), 1.45-3.42 (m, 13H, NH-cycloheptyl-H).

KHG24128 (2-cycloheptylimino-3-methyl-1,3-thiazolidine-4-yl)-N-(5-chloro-2-fluorophenyl)-acetamide hydrochloride [R$_1$=H, R$_2$=2-F, R$_3$=5-Cl, R$_4$=H, R$_5$=CH$_3$, R$_6$=C$_7$H$_{13}$, n=1, m=0, X=Cl]

yield: 54.7%; melting point: 163-165° C.

$^1$H NMR (300 MHz, DMSO-d$_6$) δ 9.67-9.70 (d, 1H, J=7.2 Hz NH—Ar), 7.22-8.04 (m, 3H, Ar—H), 7.05 (s, 1H, vinyl-H), 4.05 (s, 2H, COCH$_2$), 3.57 (s, 3H, N—CH$_3$), 1.43-3.46 (m, 13H, NH-cycloheptyl-H).

KHG24129 (2-cycloheptylimino-3-methyl-1,3-thiazolidine-4-yl)-N-(2-fluoro-5-nitrophenyl)-acetamide hydrochloride [R$_1$=H, R$_2$=2-F, R$_3$=5-NO$_2$, R$_4$=H, R$_5$=CH$_3$, R$_6$=C$_7$H$_{13}$, n=1, m=0, X=Cl]

yield: 46.6%; melting point: 223-223.5° C.

$^1$H NMR (300 MHz, DMSO-d$_6$) δ 9.71-9.73 (d, 1H, J=7.2 Hz NH—Ar), 7.58-8.95 (m, 3H, Ar—H), 7.08 (s, 1H, vinyl-H), 4.11 (s, 2H, COCH$_2$), 3.59 (s, 3H, N—CH$_3$), 1.44-3.42 (m, 13H, NH-cycloheptyl-H).

KHG24130 (2-cycloheptylimino-3-methyl-1,3-thiazolidine-4-yl)-N-(4-chloro-2-fluorophenyl)-acetamide hydrochloride [R$_1$=H, R$_2$=2-F, R$_3$=4-Cl), R$_4$=H, R$_5$=CH$_3$, R$_6$=C$_7$H$_{13}$, n=1, m=0, X=Cl]

yield: 67.8%; melting point: 204.5-205° C.

$^1$H NMR (300 MHz, DMSO-d$_6$) δ 9.71-9.73 (d, 1H, J=7.3 Hz NH—Ar), 7.26-7.90 (m, 3H, Ar—H), 7.04 (s, 1H, vinyl-H), 4.02 (s, 2H, COCH$_2$), 3.55 (s, 3H, N—CH$_3$), 1.43-3.42 (m, 13H, NH-cycloheptyl-H).

KHG24131 (2-cycloheptylimino-3-methyl-1,3-thiazolidine-4-yl)-N-(4-chlorophenyl)-acetamide hydrochloride [$R_1$=H, $R_2$=4-Cl, $R_3$=$R_4$=H, $R_5$=$CH_3$, $R_6$=$C_7H_{13}$, n=1, m=0, X=Cl]

yield: 77.6%; melting point: 215-217° C.

$^1$H NMR (400 MHz, DMSO-$d_6$) δ 9.69-9.71 (d, 1H, J=7.0 Hz NH—Ar), 7.36-7.68 (m, 4H, Ar—H), 7.06 (s, 1H, vinyl-H), 4.00 (s, 2H, COCH$_2$), 3.59 (s, 3H, N—CH$_3$), 1.52-3.42 (m, 13H, NH-cycloheptyl-H).

KHG24132 (2-cycloheptylimino-3-methyl-1,3-thiazolidine-4-yl)-N-phenyl-acetamide hydrochloride [$R_1$=H, $R_2$=$R_3$=$R_4$=H, $R_5$=$CH_3$, $R_6$=$C_7H_{13}$, n=1, m=0, X=Cl]

yield: 64.3%; melting point: 174-176° C.

$^1$H NMR (300 MHz, DMSO-$d_6$) δ 9.67-9.69 (d, 1H, J=6.7 Hz NH—Ar), 7.06-7.63 (s, 5H, Ar—H), 7.05 (s, 1H, vinyl-H), 3.99 (s, 2H, COCH$_2$), 3.59 (s, 3H, N—CH$_3$), 1.46-3.43 (m, 13H, NH-cycloheptyl-H).

KHG24133 (2-cycloheptylimino-3-methyl-1,3-thiazolidine-4-yl)-N-(4-isopropylphenyl)-acetamide hydrochloride [$R_1$=H, $R_2$=4-CH(CH$_3$)$_2$, $R_3$=$R_4$=H, $R_5$=$CH_3$, $R_6$=$C_7H_{13}$, n=1, m=0, X=Cl]

yield: 87.2%; melting point: 242-242.5° C.

$^1$H NMR (300 MHz, DMSO-$d_6$) δ 19.57-9.59 (d, 1H, J=7.2 Hz NH—Ar), 7.16-7.52 (m, 4H, Ar—H), 7.03 (s, 1H, vinyl-H), 3.94 (s, 2H, COCH$_2$), 3.56 (s, 3H, N—CH$_3$), 2.79-2.85 (q, 1H, J=6.8 Hz Ar—CH(CH$_3$)$_2$, 1.56-3.42 (m, 13H, NH-cycloheptyl-H), 1.15-1.18 (d, 6H, J=6.8 Hz Ar—CH(CH$_3$)$_2$).

KHG24134 (2-cycloheptylimino-3-methyl-1,3-thiazolidine-4-yl)-N-(4-n-butylphenyl)-acetamide hydrochloride [$R_1$=H, $R_2$=4-n-C$_4$H$_9$, $R_3$=$R_4$=H, $R_5$=$CH_3$, $R_6$=$C_7H_{13}$, n=1, m=0, X=Cl]

yield: 49.0%; melting point: 209.5-210° C.

$^1$H NMR (400 MHz, DMSO-$d_6$) δ 9.66-9.67 (d, 1H, J=7.0 Hz NH—Ar), 7.11-7.52 (m, 4H, Ar—H), 7.04 (s, 1H, vinyl-H), 3.96 (s, 2H, COCH$_2$), 3.58 (s, 3H, N—CH$_3$), 1.27-3.42 (m, 19H, NH-cycloheptyl-H, Ar—(CH$_2$)$_3$CH$_3$), 0.86-0.90 (t, 3H, J=7.3 Hz Ar—(CH$_2$)$_3$CH$_3$).

KHG24135 (2-cyclopropylimino-3-methyl-1,3-thiazolidine-4-yl)-N-(4-ethoxyphenyl)-acetamide hydrochloride [$R_1$=H, $R_2$=4-OC$_2$H$_5$, $R_3$H, $R_5$=$CH_3$, $R_6$=$C_3H_5$, n=1, m=0, X=Cl]

yield: 90.3%; melting point: 219-220° C.

$^1$H NMR (400 MHz, DMSO-$d_6$) δ 10.26 (s, 1H, NH—Ar), 7.13-7.52 (m, 4H, Ar—H), 7.08 (s, 1H, vinyl-H), 3.98 (s, 2H, COCH$_2$), 3.57 (s, 3H, N—CH$_3$), 2.51-2.57 (q, J=7.5 Hz, 2H, CH$_2$CH$_3$), 1.12-1.16 (t, J=7.5 Hz, 3H, CH$_2$CH$_3$), 0.80-2.80 (m, 5H, NH-cyclopropyl-H).

KHG24136 (2-cyclopropylimino-3-methyl-1,3-thiazolidine-4-yl)-N-(4-fluorophenyl)-acetamide hydrochloride [$R_1$=H, $R_2$=4-F, $R_3$=$R_4$=H, $R_5$=$CH_3$, $R_6$=$C_3H_5$, n=1, m=0, X=Cl]

yield: 75.5%; melting point: 252-253.5° C.

$^1$H NMR (300 MHz, DMSO-$d_6$) δ10.31 (s, 1H, NH—Ar), 7.08-7.67 (m, 4H, Ar—H), 7.04 (s, 1H, vinyl-H), 4.00 (s, 2H, COCH$_2$), 3.57 (s, 3H, N—CH$_3$), 0.89-2.77 (m, 5H, NH-cyclopropyl-H).

KHG24137 (2-cyclopropylimino-3-methyl-1,3-thiazolidine-4-yl)-N-(4-methoxyphenyl)-acetamide hydrochloride [$R_1$=H, $R_2$=4-OCH$_3$, $R_3$=$R_4$=H, $R_5$=$CH_3$, $R_6$=$C_3H_5$, n=1, m=0, X=Cl]

yield: 94.1%; melting point: 119-200° C.

$^1$H NMR (400 MHz, DMSO-$d_6$) δ 10.26 (s, 1H, NH—Ar), 6.86-7.54 (m, 4H, Ar—H), 7.07 (s, 1H, vinyl-H), 3.95 (s, 2H, COCH$_2$), 3.71 (s, 3H, OCH$_3$), 3.57 (s, 3H, N—CH$_3$), 0.79-2.80 (m, 5H, NH-cyclopropyl-H).

KHG24138 (2-cyclopropylimino-3-methyl-1,3-thiazolidine-4-yl)-N-(2-chloro-4-fluorophenyl)-acetamide hydrochloride [$R_1$=H, $R_2$=2-Cl, $R_3$=4-F, $R_4$=H, $R_5$=$CH_3$, $R_6$=$C_3H_5$, n=1, m=0, X=Cl]

yield: 89.3%; melting point: 237-239° C.

$^1$H NMR (400 MHz, DMSO-$d_6$) δ 10.22 (s, 1H, NH—Ar), 7.22-7.63 (m, 3H, Ar—H), 7.09 (s, 1H, vinyl-H), 4.04 (s, 2H, COCH$_2$), 3.59 (s, 3H, N—CH$_3$), 0.81-2.80 (m, 5H, NH-cyclopropyl-H).

KHG24139 (2-cyclopropylimino-3-methyl-1,3-thiazolidine-4-yl)-N-(4-cyanomethylphenyl)-acetamide hydrochloride [$R_1$=H, $R_2$=4-CH$_2$CN, $R_3$=$R_4$=H, $R_5$=$CH_3$, $R_6$=$C_3H_5$, n=1, m=0, X=Cl]

yield: 91.1%; melting point: 245-245.5° C.

$^1$H NMR (300 MHz, DMSO-$d_6$) δ 10.25 (s, 1H, NH—Ar), 7.28-7.65 (m, 4H, Ar—H), 7.09 (s, 1H, vinyl-H), 3.97 (s, 2H, COCH$_2$), 3.97-4.01 (d, J=9.6 Hz, 4H, CN—CH$_2$, COCH$_2$), 3.57 (s, 3H, N—CH$_3$), 0.81-2.79 (m, 5H, NH-cyclopropyl-H).

KHG24140 (2-cyclopropylimino-3-methyl-1,3-thiazolidine-4-yl)-N-(4-bromophenyl)-acetamide hydrochloride [$R_1$=H, $R_2$=4-Br, $R_3$=$R_4$=H, $R_5$=$CH_3$, $R_6$=$C_3H_5$, n=1, m=0, X=Cl]

yield: 82.9%; melting point: 227-228.5° C.

$^1$H NMR (300 MHz, DMSO-$d_6$) δ 10.32 (s, 1H, NH—Ar), 7.48-7.64 (m, 4H, Ar—H), 7.10 (s, 1H, vinyl-H), 4.03 (s, 2H, COCH$_2$), 3.58 (s, 3H, N—CH$_3$), 0.81-2.79 (m, 5H, NH-cyclopropyl-H).

KHG24141 (2-cyclopropylimino-3-methyl-1,3-thiazolidine-4-yl)-N-(4-phenoxyphenyl)-acetamide hydrochloride [$R_1$=H, $R_2$=4-OC$_6$H$_5$, $R_3$=$R_4$=H, $R_5$=$CH_3$, $R_6$=$C_3H_5$, n=1, m=0, X=Cl]

yield: 84.3%; melting point: 219.5-220° C.

$^1$H NMR (300 MHz, DMSO-$d_6$) δ 10.28 (s, 1H, NH—Ar), 6.93-7.65 (m, 10H, O—Ar—H, Ar—H, vinyl-H), 4.00 (s, 2H, COCH$_2$), 3.58 (s, 3H, N—CH$_3$), 0.81-2.78 (m, 5H, NH-cyclopropyl-H).

KHG24142 (2-cyclopropylimino-3-methyl-1,3-thiazolidine-4-yl)-N-(2-chloro-4-methylphenyl)-acetamide hydrochloride [$R_1$=H, $R_2$=2-Cl, $R_3$=4-CH$_3$, $R_4$=H, $R_5$=$CH_3$, $R_6$=$C_3H_5$, n=1, m=0, X=Cl]

yield: 80.2%; melting point: 212-212.5° C.

$^1$H NMR (300 MHz, DMSO-$d_6$) δ 10.06 (s, 1H, NH—Ar), 7.12-7.49 (m, 3H, Ar—H), 7.08 (s, 1H, vinyl-H), 4.03 (s, 2H, COCH$_2$), 3.60 (s, 3H, N—CH$_3$), 2.28 (s, 3H, Ar—CH$_3$), 0.82-2.79 (m, 5H, NH-cyclopropyl-H).

KHG24143 (2-cyclopropylimino-3-methyl-1,3-thiazolidine-4-yl)-N-(3,5-dichlorophenyl)-acetamide hydrochloride [$R_1$=H, $R_2$=3-Cl, $R_3$=5-Cl, $R_4$=H, $R_5$=$CH_3$, $R_6$=$C_3H_5$, n=1, m=0, X=Cl]

yield: 88.3%; melting point: 260.5-261° C.

$^1$H NMR (300 MHz, DMSO-$d_6$) δ 10.15 (s, 1H, NH—Ar), 7.30-7.72 (m, 3H, Ar—H), 7.10 (s, 1H, vinyl-H), 4.04 (s, 2H, COCH$_2$), 3.54 (s, 3H, N—CH$_3$), 0.80-2.81 (m, 5H, NH-cyclopropyl-H).

KHG24144 (2-cyclopropylimino-3-methyl-1,3-thiazolidine-4-yl)-N-(2-fluoro-4-methylphenyl)-acetamide hydrochloride [$R_1$=H, $R_2$=2-F, $R_3$=4-CH$_3$, $R_4$=H, $R_5$=$CH_3$, $R_6$=$C_3H_5$, n=1, m=0, X=Cl]

yield: 91.2%; melting point: 199.5-200.5° C.

$^1$H NMR (300 MHz, DMSO-$d_6$) δ 10.16 (s, 1H, NH—Ar), 6.95-7.66 (m, 4H, Ar—H, vinyl), 4.01 (s, 2H, COCH$_2$), 3.62 (s, 3H, N—CH$_3$), 2.28 (s, 3H, Ar—CH$_3$), 0.81-2.78 (m, 5H, NH-cyclopropyl-H).

KHG24145 (2-cyclopropylimino-3-methyl-1,3-thiazolidine-4-yl)-N-(2,4-difluorophenyl)-acetamide hydrochloride [$R_1$=H, $R_2$=2-F, $R_3$=4-F, $R_4$=H, $R_5$=$CH_3$, $R_6$=$C_3H_5$, n=1, m=0, X=Cl]

yield: 75.2%; melting point: 245-246° C.

$^1$H NMR (300 MHz, DMSO-$d_6$) δ 10.36 (s, 1H, NH—Ar), 7.07-7.78 (m, 3H, Ar—H), 7.04 (s, 1H, vinyl-H), 4.03 (s, 2H, $COCH_2$), 3.57 (s, 3H, N—$CH_3$), 0.81-2.78 (m, 5H, NH-cyclopropyl-H).

KHG24146 (2-cyclopropylimino-3-methyl-1,3-thiazolidine-4-yl)-N-(5-chloro-2-fluorophenyl)-acetamide hydrochloride [$R_1$=H, $R_2$=2-F, $R_3$=5-Cl, $R_4$=H, $R_5$=$CH_3$, $R_6$=$C_3H_5$, n=1, m=0, X=Cl]

yield: 78.9%; melting point: 233.5-234.5° C.

$^1$H NMR (300 MHz, DMSO-$d_6$) δ 010.40 (s, 1H, NH—Ar), 7.21-8.01 (m, 3H, Ar—H), 7.08 (s, 1H, vinyl-H), 4.07 (s, 2H, $COCH_2$), 3.57 (s, 3H, N—$CH_3$), 0.81-2.78 (m, 5H, NH-cyclopropyl-H).

KHG24147 (2-cyclopropylimino-3-methyl-1,3-thiazolidine-4-yl)-N-(2-fluoro-5-nitrophenyl)-acetamide hydrochloride [$R_1$=H, $R_2$=2-F, $R_3$=5-$NO_2$, $R_4$=H, $R_5$=$CH_3$, $R_6$=$C_3H_5$, n=1, m=0, X=Cl]

yield: 88.0%; melting point: 237.5-238° C.

$^1$H NMR (300 MHz, DMSO-$d_6$) δ 10.31 (s, 1H, NH—Ar), 7.57-8.93 (m, 3H, Ar—H), 7.10 (s, 1H, vinyl-H), 4.12 (s, 2H, $COCH_2$), 3.57 (s, 3H, N—$CH_3$), 0.81-2.80 (m, 5H, NH-cyclopropyl-H).

KHG24148 (2-cyclopropylimino-3-methyl-1,3-thiazolidine-4-yl)-N-(4-chloro-2-fluorophenyl)-acetamide hydrochloride [$R_1$=H, $R_2$=2-F, $R_3$=4-Cl, =H, $R_5$=$CH_3$, $R_6$=$C_3H_5$, n=1, m=0, X=Cl]

yield: 82.8%; melting point: 237-237.5° C.

$^1$H NMR (300 MHz, DMSO-$d_6$) δ 10.38 (d, 1H, NH—Ar), 7.25-7.87 (m, 3H, Ar—H), 7.07 (s, 1H, vinyl-H), 4.05 (s, 2H, $COCH_2$), 3.56 (s, 3H, N—$CH_3$), 0.78-2.78 (m, 5H, NH-cyclopropyl-H).

KHG24149 (2-cyclopropylimino-3-methyl-1,3-thiazolidine-4-yl)-N-(4-chlorophenyl)-acetamide hydrochloride [$R_1$=H, $R_2$=4-Cl, $R_3$=H, $R_5$=$CH_3$, $R_6$=$C_3H_5$, n=1, m=0, X=Cl]

yield: 90.7%; melting point: 241.5-242.5° C.

$^1$H NMR (400 MHz, DMSO-$d_6$) δ 10.26 (s, 1H, NH—Ar), 7.34-7.67 (m, 4H, Ar—H), 7.08 (s, 1H, vinyl-H), 4.01 (s, 2H, $COCH_2$), 3.56 (s, 3H, N—$CH_3$), 0.80-2.78 (m, 5H, NH-cyclopropyl-H).

KHG24150 (2-cyclopropylimino-3-methyl-1,3-thiazolidine-4-yl)-N-phenyl-acetamide hydrochloride [$R_1$=H, $R_2$=$R_3$H, $R_5$=$CH_3$, $R_6$=$C_3H_5$, n=1, m=0, X=Cl]

yield: 79.3%; melting point: 240.5-241° C.

$^1$H NMR (300 MHz, DMSO-$d_6$) δ 10.34 (a, 1H, NH—Ar), 7.02-7.63 (m, 6H, Ar—H, vinyl-H), 4.01 (s, 2H, $COCH_2$), 3.58 (s, 3H, N—$CH_3$), 0.81-2.78 (m, 13H, NH-cyclopropyl-H).

KHG24151 (2-cyclopropylimino-3-methyl-1,3-thiazolidine-4-yl)-N-(4-isopropylphenyl)-acetamide hydrochloride [$R_1$=H, $R_2$=4-CH($CH_3$)$_2$, $R_3$=$R_4$=H, $R_5$=$CH_3$, $R_6$=$C_3H_5$, n=1, m=0, X=Cl]

yield: 86.6%; melting point: 238-238.5° C.

$^1$H NMR (300 MHz, DMSO-$d_6$) δ 10.35 (s, 1H, NH—Ar), 7.14-7.60 (m, 4H, Ar—H), 7.07 (s, 1H, vinyl-H), 3.98 (s, 2H, $COCH_2$), 3.58 (s, 3H, N—$CH_3$), 0.81-2.86 (m, 12H, NH-cyclopropyl-H, Ar—CH($CH_3$)$_2$).

KHG24152 (2-cyclopropylimino-3-methyl-1,3-thiazolidine-4-yl)-N-(4-n-butylphenyl)-acetamide hydrochloride [$R_1$=H, $R_2$=4-n-$C_4H_9$, $R_3$=$R_4$=H, $R_5$=$CH_3$, $R_6$=$C_3H_5$, n=1, m=0, X=Cl]

yield: 84.4%; melting point: 227.5-228.5° C.

$^1$H NMR (400 MHz, DMSO-$d_6$) δ 10.26 (s, 1H, NH—Ar), 7.10-7.51 (m, 4H, Ar—H), 7.07 (s, 1H, vinyl-H), 3.97 (s, 2H, $COCH_2$), 3.56 (s, 3H, N—$CH_3$), 0.86-2.76 (m, 14H, NH-cyclopropyl-H, Ar—($CH_2$)$_3CH_3$).

KHG24153 (2-cyclopropylimino-3-methyl-1,3-thiazolidine-4-yl)-N-(4-fluorobenzyl)-acetamide hydrochloride [$R_1$=H, $R_2$=4-F, $R_3$=$R_4$=H, $R_5$=$CH_3$, $R_6$=$C_3H_5$, n=1, m=1, X=Cl]

yield: 72.3%; melting point: 200.5-202.5° C.

$^1$H NMR (300 MH$_z$, DMSO-$d_6$) δ 10.26 (s, 1H, HCl), 8.90 (t, 1H, J=5.3 H$_z$, NH), 7.12-7.34 (m, 4H, Ar—H), 6.99 (s, 1H, vinyl-H), 4.28 (d, 2H, J=5.7 H$_z$, N—$CH_2$), 3.78 (s, 2H, $COCH_2$), 3.50 (s, 3H, N—$CH_3$), 0.80-2.78 (m, 5H, cyclopropyl-H).

KHG24154 (2-cyclopropylimino-3-methyl-1,3-thiazolidine-4-yl)-N-(4-chlorobenzyl)-acetamide hydrochloride [$R_1$=H, $R_2$=4-Cl, $R_3$=$R_4$=H, $R_5$=$CH_3$, $R_6$=$C_3H_5$, n=1, m=1, X=Cl]

yield: 78.7%; melting point: 225.5-227° C.

$^1$H NMR (300 MH$_z$, DMSO-$d_6$) δ 10.34 (s, 1H, HCl), 8.98 (t, 1H, J=5.7 H$_z$, NH), 7.28-7.39 (m, 4H, Ar—H), 6.99 (s, 1H, vinyl-H), 4.27 (d, 2H, J=5.7 H$_z$, N—$CH_2$), 3.79 (s, 2H, $COCH_2$), 3.51 (s, 3H, N—$CH_3$), 0.80-2.76 (m, 5H, cyclopropyl-H).

KHG24155 (2-cyclopropylimino-3-methyl-1,3-thiazolidine-4-yl)-N-(4-methoxybenzyl)-acetamide hydrochloride [$R_1$=H, $R_2$=4-$OCH_3$, $R_3$H, $R_5$=$CH_3$, $R_6$=$C_3H_5$, n=1, m=1, X=Cl]

yield: 78.2%; melting point: 220.5-222° C.

$^1$H NMR (300 MH$_z$, DMSO-$d_6$) δ 10.31 (s, 1H, J=6.2 Hz, HCl), 8.84 (t, 1H, J=5.6 H$_z$, NH), 6.85-7.20 (m, 4H, Ar—H), 6.98 (s, 1H, vinyl-H), 4.21 (d, 2H, J=5.7 H$_z$, N—$CH_2$), 3.76 (s, 2H, $COCH_2$), 3.72 (s, 3H, Ar—$OCH_3$), 3.52 (s, 3H, N—$CH_3$), 0.77-2.76 (m, 5H, cyclopropyl-H).

KHG24156 (2-cyclopentylimino-3-methyl-1,3-thiazolidine-4-yl)-N-(4-fluorobenzyl)-acetamide hydrochloride [$R_1$=H, $R_2$=4-F, $R_3$=$R_4$=H, $R_5$=$CH_3$, $R_6$=$C_5H_9$, n=1, m=1, X=Cl]

yield: 36.8%; melting point: 160.5-162° C.

$^1$H NMR (300 MH$_z$, DMSO-$d_6$) δ 9.76 (s, 1H, HCl), 8.92 (t, 1H, J=5.3 H$_z$, NH), 7.03-7.34 (m, 4H, Ar—H), 6.97 (s, 1H, vinyl-H), 4.28 (d, 2H, J=5.7 H$_z$, N—$CH_2$), 3.77 (s, 3H, $COCH_2$, Ar—C$^1$H), 3.54 (s, 3H, N—$CH_3$), 1.58-2.03 (m, 8H, cyclopentyl-H).

KHG24157 (2-cyclopentylimino-3-methyl-1,3-thiazolidine-4-yl)-N-(4-chlorobenzyl)-acetamide hydrochloride [$R_1$=H, $R_2$=4-Cl, $R_3$=$R_4$=H, $R_5$=$CH_3$, $R_6$=$C_5H_9$, n=1, m=1, X=Cl]

yield: 71.3%; melting point: 180-182° C.

$^1$H NMR (300 MH$_z$, DMSO-$d_6$) δ 9.76 (s, 1H, HCl), 8.98 (t, 1H, J=5.4 H$_z$, NH), 7.28-7.39 (m, 4H, Ar—H), 6.99 (s, 1H, vinyl-H), 4.27 (d, 2H, J=5.7 H$_z$, N—$CH_2$), 3.78 (s, 3H, $COCH_2$, Ar—C$^1$H), 3.54 (s, 3H, N—$CH_3$), 1.58-2.03 (m, 8H, cyclopentyl-H).

KHG24158 (2-cyclopentylimino-3-methyl-1,3-thiazolidine-4-yl)-N-(4-methoxybenzyl)-acetamide hydrochloride [$R_1$=H, $R_2$=4-$OCH_3$, $R_3$=$R_4$=H, $R_5$=$CH_3$, $R_6$=$C_5H_9$, n=1, m=1, X=Cl]

yield: 56.4%; melting point: 172-173.5° C.

$^1$H NMR (300 MH$_z$, DMSO-$d_6$) δ 9.83 (s, 1H, J=6.2 Hz, HCl), 8.84 (t, 1H, J=5.6 H$_z$, NH), 6.86-7.26 (m, 4H, Ar—H), 6.97 (s, 1H, vinyl-H), 3.75 (d, 6H, J=7.3 H$_z$, $COCH_2$, Ar—C$^1$H, $OCH_3$), (d, 2H, J=5.6 H$_z$, N—$CH_2$), 3.56 (s, 3H, N—$CH_3$), 1.58-2.03 (m, 8H, cyclopentyl-H).

KHG24159 (2-cycloheptylimino-3-methyl-1,3-thiazolidine-4-yl)-N-(4-fluorobenzyl)-acetamide hydrochloride [$R_1$=H, $R_2$=4-F, $R_3$H, $R_5$=CH$_3$, $R_6$=C$_7$H$_{13}$, n=1, m=1, X=Cl]

yield: 65.0%; melting point: 210.5-211.5° C.

$^1$H NMR (300 MH$_z$, DMSO-d$_6$) δ 9.65 (d, 1H, J=6.7H$_z$, HCl), 8.90 (t, 1H, J=5.4 H$_z$, NH), 7.11-7.33 (m, 4H, Ar—H), 6.95 (s, 1H, vinyl-H), 4.27 (d, 2H, J=5.7 H$_z$, N—CH$_2$), 3.75 (s, 2H, COCH$_2$), 3.50 (s, 3H, N—CH$_3$), 1.45-3.41 (m, 13H, cycloheptyl1H).

KHG24160 (2-cycloheptylimino-3-methyl-1,3-thiazolidine-4-yl)-N-(4-chlorobenzyl)-acetamide hydrochloride [$R_1$=H, $R_2$=4-Cl, $R_3$=$R_4$=H, $R_5$=CH$_3$, $R_6$=C$_7$H$_{13}$, n=1, m=1, X=Cl]

yield: 81.2%; melting point: 216-216.5° C.

$^1$H NMR (300 MHz, DMSO-d$_6$) δ 9.65 (d, 1H, J=6.6H$_z$, HCl), 8.94 (t, 1H, J=5.4 H$_z$, NH), 7.28-7.39 (m, 4H, Ar—H), 6.95 (s, 1H, vinyl-H), 4.27 (d, 2H, J=5.7 H$_z$, N—CH$_2$), 3.76 (s, 2H, COCH$_2$), 3.51 (s, 3H, N—CH$_3$), 1.45-3.40 (m, 13H, cycloheptyl-H).

KHG24161 (2-cycloheptylimino-3-methyl-1,3-thiazolidine-4-yl)-N-(4-methoxybenzyl)-acetamide hydrochloride [$R_1$=H, $R_2$=4-OCH$_3$, $R_3$=$R_4$=H, $R_5$=CH$_3$, $R_6$=C$_7$H$_{13}$, n=1, m=1, X=Cl]

yield: 70.8%; melting point: 188-190° C.

$^1$H NMR (300 MHz, DMSO-d$_6$) δ 9.68 (s, 1H, J=6.9 Hz, HCl), 8.79 (t, 1H, J=5.7 H$_z$, NH), 6.86-7.20 (m, 4H, Ar—H), 6.95 (s, 1H, vinyl-H), 4.21 (d, 2H, J=5.7 H$_z$, N—CH$_2$), 3.77 (d, 3H, J=9.1 H$_z$, Ar—OCH$_3$, COCH$_2$), 3.51 (s, 3H, N—CH$_3$), 1.45-3.41 (m, 13H, cycloheptyl-H).

KHG24216 (2-phenethylimino-3-methyl-1,3-thiazolidine-4-yl)-N-(3,5-ditrifluoromethylphenyl)-acetamide hydrochloride [$R_1$=H, $R_2$=3-CF$_3$, $R_3$=5-CF$_3$, $R_4$=H, $R_5$=CH$_3$, $R_6$=CH$_2$CH$_2$C$_6$H$_5$, n=1, m=0, X=Cl]

yield: 43.5%; melting point: 221.3° C.

$^1$H NMR (400 MHz, CD$_3$OD) δ 8.22 (s, 2H, ArH-2' and ArH-6'), 7.69 (s, 1H, ArH-4'), 7.22-7.34 (m, 5H, benzyl), 6.90 (s, 1H, vinyl-H), 4.01 (s, 2H, COCH$_2$), 3.67 (t, 2H, J=7.15 Hz, NCH$_2$CH$_2$), 3.58 (s. 3H, NCH$_3$), 3.06 (t, 2H, J=7.15 Hz, NCH$_2$CH$_2$).

KHG24218 (2-cyclohexylmethylimino-3-methyl-1,3-thiazolidine-4-yl)-N-(3,5-ditrifluoromethylphenyl)-acetamide hydrochloride [$R_1$=H, $R_2$=3-CF$_3$, $R_3$=5-CF$_3$, $R_5$=CH$_3$, $R_6$=CH$_2$C$_6$H$_{11}$, n=1, m=0, X=Cl]

yield: 91.6%; melting point: 119.6° C.

$^1$H NMR (400 MHz, CD$_3$OD) δ 8.21 (s, 2H, ArH-2' and ArH-6'), 7.69 (s, 1H, ArH-4'), 6.89 (s, 1H, vinyl-H), 4.01 (s, 2H, COCH$_2$), 3.58 (s, 3H, NCH$_3$), 3.25 (d, 2H, J=6.77 Hz, NCH$_2$CH), 1.71-1.87 (m, 6H, cyclohexyl), 1.19-1.34 (m, 3H, cyclohexyl), 1.04-1.10 (m, 2H, cyclohexyl).

KHG24220 (2-phenethylimino-3-methyl-1,3-thiazolidine-4-yl)-N-(4-isopropylphenyl)-acetamide hydrochloride [$R_1$=H, $R_2$=4-CH(CH$_3$)$_2$, $R_3$H, $R_5$=CH$_3$, $R_6$=CH$_2$CH$_2$C$_6$H$_5$, n=1, m=0, X=Cl]

yield: 90%; melting point: 225° C.

$^1$H NMR (300 MHz, DMSO-d$_6$) δ 10.51 (s, 1H, HCl), 10.06 (br. s, 1H, NH), 7.50-7.15 (m, 9H, ArH), 7.00 (s, 1H, vinyl-H), 3.93 (s, 2H, 4-CH$_2$), 3.55 (s, 3H, N—CH$_3$), 3.02-2.98 (m, 4H, (CH$_2$)$_2$C$_6$H$_5$), 2.85-2.79 (m, 1H, isopropyl CH), 1.16 (d, J=5.2 Hz, 6H, isopropyl(CH$_3$)$_2$).

KHG24222 (2-cyclohexylmethylimino-3-methyl-1,3-thiazolidine-4-yl)-N-(4-isopropylphenyl)-acetamide hydrochloride [$R_1$=H, $R_2$=4-CH(CH$_3$)$_2$, $R_3$H, $R_5$=CH$_3$, $R_6$=CH$_2$C$_6$H$_{11}$, n=1, m=0, X=Cl]

yield: 94.4%; melting point: 250.7° C.

$^1$H NMR (400 MHz, CD$_3$OD) δ 7.47 (d, 2H, J=8.43 Hz, ArH-2' and ArH-6'), 7.20 (d, 2H, J=8.44 Hz, ArH-3' and ArH-5'), 6.92 (s, 1H, vinyl-H), 3.95 (s, 2H, COCH$_2$), 3.60 (s, 3H, NCH$_3$), 3.27 (d, 2H, J=6.76 Hz, NCH$_2$CH), 2.88 (septet, 1H, J=6.91 Hz, CH(CH$_3$)$_2$), 1.71-1.86 (m, 6H, cyclohexyl), 1.24-1.37 (m, 3H, cyclohexyl), 1.04-1.10 (m, 2H, cyclohexyl).

KHG24224 (2-phenethylimino-3-methyl-1,3-thiazolidine-4-yl)-N-(4-phenoxyphenyl)-acetamide hydrochloride [$R_1$=H, $R_2$=4-OC$_6$H$_5$, $R_3$=$R_4$=H, $R_5$=CH$_3$, $R_6$=CH$_2$CH$_2$C$_6$H$_5$, n=1, m=0, X=Cl]

yield: 72.8%; melting point: 225.5° C.

$^1$H NMR (400 MHz, CD$_3$OD) δ 7.55 (d, 2H, J=8.94 Hz, ArH-2' and ArH-6'), 7.22-7.36 (m, 7H, ArH-3", ArH-5" and benzyl), 7.09 (t, 1H, J=7.38 Hz, ArH-4"), 6.97 (d, 2H, J=8.99 Hz, ArH-3' and ArH-5'), 6.96 (dd, J=8.22, 1.05 Hz, ArH-2" and ArH-4"), 6.88 (s, 1H, vinyl-H), 3.93 (s, 2H, COCH$_2$), 3.67 (t, 2H, J=7.22 Hz, NCH$_2$CH$_2$), 3.57 (s, 3H, NCH$_3$), 3.06 (t, 2H, J=7.20 Hz, NCH$_2$CH$_2$).

KHG24226 (2-cyclohexylmethylimino-3-methyl-1,3-thiazolidine-4-yl)-N-(4-phenoxyphenyl)-acetamide hydrochloride [$R_1$=H, $R_2$=4-OC$_6$H$_5$, $R_3$H, $R_5$=CH$_3$, $R_6$=CH$_2$C$_6$H$_{11}$, n=1, m=0, X=Cl]

yield: 80.6%; melting point: 250.8° C.

$^1$H NMR (400 MHz, CD$_3$OD) δ 7.55 (d, 2H, J=8.68 Hz, ArH-2' and ArH-6'), 7.34 (t, 2H, J=7.66 Hz, ArH-3" and ArH-5"), 7.09 (t, 1H, J=6.74 Hz, ArH-4"), 6.95-6.97 (m, 4H, ArH-3', ArH-5', ArH-2" and ArH-4"), 6.92 (s, 1H, vinyl-H), 3.95 (s, 2H, COCH$_2$), 3.60 (s, 3H, NCH$_3$), 3.13-3.26 (br s, 2H, NCH$_2$CH and CD$_3$OD), 1.70-1.86 (m, 6H, cyclohexyl), 1.28-1.34 (m, 3H, cyclohexyl), 1.04-1.07 (m, 2H, cyclohexyl).

KHG24228 (2-phenethylimino-3-methyl-1,3-thiazolidine-4-yl)-N-(4-chlorophenyl)-acetamide hydrochloride [$R_1$=H, $R_2$=4-Cl, $R_3$=$R_4$=H, $R_5$=CH$_3$, $R_6$=CH$_2$CH$_2$C$_6$H$_5$, n=1, m=0, X=Cl]

yield: 39.4%; melting point: 226.7° C.

$^1$H NMR (400 MHz, CD$_3$OD) δ 7.57 (d, 2H, J=8.67 Hz, ArH-2' and ArH-6'), 7.24-7.33 (m, 7H, ArH-3", ArH-5" and benzyl), 6.91 (s, 1H, vinyl-H), 3.95 (s, 2H, COCH$_2$), 3.68 (t, 2H, J=7.11 Hz, NCH$_2$CH$_2$), 3.48 (s, 3H, NCH$_3$), 3.06 (t, 2H, J=6.98 Hz, NCH$_2$CH$_2$).

KHG24230 (2-cyclohexylmethylimino-3-methyl-1,3-thiazolidine-4-yl)-N-(4-chlorophenyl)-acetamide hydrochloride [$R_1$=H, $R_2$=4-Cl, $R_3$=$R_4$=H, $R_5$=CH$_3$, $R_6$=CH$_2$C$_6$H$_{11}$, n=1, m=0, X=Cl]

yield: 94.7%; melting point: 177.1° C.

$^1$H NMR (400 MHz, DMSO) δ 9.63 (s, 1H, CONH), 7.62 (d, 2H, J=9.00 Hz, ArH-2' and ArH-6'), 7.39 (d, 2H, J=8.88 Hz, ArH-3' and ArH-5'), 7.02 (s, 1H, vinyl-H), 3.95 (s, 2H, COCH$_2$), 3.52 (s, 3H, NCH$_3$), 3.18 (s, 2H, NCH$_2$CH), 1.66-1.74 (m, 6H, cyclohexyl), 0.86-1.23 (m, 5H, cyclohexyl).

KHG24232 (2-phenethylimino-3-methyl-1,3-thiazolidine-4-yl)-N-(2-fluoro-5-nitrophenyl)-acetamide hydrochloride [$R_1$=H, $R_2$=2-F, $R_3$=5-NO$_2$, $R_4$=H, $R_5$=CH$_3$, $R_6$=CH$_2$CH$_2$C$_6$H$_5$, n=1, m=0, X=Cl]

yield: 99%; melting point: 196.4° C.:

$^1$H NMR (400 MHz, CD$_3$OD) δ 9.07 (t, 1H, J=3.29 Hz, ArH-6'), 8.09 (t, 1H, J=4.53 Hz, ArH-4'), 7.45 (t, 1H, J=9.51 Hz, ArH-5'), 7.22-7.35 (m, 5H, benzyl), 6.88 (s, 1H, vinyl-H), 4.05 (s, 2H, COCH$_2$), 3.66 (d, 2H, J=7.20 Hz, NCH$_2$CH), 3.57 (s, 3H, NCH$_3$), 3.06 (t, 2H, J=7.18 Hz, NCH$_2$CH$_2$).

KHG24234 (2-cyclohexylmethylimino-3-methyl-1,3-thiazolidine-4-yl)-N-(2-fluoro-5-nitrophenyl)-acetamide hydrochloride [$R_1$=H, $R_2$=2-F, $R_3$=5-NO$_2$), $R_4$=H, $R_5$=CH$_3$, $R_6$=CH$_2$C$_6$H$_{11}$, n=1, m=0, X=Cl]

yield: 63.5%; melting point: 225.0° C.

$^1$H NMR (400 MHz, CD$_3$OD) δ 9.07 (dd, 1H, J=6.66, 7.81 Hz, ArH-6'), 8.11 (ddt, 1H, J=6.78, 4.30, 2.97 Hz, ArH-4'), 7.45 (t, 1H, J=9.76 Hz, ArH-3'), 6.96 (s, 1H, vinyl-H), 4.09 (s, 2H, COCH$_2$), 3.63 (s, 3H, NCH$_3$), 3.29 (d, 2H, J=6.85 Hz, NCH$_2$CH), 1.72-1.89 (m, 6H, cyclohexyl), 1.19-1.36 (m, 3H, cyclohexyl), 1.02-1.13 (m, 2H, cyclohexyl).

KHG24235 [2-(1-adamantyl)imino-3-methyl-1,3-thiazolidine-4-yl]-N-(4-methylphenyl)-acetamide hydrochloride [$R_1$=H, $R_2$=4-CH$_3$, $R_3$=$R_4$=H, $R_5$=CH$_3$, $R_6$=1-adamantyl, n=1, m=0, X=Cl]

yield: 36.0%; melting point: 119.6° C.

$^1$H NMR (300 MHz, CD$_3$OD) δ 7.44 (d, 2H, J=8.46 Hz, ArH-3' and ArH-5'), 7.15 (d, 2H, J=8.21 Hz, ArH-2' and ArH-6'), 7.00 (s, 1H, vinyl-H), 3.97 (s, 2H, COCH$_2$), 3.63 (s, 3H, NCH$_3$), 2.31 (s, 3H, CCH$_3$), 2.16-2.24 (m, 9H, adamantyl), 1.74-1.81 (m, 6H, adamantyl).

KHG24236 [2-(1-adamantyl)imino-3-methyl-1,3-thiazolidine-4-yl]-N-(4-ethylphenyl)-acetamide hydrochloride [$R_1$=H, $R_2$=4-CH$_2$CH$_3$, $R_3$=$R_4$=H, $R_5$=CH$_3$, $R_6$=1-adamantyl, n=1, m=0, X=Cl]

yield: 80.9%; melting point: 219.2° C.

$^1$H NMR (300 MHz, CD$_3$OD) δ 7.46 (d, 2H, J=8.50 Hz, ArH-3' and ArH-5'), 7.18 (d, 2H, J=8.56 Hz, ArH-2' and ArH-6'), 7.00 (s, 1H, vinyl-H), 3.97 (s, 2H, COCH$_2$), 3.63 (s, 3H, NCH$_3$), 2.62 (q, 2H, 7.60 Hz, CH$_2$CH$_3$), 2.20-2.24 (m, 9H, adamantyl), 1.81 (br s, 6H, adamantyl), 1.22 (t, 3H, J=7.60 Hz, CH$_2$CH$_3$).

KHG24237 [2-(1-adamantyl)imino-3-methyl-1,3-thiazolidine-4-yl]-N-(4-fluorophenyl)-acetamide hydrochloride [$R_1$=H, $R_2$=4-F, $R_3$=$R_4$=H, $R_5$=CH$_3$, $R_6$=1-adamantyl, n=1, m=0, X=Cl]

yield: 96.8%; melting point: 201.9° C.

$^1$H NMR (300 MHz, CD$_3$OD) δ 7.58 (dd, 2H, J=9.06, 4.84 Hz, ArH-3' and ArH-5'), 7.08 (dd, 2H, J=8.78, 8.77 Hz, ArH-2' and ArH-6'), 6.99 (s, 1H, vinyl-H), 3.99 (s, 2H, COCH$_2$), 3.63 (s, 3H, NCH$_3$), 2.20-2.24 (m, 9H, adamantyl), 1.81 (br s, 6H, adamantyl).

KHG24238 [2-(1-adamantyl)imino-3-methyl-1,3-thiazolidine-4-yl]-N-(4-chlorophenyl)-acetamide hydrochloride [$R_1$=H, $R_2$=4-Cl, $R_3$=$R_4$=H, $R_5$=CH$_3$, $R_6$=1-adamantyl, n=1, m=0, X=Cl]

yield: 87.1%; melting point: 228.3° C.

$^1$H NMR (300 MHz, CD$_3$OD) δ 7.59 (d, 2H, J=8.81 Hz, ArH-3' and ArH-5'), 7.33 (d, 2H, J=8.83 Hz, ArH-2' and ArH-6'), 6.70 (s, 1H, vinyl-H), 4.00 (s, 2H, COCH$_2$), 3.63 (s, 3H, NCH$_3$), 2.20-2.24 (m, 9H, adamantyl), 1.73-1.86 (m, 6H, adamantyl).

KHG24239 [2-(1-adamantyl)imino-3-methyl-1,3-thiazolidine-4-yl]-N-(4-bromophenyl)-acetamide hydrochloride [$R_1$=H, $R_2$=4-Br, $R_3$=$R_4$=H, $R_5$=CH$_3$, $R_6$=1-adamantyl, n=1, m=0, X=Cl]

yield: 81.9%; melting point: 237.4° C.

$^1$H NMR (300 MHz, CD$_3$OD) δ 7.50 (ddd, 4H, J=9.07, 18.48, 4.50 Hz, Ar—H), 6.97 (s, 1H, vinyl-H), 3.98 (s, 2H, COCH$_2$), 3.62 (s, 3H, NCH$_3$), 2.20-2.24 (m, 9H, adamantyl), 1.81 (br s, 6H, adamantyl).

KHG24240 [2-(1-adamantyl)imino-3-methyl-1,3-thiazolidine-4-yl]-N-(4-trifluoromethylphenyl)-acetamide hydrochloride [$R_1$=H, $R_2$=4-CF$_3$, $R_3$=$R_4$=H, $R_5$=CH$_3$, $R_6$=1-adamantyl, n=1, m=0, X=Cl]

yield: 41.3%; melting point: 238.7° C.

$^1$H NMR (300 MHz, CD$_3$OD) δ 7.79 (d, 2H, J=8.60 Hz, ArH-3' and ArH-5'), 7.64 (d, 2H, J=8.68 Hz, ArH-2' and ArH-6'), 6.70 (s, 1H, vinyl-H), 4.03 (s, 2H, COCH$_2$), 3.63 (s, 3H, NCH$_3$), 2.20-2.24 (m, 9H, adamantyl), 1.81 (br s, 6H, adamantyl).

KHG24241 [2-(1-adamantyl)imino-3-methyl-1,3-thiazolidine-4-yl]-N-(3,5-ditrifluoromethylphenyl)-acetamide hydrochloride [$R_1$=H, $R_2$=3-CF$_3$, $R_3$=5-CF$_3$, $R_4$=H, $R_5$=CH$_3$, $R_6$=1-adamantyl, n=1, m=0, X=Cl]

yield: 63.0%; melting point: 204.8° C.

$^1$H NMR (300 MHz, CD$_3$OD) δ 8.23 (s, 2H, ArH-2' and ArH-6'), 7.70 (s, 1H, ArH-4'), 7.02 (s, 1H, vinyl-H), 4.07 (s, 2H, COCH$_2$), 3.65 (s, 3H, NCH$_3$), 2.21-2.24 (m, 9H, adamantyl), 1.81 (br s, 6H, adamantyl).

KHG24242 [2-(1-adamantyl)imino-3-methyl-1,3-thiazolidine-4-yl]-N-(5-chloro-2-fluorophenyl)-acetamide hydrochloride [$R_1$=H, $R_2$=2-F, $R_3$=5-Cl, $R_4$=H, $R_5$=CH$_3$, $R_6$=1-adamantyl, n=1, m=0, X=Cl]

yield: 62.5%; melting point: 232.8° C.

$^1$H NMR (300 MHz, CD$_3$OD) δ 7.94 (dd, 1H, J=8.47, 8.57 Hz, ArH-6'), 7.31 (dd, 1H, J=10.62, 2.30 Hz, ArH-4'), 7.21 (ddd, 1H, J=8.75, 2.24, 1.34 Hz, ArH-3'), 7.00 (s, 1H, vinyl-H), 4.06 (s, 2H, COCH$_2$), 3.63 (s, 3H, CH$_3$), 2.20-2.24 (m, 9H, adamantyl), 1.81 (br s, 6H, adamantyl).

KHG24243 [2-(1-adamantyl)imino-3-methyl-1,3-thiazolidine-4-yl]-N-(4-isopropylphenyl)-acetamide hydrochloride [$R_1$=H, $R_2$=4-CH(CH$_3$)$_2$, $R_3$=$R_4$=H, $R_5$=CH$_3$, $R_6$=1-adamantyl, n=1, m=0, X=Cl]

yield: 32.9; melting point: 221.4° C.

$^1$H NMR (300 MHz, CD$_3$OD) δ 7.29 (d, 2H, J=8.56 Hz, ArH-2' and ArH-6'), 7.21 (d, 2H, J=8.48 Hz, ArH-3' and ArH-5'), 6.99 (s, 1H, vinyl-H), 3.98 (s, 2H, COCH$_2$), 3.63 (s, 3H, CH$_3$), 2.89 (septet, 1H, J=6.90 Hz, CH$_3$CH$_2$CH$_3$), 2.20-2.24 (m, 9H, adamantyl), 1.77-1.81 (m, 6H, adamantyl), 1.24 (d, 6H, J=6.92 Hz, CH$_3$CH$_2$CH$_3$).

KHG24244 [2-(1-adamantyl)imino-3-methyl-1,3-thiazolidine-4-yl]-N-(4-phenoxyphenyl)-acetamide hydrochloride [$R_1$=H, $R_2$=4-OC$_6$H$_5$, $R_3$=$R_4$=H, $R_5$=CH$_3$, $R_6$=1-adamantyl, n=1, m=0, X=Cl]

yield: 72.7%; melting point: 255.1° C.

$^1$H NMR (300 MHz, CD$_3$OD) δ 7.56 (d, 2H, J=9.07 Hz, ArH-2' and ArH-6'), 7.35 (t, 2H, J=6.00 Hz, ArH-3" and ArH-5"), 7.10 (t, 1H, J=7.41 Hz, ArH-4"), 6.94-7.00 (m, 5H, ArH-3', ArH-5', ArH-2", ArH-4" and vinyl-H), 3.99 (s, 2H, COCH$_2$), 3.64 (s, 3H, NCH$_3$), 2.17-2.24 (m, 9H, adamantyl), 1.77-1.86 (m, 6H, adamantyl).

KHG24261 [2-cyclohexylimino-3-ethyl-1,3-thiazolidine-4-yl]-N-(3,5-ditrifluoromethylphenyl)-acetamide hydrochloride [$R_1$=H, $R_2$=3-CF$_3$, $R_3$=5-CF$_3$, $R_4$=H, $R_5$=CH$_2$CH$_3$, $R_6$=C$_6$H$_{11}$, n=1, m=0, X=Cl]

yield: 67.3%; melting point: 226.4° C.

$^1$H NMR (300 MHz, DMSO-d$_6$) δ 11.73 (s, 1H, NH), 8.34 (s, 2H, Ar—H), 7.79 (s, 1H, Ar—H), 7.10 (s, 1H, vinyl-H), 4.18-4.13 (m, 2H, N—CH$_2$CH$_3$), 4.05 (s, 2H, 4-methylene CH$_2$), 3.22 (m, 1H, 1-cyclohexyl H), 1.99-1.27 (m, 10H, cyclohexyl-H), 1.21-1.16 (m, 3H, N—CH$_2$CH$_3$).

KHG24262 [2-cyclohexylimino-3-(n-butyl)-1,3-thiazolidine-4-yl]-N-(4-chlorophenyl)-acetamide hydrochloride [$R_1$=H, $R_2$=4-Cl, $R_3$=$R_4$=H, $R_5$=n-C$_4$H$_9$, $R_6$=C$_6$H$_{11}$, n=1, m=0, X=Cl]

yield: 61.2%; melting point: 194.3° C.

$^1$H NMR (300 MHz, DMSO-d$_6$) δ 11.05 (s, 1H, NH), 7.67 (s, 2H, J=8.9 Hz, Ar—H), 7.38 (s, 2H, J=8.9 Hz, Ar—H), 7.05 (s, 1H, vinyl-H), 4.12 (t, 2H, J≅7.8 Hz, N—CH$_2$CH$_2$CH$_2$CH$_3$), 3.97 (s, 2H, 4-methylene CH$_2$), 3.21 (m, 1H, 1-cyclohexyl H), 1.98-1.11 (m, 10H, cyclohexyl-H), 1.39-1.22 (m, 4H, N—CH$_2$CH$_2$CH$_2$CH$_3$), 0.77 (t, 3H, J=7.3 Hz, N—(CH$_2$)$_3$CH$_3$).

KHG24263 [2-cyclohexylimino-3-(n-butyl)-1,3-thiazolidine-4-yl]-N-(4-bromophenyl)-acetamide hydrochloride [$R_1$=H, $R_2$=4-Br, $R_3$=$R_4$=H, $R_5$=n-C$_4$H$_9$, $R_6$=C$_6$H$_{11}$, n=1, m=0, X=Cl]

yield: 63.5%; melting point: 215.2° C.

$^1$H NMR (300 MHz, DMSO-d$_6$) δ 11.04 (s, 1H, NH), 7.64-7.49 (m, 4H, Ar—H), 7.05 (s, 1H, vinyl-H), 4.11 (t, 2H, J≅7.8 Hz, N—CH$_2$CH$_2$CH$_2$CH$_3$), 3.97 (s, 2H, 4-methylene CH$_2$), 3.08 (m, 1H, 1-cyclohexyl H), 1.98-1.49 (m, 10H, cyclohexyl-H), 1.39-1.25 (m, 4H, N—CH$_2$CH$_2$CH$_2$CH$_3$), 0.77 (m, 3H, J=7.3 Hz, N—(CH$_2$)$_3$CH$_3$).

KHG24264 [2-cyclohexylimino-3-(n-butyl)-1,3-thiazolidine-4-yl]-N-(4-3,5-ditrifluoromethylphenyl)-acetamide hydrochloride [R$_1$=H, R$_2$=3-CF$_3$, R$_3$=5-CF$_3$, R$_4$=H, R$_5$=n-C$_4$H$_9$, R$_6$=C$_6$H, n=1, m=0, X=Cl]

yield: 11.3%; melting point: 230.9° C.

$^1$H NMR (300 MHz, DMSO-d$_6$) δ 11.77 (s, 1H, NH), 8.35 (s, 1H, Ar—H), 7.81 (s, 1H, Ar—H), 7.11 (s, 1H, vinyl-H), 4.13-4.05 (m, 4H, N—CH$_2$CH$_2$CH$_2$CH$_3$, 4-methylene CH$_2$), 3.29 (m, 1H, 1-cyclohexyl H), 1.99-1.27 (m, 14H, cyclohexyl-H, N—CH$_2$CH$_2$CH$_2$CH$_3$), 0.77 (m, 3H, J=7.3 Hz, N—(CH$_2$)$_3$CH$_3$).

KHG24265 [2-cyclohexylimino-3-cyclohexyl-1,3-thiazolidine-4-yl]-N-(4-bromophenyl)-acetamide hydrochloride [R$_1$=H, R$_2$=4-Br, R$_3$=R$_4$=H, R$_5$=C$_6$H$_{11}$, R$_6$=C$_6$H$_{11}$, n=1, m=0, X=Cl]

yield: 85.0%; melting point: 233.9° C.

$^1$H NMR (300 MHz, DMSO-d$_6$) δ 10.82 (s, 1H, NH), 7.59-7.06 (dd, 4H, J≅8.9 Hz, Ar—H), 7.06 (s, 1H, vinyl-H), 4.04 (s, 2H, 4-CH$_2$), 3.28-3.25 (m, 2H, cyclohexyl-H), 2.26-1.11 (m, 22H, cyclohexyl-H).

KHG24266 [2-cyclohexylimino-3-cyclohexyl-1,3-thiazolidine-4-yl]-N-(4-chlorophenyl)-acetamide hydrochloride [R$_1$=H, R$_2$=4-C$_1$, R$_3$=R$_4$=H, R$_5$=C$_6$H$_{11}$, R$_6$=C$_6$H$_{11}$, n=1, m=0, X=Cl]

yield: 81.0%; melting point: 244.4° C.

$^1$H NMR (300 MHz, DMSO-d$_6$) δ 10.80 (s, 1H, NH), 7.74-7.39 (dd, 4H, Ar—H), 7.06 (s, 1H, vinyl-H), 4.04 (s, 2H, 4-CH$_2$), 3.28-3.25 (m, 2H, cyclohexyl-H), 2.23-0.89 (m, 22H, cyclohexyl-H).

KHG24267 [2-cyclohexylimino-3-cyclopropyl-1,3-thiazolidine-4-yl]-N-(3,5-ditrifluoromethylphenyl)-acetamide hydrochloride [R$_1$=H, R$_2$=3-CF$_3$, R$_3$=5-CF$_3$, R$_4$=H, R$_5$=C$_3$H$_5$, R$_6$=C$_6$H$_{11}$, n=1, m=0, X=Cl]

yield: 76%; melting point: 197.3° C.

$^1$H NMR (300 MHz, DMSO-d$_6$) δ 11.65 (s, 1H, NH), 9.26 (d, 1H, J=8.0 Hz, HCl), 8.36 (s, 2H, Ar—H), 7.79 (s, 1H, Ar—H), 7.03 (s, 1H, vinyl-H), 4.10 (s, 2H, CH$_2$), 3.28-3.26 (m, 1H, N-cyclohexyl-H), 2.99 (m, 1H, N-cyclopropyl-H), 1.99-1.03 (m, 14H, N-cyclohexyl-H, N-cyclopropyl-H).

KHG24268 [2-cyclohexylimino-3-cyclopropyl-1,3-thiazolidine-4-yl]-N-(4-trifluoromethylphenyl)-acetamide hydrochloride [R$_1$=H, R$_2$=4-CF$_3$, R$_3$=R$_4$=H, R$_5$=C$_3$H$_5$, R$_6$=C$_6$H$_{11}$, n=1, m=0, X=Cl]

yield: 32.7%; melting point: 240.8° C.

$^1$H NMR (300 MHz, DMSO-d$_6$) δ 11.13 (s, 1H, NH), 9.30 (d, 1H, J=6.5 Hz, HCl), 7.85 (d, 2H, J=8.5 Hz, Ar—H), 7.69 (d, 2H, J=8.7 Hz, Ar—H), 7.00 (s, 1H, vinyl-H), 4.07 (s, 2H, CH$_2$), 2.98 (m, 1H, N-cyclopropyl-H), 1.99-1.04 (m, 14H, N-cyclohexyl-H, N-cyclopropyl-H).

KHG24270 [2-cyclohexylimino-3-cyclopropyl-1,3-thiazolidine-4-yl]-N-(4-n-butylphenyl)-acetamide hydrochloride [R$_1$=H, R$_2$=4-n-C$_4$H$_9$, R$_3$=R$_4$=H, R$_5$=C$_3$H$_5$, R$_6$=C$_6$H$_{11}$, n=1, m=0, X=Cl]

yield: 8.5%; melting point: 195.6° C.

$^1$H NMR (400 MHz, DMSO-d$_6$) δ 10.55 (s, 1H, NH), 9.31 (d, 1H, J=8.0 Hz, HCl), 7.51 (d, 2H, J=8.5 Hz, Ar—H), 7.12 (d, 2H, J=8.4 Hz, Ar—H), 6.97 (s, 1H, vinyl-H), 3.98 (s, 2H, CH$_2$), 3.28-3.24 (m, 1H, N-cyclohexyl-H), 2.99-2.95 (m, 1H, N-cyclopropyl-H), 2.55 (m, 2H, ArCH$_2$CH$_2$), 1.53-1.49 (m, 2H, CH$_2$CH$_2$CH$_2$), 1.35-1.32 (m, 2H, CH$_2$CH$_2$CH$_3$), 1.99-1.02 (m, 14H, N-cyclohexyl-H, N-cyclopropyl-H), 0.88 (t, 3H, J=7.3 Hz, CH$_2$CH$_3$).

KHG24271 [2-cyclohexylimino-3-cyclopropyl-1,3-thiazolidine-4-yl]-N-(5-chloro-2-fluorophenyl)-acetamide hydrochloride [R$_1$=H, R$_2$=2-F, R$_3$=5-Cl, R$_4$=H, R$_5$=C$_3$H$_5$, R$_6$=C$_6$H$_{11}$, n=1, m=0, X=Cl]

yield: 76%; melting point: 183.7° C.

$^1$H NMR (400 MHz, DMSO-d$_6$) δ 10.51 (s, 1H, NH), 9.35 (d, 1H, J=8.1 Hz, HCl), 8.01 (d, 2H, J=6.8 Hz, Ar—H), 7.36 (t, 1H, J=8.8 Hz, Ar—H), 7.26-7.23 (m, 1H, Ar—H), 6.99 (s, 1H, vinyl-H), 4.09 (s, 2H, CH$_2$), 3.32-3.25 (m, 1H, N-cyclohexyl-H), 3.00-2.96 (m, 1H, N-cyclopropyl-H), 1.99-1.01 (m, 14H, N-cyclohexyl-H, N-cyclopropyl-H).

KHG24272 [2-cyclohexylimino-3-cyclopropyl-1,3-thiazolidine-4-yl]-N-(4-ethylphenyl)-acetamide hydrochloride [R$_1$=H, R$_2$=4-C$_2$H$_5$, R$_3$=R$_4$=H, R$_5$=C$_3$H$_5$, R$_6$=C$_6$H$_{11}$, n=1, m=0, X=Cl]

yield: 36%; melting point: 194.2° C.

$^1$H NMR (400 MHz, DMSO-d$_6$) δ 10.51 (s, 1H, NH), 9.28 (d, 1H, J=8.1 Hz, HCl), 7.50 (d, 2H, J=6.5 Hz, Ar—H), 7.15 (d, 2H, J=8.4 Hz, Ar—H), 6.97 (s, 1H, vinyl-H), 3.98 (s, 2H, CH$_2$), 3.28-3.24 (m, 1H, N-cyclohexyl-H), 2.99-2.95 (m, 1H, N-cyclopropyl-H), 2.53 (q, 2H, J=7.6 Hz, CH$_2$CH$_3$), 1.15 (t, 3H, J=7.6 Hz, CH$_2$CH$_3$), 1.99-1.02 (m, 14H, N-cyclohexyl-H, N-cyclopropyl-H).

KHG24273 [2-cyclohexylimino-3-cyclopropyl-1,3-thiazolidine-4-yl]-N-(4-bromophenyl)-acetamide hydrochloride [R$_1$=H, R$_2$=4-Br, R$_3$=H, R$_5$=C$_3$H$_5$, R$_6$=C$_6$H$_{11}$, n=1, m=0, X=Cl]

yield: 24.8%; melting point: 188.9° C.

$^1$H NMR (300 MHz, DMSO-d$_6$) δ 11.86 (s, 1H, NH), 9.29 (d, 1H, J=7.9 Hz, HCl), 7.62 (d, 2H, J=8.9 Hz, Ar—H), 7.50 (d, 2H, J=8.9 Hz, Ar—H), 6.98 (s, 1H, vinyl-H), 4.01 (s, 2H, CH$_2$), 3.27 (m, 1H, N-cyclohexyl-H), 2.98-2.96 (m, 1H, N-cyclopropyl-H), 1.99-1.02 (m, 14H, N-cyclohexyl-H, N-cyclopropyl-H).

KHG24274 [2-cyclohexylimino-3-cyclopropyl-1,3-thiazolidine-4-yl]-N-(4-methylphenyl)-acetamide hydrochloride [R$_1$=H, R$_2$=4-CH$_3$, R$_3$=R$_4$=H, R$_5$=C$_3$H$_5$, R$_6$=C$_6$H$_{11}$, n=1, m=0, X=Cl]

yield: 74.0%; melting point: 216.4° C.

$^1$H NMR (300 MHz, DMSO-d$_6$) δ 9.22 (s, 1H, NH), 7.55-7.10 (m, 4H, Ar—H), 6.96 (s, 1H, vinyl-H), 3.96 (s, 2H, CH$_2$), 3.44 (s, 3H, CH$_3$), 3.27 (m. 1H, cyclopropyl C$_1$—H), 3.97 (m, 1H, cyclohexyl-H), 2.25 (s, 4H, cyclopropyl-H), 1.83-1.24 (m, 8H, cyclohexyl-H).

KHG24275 [2-cyclohexylimino-3-ethyl-1,3-thiazolidine-4-yl]-N-(4-chlorophenyl)-acetamide hydrochloride [R$_1$=H, R$_2$=4-Cl, R$_3$=R$_4$=H, R$_5$=C$_2$H$_5$, R$_6$=C$_6$H$_{11}$, n=1, m=0, X=Cl]

yield: 58.3%; melting point: 218.3° C.

$^1$H NMR (300 MHz, DMSO-d$_6$) δ 11.07 (s, 1H, NH), 7.68 (d, 2H, J=8.9 Hz, ArH), 7.37 (d, 2H, J=8.8 Hz, ArH), 7.05 (s, 1H, vinyl H), 4.21-4.19 (m, 2H, NCH$_2$CH$_3$), 3.99 (s, 2H, CH$_2$), 3.22 (br s, 1H, 1-cyclohexyl H), 1.98-1.26 (m, 10H, cyclohexyl-H), 1.19-1.15 (m, 3H, NCH$_2$CH$_3$).

KHG24276 [2-cyclohexylimino-3-ethyl-1,3-thiazolidine-4-yl]-N-(4-phenoxyphenyl)-acetamide hydrochloride [R$_1$=H, R$_2$=4-OC$_6$H$_5$, R$_3$H, R$_5$=C$_2$H$_5$, R$_6$=C$_6$H$_{11}$, n=1, m=0, X=Cl]

yield: 62.4%; melting point: 160.3° C.

$^1$H NMR (300 MHz, DMSO-d$_6$) δ 10.49 (s, 1H, NH), 7.67-7.33 (m, 9H, ArH), 6.74 (s, 1H, vinyl H), 3.74-3.64 (m, 2H, NCH$_2$CH$_3$), 3.24-3.22 (m, 1H, 1-cyclohexyl H), 3.85 (s, 2H, CH$_2$), 1.99-1.02 (m, 10H, cyclohexyl-H), 1.19-1.13 (m, 3H, NCH$_2$CH$_3$).

KHG24277 [2-cyclohexylimino-3-ethyl-1,3-thiazolidine-4-yl]-N-(4-n-butylphenyl)-acetamide hydrochloride [$R_1$=H, $R_2$=4-n-$C_4H_9$, $R_3$=$R_4$=H, $R_5$=$C_2H_5$, $R_6$=$C_6H_{11}$, n=1, m=0, X=Cl]

yield: 57.0%; melting point: 158.4° C.

$^1$H NMR (300 MHz, DMSO-$d_6$) δ 10.61 and 10.36 (A:B=0.3:1) (s, 1H, NH), 7.54-7.09 (m, 4H, ArH), 7.71 (s, 1H, 4-OH), 3.73-3.66 (m, 2H, N$CH_2$$CH_3$), 3.23-3.20 (m, 1H, 1-cyclohexyl H), 3.86 (ABq, 2H, Japp≅12.0 Hz, $CH_2$), 3.73-3.50 (m, 2H, Ar$CH_2$$CH_2$$CH_2$$CH_3$) 2.97 (ABq, 2H, J=14.3 Hz, 5-methylene $CH_2$), 1.99-1.43 (m, 10H, cyclohexyl-H), 1.33-1.05 (m, 7H, Ar$CH_2$$CH_2$$CH_2$$CH_3$), 0.87 (t, 3H, J=7.3 Hz, N$CH_2$$CH_3$).

KHG24278 [2-cyclohexylimino-3-ethyl-1,3-thiazolidine-4-yl]-N-(2-fluoro-5-nitrophenyl)-acetamide hydrochloride [$R_1$=H, $R_2$=2-F, $R_3$=4-$NO_2$, $R_4$=H, $R_5$=$C_2H_5$, $R_6$=$C_6H_{11}$, n=1, m=0, X=Cl]

yield: 31.6%; melting point: 177.0° C.

$^1$H NMR (300 MHz, DMSO-$d_6$) δ 10.83 and 10.59 (A:B=1.0:1.2) (s, 1H, NH), 8.11-7.53 (m, 3H, ArH), 7.85 (s, 1H, 4-OH), 7.08 (s, 1H, vinyl H), 3.25-3.22 (m, 1H, 1-cyclohexyl H), 3.86 (ABq, 2H, Japp≅12.4 Hz, $CH_2$), 3.16 (ABq, 2H, J=14.2 Hz, 5-methylene $CH_2$), 1.98-1.05 (m, 10H, cyclohexyl-H), 1.21-1.14 (m, 3H, N$CH_2$$CH_3$).

KHG24279 [2-cyclohexylimino-3-ethyl-1,3-thiazolidine-4-yl]-N-(4-methylphenyl)-acetamide hydrochloride [$R_1$=H, $R_2$=4-$CH_3$, $R_3$=$R_4$=H, $R_5$=$C_2H_5$, $R_6$=$C_6H_{11}$, n=1, m=0, X=Cl]

yield: 19.1%; melting point: 211.9° C.

$^1$H NMR (300 MHz, DMSO-$d_6$) δ 10.65 and 10.39 (A:B=0.3:1) (s, 1H, NH), 7.73 (s, 1H, 4-OH), 7.54-7.09 (m, 4H, Ar—H), 3.73-3.63 (m, 2H, N$CH_2$$CH_3$), 3.25-3.22 (m, 1H, 1-cyclohexyl H), 3.83 (ABq, 2H, Japp≅12.0 Hz, $CH_2$), 2.98 (ABq, 2H, J=14.2 Hz, 5-methylene $CH_2$), 1.96-1.10 (m, 10H, cyclohexyl-H), 1.20-1.10 (m, 3H, N$CH_2$$CH_3$).

KHG24280 [2-cyclohexylimino-3-ethyl-1,3-thiazolidine-4-yl]-N-(4-trifluoromethylphenyl)-acetamide hydrochloride [$R_1$=H, $R_2$=4-$CF_3$, $R_3$=$R_4$H, $R_5$=$C_2H_5$, $R_6$=$C_6H_{11}$, n=1, m=0, X=Cl]

yield: 89%; melting point: 191° C.

$^1$H NMR (300 MHz, DMSO-$d_6$) δ 11.26 (s, 1H, NH), 9.69 (d, 1H, J=7.8 Hz, HCl), 7.85 (d, 2H, J=8.6 Hz, ArH), 7.68 (d, 2H, J=8.64 Hz, ArH), 4.17 (q, 2H, J=7.0 Hz, $CH_2$$CH_3$), 3.98 (s, 2H, $CH_2$), 3.25-3.22 (m, 1H, 1-cyclohexyl CH), 1.98-1.05 (m, 13H, cyclohexyl CH, $CH_2$$CH_3$).

KHG24281 [2-cyclohexylimino-3-(n-butyl)-1,3-thiazolidine-4-yl]-N-(4-phenoxyphenyl)-acetamide hydrochloride [$R_1$=H, $R_2$=4-O$C_6H_5$, $R_3$=$R_4$=H, $R_5$=n-$C_4H_9$, $R_6$=$C_6H_{11}$, n=1, m=0, X=Cl]

yield: 92.2%; melting point: 213.3° C.

$^1$H NMR (300 MHz, DMSO-$d_6$) δ 10.75 (s, 1H, NH), 7.63 (d, 2H, J=9.0 Hz, ArH), 7.39-7.34 (m, 2H, ArH), 7.13-6.94 (m, 5H, ArO$C_6H_5$, vinyl H), 4.10 (t, 2H, N$CH_2$$CH_2$$CH_2$$CH_3$), 3.93 (s, 2H, $CH_2$), 3.25 (m, 1H, 1-cyclohexyl H), 1.99-1.51 (m, 10H, cyclohexyl-H), 1.36-1.26 (m, 4H, N$CH_2$$CH_2$$CH_2$$CH_3$), 0.79 (t, 3H, J=7.3 Hz, N($CH_2$)$_3$$CH_3$).

KHG24282 [2-cyclohexylimino-3-(n-butyl)-1,3-thiazolidine-4-yl]-N-(4-n-butylphenyl)-acetamide hydrochloride [$R_1$=H, $R_2$=4-n-$C_4H_9$, $R_3$H, $R_5$=n-$C_4H_9$, $R_6$=$C_6H_{11}$, n=1, m=0, X=Cl]

yield: 96.1%; melting point: 209.1° C.

$^1$H NMR (300 MHz, DMSO-$d_6$) δ 10.68 (s, 1H, NH), 7.50 (d, 2H, J=8.4 Hz, ArH), 7.12 (m, 2H, J=8.4 Hz, ArH), 7.04 (s, 1H, vinyl H), 4.11 (t, 2H, J=7.6 Hz, N$CH_2$$CH_2$$CH_2$$CH_3$), 3.93 (s, 2H, $CH_2$), 3.28 (m, 1H, 1-cyclohexyl H), 1.98-1.10 (m, 22H, cyclohexyl-H, Ar($CH_2$)$_3$$CH_3$, N$CH_2$$CH_2$$CH_2$$CH_3$), 0.87 (t, 3H, Ar($CH_2$)$_3$$CH_3$), 0.76 (t, 3H, J=7.3 Hz, N($CH_2$)$_3$$CH_3$).

KHG24283 [2-cyclohexylimino-3-(n-butyl)-1,3-thiazolidine-4-yl]-N-(4-isopropylphenyl)-acetamide hydrochloride [$R_1$=H, $R_2$=4-CH($CH_3$)$_2$, $R_3$H, $R_5$ n-$C_4H_9$, $R_6$=$C_6H_{11}$, n=1, m=0, X=Cl]

yield: 75.6%; melting point: 215.6° C.

$^1$H NMR (300 MHz, DMSO-$d_6$) δ 10.66 (s, 1H, NH), 7.52 (d, 2H, J=8.4 Hz, ArH), 7.18 (m, 2H, J=8.4 Hz, ArH), 7.10 (s, 1H, vinyl H), 4.10 (s, 2H, N$CH_2$$CH_2$$CH_2$$CH_3$), 3.93 (s, 2H, $CH_2$), 3.22 (m, 1H, 1-cyclohexyl H), 1.92-1.15 (m, 16H, cyclohexyl-H, N$CH_2$$CH_2$$CH_2$$CH_3$, ArCH($CH_3$)$_2$), 0.78 (t, 3H, J=7.3 Hz, N($CH_2$)$_3$$CH_3$).

KHG24284 [2-cyclohexylimino-3-(n-butyl)-1,3-thiazolidine-4-yl]-N-(4-fluorophenyl)-acetamide hydrochloride [$R_1$=H, $R_2$=4-F, $R_3$=H, $R_5$=n-$C_4H_9$, $R_6$=$C_6H_{11}$, n=1, m=0, X=Cl]

yield: 69.2%; melting point: 203.5° C.

$^1$H NMR (300 MHz, DMSO-$d_6$) δ 10.82 (s, 1H, NH), 7.67-7.13 (m, 4H, ArH), 7.05 (s, 1H, vinyl H), 4.09 (t, 2H, Japp≅7.7 Hz, N$CH_2$$CH_2$$CH_2$$CH_3$), 3.93 (s, 2H, $CH_2$), 3.27 (m, 1H, 1-cyclohexyl H), 1.98-1.07 (m, 14H, cyclohexyl-H, N$CH_2$$CH_2$$CH_2$$CH_3$), 0.78 (t, 3H, Japp≅7.3 Hz, N($CH_2$)$_3$$CH_3$).

KHG24285 [2-cyclohexylimino-3-(n-butyl)-1,3-thiazolidine-4-yl]-N-(4-methylphenyl)-acetamide hydrochloride [$R_1$=H, $R_2$=4-$CH_3$, $R_3$=$R_4$=H, $R_5$=n-$C_4H_9$, $R_6$=$C_6H_{11}$, n=1, m=0, X=Cl]

yield: 84.1%; melting point: 183.4° C.

$^1$H NMR (300 MHz, DMSO-$d_6$) δ 10.76 (s, 1H, NH), 7.52 (d, 2H, J=8.4 Hz, ArH), 7.14 (d, 2H, J=8.4 Hz, ArH), 7.05 (s, 1H, vinyl H), 4.15 (t, 2H, Japp≅7.6 Hz, N$CH_2$$CH_2$$CH_2$$CH_3$), 3.92 (s, 2H, $CH_2$), 3.23 (m, 1H, 1-cyclohexyl H), 2.25 (s, 3H, Ar$CH_3$), 1.98-1.11 (m, 14H, cyclohexyl-H, N$CH_2$$CH_2$$CH_2$$CH_3$), 0.78 (t, 3H, Japp≅7.2 Hz, N($CH_2$)$_3$$CH_3$).

KHG24286 [2-cyclohexylimino-3-(n-butyl)-1,3-thiazolidine-4-yl]-N-(4-ethylphenyl)-acetamide hydrochloride [$R_1$=H, $R_2$=4-$C_2H_5$, $R_3$=$R_4$=H, $R_5$=n-$C_4H_9$, $R_6$=$C_6H_{11}$, n=1, m=0, X=Cl]

yield: 69.4%; melting point: 221.2° C.

$^1$H NMR (300 MHz, DMSO-$d_6$) δ 10.68 (s, 1H, NH), 7.52 (d, 2H, J=8.4 Hz, ArH), 7.12 (d, 2H, J=8.3 Hz, ArH), 7.03 (s, 1H, vinyl H), 4.12 (s, 2H, N$CH_2$$CH_2$$CH_2$$CH_3$), 3.95 (s, 2H, $CH_2$), 3.22 (m, 1H, 1-cyclohexyl H), 2.58-2.53 (m, 2H, Ar$CH_2$$CH_3$), 1.96-1.25 (m, 13H, cyclohexyl-H, Ar$CH_2$$CH_3$), 1.19-1.12 (m, 4H, N$CH_2$$CH_2$$CH_2$$CH_3$), 0.78 (t, 3H, Japp≅7.2 Hz, N($CH_2$)$_3$$CH_3$).

KHG24287 [2-cyclohexylimino-3-(n-propyl)-1,3-thiazolidine-4-yl]-N-(4-chlorophenyl)-acetamide hydrochloride [$R_1$=H, $R_2$=4-Cl, $R_3$=$R_4$=H, $R_5$=n-$C_3H_7$, $R_6$=$C_6H_{11}$, n=1, m=0, X=Cl]

yield: 61.6%; melting point: 206.8° C.

$^1$H NMR (300 MHz, DMSO-$d_6$) δ 11.04 (s, 1H, NH), 7.66 (m, 2H, ArH), 7.38 (d, 2H, J=8.8 Hz, ArH), 7.06 (s, 1H, vinyl H), 4.09 (t, 2H, Japp≅7.8 Hz, N$CH_2$$CH_3$), 3.97 (s, 2H, $CH_2$), 3.26 (m, 1H, 1-cyclohexyl H), 1.97-1.06 (m, 12H, cyclohexyl-H, N$CH_2$$CH_3$), 0.85 (t, 3H, Japp≅7.3 Hz, N$CH_2$$CH_2$$CH_3$).

KHG24288 [2-cyclohexylimino-3-(n-propyl)-1,3-thiazolidine-4-yl]-N-(4-bromophenyl)-acetamide hydrochloride [$R_1$=H, $R_2$=4-Br, $R_3$=$R_4$=H, $R_5$=n-$C_3H_7$, $R_6$=$C_6H_{11}$, n=1, m=0, X=Cl]

yield: 75.7%; melting point: 219.1° C.

$^1$H NMR (300 MHz, DMSO-$d_6$) δ 11.02 (d, 1H, NH), 7.61 (m, 2H, ArH), 7.50 (d, 2H, J=8.9 Hz, ArH), 7.05 (s, 1H, vinyl H), 4.09 (t, 2H, Japp≅7.7 Hz, NCH$_2$CH$_2$CH$_3$), 3.97 (s, 2H, CH$_2$), 3.28 (m, 1H, 1-cyclohexyl), 1.97-1.10 (m, 12H, cyclohexyl-H, NCH$_2$CH$_2$CH$_3$), 0.85 (t, 3H, Japp≅7.2 Hz, NCH$_2$CH$_2$CH$_3$).

KHG24289 [2-cyclohexylimino-3-(n-propyl)-1,3-thiazolidine-4-yl]-N-(3,5-ditrifluoromethylphenyl)-acetamide hydrochloride [R$_1$=H, R$_2$=3-CF$_3$, R$_3$=5-CF$_3$, R$_4$=H, R$_5$=n-C$_3$H$_7$, R$_6$=C$_6$H$_{11}$, n=1, m=0, X=Cl]

yield: 61.2%; melting point: 243.4° C.

$^1$H NMR (300 MHz, DMSO-d$_6$) δ 11.69 (s, 1H, NH), 8.34 (s, 2H, ArH), 7.82 (s, 1H, ArH), 7.11 (s, 1H, vinyl H), 4.10-4.04 (m, 4H, NCH$_2$CH$_2$CH$_3$, CH$_2$), 3.26 (m, 1H, 1-cyclohexyl H), 1.99-1.16 (m, 12H, cyclohexyl-H, NCH$_2$CH$_2$CH$_3$), 0.88 (t, 3H, Japp≅7.3 Hz, NCH$_2$CH$_2$CH$_3$).

KHG24290 [2-cyclohexylimino-3-(n-propyl)-1,3-thiazolidine-4-yl]-N-(4-phenoxyphenyl)-acetamide hydrochloride [R$_1$=H, R$_2$=4-OC$_6$H$_5$, R$_3$=R$_4$=H, R$_5$=n-C$_3$H$_7$, R$_6$=C$_6$H$_{11}$, n=1, m=0, X=Cl]

yield: 79.5%; melting point: 230.3° C.

$^1$H NMR (300 MHz, DMSO-d$_6$) δ 10.91 (s, 1H, NH), 7.67-7.34 (m, 4H, ArH), 7.12-6.94 (m, 6H, OC$_6$H$_5$, vinyl H), 4.13 (t, 2H, NCH$_2$CH$_2$CH$_3$), 3.95 (s, 2H, CH$_2$), 1.97-1.06 (m, 12H, cyclohexyl-H, NCH$_2$CH$_2$CH$_3$), 0.87 (t, 3H, Japp≅7.2 Hz, NCH$_2$CH$_2$CH$_3$).

KHG24291 [2-cyclohexylimino-3-(n-propyl)-1,3-thiazolidine-4-yl]-N-(4-n-butylphenyl)-acetamide hydrochloride [R$_1$=H, R$_2$=4-n-C$_4$H$_9$, R$_3$=R$_4$=H, R$_5$=n-C$_3$H$_7$, R$_6$=C$_6$H$_{11}$, n=1, m=0, X=Cl]

yield: 72.2%; melting point: 201.4° C.

$^1$H NMR (300 MHz, DMSO-d$_6$) δ 10.67 (s, 1H, NH), 7.51 (d, 2H, J=8.4 Hz, ArH), 7.12 (d, 2H, J=8.4 Hz, ArH), 7.04 (s, 1H, vinyl H), 4.10 (t, 2H, Japp≅7.7 Hz, NCH$_2$CH$_2$CH$_3$), 3.92 (s, 2H, CH$_2$), 3.24 (m, 1H, 1-cyclohexyl H), 1.97-1.11 (m, 19H, cyclohexyl-H, Ar(CH$_2$)$_3$CH$_3$), 0.90-0.84 (m, 5H, NCH$_2$CH$_2$CH$_3$).

KHG24292 (2-cyclohexylimino-3-ethyl-1,3-thiazolidine-4-yl)-N-(4-methylbenzyl)-acetamide hydrochloride [R$_1$=H, R$_2$=4-CH$_3$, R$_3$=R$_4$=H, R$_5$=C$_2$H$_5$, R$_6$=C$_6$H$_{11}$, n=1, m=1, X=Cl]

yield: 39.3%; melting point: 172.6° C.

$^1$H NMR (300 MHz, DMSO-d$_6$) δ 8.89 (t, 1H, J=5.8 Hz, NH), 7.18-7.12 (m, 4H, ArH), 6.96 (s, 1H, vinyl H), 4.25-4.24 (d, 2H, J=5.8 Hz, NCH$_2$C$_6$H$_5$), 4.14 (q, 2H, J=7.0 Hz, NCH$_2$CH$_3$), 3.74 (s, 2H, CH$_2$), 3.20 (m, 1H, 1-cyclohexyl H), 2.28 (s, 3H, ArCH$_3$), 1.97-1.26 (m, 10H, cyclohexylH), 1.13 (t, 3H, J≅6.6 Hz, NCH$_2$CH$_3$).

KHG24293 [2-cyclohexylimino-3-(n-propyl)-1,3-thiazolidine-4-yl]-N-(4-methylbenzyl)-acetamide hydrochloride [R$_1$=H, R$_2$=4-CH$_3$, R$_3$=R$_4$=H, R$_5$=n-C$_4$H$_9$, R$_6$=C$_6$H$_{11}$, n=1, m=1, X=Cl]

yield: 63.7%; melting point: 189.5-191.2° C.

$^1$H NMR (300 MHz, DMSO-d$_6$) δ 8.80 (t, 1H, J=5.7 Hz, NH), 7.18-7.12 (m, 4H, ArH), 6.96 (s, 1H, vinyl H), 4.24 (d, 2H, J=5.7 Hz, NCH$_2$C$_6$H$_5$), 4.01 (q, 2H, J=7.8 Hz, NCH$_2$CH$_2$CH$_3$), 3.71 (s, 2H, 4-CH$_2$), 2.28 (s, 3H, ArCH$_3$), 1.98-1.46 (m, 10H, cyclohexyl-H), 1.40-1.24 (m, 4H, NCH$_2$CH$_2$CH$_3$), 0.88-0.83 (t, 3H, Japp≅7.3 Hz, N—(CH$_2$)$_3$CH$_3$).

KHG24294 [2-cyclohexylimino-3-(n-propyl)-1,3-thiazolidine-4-yl]-N-(4-isopropylphenyl)-acetamide hydrochloride [R$_1$=H, R$_2$=4-CH(CH$_3$)$_2$, R$_3$=R$_4$=H, R$_5$=n-C$_3$H$_7$, R$_6$=C$_6$H$_{11}$, n=1, m=0, X=Cl]

yield: 75.5%; melting point: 207.0° C.

$^1$H NMR (300 MHz, DMSO-d$_6$) δ 10.67 (s, 1H, NH), 7.52 (s, 2H, J=8.5 Hz, ArH), 7.18 (m, 2H, J=8.5 Hz, ArH), 7.05 (s, 1H, vinyl H), 4.10 (t, 2H, Japp≅8.3 Hz, NCH$_2$CH$_2$CH$_3$), 3.93 (s, 2H, CH$_2$), 3.25 (m, 1H, 1-cyclohexyl H), 1.95-1.49 (m, 10H, cyclohexyl-H), 1.33 (q, 2H, Japp≅12.8 Hz, NCH$_2$CH$_2$CH$_3$), 1.17 (d, 6H, J=6.9 Hz, ArCH(CH$_3$)$_2$), 0.87 (t, 3H, Japp≅7.3 Hz, NCH$_2$CH$_2$CH$_3$).

KHG24295 [2-cyclohexylimino-3-(n-propyl)-1,3-thiazolidine-4-yl]-N-(2-fluoro-5-nitrophenyl)-acetamide hydrochloride [R$_1$=H, R$_2$=2-F, R$_3$=5-NO$_2$, R$_4$=H, R$_5$=n-C$_3$H$_7$, R$_6$=C$_6$H$_{11}$, n=1, m=0, X=Cl]

yield: 88.4%; melting point: 139.2° C.

$^1$H NMR (300 MHz, DMSO-d$_6$) δ 10.83 (s, 1H, NH), 8.94-8.06 (m, 3H, ArH), 7.08 (s, 1H, vinyl H), 4.14 (s, 2H, NCH$_2$CH$_2$CH$_3$), 4.10 (s, 2H, CH$_2$), 3.24 (m, 1H, 1-cyclohexyl H), 1.98-1.56 (m, 10H, cyclohexyl-H), 1.33 (q, 2H, Japp≅12.8 Hz, NCH$_2$CH$_2$CH$_3$), 0.89 (t, 3H, Japp≅7.3 Hz, NCH$_2$CH$_2$CH$_3$).

KHG24296 [2-cyclohexylimino-3-(n-propyl)-1,3-thiazolidine-4-yl]-N-(4-fluorophenyl)-acetamide hydrochloride [R$_1$=H, R$_2$=4-F, R$_3$=R$_4$=H, R$_5$=n-C$_3$H$_7$, R$_6$=C$_6$H$_{11}$, n=1, m=0, X=Cl]

yield: 75.0%; melting point: 169.7° C.

$^1$H NMR (300 MHz, DMSO-d$_6$) δ 11.03 (s, 1H, NH), 7.70-7.14 (m, 4H, ArH), 7.07 (s, 1H, vinyl H), 4.14 (t, 2H, J=7.7 Hz, NCH$_2$CH$_2$CH$_3$), 3.97 (s, 2H, 4-CH$_2$), 3.22 (m, 1H, 1-cyclohexyl H), 1.98-1.52 (m, 10H, cyclohexyl-H), 1.33 (q, 2H, Japp≅12.8 Hz, NCH$_2$CH$_2$CH$_3$), 0.87 (t, 3H, Japp≅7.7 Hz, NCH$_2$CH$_2$CH$_3$).

KHG24297 [2-cyclohexylimino-3-(n-propyl)-1,3-thiazolidine-4-yl]-N-(4-methylphenyl)-acetamide hydrochloride [R$_1$=H, R$_2$=4-CH$_3$, R$_3$=R$_4$=H, R$_5$=n-C$_3$H$_7$, R$_6$=C$_6$H$_{11}$, n=1, m=0, X=Cl]

yield: 56.5%; melting point: 188.9° C.

$^1$H NMR (300 MHz, DMSO-d$_6$) δ 10.71 (s, 1H, NH), 7.50 (d, 2H, J=8.4 Hz, ArH), 7.11 (d, 2H, J=8.4 Hz, ArH), 7.04 (s, 1H, vinyl H), 4.12 (t, 2H, J=7.7 Hz, NCH$_2$CH$_2$CH$_3$), 3.93 (s, 2H, CH$_2$), 3.23 (m, 1H, 1-cyclohexyl H), 2.24 (s, 1H, ArCH$_3$), 1.98-1.55 (m, 10H, cyclohexyl-H), 1.33 (q, 2H, J=12.8 Hz, NCH$_2$CH$_2$CH$_3$), 0.86 (t, 3H, Japp≅7.3 Hz, NCH$_2$CH$_2$CH$_3$).

KHG24298 [2-cyclohexylimino-3-(n-propyl)-1,3-thiazolidine-4-yl]-N-(4-ethylphenyl)-acetamide hydrochloride [R$_1$=H, R$_2$=4-C$_2$H$_5$, R$_3$=R$_4$=H, R$_5$=n-C$_3$H$_7$, R$_6$=C$_6$H$_{11}$, n=1, m=0, X=Cl]

yield: 72.0%; melting point: 221.4° C.

$^1$H NMR (300 MHz, DMSO-d$_6$) δ 10.69 (s, 1H, NH), 7.53 (d, 2H, J=8.4 Hz, ArH), 7.15 (d, 2H, J=8.4 Hz, ArH), 7.05 (s, 1H, vinyl H), 4.12 (t, 2H, J=7.7 Hz, NCH$_2$CH$_2$CH$_3$), 3.94 (s, 2H, CH$_2$), 2.57-2.54 (m, 2H, Japp≅7.6 Hz, ArCH$_2$CH$_3$), 1.95-1.55 (m, 10H, cyclohexyl-H), 1.33 (m, 2H, NCH$_2$CH$_2$CH$_3$), 1.15 (t, 3H, J=7.6 Hz, ArCH$_2$CH$_3$), 0.87 (t, 3H, Japp≅7.2 Hz, NCH$_2$CH$_2$CH$_3$).

KHG24299 (2-cyclohexylimino-3-benzyl-1,3-thiazolidine-4-yl)-N-(4-chlorophenyl)-acetamide hydrochloride [R$_1$=H, R$_2$=4-Cl, R$_3$=R$_4$=H, R$_5$=CH$_2$C$_6$H$_5$, R$_6$=C$_6$H$_{11}$, n=1, m=0, X=Cl]

yield: 39.9%; melting point: 199.0° C.

$^1$H NMR (300 MHz, DMSO-d$_6$) δ 10.71 (s, 1H, NH), 7.55-7.07 (m, 10H, ArH, NCH$_2$C$_6$H$_5$, vinyl H), 5.55 (s, 2H, NCH$_2$C$_6$H$_5$), 3.79 (s, 2H, CH$_2$), 3.29 (m, 1H, 1-cyclohexyl H), 1.94-1.12 (m, 10H, cyclohexyl-H).

KHG24300 (2-cyclohexylimino-3-benzyl-1,3-thiazolidine-4-yl)-N-(4-bromophenyl)-acetamide hydrochloride [R$_1$=H, R$_2$=4-Br, R$_3$=R$_4$=H, R$_5$=CH$_2$C$_6$H$_5$, R$_6$=C$_6$H$_{11}$, n=1, m=0, X=Cl]

yield: 93.0%; melting point: 181.4° C.

$^1$H NMR (300 MHz, DMSO-d$_6$) δ 10.75 (s, 1H, NH), 7.51-7.44 (m, 4H, Japp≅4.3 Hz, ArH), 7.36-7.08 (m, 6H, NCH$_2$C$_6$H$_5$, vinyl H), 5.57 (s, 2H, NCH$_2$C$_6$H$_5$), 3.80 (s, 2H, CH$_2$), 3.30 (m, 1H, 1-cyclohexyl H), 1.95-1.03 (m, 10H, cyclohexyl-H).

KHG24301 (2-cyclohexylimino-3-benzyl-1,3-thiazolidine-4-yl)-N-(3,5-ditrifluoromethylphenyl)-acetamide hydrochloride [$R_1$=H, $R_2$=3-$CF_3$, $R_3$=5-$CF_3$, $R_4$=H, $R_5$=$CH_2C_6H_5$, $R_6$=$C_6H_{11}$, n=1, m=0, X=Cl]

yield: 76.2%; melting point: 234.6° C.

$^1$H NMR (300 MHz, DMSO-$d_6$) δ 11.44 (s, 1H, NH), 8.12 (s, 2H, ArH), 7.74 (m, 1H, ArH), 7.26-7.03 (m, 6H, $NCH_2C_6H_5$, vinyl H), 5.56 (s, 2H, $NCH_2C_6H_5$), 3.91 (s, 2H, $CH_2$), 3.33 (m, 1H, 1-cyclohexyl H), 1.97-1.03 (m, 10H, cyclohexyl-H).

KHG24302 (2-cyclohexylimino-3-benzyl-1,3-thiazolidine-4-yl)-N-(4-phenoxyphenyl)-acetamide hydrochloride [$R_1$=H, $R_2$=4-$OC_6H_5$, $R_3$=$R_4$=H, $5_3$=$CH_2C_6H_5$, $R_6$=$C_6H_{11}$, n=1, m=0, X=Cl]

yield: 90.2%; melting point: 209.5° C.

$^1$H NMR (300 MHz, DMSO-$d_6$) δ 10.57 (s, 1H, NH), 7.54-6.93 (m, 15H, ArH, $ArOC_6H_5$, $NCH_2C_6H_5$, vinyl H), 5.57 (s, 2H, $NCH_2C_6H_5$), 3.77 (s, 2H, $CH_2$), 3.28 (m, 1H, 1-cyclohexyl H), 1.94-1.02 (m, 10H, cyclohexyl-H).

KHG24303 (2-cyclohexylimino-3-benzyl-1,3-thiazolidine-4-yl)-N-(4-isopropylphenyl)-acetamide hydrochloride [$R_1$=H, $R_2$=4-$CH(CH_3)_2$, $R_3$=$R_4$=H, $R_5$=$CH_2C_6H_5$, $R_6$=$C_6H_{11}$, n=1, m=0, X=Cl]

yield: 79.5%; melting point: 202.9° C.

$^1$H NMR (300 MHz, DMSO-$d_6$) δ 10.42 (s, 1H, NH), 7.44-7.09 (m, 10H, ArH, $NCH_2C_6H_5$, vinyl H), 5.56 (s, 2H, $NCH_2C_6H_5$), 3.74 (s, 2H, $CH_2$), 3.29 (m, 1H, 1-cyclohexyl H), 2.83 (m, 1H, $ArCH(CH_3)_2$), 1.95-1.26 (m, 10H, cyclohexyl-H), 1.17 (d, 6H, J=6.9 Hz, $ArCH(CH_3)_2$).

KHG24304 (2-cyclohexylimino-3-benzyl-1,3-thiazolidine-4-yl)-N-(2-fluoro-5-nitrophenyl)-acetamide hydrochloride [$R_1$=H, $R_2$=2-F, $R_3$=5-$NO_2$, $R_4$=H, $R_5$=$CH_2C_6H_5$, $R_6$=$C_6H_{11}$, n=1, m=0, X=Cl]

yield: 86.0%; melting point: 166.4° C.

$^1$H NMR (300 MHz, DMSO-$d_6$) δ 10.57 (d, 1H, NH), 8.73-7.53 (m, 3H, ArH), 7.33-7.06 (m, 6H, $NCH_2C_6H_5$, vinyl H), 5.55 (s, 2H, $NCH_2C_6H_5$), 3.95 (s, 2H, $CH_2$), 1.96-1.03 (m, 10H, cyclohexyl-H).

KHG24305 (2-cyclohexylimino-3-benzyl-1,3-thiazolidine-4-yl)-N-(4-fluorophenyl)-acetamide hydrochloride [$R_1$=H, $R_2$=4-F, $R_3$=$R_4$=H, $R_5$=$CH_2C_6H_5$, $R_6$=$C_6H_{11}$, n=1, m=0, X=Cl]

yield: 74.6%; melting point: 214.1° C.

$^1$H NMR (300 MHz, DMSO-$d_6$) δ 10.58 (s, 1H, NH), 7.54-7.08 (m, 10H, ArH, $NCH_2C_6H_5$, vinyl H), 5.55 (s, 2H, $NCH_2C_6H_5$), 3.75 (s, 2H, $CH_2$), 1.95-1.08 (m, 10H, cyclohexyl-H).

KHG24306 (2-cyclohexylimino-3-benzyl-1,3-thiazolidine-4-yl)-N-(4-ethylphenyl)-acetamide hydrochloride [$R_1$=H, $R_2$=4-$C_2H_5$, $R_3$H, $R_5$=$CH_2C_6H_5$, $R_6$=$C_6H_{11}$, n=1, m=0, X=Cl]

yield: 87.0%; melting point: 146.4° C.

$^1$H NMR (300 MHz, DMSO-$d_6$) δ 10.43 (s, 1H, NH), 7.43-7.09 (m, 10H, ArH, $NCH_2C_6H_5$, vinyl H), 5.56 (s, 2H, $NCH_2C_6H_5$), 3.75 (s, 2H, $CH_2$), 2.55-2.49 (m, 2H, $ArCH_2CH_3$), 1.94-1.25 (m, 10H, cyclohexyl-H), 1.16-1.03 (m, 3H, $ArCH_2CH_3$).

KHG24307 (2-cyclohexylimino-3-cyclohexyl-1,3-thiazolidine-4-yl)-N-(3,5-ditrifluoromethylphenyl)-acetamide hydrochloride [$R_1$=H, $R_2$=3-$CF_3$, $R_3$=5-$CF_3$, $R_4$=H, $R_5$=$C_6H_{11}$, $R_6$=$C_6H_{11}$, n=1, m=0, X=Cl]

yield: 71.4%; melting point: 193.3° C.

$^1$H NMR (300 MHz, DMSO-$d_6$) δ 12.06 (s, 1H, NH), 8.37 (s, 2H, ArH), 7.79 (s, 1H, ArH), 7.11 (s, 1H, vinyl H), 4.21 (s, 2H, $CH_2$), 3.27-3.24 (m, 1H, cyclohexyl-H), 1.66-1.28 (m, 21H, cyclohexyl-H, 2-cyclohexyl-H).

KHG24308 (2-cyclohexylimino-3-cyclohexyl-1,3-thiazolidine-4-yl)-N-(4-isopropylphenyl)-acetamide hydrochloride [$R_1$=H, $R_2$=4-$CH(CH_3)_2$, $R_3$=$R_4$=H, $R_5$=$C_6H_{11}$, $R_6$=$C_6H_{11}$, n=1, m=0, X=Cl]

yield: 51.2%; melting point: 199.7° C.

$^1$H NMR (300 MHz, DMSO-$d_6$) δ 10.79 (s, 1H, NH), 7.52-7.16 (m, 4H, ArH), 7.05 (s, 1H, vinyl H), 4.06 (s, 2H, $CH_2$), 3.44-3.41 (m, 1H, 3-cyclohexyl-H), 1.98-1.26 (m, 21H, cyclohexyl-H, 2-cyclohexyl-H), 1.17-1.15 (2s, 6H, $CH(CH_3)_2$).

KHG24309 (2-cyclohexylimino-3-cyclohexyl-1,3-thiazolidine-4-yl)-N-(4-phenoxyphenyl)-acetamide hydrochloride [$R_1$=H, $R_2$=4-$OC_6H_5$, $R_3$=$R_4$=H, $R_5$=$C_6H_{11}$, $R_6$=$C_6H_{11}$, n=1, m=0, X=Cl]

yield: 84.9%; melting point: 199.3° C.

$^1$H NMR (300 MHz, DMSO-$d_6$) δ 10.99 (s, 1H, NH), 7.66-6.94 (m, 9H, ArH), 7.07 (s, 1H, vinyl H), 4.08 (s, 2H, $CH_2$), 3.26-3.24 (br s, 1H, 3-cyclohexyl-H), 2.15-1.14 (m, 21H, cyclohexyl-H, 2-cyclohexyl-H).

KHG24310 (2-cyclohexylimino-3-cyclohexyl-1,3-thiazolidine-4-yl)-N-(4-trifluoromethylphenyl)-acetamide hydrochloride [$R_1$=H, $R_2$=4-$CF_3$, $R_3$=$R_4$=H, $R_5$=$C_6H_{11}$, $R_6$=$C_6H_{11}$, n=1, m=0, X=Cl]

yield: 82.09%; melting point: 220.0° C.

$^1$H NMR (300 MHz, DMSO-$d_6$) δ 11.50 (s, 1H, NH), 7.89-7.68 (m, 4H, ArH), 7.09 (s, 1H, vinyl H), 4.17 (s, 2H, $CH_2$), 3.24 (br s, 1H, 3-cyclohexyl-H), 2.17-1.09 (m, 21H, cyclohexyl-H, 2-cyclohexyl-H).

KHG24311 (2-cyclohexylimino-3-cyclohexyl-1,3-thiazolidine-4-yl)-N-(4-n-butylphenyl)-acetamide hydrochloride [$R_1$=H, $R_2$=4-n-$C_4H_9$, $R_3$=$R_4$=H, $R_5$=$C_6H_{11}$, $R_6$=$C_6H_{11}$, n=1, m=0, X=Cl]

yield: 65.9%; melting point: 153.3° C.

$^1$H NMR (300 MHz, DMSO-$d_6$) δ 10.91 (s, 1H, NH), 7.53-7.10 (m, 4H, ArH), 7.06 (s, 1H, vinyl H), 4.08 (s, 2H, $CH_2$), 3.23 (br s, 1H, 3-cyclohexyl-H), 2.16-1.04 (m, 23H, $CH_3CH_2CH_2CH_2$, cyclohexyl-H, 2-cyclohexyl-H), 1.48 (m, 2H, J=7.3 Hz, $CH_3CH_2CH_2$), 1.28 (m, 2H, J=7.3 Hz, $CH_3CH_2CH_2$), 0.87 (t, 3H, J=7.3 Hz, $CH_3CH_2CH_2$).

KHG24312 (2-cyclohexylimino-3-cyclohexyl-1,3-thiazolidine-4-yl)-N-(4-n-fluorophenyl)-acetamide hydrochloride [$R_1$=H, $R_2$=4-F, $R_3$=$R_4$=H, $R_5$=$C_6H_{11}$, $R_6$=$C_6H_{11}$, n=1, m=0, X=Cl]

yield: 74.8%; melting point: 244.0° C.

$^1$H NMR (300 MHz, DMSO-$d_6$) δ 11.03 (s, 1H, NH), 7.67-7.13 (m, 4H, ArH), 7.06 (s, 1H, vinyl H), 4.07 (s, 2H, $CH_2$), 3.24 (br s, 1H, 3-cyclohexyl-H), 2.16-1.10 (m, 21H, cyclohexyl-H, 2-cyclohexyl-H).

KHG24313 (2-cyclohexylimino-3-cyclohexyl-1,3-thiazolidine-4-yl)-N-(4-methylphenyl)-acetamide hydrochloride [$R_1$=H, $R_2$=4-$CH_3$, $R_3$=$R_4$=H, $R_5$=$C_6H_{11}$, $R_6$=$C_6H_{11}$, n=1, m=0, X=Cl]

yield: 51.2%; melting point: 234.0° C.

$^1$H NMR (300 MHz, DMSO-$d_6$) δ 10.78 (s, 1H, NH), 7.50-7.09 (m, 4H, ArH), 7.05 (s, 1H, vinyl H), 4.05 (s, 2H, $CH_2$), 3.24 (br s, 1H, 3-cyclohexyl-H), 2.24 (s. 3H, $CH_3$), 2.14-1.10 (m, 21H, cyclohexyl-H, 2-cyclohexyl-H).

KHG24314 (2-cyclohexylimino-3-cyclohexyl-1,3-thiazolidine-4-yl)-N-(4-ethylphenyl)-acetamide hydrochloride [$R_1$=H, $R_2$=4-$C_2H_5$, $R_3$=$R_4$=H, $R_5$=$C_6H_{11}$, $R_6$=$C_6H_{11}$, n=1, m=0, X=Cl]

yield: 79.7%; melting point: 222.7° C.

$^1$H NMR (300 MHz, DMSO-$d_6$) δ 10.74 (s, 1H, NH), 7.52-7.13 (m, 4H, ArH), 7.05 (s, 1H, vinyl H), 4.05 (s, 2H, $CH_2$), 3.24 (br s, 1H, 3-cyclohexyl-H), 2.54 (q, 2H, J=7.5 Hz, $CH_2CH_3$), 2.13-1.12 (m, 21H, cyclohexyl-H, 2-cyclohexyl-H), 1.14 (t, 3H, J=7.6 Hz, $CH_2CH_3$).

KHG24315 (2-cyclohexylimino-3-cyclopropyl-1,3-thiazolidine-4-yl)-N-(4-phenoxyphenyl)-acetamide hydrochloride [$R_1$=H, $R_2$=4-OC$_6$H$_5$, $R_3$=$R_4$=H, $R_5$=C$_3$H$_5$, $R_6$=C$_6$H$_{11}$, n=1, m=0, X=Cl]

yield: 10.3%; melting point: 195.0° C.

$^1$H NMR (300 MHz, DMSO-d$_6$) δ 10.71 (s, 1H, NH), 9.32 (d, 1H, J=8.0 Hz, HCl), 7.63 (d, 2H, J=8.8 Hz, ArH), 7.36 (t, 2H, J=7.9 Hz, ArH), 7.10 (t, 1H, J=7.3 Hz, ArH), 6.98 (t, 5H, J=10.2 Hz, ArH, vinyl H), 4.00 (s, 2H, CH$_2$), 3.25 (m, 1H, cyclohexyl-H), 2.99 (m, 1H, cyclopropyl-H), 1.99-1.03 (m, 14H, cyclohexyl-H, cyclopropyl-H).

KHG24336 (2-cycloheptylimino-3-methyl-1,3-thiazolidine-4-yl)-N-(3-chlorobenzyl)-carboxamide hydrochloride [$R_1$=H, $R_2$=3-Cl, $R_3$=$R_4$=H, $R_5$=CH$_3$, $R_6$=C$_7$H$_{13}$, n=0, m=1, X=Cl]

yield: 68%; melting point: 230-231° C., $^1$H NMR (300 MHz, DMSO-d$_6$) δ 9.10 (br. s, 1H, NH), 7.36-7.27 (m, 4H, ArH), 6.70 (s, 1H, vinyl-H), 4.36 (d, J=5.94 Hz, 2H, benzyl-H), 3.25 (s, 3H, methyl-H), 2.90 (m, 1H, 2-imino N—CH), 1.69-1.43 (m, 12H, cycloheptyl-H).

KHG24337 (2-cycloheptylimino-3-methyl-1,3-thiazolidine-4-yl)-N-(4-chlorobenzyl)-carboxamide hydrochloride [$R_1$=H, $R_2$=4-Cl, $R_3$=$R_4$=H, $R_5$=CH$_3$, $R_6$=C$_7$H$_{13}$, n=0, m=1, X=Cl]

yield: 65%; melting point: 220-222° C., $^1$H NMR (300 MHz, DMSO-d$_6$) δ 9.10 (br. s, 1H, NH), 7.38 (d, J=8.55 Hz, 2H, ArH), 7.33 (d, J=8.55 Hz, 2H, ArH), 4.34 (d, J=6.03 Hz, 2H, benzyl-H), 3.24 (s, 3H, methyl-H), 2.91-2.89 (m, 1H, 2-imino N—CH), 1.70-1.53 (m, 12H, cyclohexyl-H).

KHG24338 (2-cycloheptylimino-3-methyl-1,3-thiazolidine-4-yl)-N-(3,4-dichlorobenzyl)-carboxamide hydrochloride [$R_1$=H, $R_2$=3-Cl, $R_3$=4-Cl, $R_4$=H, $R_5$=CH$_3$, $R_6$=C$_7$H$_{13}$, n=0, m=1, X=Cl]

yield: 70%; melting point: 218-219° C., $^1$H NMR (300 MHz, DMSO-d$_6$) δ 9.07 (t, J=5.79 Hz, 1H, NH), 7.61-7.55 (m, 2H, ArH), 7.31-7.27 (m, 1H, ArH), 4.35 (d, J=6.0 Hz, 2H, benzyl-H), 3.24 (s, 3H, methyl-H), 2.88-2.85 (m, 1H, 2-imino N—CH), 1.49-1.36 (m, 12H, cyclohexyl-H).

KHG24339 (2-cycloheptylimino-3-methyl-1,3-thiazolidine-4-yl)-N-(4-methoxybenzyl)-carboxamide hydrochloride [$R_1$=H, $R_2$=4-OCH$_3$, $R_3$=$R_4$=H, $R_5$=CH$_3$, $R_6$=C$_7$H$_{13}$, n=0, m=1, X=Cl]

yield: 67%; melting point: 156-159° C., $^1$H NMR (300 MHz, DMSO-d$_6$) δ 7.26 (d, J=8.19 Hz, 2H, ArH), 6.88 (d, J=8.55 Hz, 2H, ArH), 4.46 (d, J=5.70 Hz, 2H, benzyl-H), 3.52 (s, 3H, methyl-H), 2.95-2.91 (m, 1H, 2-imino N—CH), 1.85-1.44 (m, 12H, cyclohexyl-H).

KHG24403 (2-cyclohexylimino-3-ethyl-1,3-thiazolidine-4-yl)-N-(4-fluorophenyl)-acetamide hydrochloride [$R_1$=H, $R_2$=4-F, $R_3$=$R_4$=H, $R_5$=C$_2$H$_5$, $R_6$=C$_6$H$_{11}$, n=1, m=0, X=Cl]

yield: 94.7%; melting point: 196.5° C.

$^1$H NMR (300 MHz, DMSO-d$_6$) δ 10.91 (s, 1H, NH), 7.67-7.13 (m, 2H, ArH), 7.19-7.13 (t, 2H, J=8.8 Hz, ArH), 7.05 (s, 1H, vinyl H), 4.20 (q, 2H, Japp≅6.9 Hz, NCH$_2$CH$_3$), 3.96 (s, 2H, CH$_2$), 3.25-3.19 (m, 1H, 1-cyclohexyl-H), 1.98-1.11 (m, 10H, cyclohexyl-H), 1.05 (t, 3H, NCH$_2$CH$_3$).

KHG24404 [2-cyclohexylimino-3-(n-propyl)-1,3-thiazolidine-4-yl]-N-(4-trifluoromethylphenyl)-acetamide hydrochloride [$R_1$=H, $R_2$=4-CF$_3$, $R_3$=$R_4$=H, $R_5$=n-C$_3$H$_5$, $R_6$=C$_6$H$_{11}$, n=1, m=0, X=Cl]

yield: 73.2%; melting point: 173.6-174.8° C.

$^1$H NMR (300 MHz, DMSO-d$_6$) δ 11.3 (s, 1H, NH), 7.94-7.67 (m, 4H, ArH), 7.08 (s, 1H, vinyl H), 4.12 (t, 2H, J=7.6 Hz, NCH$_2$CH$_2$CH$_3$), 4.03 (s, 2H, CH$_2$), 3.25 (m, 1H, 1-cyclohexyl H), 1.98-1.10 (m, 12H, cyclohexyl-H, NCH$_2$CH$_2$CH$_3$), 0.86 (t, 3H, J=7.2 Hz, NCH$_2$CH$_2$CH$_3$).

KHG24405 (2-cyclohexylimino-3-(n-propyl)-1,3-thiazolidine-4-yl)-N-(3-chloro-4-methylphenyl)-acetamide hydrochloride [$R_1$=H, $R_2$=3-Cl, $R_3$=4-CH$_3$, $R_4$=H, $R_5$=n-C$_3$H$_5$, $R_6$=C$_6$H$_{11}$, n=1, m=0, X=Cl]

yield: 46.6%; melting point: 204.9° C.

$^1$H NMR (300 MHz, DMSO-d$_6$) δ 10.89 (s, 1H, NH), 7.81-7.28 (m, 2H, ArH), 7.05 (s, 1H, vinyl H), 4.08 (t, 2H, J=7.6 Hz, NCH$_2$CH$_2$CH$_3$), 3.94 (s, 2H, CH$_2$), 3.26 (m, 1H, 1-cyclohexyl H), 2.27 (s, 3H, ArCH$_3$), 1.98-1.11 (m, 12H, cyclohexyl-H, NCH$_2$CH$_2$CH$_3$), 0.86 (t, 3H, J=7.2 Hz, NCH$_2$CH$_2$CH$_3$).

KHG24406 (2-cyclohexylimino-3-benzyl-1,3-thiazolidine-4-yl)-N-(4-n-butylphenyl)-acetamide hydrochloride [$R_1$=H, $R_2$=4-n-C$_4$H$_9$, $R_3$=$R_4$=H, $R_5$=CH$_2$C$_6$H$_5$, $R_6$=C$_6$H$_{11}$, n=1, m=0, X=Cl]

yield: 78.0%; melting point: 156.2° C.

$^1$H NMR (300 MHz, DMSO-d$_6$) δ 10.44 (s, 1H, NH), 7.42-7.08 (m, 10H, ArH, NCH$_2$C$_6$H$_5$, vinyl H), 5.57 (s, 2H, NCH$_2$C$_6$H$_5$), 3.75 (s, 2H, CH$_2$), 3.35-3.31 (m, 1H, 1-cyclohexyl H), 2.53-2.50 (m, 2H, CH$_2$CH$_2$CH$_2$CH$_3$), 1.94-1.08 (m, 14H, cyclohexyl-H, CH$_2$CH$_2$CH$_2$CH$_3$), 0.88 (t, 3H, J=7.2 Hz, N(CH$_2$)$_3$CH$_3$).

KHG24407 (2-cyclohexylimino-3-benzyl-1,3-thiazolidine-4-yl)-N-(4-trifluoromethylphenyl)-acetamide hydrochloride [$R_1$=H, $R_2$=4-CF$_3$, $R_3$=$R_4$=H, $R_5$=CH$_2$C$_6$H$_5$, $R_6$=C$_6$H$_{11}$, n=1, m=0, X=Cl]

yield: 61.9%; melting point: 238.5° C.

$^1$H NMR (300 MHz, DMSO-d$_6$) δ 10.98 (s, 1H, NH), 7.73-7.63 (m, 4H, ArH), 7.35-7.07 (m, 6H, NCH$_2$C$_6$H$_5$, vinyl H), 5.56 (s, 2H, NCH$_2$C$_6$H$_5$), 3.85 (s, 2H, CH$_2$), 3.37-3.29 (m, 1H, 1-cyclohexyl H), 1.95-1.08 (m, 10H, cyclohexyl-H).

KHG24408 (2-cyclohexylimino-3-benzyl-1,3-thiazolidine-4-yl)-N-(5-chloro-2-fluorophenyl)-acetamide hydrochloride [$R_1$=H, $R_2$=2-F, $R_3$=5-Cl, $R_4$=H, $R_5$=CH$_2$C$_6$H$_5$, $R_6$=C$_6$H$_{11}$, n=1, m=0, X=Cl]

yield: 69.8%; melting point: 194.8° C.

$^1$H NMR (300 MHz, DMSO-d$_6$) δ 10.35 (s, 1H, NH), 7.80-7.77 (m, 1H, ArH), 7.37-7.07 (m, 8H, ArH, NCH$_2$C$_6$H$_5$, vinyl H), 5.56 (s, 2H, NCH$_2$C$_6$H$_5$), 3.90 (s, 2H, CH$_2$), 3.31 (m, 1H, 1-cyclohexyl H), 1.95-1.09 (m, 10H, cyclohexyl-H).

KHG24409 [2-(1-adamantylimino-3-methyl-1,3-thiazolidine-4-yl]-N-(4-n-butylphenyl)-acetamide hydrochloride [$R_1$=H, $R_2$=4-n-C$_4$H$_9$, $R_3$=$R_4$=H, $R_5$=CH$_3$, $R_6$=1-adamantyl, n=1, m=0, X=Cl]

yield: 76%; melting point: 178.4° C.

$^1$H NMR (300 MHz, DMSO-d$_6$) δ 10.54 (s, 1H, NH), 7.51-7.11 (m, 4H, ArH, vinyl H), 3.98 (s, 2H, CH$_2$), 3.59 (s, 3H, NCH$_3$), 2.16-1.21 (m, 15H, adamantyl-H), 0.91-0.85 (m, 3H, (CH$_2$)$_3$CH$_3$).

KHG24410 [2-(1-adamantylimino-3-methyl-1,3-thiazolidine-4-yl]-N-(3,5-dichlorophenyl)-acetamide hydrochloride [$R_1$=H, $R_2$=3-Cl, $R_3$=5-Cl, $R_4$=H, $R_5$=CH$_3$, $R_6$=1-adamantyl, n=1, m=0, X=Cl]

yield: 96.2%; melting point: 231.0° C.

$^1$H NMR (300 MHz, DMSO-d$_6$) δ 10.23 (s, 1H, NH), 7.70-7.42 (m, 3H, ArH), 7.13 (s, 1H, vinyl H), 4.08 (s, 2H, CH$_2$), 3.61 (s, 3H, NCH$_3$), 2.16-1.63 (m, 15H, adamantyl-H).

KHG24411 [2-(1-adamantylimino-3-methyl-1,3-thiazolidine-4-yl]-N-(4-chloro-2-fluorophenyl)-acetamide hydrochloride [$R_1$=H, $R_2$=2-F, $R_3$=4-Cl, $R_4$=H, $R_5$=CH$_3$, $R_6$=1-adamantyl, n=1, m=0, X=Cl]

yield: 68.5%; melting point: 211.2° C.

$^1$H NMR (300 MHz, DMSO-d$_6$) δ 10.41 (s, 1H, NH), 7.89-7.26 (m, 3H, ArH), 7.12 (s, 1H, vinyl H), 4.07 (s, 2H, CH$_2$), 3.59 (s, 3H, NCH$_3$), 2.16-1.63 (m, 15H, adamantyl-H).

KHG24412 [2-(1-adamantylimino-3-methyl-1,3-thiazolidine-4-yl]-N-phenyl-acetamide hydrochloride [$R_1$=H, $R_2$=$R_3$=$R_4$=H, $R_5$=$CH_3$, $R_6$=1-adamantyl, n=1, m=0, X=Cl]

yield: 88%; melting point: 232-234° C.

$^1$H NMR (300 MHz, DMSO-$d_6$) δ 10.82 (s, 1H, HCl), 8.59 (br. s, 1H, NH), 7.63-7.03 (m, 5H, ArH), 7.05 (s, 1H, vinyl-H), 4.03 (s, 2H, 4-$CH_2$), 3.62 (s, 3H, N—$CH_3$), 2.15-1.53 (m, 17H, adamantyl).

KHG24413 [2-(1-adamantylimino-3-methyl-1,3-thiazolidine-4-yl]-N-(2-chloro-4-methylphenyl)-acetamide hydrochloride [$R_1$=H, $R_2$=2-Cl, $R_3$=4-$CH_3$, $R_4$=H, $R_5$=$CH_3$, $R_6$=1-adamantyl, n=1, m=0, X=Cl]

yield: 90.1%; melting point: 151.6° C.

$^1$H NMR (300 MHz, DMSO-$d_6$) δ 10.03 (s, 1H, NH), 7.49-7.12 (m, 4H, ArH, vinyl H), 4.03 (s, 2H, $CH_2$), 3.62 (s, 3H, $NCH_3$), 2.29 (s, 3H, $ArCH_3$), 2.16-1.63 (m, 15H, adamantyl-H).

KHG24414 (2-cyclohexylimino-3-ethyl-1,3-thiazolidine-4-yl)-N-(3,5-dichlorophenyl)-acetamide hydrochloride [$R_1$=H, $R_2$=3-Cl, $R_3$=5-Cl, $R_4$=H, $R_5$=$C_2H_5$, $R_6$=$C_6H_{11}$, n=1, m=0, X=Cl]

yield: %; melting point: 100.5° C.

$^1$H NMR (300 MHz, DMSO-$d_6$) δ 10.27 (s, 1H, NH), 7.71-7.42 (m, 3H, Ar—H), 7.05 (s, 1H, vinyl H), 4.21-4.17 (m, 2H, $NCH_2CH_3$), 4.04 (s, 2H, $CH_2$), 3.25-3.23 (m, 1H, 1-cyclohexyl H), 1.98-1.15 (m, 10H, cyclohexyl-H), 1.07-1.02 (m, 3H, $NCH_2CH_3$).

KHG24415 [2-cyclohexylimino-3-(n-propyl)-1,3-thiazolidine-4-yl]-N-(3,5-dichlorophenyl)-acetamide hydrochloride [$R_1$=H, $R_2$=3-Cl, $R_3$=5-Cl, $R_4$=H, $R_5$=n-$C_3H_7$, $R_6$=$C_6H$, n=1, m=0, X=Cl]

yield: 64.2%; melting point: 109.2° C.

$^1$H NMR (300 MHz, DMSO-$d_6$) δ 10.25 (s, 1H, NH), 7.71-7.42 (m, 3H, Ar—H), 7.05 (s, 1H, vinyl H), 4.13-4.08 (m, 2H, $NCH_2CH_2CH_3$), 4.03 (s, 2H, $CH_2$), 3.25-3.22 (m, 1H, 1-cyclohexyl H), 1.97-0.99 (m, 12H, cyclohexyl-H, $NCH_2CH_2CH_3$), 0.93-0.88 (m, 3H, $NCH_2CH_2CH_3$).

KHG24416 [2-cyclohexylimino-3-(n-butyl)-1,3-thiazolidine-4-yl]-N-(3,5-dichlorophenyl)-acetamide hydrochloride [$R_1$=H, $R_2$=3-Cl, $R_3$=5-Cl, $R_4$=H, $R_5$=n-$C_4H_9$, $R_6$=$C_6H_{11}$, n=1, m=0, X=Cl]

yield: 74%; melting point: 153-154° C.

$^1$H NMR (300 MHz, DMSO-$d_6$) δ 10.28 (s, 1H, HCl), 9.96 (br. s, 1H, NH), 7.70-7.35 (m, 3H, ArH), 7.05 (s, 1H, vinyl-H), 4.03 (s, 2H, 4-$CH_2$), 3.41 (s, 3H, N—$CH_3$), 3.32 (br. s, 1H, cyclohexyl-$C_1$H), 1.95-1.02 (m, 16H, butyl-$(CH_2)_3$ and cyclohexyl), 0.84 (t, J=5.42 Hz, 3H, N-butyl-$CH_3$).

KHG24417 [2-(1-adamantyl)imino-3-methyl-1,3-thiazolidine-4-yl]-N-(3,5-dichlorophenyl)-acetamide hydrochloride [$R_1$=H, $R_2$=3-Cl, $R_3$=5-Cl, $R_4$=H, $R_5$=$CH_3$, $R_6$=$C_6H_{11}$, n=1, m=0, X=Cl]

yield: 91%; melting point: 238-240° C.

$^1$H NMR (300 MHz, DMSO-$d_6$) δ 10.26 (s, 1H, HCl), 8.58 (br. s, 1H, NH), 7.68-7.41 (m, 3H, ArH), 7.13 (s, 1H, vinyl-H), 4.07 (s, 2H, 4-$CH_2$), 3.61 (s, 3H, N—$CH_3$), 2.15-1.53 (m, 17H, adamantyl).

KHG24418 [2-(1-adamantyl)imino-3-methyl-1,3-thiazolidine-4-yl]-N-(2-chloro-4-methylphenyl)-acetamide hydrochloride [$R_1$=H, $R_2$=2-Cl, $R_3$=4-$CH_3$, $R_4$=H, $R_5$=$CH_3$, $R_6$=$C_6H_{11}$, n=1, m=0, X=Cl]

($R_1$=H, $R_2$=2-Cl, 5-$CH_3$, $R_3$=$CH_3$, $R_4$=adamantyl, n=1, m=0, X=HCl)

yield: 75%; melting point: 234-236° C.

$^1$H NMR (300 MHz, DMSO-$d_6$) δ 10.11 (s, 1H, HCl), 8.43 (br. s, 1H, NH), 7.65-6.89 (m, 3H, ArH), 7.10 (s, 1H, vinyl-H), 4.01 (s, 2H, 4-$CH_2$), 3.57 (s, 3H, N—$CH_3$), 2.31-1.63 (m, 17H, adamantyl).

KHG24419 [2-(1-adamantyl)imino-3-methyl-1,3-thiazolidine-4-yl]-N-(4-methoxyphenyl)-acetamide hydrochloride [$R_1$=H, $R_2$=4-$OCH_3$, $R_3$=$R_4$=H, $R_5$=$CH_3$, $R_6$=$C_6H_{11}$, n=1, m=0, X=Cl]

yield: 69%; melting point: 227-229° C.

$^1$H NMR (300 MHz, DMSO-$d_6$) δ 10.49 (s, 1H, HCl), 8.48 (br. s, 1H, NH), 7.51-6.86 (m, 4H, ArH), 7.10 (s, 1H, vinyl-H), 3.96 (s, 2H, 4-$CH_2$), 3.70 (s, 3H, $OCH_3$), 3.59 (s, 3H, N—$CH_3$), 2.15-1.67 (m, 17H, adamantyl).

KHG24420 (2-cyclohexylimino-3-ethyl-1,3-thiazolidine-4-yl)-N-(2-chloro-4-methylphenyl)-acetamide hydrochloride [$R_1$=H, $R_2$=2-Cl, $R_3$=4-$CH_3$, $R_4$=H, $R_5$=$C_2H_5$, $R_6$=$C_6H_{11}$, n=1, m=0, X=Cl]

yield: 82%; melting point: 115° C.

$^1$H NMR (300 MHz, DMSO-$d_6$) δ 10.90 (s, 1H, HCl), 9.61 (br. s, 1H, NH), 7.80-7.21 (m, 3H, ArH), 7.04 (s, 1H, vinyl-H), 4.20-4.11 (m, 2H, ethyl-$CH_2$), 3.95 (s, 2H, 4-$CH_2$), 3.35 (s, 3H, N—$CH_3$), 3.22 (br. s. 1H, adamantyl $C_1$H), 2.25 (s, 3H, $CH_3$), 1.97-1.26 (m, 17H, adamantyl), 1.16 (t, 3H, J=5.40 Hz, ethyl-$CH_3$).

KHG24421 (2-cyclohexylimino-3-(n-butyl)-1,3-thiazolidine-4-yl)-N-(2-chloro-4-methylphenyl)-acetamide hydrochloride [$R_1$=H, $R_2$=2-Cl, $R_3$=4-$CH_3$, $R_4$=H, $R_5$=n-$C_4H_9$, $R_6$=$C_6H_{11}$, n=1, m=0, X=Cl]

yield: 74%; melting point: 143-144° C.

$^1$H NMR (300 MHz, DMSO-$d_6$) δ 10.11 (s, 1H, HCl), 9.79 (d, J=5.8 Hz, 1H, NH), 7.81-7.26 (m, 3H, ArH), 7.05 (s, 1H, vinyl-H), 4.13 (t, 2H, J=5.72 Hz, N-butyl-$CH_2$), 3.97 (s, 2H, 4-$CH_2$), 3.34 (s, 3H, N—$CH_3$), 3.22 (br. s, 1H, cyclohexyl-$C_1$H), 2.25 (s, 3H, p-$CH_3$), 1.95-1.07 (m, 14H, N-butyl-$(CH_2)_2$ and cyclohexyl), 0.76 (t, J=5.36 Hz, 3H, N-butyl-$CH_3$).

KHG24422 (2-cyclohexylimino-3-benzyl-1,3-thiazolidine-4-yl)-N-(3,5-dichlorophenyl)-acetamide hydrochloride [$R_1$=H, $R_2$=3-Cl, $R_3$=5-Cl, $R_4$=H, $R_5$=$CH_2C_6H_5$, $R_6$=$C_6H_{11}$, n=1, m=0, X=Cl]

yield: 63%; melting point: 178-179° C.

$^1$H NMR (300 MHz, DMSO-$d_6$) δ 10.07 (s, 1H, HCl), 10.03 (d, J=5.5 Hz, 1H, NH), 7.65-7.08 (m, 8H, ArH), 7.15 (s, 1H, vinyl-H), 5.55 (s, 3H, N-benzyl-$CH_2$), 3.86 (s, 2H, 4-$CH_2$), 3.34 (s, 3H, N—$CH_3$), 3.25 (br. s, 1H, cyclohexyl-$C_1$H), 1.93-1.04 (m, 10H, cyclohexyl).

KHG24445 (2-cycloheptylimino-3-methyl-1,3-thiazolidine-4-yl)-N-(4-nitrophenyl)-acetamide hydrochloride [$R_1$=H, $R_2$=4-$NO_2$, $R_3$=$R_4$=H, $R_5$=$CH_3$, $R_6$=$C_7H_{13}$, n=1, m=0, X=Cl]

yield: 74%; melting point: 242° C.

$^1$H NMR (300 MHz, $CD_3OD$) δ 8.23-7.81 (m, 4H, Ar—H), 6.96 (s, 1H, vinyl-H), 4.03 (s, 2H, 4-$CH_2$), 3.59 (s, 3H, N—$CH_3$), 3.51-3.48 (m, 1H, cycloheptyl-$C_1$H), 2.14-1.54 (m, 12H, cycloheptyl-H).

KHG24446 (2-cycloheptylimino-3-methyl-1,3-thiazolidine-4-yl)-N-(4-aminophenyl)-acetamide hydrochloride [$R_1$=H, $R_2$=4—$NH_2$, $R_3$=$R_4$=H, $R_5$=$CH_3$, $R_6$=$C_7H_{13}$, n=1, m=, X=Cl]

yield: 77%; melting point: 77° C.

$^1$H NMR (300 MHz, $CD_3OD$) δ 7.29-6.68 (m, 4H, Ar—H), 6.87 (s, 1H, vinyl-H), 3.89 (s, 2H, 4-$CH_2$), 3.57 (s, 3H, N—$CH_3$), 3.52-3.41 (m, 1H, cycloheptyl-$C_1$H), 2.10-1.57 (m, 12H, cycloheptyl-H).

KHG24447 (2-cycloheptylimino-3-methyl-1,3-thiazolidine-4-yl)-N-(4-aminophenyl)-acetamide hydrochloride [$R_1$=H, $R_2$=4—NHMs, $R_3$=$R_4$=H, $R_5$=$CH_3$, $R_6$=$C_7H_{13}$, n=1, m=0, X=Cl]

yield: 31%; melting point: 176° C.

$^1$H NMR (300 MHz, $CD_3OD$) δ 7.60-7.00 (m, 8H, Ar—H), 6.73 (s, 1H, vinyl-H), 3.85 (s, 2H, 4-$CH_2$), 3.49 (s, 3H, N—CH$_3$), 3.56-3.45 (m, 1H, cycloheptyl-C$_1$H), 2.03-1.52 (m, 12H, cycloheptyl-H), 2.01 (s, 3H, —CH$_3$).

KHG24448 (2-cycloheptylimino-3-methyl-1,3-thiazolidine-4-yl)-N-(4-aminophenyl)-acetamide hydrochloride [R$_1$=H, R$_2$=4-NHTs, R$_3$=R$_4$=H, R$_5$=CH$_3$, R$_6$=C$_7$H$_{13}$, n=1, m=0, X=Cl]

yield: 8%; melting point: 130° C.

$^1$H NMR (300 MHz, CD$_3$OD) δ 7.76-7.12 (m, 8H, Ar—H), 6.94 (s, 1H, vinyl-H), 3.96 (s, 2H, 4-CH$_2$), 3.54-3.47 (m, 1H, cycloheptyl-C$_1$H), 3.60 (s, 3H, N—CH$_3$), 2.92 (s, 3H, p-CH$_3$), 2.16-1.58 (m, 12H, cycloheptyl-H).

KHG24449 (2-cycloheptylimino-3-methyl-1,3-thiazolidine-4-yl)-N-(4-aminobenzyl)-acetamide hydrochloride [R$_1$=H, R$_2$=4-NHTs, R$_3$=R$_4$=H, R$_5$=CH$_3$, R$_6$=C$_7$H$_{13}$, n=1, m=1, X=Cl]

yield: 83%; melting point: 143° C.

$^1$H NMR (300 MHz, CD$_3$OD) δ 7.64-7.04 (m, 8H, Ar—H), 6.78 (s, 1H, vinyl-H), 4.29 (s, 2H, benzyl-CH$_2$), 3.74 (s, 2H, 4-CH$_2$), 3.52-3.38 (m, 1H, cycloheptyl-C$_1$H), 3.48 (s, 3H, N—CH$_3$), 2.36 (s, 3H, p-CH$_3$), 2.08-1.53 (m, 12H, cycloheptyl-H).

KHG24450 (2-cycloheptylimino-3-methyl-1,3-thiazolidine-4-yl)-N-(4-aminobenzyl)-acetamide hydrochloride [R$_1$=H, R$_2$=4-NHMs, R$_3$=R$_4$=H, R$_5$=CH$_3$, R$_6$=C$_7$H$_{13}$, n=1, m=1, X=Cl]

yield: 82%; melting point: 68° C.

$^1$H NMR (300 MHz, CD$_3$OD) δ 7.31-7.20 (m, 4H, Ar—H), 6.85 (s, 1H, vinyl-H), 4.37 (s, 2H, benzyl-CH$_2$), 3.79 (s, 2H, 4-CH$_2$), 3.62-3.48 (m, 1H, cycloheptyl-C$_1$H), 3.35 (s, 3H, N—CH$_3$), 2.93 (s, 3H, CH$_3$), 1.83-1.60 (m, 12H, cycloheptyl-H).

KHG24480 (2-cyclohexylimino-3,5-dimethyl-1,3-thiazolidine-4-yl)-N-(4-chlorophenyl)-acetamide [R$_1$=CH$_3$, R$_2$=4-Cl, R$_3$=R$_4$=H, R$_5$=CH$_3$, R$_6$=C$_6$H$_{11}$, n=1, m=0]

yield: 66%; melting point: 262-264° C.

$^1$H NMR (300 MHz, DMSO-d$_6$) δ 10.60 (s, 1H, HCl), 9.34 (s, 1H, NH), 7.63-7.36 (m, 4H, ArH), 3.91 (s, 2H, CH$_2$), 3.52 (s, 3H, N—CH$_3$), 3.19 (m, 1H, cyclohexyl C$_1$-H), 2.29 (s, 3H, 5-CH$_3$), 2.00-1.16 (m, 10H, cyclohexyl-H).

KHG24481 (2-cyclohexylimino-3,5-dimethyl-1,3-thiazolidine-4-yl)-N-(4-methoxyphenyl)-acetamide [R$_1$=CH$_3$, R$_2$=4-OCH$_3$, R$_3$=R$_4$=H, R$_5$=CH$_3$, R$_6$=C$_6$H$_{11}$, n=1, m=0]

yield: 24%; melting point: 258-260° C.

$^1$H NMR (300 MHz, DMSO-d$_6$) δ 10.39 (s, 1H, HCl), 9.40 (s, 1H, NH), 7.52-6.87 (m, 4H, ArH), 3.90 (s, 2H, CH$_2$), 3.71 (s, 3H, OCH$_3$), 3.56 (s, 3H, N—CH$_3$), 3.19 (m, 1H, cyclohexyl C$_1$—H), 2.30 (s, 3H, 5-CH$_3$), 1.99-1.13 (m, 10H, cyclohexyl-H).

KHG24482 (2-cyclohexylimino-3,5-dimethyl-1,3-thiazolidine-4-yl)-N-(4-bromophenyl)-acetamide [R$_1$=CH$_3$, R$_2$=4-Br, R$_3$=R$_4$=H, R$_5$=CH$_3$, R$_6$=C$_6$H$_{11}$, n=1, m=0]

yield: 50%; melting point: 260-262° C.

$^1$H NMR (300 MHz, DMSO-d$_6$) δ 10.60 (s, 1H, HCl), 9.34 (s, 1H, NH), 7.58-7.49 (m, 4H, ArH), 3.91 (s, 2H, CH$_2$), 3.52 (s, 3H, NCH$_3$), 3.20 (m, 1H, cyclohexyl C$_1$-H), 2.29 (s, 3H, 5-CH$_3$), 1.99-1.13 (m, 10H, cyclohexyl-H).

KHG24483 (2-cyclohexylimino-3,5-dimethyl-1,3-thiazolidine-4-yl)-N-(3,5-dichlorophenyl)-acetamide [R$_1$=CH$_3$, R$_2$=3-Cl, R$_3$=5-Cl, R$_4$=H, R$_5$=CH$_3$, R$_6$=C$_6$H$_{11}$, n=1, m=0]

yield: 32%; melting point: 264-265° C.

$^1$H NMR (300 MHz, DMSO-d$_6$) δ 11.01 (s, 1H, HCl), 9.39 (s, 1H, NH), 7.70-7.31 (m, 3H, ArH), 3.96 (s, 2H, CH$_2$), 3.53 (s, 3H, NCH$_3$), 3.21 (m, 1H, cyclohexyl C$_1$-H), 2.30 (s, 3H, 5-CH$_3$), 1.99-1.10 (m, 10H, cyclohexyl-H).

KHG24484 (2-cyclohexylimino-3,5-dimethyl-1,3-thiazolidine-4-yl)-N-(2-fluoro-5-nitrophenyl)-acetamide [R$_1$=CH$_3$, R$_2$=2-F, R$_3$=5-NO$_2$, R$_4$=H, R$_5$=CH$_3$, R$_6$=C$_6$H$_{11}$, n=1, m=0]

yield: 5%; melting point: 249-251° C.

$^1$H NMR (300 MHz, DMSO-d$_6$) δ 10.68 (s, 1H, HCl), 9.47 (s, 1H, NH), 8.98-7.59 (m, 3H, ArH), 4.08 (s, 2H, CH$_2$), 3.56 (s, 3H, NCH$_3$), 3.24 (m, 1H, cyclohexyl C$_1$-H), 2.30 (s, 3H, 5-CH$_3$), 2.00-1.13 (m, 10H, cyclohexyl-H).

KHG24485 (2-cycloheptylimino-3,5-dimethyl-1,3-thiazolidine-4-yl)-N-(4-methoxyphenyl)-acetamide [R$_1$=CH$_3$, R$_2$=4-OCH$_3$, R$_3$=R$_4$=H, R$_5$=CH$_3$, R$_6$=C$_7$H$_{13}$, n=1, m=0]

yield: 20%; melting point: 250-251° C.

$^1$H NMR (300 MHz, DMSO-d$_6$) δ 10.32 (s, 1H, HCl), 9.38 (s, 1H, NH), 7.51-6.88 (m, 4H, ArH), 3.87 (s, 2H, CH$_2$), 3.71 (s, 3H, OCH$_3$), 3.54 (s, 3H, NCH$_3$), 3.39 (m, 1H, cycloheptyl C$_1$-H), 2.30 (s, 3H, 5-CH$_3$), 2.00-1.43 (m, 10H, cycloheptyl-H).

KHG24486 (2-cycloheptylimino-3,5-dimethyl-1,3-thiazolidine-4-yl)-N-(4-bromophenyl)-acetamide [R$_1$=CH$_3$, R$_2$=4-Br, R$_3$=R$_4$=H, R$_5$=CH$_3$, R$_6$=C$_7$H$_{13}$, n=1, m=0]

yield: 28%; melting point: 253-254° C.

$^1$H NMR (300 MHz, DMSO-d$_6$) δ 10.80 (s, 1H, HCl), 9.48 (s, 1H, NH), 7.61-7.49 (m, 4H, ArH), 3.95 (s, 2H, CH$_2$), 3.55 (s, 3H, NCH$_3$), 3.39 (m, 1H, cycloheptyl C$_1$-H), 2.30 (s, 3H, 5-CH$_3$), 2.00-1.46 (m, 10H, cycloheptyl-H).

KHG24516 (2-cycloheptylimino-3,5-dimethyl-1,3-thiazolidine-4-yl)-N-(4-n-butylphenyl)-acetamide hydrochloride [R$_1$=CH$_3$, R$_2$=4-n-C$_4$H$_9$, R$_3$=R$_4$=H, R$_5$=CH$_3$, R$_6$=C$_7$H$_{13}$, n=1, m=0, X=Cl]

yield: 20%; melting point: 247-249° C.

$^1$H NMR (300 MHz, DMSO-d$_6$) δ 10.28 (s, 1H, HCl), 9.29 (s, 1H, NH), 7.48-7.12 (m, 4H, ArH), 3.88 (s, 2H, CH$_2$), 3.52 (s, 3H, NCH$_3$), 3.39 (m, 1H, cycloheptyl C$_1$-H), 2.54 (m, 2H, CH$_2$CH$_2$CH$_2$CH$_3$), 2.30 (s, 3H, 5-CH$_3$), 2.01-1.43 (m, 12H, cycloheptyl-H), 1.50 (m, 2H, CH$_2$CH$_2$CH$_2$CH$_3$), 1.28 (m, J=5.5 Hz, 2H, CH$_2$CH$_2$CH$_2$CH$_3$), 0.88 (t, 3H, J=5.4 Hz, CH$_2$CH$_2$CH$_2$CH$_3$).

KHG24517 (2-cycloheptylimino-3,5-dimethyl-1,3-thiazolidine-4-yl)-N-(4-ethylphenyl)-acetamide hydrochloride [R$_1$=CH$_3$, R$_2$=4-C$_2$H$_5$, R$_3$=R$_4$=H, R$_5$=CH$_3$, R$_6$=C$_7$H$_{13}$, n=1, m=0, X=Cl]

yield: 25%; melting point: 262-264° C.

$^1$H NMR (300 MHz, DMSO-d$_6$) δ 10.29 (s, 1H, HCl), 9.29 (s, 1H, NH), 7.49-7.14 (m, 4H, ArH), 3.88 (s, 2H, CH$_2$), 3.52 (s, 3H, NCH$_3$), 3.39 (m, 1H, cycloheptyl C$_1$-H), 2.53 (m, 2H, J=7.5 Hz, CH$_2$CH$_3$), 2.30 (s, 3H, 5-CH$_3$), 1.99-1.47 (m, 12H, cycloheptyl-H), 1.14 (t, 3H, J=7.5 Hz, CH$_2$CH$_3$).

KHG24518 (2-cycloheptylimino-3,5-dimethyl-1,3-thiazolidine-4-yl)-N-(4-fluorophenyl)-acetamide hydrochloride [R$_1$=CH$_3$, R$_2$=4-F, R$_3$=R$_4$=H, R$_5$=CH$_3$, R$_6$=C$_7$H$_{13}$, n=1, m=0, X=Cl]

yield: 17%; melting point: 229-231° C.

$^1$H NMR (300 MHz, DMSO-d$_6$) δ 10.45 (s, 1H, HCl), 9.30 (s, 1H, NH), 7.62-7.14 (m, 4H, ArH), 3.89 (s, 2H, CH$_2$), 3.52 (s, 3H, NCH$_3$), 3.37 (m, 1H, cycloheptyl C$_1$-H), 2.30 (s, 3H, 5-CH$_3$), 2.00-1.44 (m, 12H, cycloheptyl-H).

KHG24519 (2-cycloheptylimino-3,5-dimethyl-1,3-thiazolidine-4-yl)-N-(4-isopropylphenyl)-acetamide hydrochloride [R$_1$=CH$_3$, R$_2$=4-CH(CH$_3$)$_2$, R$_3$=R$_4$=H, R$_5$=CH$_3$, R$_6$=C$_7$H$_{13}$, n=1, m=0, X=Cl]

yield: 15%; melting point: 260-262° C.

$^1$H NMR (300 MHz, DMSO-d$_6$) δ 10.35 (s, 1H, HCl), 9.32 (s, 1H, NH), 7.50-7.17 (m, 4H, ArH), 3.89 (s, 2H, CH$_2$), 3.53 (s, 3H, NCH$_3$), 3.39 (m, 1H, cycloheptyl C$_1$-H), 2.84 (m, 1H, J=5.1 Hz, isopropyl $C_1$—H), 2.30 (s, 3H, 5-CH$_3$), 2.00-1.44 (m, 12H, cycloheptyl-H), 1.17 (d, 6H, J=5.1 Hz, 2∪ isopropyl-CH$_3$).

KHG24520 (2-cycloheptylimino-3,5-dimethyl-1,3-thiazolidine-4-yl)-N-(4-trifluoromethylphenyl)-acetamide hydrochloride [$R_1$=CH$_3$, $R_2$=4-CF$_3$, $R_3$=$R_4$=H, $R_5$=CH$_3$, $R_6$=C$_7$H$_{13}$, n=1, m=0, X=Cl]

yield: 16%; melting point: 261-263° C.

$^1$H NMR (300 MHz, DMSO-d$_6$) δ 10.83 (s, 1H, HCl), 9.34 (s, 1H, NH), 7.69-7.83 (m, 4H, ArH), 3.97 (s, 2H, CH$_2$), 3.51 (s, 3H, NCH$_3$), 3.37 (m, 1H, cycloheptyl $C_1$-H), 2.30 (s, 3H, 5-CH$_3$), 1.44-1.98 (m, 12H, cycloheptyl-H).

KHG24521 (2-cycloheptylimino-3,5-dimethyl-1,3-thiazolidine-4-yl)-N-(4-t-butylphenyl)-acetamide hydrochloride [$R_1$=CH$_3$, $R_2$=4-t-C$_4$H$_9$, $R_3$=$R_4$=H, $R_5$=CH$_3$, $R_6$=C$_7$H$_{13}$, n=1, m=0, X=Cl]

yield: 18%; melting point: 239-241° C.

$^1$H NMR (300 MHz, DMSO-d$_6$) δ 10.30 (s, 1H, HCl), 9.28 (s, 1H, NH), 7.50-7.32 (m, 4H, ArH), 3.88 (s, 2H, CH$_2$), 3.52 (s, 3H, NCH$_3$), 3.38 (m, 1H, cycloheptyl $C_1$-H), 2.30 (s, 3H, 5-CH$_3$), 2.01-1.42 (m, 12H, cycloheptyl-H), 1.25 (s, 9H, tert-butyl-H).

KHG24522 (2-cyclohexylimino-3,5-dimethyl-1,3-thiazolidine-4-yl)-N-(3,5-difluoromethylphenyl)-acetamide hydrochloride [$R_1$=CH$_3$, $R_2$=3-CF$_3$, $R_3$=5-CF$_3$, $R_4$=H, $R_5$=CH$_3$, $R_6$=C$_6$H$_{11}$, n=1, m=0, X=Cl]

yield: 20%; melting point: 244-246° C.

$^1$H NMR (300 MHz, DMSO-d$_6$) δ 11.29 (s, 1H, HCl), 9.37 (s, 1H, NH), 8.29 (s, 2H, ArH), 7.82 (s, 1H, ArH), 3.99 (s, 2H, CH$_2$), 3.53 (s, 3H, NCH$_3$), 3.22 (m, 1H, cyclohexyl $C_1$—H), 2.31 (s, 3H, 5-CH$_3$), 2.00-1.31 (m, 10H, cyclohexyl-H).

KHG24523 (2-cyclohexylimino-3,5-dimethyl-1,3-thiazolidine-4-yl)-N-(4-ethylphenyl)-acetamide hydrochloride [$R_1$=CH$_3$, $R_2$=4-C$_2$H$_5$, $R_3$=$R_4$=H, $R_5$=CH$_3$, $R_6$=C$_6$H$_{11}$, n=1, m=0, X=Cl]

yield: 15%; melting point: 265-266° C.

$^1$H NMR (300 MHz, DMSO-d$_6$) δ 10.44 (s, 1H, HCl), 9.42 (s, 1H, NH), 7.51-7.13 (m, 4H, ArH), 3.91 (s, 2H, CH$_2$), 3.55 (s, 3H, NCH$_3$), 3.19 (m, 1H, cyclohexyl $C_1$-H), 2.55 (q, 2H, J=7.5 Hz, CH$_2$CH$_3$), 2.30 (s, 3H, 5-CH$_3$), 2.00-1.26 (m, 10H, cyclohexyl-H), 1.14 (t, 3H, J=7.5 Hz, CH$_2$CH$_3$).

KHG24524 (2-cyclohexylimino-3,5-dimethyl-1,3-thiazolidine-4-yl)-N-(4-trifluoromethoxyphenyl)-acetamide hydrochloride [$R_1$=CH$_3$, $R_2$=4-OCF$_3$, $R_3$=$R_4$=H, $R_5$=CH$_3$, $R_6$=C$_6$H$_{11}$, n=1, m=0, X=Cl]

yield: 20%; melting point: 178-180° C.

$^1$H NMR (300 MHz, DMSO-d$_6$) δ 10.57 (s, 1H, HCl), 9.36 (s, 1H, NH), 7.71-7.32 (m, 4H, ArH), 3.79 (s, 2H, CH$_2$), 3.32 (s, 3H, NCH$_3$), 2.96 (m, 1H, cyclohexyl $C_1$-H), 2.19 (s, 3H, 5-CH$_3$), 1.84-1.15 (m, 10H, cyclohexyl-H).

KHG24525 (2-cyclohexylimino-3,5-dimethyl-1,3-thiazolidine-4-yl)-N-(4-fluorophenyl)-acetamide hydrochloride [$R_1$=CH$_3$, $R_2$=4-F, $R_3$=$R_4$=H, $R_5$=CH$_3$, $R_6$=C$_6$H$_{11}$, n=1, m=0, X=Cl]

yield: 33%; melting point: 267-269° C.

$^1$H NMR (300 MHz, DMSO-d$_6$) δ 10.56 (s, 1H, HCl), 9.38 (s, 1H, NH), 7.64-7.13 (m, 4H, ArH), 3.91 (s, 2H, CH$_2$), 3.54 (s, 3H, NCH$_3$), 3.20 (m, 1H, cyclohexyl $C_1$-H), 2.30 (s, 3H, 5-CH$_3$), 2.00-1.30 (m, 10H, cyclohexyl-H).

KHG24526 (2-cyclohexylimino-3,5-dimethyl-1,3-thiazolidine-4-yl)-N-(4-isopropylphenyl)-acetamide hydrochloride [$R_1$=CH$_3$, $R_2$=4-CH(CH$_3$)$_2$, $R_3$=$R_4$=H, $R_5$=CH$_3$, $R_6$=C$_6$H$_{11}$, n=1, m=0, X=Cl]

yield: 47%; melting point: 265-267° C.

$^1$H NMR (300 MHz, DMSO-d$_6$) δ 10.38 (s, 1H, HCl), 9.37 (s, 1H, NH), 7.51-7.17 (m, 4H, ArH), 3.89 (s, 2H, CH$_2$), 3.54 (s, 3H, N—CH$_3$), 3.20 (m, 1H, cyclohexyl $C_1$—H), 2.83 (m, 1H, J=6.7 Hz, isopropyl $C_1$—H), 2.30 (s, 3H, 5-CH$_3$), 2.00-1.26 (m, 10H, cyclohexyl-H), 1.17 (d, 6H, J=6.7 Hz, 2∪ isopropyl-CH$_3$).

KHG24527 (2-cyclohexylimino-3,5-dimethyl-1,3-thiazolidine-4-yl)-N-(4-trifluoromethylphenyl)-acetamide hydrochloride [$R_1$=CH$_3$, $R_2$=4-CF$_3$, $R_3$=$R_4$=H, $R_5$=CH$_3$, $R_6$=C$_6$H$_{11}$, n=1, m=0, X=Cl]

yield: 8%; melting point: 190-192° C.

$^1$H NMR (300 MHz, DMSO-d$_6$) δ 10.77 (s, 1H, HCl), 9.40 (s, 1H, NH), 7.82-7.68 (m, 4H, ArH), 3.84 (s, 2H, CH$_2$), 3.39 (s, 3H, NCH$_3$), 2.97 (m, 1H, cyclohexyl $C_1$—H), 2.20 (s, 3H, 5-CH$_3$), 1.88-1.24 (m, 10H, cyclohexyl-H).

KHG24528 (2-cyclohexylimino-3-methyl-1,3-thiazolidine-4-yl)-N-(3-isopropylphenyl)-acetamide hydrochloride [$R_1$=H, $R_2$=4-CH(CH$_3$)$_2$, $R_3$=$R_4$=H, $R_5$=CH$_3$, $R_6$=C$_6$H$_{11}$, n=1, m=0, X=Cl]

yield: 95%; melting point: 160° C.

$^1$H NMR (300 MHz, DMSO-d$_6$) δ 10.58 (s, 1H, HCl), 9.64 (s, 1H, NH), 7.52-6.94 (m, 4H, ArH), 7.04 (s, 1H, vinyl H), 3.96 (s, 2H, CH$_2$), 3.58 (s, 3H, NCH$_3$), 3.28 (m, 1H, cyclohexyl CH), 2.83 (septet, 1H, J=6.9 Hz, isopropyl C—H), 1.99-1.27 (m, 10H, cyclohexyl-H), 1.17 (d, 6H, J=6.9 Hz, isopropyl-H).

KHG24529 (2-cyclohexylimino-3-methyl-1,3-thiazolidine-4-yl)-N-(3,5-ditrifluoromethylphenyl)-acetamide hydrochloride [$R_1$=H, $R_2$=3-CF$_3$, $R_3$=5-CF$_3$, $R_5$=CH$_3$, $R_6$=C$_6$H$_{11}$, n=1, m=0, X=Cl]

yield: 14%; melting point: 144° C.

$^1$H NMR (300 MHz, DMSO-d$_6$) δ 11.39 (s, 1H, HCl), 9.45 (m, 1H, NH), 8.30 (s, 2H, ArH), 7.81 (s, 1H, ArH), 7.08 (s, 1H, vinyl H), 4.05 (s, 2H, CH$_2$), 3.54 (s, 3H, N—CH$_3$), 3.27-3.15 (m, 1H, cyclohexyl-CH), 1.99-1.08 (m, 10H, cyclohexyl-H).

KHG24530 (2-cyclohexylimino-3-methyl-1,3-thiazolidine-4-yl)-N-(2,3-dichlorophenyl)-acetamide hydrochloride [$R_1$=H, $R_2$=2-Cl, $R_3$=3-Cl, $R_4$=H, $R_5$=CH$_3$, $R_6$=C$_6$H$_{11}$, n=1, m=0, X=Cl]

yield: 89%; melting point: 215° C.

$^1$H NMR (300 MHz, DMSO-d$_6$) δ 10.24 (s, 1H, HCl), 9.55 (s, 1H, NH), 7.67-7.34 (m, 3H, ArH), 7.05 (s, 1H, vinyl H), 4.04 (s, 2H, CH$_2$), 3.56 (s, 3H, CH$_3$), 3.27-3.21 (m, 1H, cyclohexyl C—H), 1.99-1.03 (m, 10H, cyclohexyl-H).

KHG24531 (2-cyclohexylimino-3-methyl-1,3-thiazolidine-4-yl)-N-(3,4-dichlorophenyl)-acetamide hydrochloride [$R_1$=H, $R_2$=3-Cl, $R_3$=4-Cl, $R_4$=H, $R_5$=CH$_3$, $R_6$=C$_6$H$_{11}$, n=1, m=0, X=Cl]

yield: 95%; melting point: 223° C.

$^1$H NMR (300 MHz, DMSO-d$_6$) δ 11.12 (s, 1H, HCl), 9.58 (s, 1H, NH), 8.05-7.55 (m, 3H, ArH), 4.54 (s, 2H, CH$_2$), 3.58 (s, 3H, CH$_3$), 3.31-3.21 (m, 1H, cyclohexyl C—H), 2.02-1.11 (m, 10H, cyclohexyl-H).

KHG24532 (2-cyclohexylimino-3-methyl-1,3-thiazolidine-4-yl)-N-(2,5-dichlorophenyl)-acetamide hydrochloride [$R_1$=H, $R_2$=2-Cl, $R_3$=5-Cl, $R_4$=H, $R_5$=CH$_3$, $R_6$=C$_6$H$_{11}$, n=1, m=0, X=Cl]

yield: 88%; melting point: 208° C.

$^1$H NMR (300 MHz, DMSO-d$_6$) δ 10.18 (s, 1H, HCl), 9.55 (s, 1H, NH), 7.87 (d, 1H, J=2.4 Hz, ArH), 7.55 (d, 1H, J=8.7 Hz, ArH), 7.29 (dd, 1H, J=8.7, 2.4 Hz, ArH), 7.06 (s, 1H, vinyl H), 4.05 (s, 2H, CH$_2$), 3.57 (s, 3H, CH$_3$), 3.31-3.20 (m, 1H, cyclohexyl CH), 1.03-2.00 (m, 10H, cyclohexyl-H).

KHG24533 (2-cyclohexylimino-3-methyl-1,3-thiazolidine-4-yl)-N-(2,4,5-trichlorophenyl)-acetamide hydrochloride [$R_1$=H, $R_2$=2-Cl, $R_3$=4-Cl, $R_4$=5-Cl, $R_5$=CH$_3$, $R_6$=C$_6$H$_{11}$, n=1, m=0, X=Cl]

yield: 99%; melting point: 186° C.

$^1$H NMR (300 MHz, DMSO-d$_6$) δ 10.25 (s, 1H, HCl), 9.50 (s, 1H, NH), 8.08 (s, 1H, ArH), 7.95 (s, 1H, ArH), 7.06 (s, 1H, vinyl H), 4.06 (s, 2H, CH$_2$), 3.55 (s, 3H, CH$_3$), 3.31-3.19 (m, 1H, cyclohexyl C—H), 1.96-1.13 (m, 10H, cyclohexyl-H).

KHG24534 (2-cyclohexylimino-3-methyl-1,3-thiazolidine-4-yl)-N-(3,5-difluorophenyl)-acetamide hydrochloride [R$_1$=H, R$_2$=3-F, R$_3$=5-F, R$_4$=H, R$_5$=CH$_3$, R$_6$=C$_6$H$_{11}$, n=1, m=0, X=Cl]

yield: 96%; melting point: 240° C.

$^1$H NMR (300 MHz, DMSO-d$_6$) δ 11.14 (s, 1H, HCl), 9.48 (s, 1H, NH), 7.35 (m, 2H, ArH), 7.05 (s, 1H, vinyl H), 6.93 (m, 1H, ArH), 4.00 (s, 2H, CH$_2$), 3.53 (s, 3H, CH$_3$), 3.31-3.21 (m, 1H, cyclohexyl C—H), 2.02-1.02 (m, 10H, cyclohexyl-H).

KHG24535 (2-cyclohexylimino-3-cyclohexyl-1,3-thiazolidine-4-yl)-N-(4-methylphenyl)-acetamide hydrochloride [R$_1$=H, R$_2$=4-CH$_3$, R$_3$=R$_4$=H, R$_5$=C$_6$H$_{11}$, R$_6$=C$_6$H$_{11}$, n=1, m=0, X=Cl]

yield: 94%; melting point: 251° C.

$^1$H NMR (300 MHz, DMSO-d$_6$) δ 10.58 (s, 1H, HCl), 7.49-7.11 (m, 4H, ArH), 7.05 (s, 1H, vinyl H), 4.02 (s, 2H, CH$_2$), 3.30-3.20 (m, 2H, cyclohexyl-CH), 2.25 (s, 3H, ArCH$_3$), 1.94-1.15 (m, 20H, cyclohexyl-H).

KHG24536 (2-cyclohexylimino-3-cyclohexyl-1,3-thiazolidine-4-yl)-N-(4-fluorophenyl)-acetamide hydrochloride [R$_1$=H, R$_2$=4-F, R$_3$=R$_4$=H, R$_5$=C$_6$H$_{11}$, R$_6$=C$_6$H$_{11}$, n=1, m=0, X=Cl]

yield: 91%; melting point: 256° C.

$^1$H NMR (300 MHz, DMSO-d$_6$) δ 10.79 (s, 1H, HCl), 7.68-7.12 (m, 4H, ArH), 7.05 (s, 1H, vinyl H), 4.05 (s, 2H, CH$_2$), 3.30-3.22 (m, 2H, cyclohexyl-CH), 2.05-1.10 (m, 20H, cyclohexyl-H).

KHG24537 (2-cyclohexylimino-3-cyclohexyl-1,3-thiazolidine-4-yl)-N-(3-chloro-4-methylphenyl)-acetamide hydrochloride [R$_1$=H, R$_2$=3-Cl, R$_3$=4-CH$_3$, R$_4$=H, R$_5$=C$_6$H$_{11}$, R$_6$=C$_6$H$_{11}$, n=1, m=0, X=Cl]

yield: 99%; melting point: 173° C.

$^1$H NMR (300 MHz, DMSO-d$_6$) δ 11.10 (s, 1H, HCl), 7.82-7.25 (m, 3H, ArH), 7.08 (s, 1H, vinyl H), 4.11 (s, 2H, CH$_2$), 3.36-3.22 (m, 2H, cyclohexyl-CH), 2.27 (s, 3H, CH$_3$), 2.02-1.12 (m, 20H, cyclohexyl-H).

KHG24538 (2-cyclohexylimino-3-cyclohexyl-1,3-thiazolidine-4-yl)-N-(4-ethylphenyl)-acetamide hydrochloride [R$_1$=H, R$_2$=4-C$_2$H$_5$, R$_3$=R$_4$=H, R$_5$=C$_6$H$_{11}$, R$_6$=C$_6$H$_{11}$, n=1, m=0, X=Cl]

yield: 91%; melting point: 236° C.

$^1$H NMR (300 MHz, DMSO-d$_6$) δ 10.59 (s, 1H, HCl), 7.55-7.15 (m, 4H, ArH), 7.08 (s, 1H, vinyl H), 4.10 (s, 2H, CH$_2$), 3.35-3.31 (m, 2H, cyclohexyl-CH), 2.60 (m, 2H, CH$_2$CH$_3$), 2.09-1.21 (m, 20H, cyclohexyl-H), 1.18 (m, 3H, CH$_2$CH$_3$).

KHG24539 (2-cyclohexylimino-3-cyclohexyl-1,3-thiazolidine-4-yl)-N-(4-chlorophenyl)-acetamide hydrochloride [R$_1$=H, R$_2$=4-Cl, R$_3$=R$_4$=H, R$_5$=C$_6$H$_{11}$, R$_6$=C$_6$H$_{11}$, n=1, m=0, X=Cl]

yield: 99%; melting point: 231° C.

$^1$H NMR (300 MHz, DMSO-d$_6$) δ 10.78 (s, 1H, HCl), 7.69-7.38 (m, 4H, ArH), 7.08 (s, 1H, vinyl H), 4.08 (s, 2H, CH$_2$), 3.39-3.31 (m, 2H, cyclohexyl-CH), 2.02-1.03 (m, 20H, cyclohexyl-H).

KHG24540 (2-cyclohexylimino-3-cyclohexyl-1,3-thiazolidine-4-yl)-N-(5-chloro-2-fluorophenyl)-acetamide hydrochloride [R$_1$=H, R$_2$=2-F, R$_3$=5-Cl, R$_4$=H, R$_5$=C$_6$H$_{11}$, R$_6$=C$_6$H$_{11}$, n=1, m=0, X=Cl]

yield: 96%; melting point: 158° C.

$^1$H NMR (300 MHz, DMSO-d$_6$) δ 10.59 (s, 1H, HCl), 7.98-7.22 (m, 3H, ArH), 7.05 (s, 1H, vinyl H), 4.21 (s, 2H, CH$_2$), 3.28-3.20 (m, 2H, cyclohexyl-CH), 2.01-0.85 (m, 20H, cyclohexyl-H).

KHG24541 (2-cyclohexylimino-3-cyclohexyl-1,3-thiazolidine-4-yl)-N-(4-n-butylphenyl)-acetamide hydrochloride [R$_1$=H, R$_2$=4-n-C$_4$H$_9$, R$_3$=R$_4$=H, R$_5$=C$_6$H$_{11}$, R$_6$=C$_6$H$_{11}$, n=1, m=0, X=Cl]

yield: 89%; melting point: 226° C.

$^1$H NMR (300 MHz, DMSO-d$_6$) δ 10.79 (s, 1H, HCl), 7.52-7.11 (m, 4H, ArH), 7.06 (s, 1H, vinyl H), 3.32-3.21 (m, 2H, cyclohexyl-CH), 1.96-0.86 (m, 20H, cyclohexyl-H), 1.07-1.02 (m, 11H, butyl-H).

KHG24542 (2-cyclohexylimino-3-cyclohexyl-1,3-thiazolidine-4-yl)-N-(4-bromophenyl)-acetamide hydrochloride [R$_1$=H, R$_2$=4-Br, R$_3$=R$_4$=H, R$_5$=C$_6$H$_{11}$, R$_6$=C$_6$H$_{11}$, n=1, m=0, X=Cl]

yield: 80%; melting point: 264° C.

$^1$H NMR (300 MHz, DMSO-d$_6$) δ 10.68 (s, 1H, HCl), 7.55-7.53 (m, 4H, ArH), 7.06 (s, 1H, vinyl H), 4.03 (s, 2H, CH$_2$), 3.31-3.28 (m, 2H, cyclohexyl-CH), 2.02-1.31 (m, 20H, cyclohexyl-H).

KHG24543 (2-cyclohexylimino-3-cyclohexyl-1,3-thiazolidine-4-yl)-N-(4-trifluoromethylphenyl)-acetamide hydrochloride [R$_1$=H, R$_2$=4-CF$_3$, R$_3$=R$_4$=H, R$_5$=C$_6$H$_{11}$, R$_6$=C$_6$H$_{11}$, n=1, m=0, X=Cl]

yield 91%; melting point: 232° C.

$^1$H NMR (300 MHz, DMSO-d$_6$) δ 10.68 (s, 1H, HCl), 7.52-7.32 (m, 4H, ArH), 7.06 (s, 1H, vinyl H), 4.04 (s, 1H, CH$_2$), 3.35-3.21 (m, 2H, cyclohexyl-CH), 2.01-1.02 (m, 20H, cyclohexyl-H).

KHG24544 (2-cyclohexylimino-3-cyclohexyl-1,3-thiazolidine-4-yl)-N-(4-chlorobenzyl)-acetamide hydrochloride [R$_1$=H, R$_2$=4-Cl, R$_3$=R$_4$=H, R$_5$=C$_6$H$_{11}$, R$_6$=C$_6$H$_{11}$, n=1, m=1, X=Cl]

yield: 96%; melting point: 152° C.

$^1$H NMR (300 MHz, DMSO-d$_6$) δ 8.99 (s, 1H, NH), 7.50-7.31 (m, 4H, ArH), 6.99 (s, 1H, vinyl H), 4.27 (s, 2H, CH$_2$), 3.86 (s, 2H, CH$_2$C$_6$H$_5$), 3.35-3.21 (m, 2H, cyclohexyl-CH), 1.96-1.12 (m, 20H, cyclohexyl-H).

KHG24545 (2-cyclohexylimino-3-cyclohexyl-1,3-thiazolidine-4-yl)-N-(4-t-butylphenyl)-acetamide hydrochloride [R$_1$=H, R$_2$=4-t-C$_4$H$_9$, R$_3$=R$_4$=H, R$_5$=C$_6$H$_{11}$, R$_6$=C$_6$H$_{11}$, n=1, m=0, X=Cl]

yield: 91%; melting point: 244° C.

$^1$H NMR (300 MHz, DMSO-d$_6$) δ 10.69 (s, 1H, HCl), 7.53-7.32 (m, 4H, ArH), 7.06 (s, 1H, vinyl H), 4.05 (s, 2H, CH$_2$), 3.33-3.21 (m, 2H, cyclohexyl-CH), 1.26 (s, 9H, C(CH$_3$)$_3$), 1.94-1.03 (m, 20H, cyclohexyl-H).

KHG24546 (2-cyclohexylimino-3-cyclohexyl-1,3-thiazolidine-4-yl)-N-(3,5-ditrifluoromethylphenyl)-acetamide hydrochloride [R$_1$=H, R$_2$=3-CF$_3$, R$_3$=5-CF$_3$, R$_4$=H, R$_5$=C$_6$H$_{11}$, R$_6$=C$_6$H$_{11}$, n=1, m=0, X=Cl]

yield 99%; melting point: 160° C.

$^1$H NMR (300 MHz, DMSO-d$_6$) δ 12.01 (s, 1H, HCl), 8.44-7.91 (m, 3H, ArH), 7.09 (s, 1H, vinyl H), 4.21 (s, 2H, CH$_2$), 3.39-3.20 (m, 2H, cyclohexyl-CH), 2.21-1.12 (m, 20H, cyclohexyl-H).

KHG24547 (2-cyclohexylimino-3-cyclohexyl-1,3-thiazolidine-4-yl)-N-(2-trifluoromethylbenzyl)-acetamide hydrochloride [R$_1$=H, R$_2$=2-CF$_3$, R$_3$=R$_4$=H, R$_5$=C$_6$H$_{11}$, R$_6$=C$_6$H$_{11}$, n=1, m=1, X=Cl]

yield: 91%; melting point: 180° C.

$^1$H NMR (300 MHz, DMSO-d$_6$) δ 8.91 (s, 1H, NH), 7.74-7.47 (m, 4H, ArH), 7.00 (s, 1H, vinyl H), 4.68 (s, 2H, CH$_2$), 3.90 (s, 2H, benzyl-CH$_2$), 3.33-3.21 (m, 2H, cyclohexyl-CH), 1.92-1.11 (m, 20H, cyclohexyl-H).

KHG24548 (2-cyclohexylimino-3-cyclohexyl-1,3-thiazolidine-4-yl)-N-(4-phenoxyphenyl)-acetamide hydrochloride [$R_1$=H, $R_2$=4-$OC_6H_5$, $R_3$=$R_4$=H, $R_5$=$C_6H_{11}$, $R_6$=$C_6H_{11}$, n=1, m=0, X=Cl]

yield: 97%; melting point: 206° C.

$^1$H NMR (300 MHz, DMSO-$d_6$) δ 10.95 (s, 1H, HCl), 7.66-7.08 (m, 9H, ArH), 6.98 (s, 1H, vinyl H), 4.08 (s, 2H, $CH_2$), 3.25-3.21 (m, 2H, cyclohexyl-CH), 2.15-1.09 (m, 20H, cyclohexyl-H).

KHG24549 (2-cyclohexylimino-3-cyclohexyl-1,3-thiazolidine-4-yl)-N-(3,5-dichlorophenyl)-acetamide hydrochloride [$R_1$=H, $R_2$=3-Cl, $R_3$=5-Cl, =H, $R_5$=$C_6H_{11}$, $R_6$=$C_6H_{11}$, n=1, m=0, X=Cl]

yield: 99%; melting point: 202° C.

$^1$H NMR (300 MHz, DMSO-$d_6$) δ 10.96 (s, 1H, HCl), 7.77-7.29 (m, 3H, ArH), 7.09 (s, 1H, vinyl H), 4.16 (s, 1H, $CH_2$), 3.26-3.21 (m, 2H, cyclohexyl-CH), 1.03-1.97 (m, 20H, cyclohexyl-H).

KHG24622 (2-cycloheptylimino-3-methyl-1,3-thiazolidine-4-yl)-N-phenyl-carboxamide [$R_1$=H, $R_2$=$R_3$=$R_4$=H, $R_5$=$CH_3$, $R_6$=$C_7H_{13}$, n=0, m=1]

yield: 59.3% melting point: 208° C.

$^1$H NMR (300 MHz, CDCl$_3$) δ 7.37-7.27 (m, 5H, ArH), 6.65 (s, 1H, NH), 6.26 (s, 1H, vinyl H), 4.49 (d, 2H, J=5.79 Hz, $CH_2NH$), 3.40 (s, 3H, $NCH_3$), 2.89-2.85 (m, 1H, cycloheptyl-H), 1.82-1.27 (m, 12H, cycloheptyl-H).

KHG24623 (2-cycloheptylimino-3-methyl-1,3-thiazolidine-4-yl)-N-phenyl-carboxamide hydrochloride [$R_1$=H, $R_2$=$R_3$=$R_4$=H, $R_5$=$CH_3$, $R_6$=$C_7H_{13}$, n=0, m=1, X=Cl]

yield: 100.0%; melting point: 211.4° C.

$^1$H NMR (300 MHz, DMSO-$d_6$) δ 9.98 (d, 1H, J=7.62 Hz, HCl), 9.69 (t, 1H, J=5.78 Hz, NH), 7.70 (s, 1H, vinyl H), 7.36-7.24 (m, 5H, ArH), 4.41 (d, 2H, J=5.88 Hz, $CH_2NH$), 3.78 (s, 3H, $NCH_3$), 3.50-3.43 (m, 1H, cycloheptyl-H), 2.00-1.42 (m, 12H, cycloheptyl-H).

KHG24624 (2-cycloheptylimino-3-methyl-1,3-thiazolidine-4-yl)-N-(2-chlorophenyl)-carboxamide [$R_1$=H, $R_2$=2-Cl, $R_3$=$R_4$=H, $R_5$=$CH_3$, $R_6$=$C_7H_{13}$, n=0, m=1]

yield: 60.3%; melting point: 198.4° C.

$^1$H NMR (300 MHz, DMSO-$d_6$) δ 9.04 (t, 1H, J=5.52 Hz, NH), 7.47-7.28 (m, 5H, ArH), 6.74 (s, 1H, vinyl H), 4.43 (d, 2H, J=5.67 Hz, $CH_2NH$), 3.25 (s, 3H, $NCH_3$), 2.88 (m, 1H, cycloheptyl-H), 1.72-1.43 (m, 12H, cycloheptyl-H).

KHG24625 (2-cycloheptylimino-3-methyl-1,3-thiazolidine-4-yl)-N-(2,5-difluorophenyl)-carboxamide [$R_1$=H, $R_2$=2-F, $R_3$=5-F, $R_4$=H, $R_5$=$CH_3$, $R_6$=$C_7H_{13}$, n=0, m=1]

yield: 78.6%; melting point: 184.2° C.

$^1$H NMR (300 MHz, CDCl$_3$) δ 7.12-6.93 (m, 4H, ArH and NH), 6.63 (s, 1H, vinyl H), 4.54 (d, 2H, J=5.97 Hz, $CH_2$), 3.54 (s, 3H, $NCH_3$), 2.98-2.97 (m, 1H, cycloheptyl-H), 1.83-1.13 (m, 12H, cycloheptyl-H).

KHG24626 (2-cycloheptylimino-3-methyl-1,3-thiazolidine-4-yl)-N-(2,5-difluorophenyl)-carboxamide hydrochloride [$R_1$=H, $R_2$=2-F, $R_3$=5-F, $R_4$=H, $R_5$=$CH_3$, $R_6$=$C_7H_{13}$, n=0, m=1, X=Cl]

yield: 95.1%; melting point: 187.9° C.

$^1$H NMR (300 MHz, DMSO-$d_6$) δ 10.00 (d, 1H, HCl), 9.74 (t, 1H, J=4.71 Hz, NH), 7.77 (s, 1H, vinyl H), 7.28-7.14 (m, 3H, ArH), 4.43 (d, 2H, J=5.52 Hz, $CH_2NH$), 3.72 (s, 3H, $NCH_3$), 3.44 (m, 1H, cycloheptyl-H), 2.07-1.42 (m, 12H, cycloheptyl-H).

KHG24627 (2-cycloheptylimino-3-methyl-1,3-thiazolidine-4-yl)-N-(3,4-difluorophenyl)-carboxamide [$R_1$=H, $R_2$=3-F, $R_3$=4-F, $R_4$=H, $R_5$=$CH_3$, $R_6$=$C_7H_{13}$, n=0, m=1]

yield: 24.5%; melting point: 209.6° C.

$^1$H NMR (300 MHz, DMSO-$d_6$) δ 9.84 (d, 1H, J=4.98 Hz, HCl), 9.70 (t, 1H, J=5.40 Hz, NH), 7.72 (s, 1H, vinyl H), 7.43-7.19 (m, 3H, ArH), 4.40 (d, 2H, J=5.73 Hz, $CH_2NH$), 3.71 (s, 3H, $NCH_3$), 3.46 (m, 1H, cycloheptyl-H), 2.00-1.43 (m, 12H, cycloheptyl-H).

KHG24628 (2-cycloheptylimino-3-methyl-1,3-thiazolidine-4-yl)-N-(4-methylphenyl)-carboxamide [$R_1$=H, $R_2$=4-$CH_3$, $R_3$=$R_4$=H, $R_5$=$CH_3$, $R_6$=$C_7H_{13}$, n=0, m=1]

yield: 69.1%; melting point: 114.9° C.

$^1$H NMR (300 MHz, CDCl$_3$) δ 7.20 (d, 2H, J=8.19 Hz, ArH-2' and ArH-6'), 7.16 (d, 2H, J=8.15 Hz, ArH-3' and ArH-5'), 6.43 (s, 1H, NH), 6.29 (s, 1H, vinyl H), 4.48 (d, 2H, J=5.71 Hz, $CH_2NH$), 3.45 (s, 3H, $NCH_3$), 2.35 (s, 3H, $CH_3$), 2.93-2.87 (m, 1H, cycloheptyl-H), 1.84-1.42 (m, 12H, cycloheptyl-H).

KHG24629 (2-cycloheptylimino-3-methyl-1,3-thiazolidine-4-yl)-N-(4-methylphenyl)-carboxamide hydrochloride [$R_1$=H, $R_2$=4-$CH_3$, $R_3$=$R_4$=H, $R_5$=$CH_3$, $R_6$=$C_7H_{13}$, n=0, m=1, X=Cl]

yield: 73.3%; melting point: 202.1° C.

$^1$H NMR (300 MHz, DMSO-$d_6$) δ 9.95 (s, 1H, HCl), 9.62 (t, 1H, NH), 7.66 (s, 1H, vinyl H), 7.21 (d, 2H, J=7.88 Hz, ArH-2' and ArH-6'), 7.13 (d, 2H, J=7.85 Hz, ArH-3' and ArH-5'), 4.36 (d, 2H, J=5.78 Hz, $CH_2NH$), 3.73 (s, 3H, $NCH_3$), 3.44-3.42 (m, 1H, cycloheptyl-H), 2.27 (s, 3H, $CH_3$), 2.00-1.42 (m, 12H, cycloheptyl-H).

KHG24630 (2-cycloheptylimino-3-methyl-1,3-thiazolidine-4-yl)-N-(3,5-ditrifluoromethylphenyl)-carboxamide [$R_1$=H, $R_2$=3-$CF_3$, $R_3$=5-$CF_3$, $R_4$=H, $R_5$=$CH_3$, $R_6$=$C_7H_{13}$, n=0, m=1]

yield: 74.4%; melting point: 124.8° C.

$^1$H NMR (300 MHz, CDCl$_3$) δ 7.82 (s, 1H, ArH-4'), 7.79 (s, 2H, ArH-2' and ArH-6'), 6.92 (s, 1H, NH), 6.51 (s, 1H, vinyl H), 4.66 (d, 2H, J=6.09 Hz, $CH_2NH$), 3.50 (s, 3H, $NCH_3$), 2.94-2.91 (m, 1H, cycloheptyl-H), 1.84-1.45 (m, 12H, cycloheptyl-H).

KHG24631 (2-cycloheptylimino-3-methyl-1,3-thiazolidine-4-yl)-N-(4-fluorophenyl)-carboxamide [$R_1$=H, $R_2$=4-F, $R_3$=$R_4$=H, $R_5$=$CH_3$, $R_6$=$C_7H_{13}$, n=0, m=1]

yield: 79.4%; melting point: 169.6° C.

$^1$H NMR (300 MHz, DMSO-$d_6$) δ 10.46 (s, 1H, NH), 7.72 (s, 1H, vinyl H), 7.64 (d, 1H, ArH-3'), 7.40-7.35 (m, 2H, ArH-4' and ArH-6'), 7.27-7.22 (m, 1H, ArH-5'), 4.45 (d, 2H, J=5.59 Hz, $CH_2NH$), 3.72 (s, 3H, $NCH_3$), 3.45-3.40 (m, 1H, cycloheptyl-H), 2.01-1.43 (m, 12H, cycloheptyl-H).

KHG24632 (2-cycloheptylimino-3-methyl-1,3-thiazolidine-4-yl)-N-(3,5-ditrifluoromethylphenyl)-carboxamide hydrochloride [$R_1$=H, $R_2$=3-$CF_3$, $R_3$=5-$CF_3$, $R_5$=$CH_3$, $R_6$=$C_7H_{13}$, n=0, m=1, X=Cl]

yield: 91.5%; melting point: 202.0° C.

$^1$H NMR (300 MHz, DMSO-$d_6$) δ 10.06 (s, 1H, HCl), 9.99 (t, 1H, NH), 8.06 (s, 2H, ArH-2' and ArH-6'), 7.99 (s, 1H, ArH-4'), 7.82 (s, 1H, vinyl H), 4.60 (d, 2H, J=5.66 Hz, $CH_2NH$), 3.73 (s, 3H, $NCH_3$), 3.45-3.40 (m, 1H, cycloheptyl-H), 1.99-1.42 (m, 12H, cycloheptyl-H).

KHG24633
(2-cycloheptylimino-3-methyl-1,3-thiazolidine-4-yl)-N-(4-bromophenyl)-carboxamide [$R_1$=H, $R_2$=4-Br, $R_3$=$R_4$=H, $R_5$=$CH_3$, $R_6$=$C_7H_{13}$, n=0, m=1]

yield: 67.1%; melting point: 109.2° C.

$^1$H NMR (300 MHz, DMSO-$d_6$) δ 9.87 (br. s, 1H, HCl), 9.66-9.62 (t, 1H, J=5.5 Hz, NH), 7.21-7.65 (m, 4H, Ar—H), 7.21 (s, 1H, vinyl-H), 4.45 (d, 2H, J=5.5 Hz, benzyl-$CH_2$), 3.47-3.36 (m, 1H, cycloheptyl-$C_1$H), 3.35 (s, 3H, N—$CH_3$), 2.00-1.43 (m, 12H, cycloheptyl-H).

KHG24634 (2-cycloheptylimino-3-methyl-1,3-thiazolidine-4-yl)-N-(2-bromophenyl)-carboxamide hydrochloride [$R_1$=H, $R_2$=2-Br, $R_3$=$R_4$=H, $R_5$=$CH_3$, $R_6$=$C_7H_{13}$, n=0, m=1, X=Cl]

yield: 87.1%; melting point: 232.8° C.
$^1$H NMR (300 MHz, DMSO-$d_6$) δ 9.88 (s, 1H, HCl), 9.65 (t, 1H, J=5.50 Hz, NH), 7.72 (s, 1H, vinyl H), 7.64 (d, 1H, ArH-3'), 7.40-7.35 (m, 2H, ArH-4' and ArH-6'), 7.27-7.22 (m, 1H, ArH-5'), 4.45 (d, 2H, J=5.59 Hz, $CH_2$NH), 3.72 (s, 3H, $NCH_3$), 3.45-3.40 (m, 1H, cycloheptyl-H), 2.01-1.43 (m, 12H, cycloheptyl-H).

KHG24635 (2-cyclohexylimino-3,5-dimethyl-1,3-thiazolidine-4-yl)-N-phenyl-acetamide hydrochloride [$R_1$=$CH_3$, $R_2$=$R_3$=$R_4$=H, $R_5$=$CH_3$, $R_6$=$C_6H_{11}$, n=1, m=0, X=Cl]

yield: 38%; melting point: 231-234° C.
$^1$H NMR (300 MHz, DMSO-$d_6$) δ 10.50 (s, 1H, HCl), 9.45 (s, 1H, NH), 7.61-7.05 (m, 5H, ArH), 3.91 (s, 2H, $CH_2$), 3.54 (s, 3H, $NCH_3$), 3.22 (m, 1H, cyclohexyl $C_1$-H), 1.98-1.26 (m, 10H, cyclohexyl-H), 2.29 (s, 3H, 5-$CH_3$).

KHG24636 (2-cyclohexylimino-3,5-dimethyl-1,3-thiazolidine-4-yl)-N-(3-fluorophenyl)-acetamide hydrochloride [$R_1$=$CH_3$, $R_2$=3-F, $R_3$=$R_4$=H, $R_5$=$CH_3$, $R_6$=$C_6H_{11}$, n=1, m=0, X=Cl]

yield: 33%; melting point: 257-259° C.
$^1$H NMR (300 MHz, DMSO-$d_6$) δ 10.84 (s, 1H, HCl), 9.45 (s, 1H, NH), 7.62-6.88 (m, 4H, ArH), 3.95 (s, 2H, $CH_2$), 3.54 (s, 3H, $NCH_3$), 3.22 (m, 1H, cyclohexyl $C_1$-H), 2.29 (s, 3H, 5-$CH_3$), 1.98-1.26 (m, 10H, cyclohexyl-H).

KHG24637 (2-cyclohexylimino-3,5-dimethyl-1,3-thiazolidine-4-yl)-N-(4-t-butylphenyl)-acetamide hydrochloride [$R_1$=$CH_3$, $R_2$=4-t-$C_4H_9$, $R_3$=$R_4$=H, $R_5$=$CH_3$, $R_6$=$C_6H_{11}$, n=1, m=0, X=Cl]

yield: 2%; melting point: 255-257° C.
$^1$H NMR (300 MHz, DMSO-$d_6$) δ 10.37 (s, 1H, HCl), 9.39 (s, 1H, NH), 7.52-7.30 (m, 4H, ArH), 3.89 (s, 2H, $CH_2$), 3.53 (s, 3H, $NCH_3$), 3.19 (m, 1H, cyclohexyl $C_1$-H), 2.29 (s, 3H, 5-$CH_3$), 1.99-1.30 (m, 10H, cyclohexyl-H), 1.24 (s, 9H, t-butyl).

KHG24638 (2-cycloheptylimino-3,5-dimethyl-1,3-thiazolidine-4-yl)-N-phenyl-acetamide hydrochloride [$R_1$=$CH_3$, $R_2$=$R_3$=H, $R_5$=$CH_3$, $R_6$=$C_7H_{13}$, n=1, m=0, X=Cl]

yield: 99%; melting point: 236-238° C.
$^1$H NMR (300 MHz, DMSO-$d_6$) δ 9.62 (s, 1H, NH), 7.62-7.04 (m, 5H, Ar—H), 3.64 (s, 2H, $CH_2$), 3.56 (s, 3H, $NCH_3$), 3.38 (m, 1H, cycloheptyl $C_1$—H), 2.30 (s, 3H, 5-$CH_3$), 2.00-1.40 (m, 12H, cycloheptyl-H), 10.59 (s, 1H, HCl).

KHG24639 (2-cycloheptylimino-3,5-dimethyl-1,3-thiazolidine-4-yl)-N-(4-methylphenyl)-acetamide hydrochloride [$R_1$=$CH_3$, $R_2$=4-$CH_3$, $R_3$=$R_4$=H, $R_5$=$CH_3$, $R_6$=$C_7H_{13}$, n=1, m=0, X=Cl]

yield: 60%; melting point: 248-250° C.
$^1$H NMR (300 MHz, DMSO-$d_6$) δ 9.45 (d, 1H, NH), 7.49-7.10 (m, 4H, ArH), 3.91 (s, 2H, $CH_2$), 3.55 (s, 3H, $NCH_3$), 3.38 (m, 1H, cycloheptyl $C_1$—H), 2.30 (s, 3H, 5-$CH_3$), 2.25 (s, 3H, Ar$CH_3$), 2.00-1.40 (m, 12H, cycloheptyl-H), 10.45 (s, 1H, HCl).

KHG24640 (2-cycloheptylimino-3,5-dimethyl-1,3-thiazolidine-4-yl)-N-(2-fluorophenyl)-acetamide hydrochloride [$R_1$=$CH_3$, $R_2$=2-F, $R_3$=$R_4$=H, $R_5$=$CH_3$, $R_6$=$C_7H_{13}$, n=1, m=0, X=Cl]

yield: 49%; melting point: 197-199° C.
$^1$H NMR (300 MHz, DMSO-$d_6$) δ 10.29 (s, 1H, HCl), 9.73 (s, 1H, NH), 7.85-7.15 (m, 4H, ArH), 4.01 (s, 2H, $CH_2$), 3.60 (s, 3H, $NCH_3$), 3.39 (m, 1H, cycloheptyl $C_1$-H), 2.30 (s, 3H, 5-$CH_3$), 1.99-1.41 (m, 12H, cycloheptyl-H).

KHG24641 (2-cycloheptylimino-3,5-dimethyl-1,3-thiazolidine-4-yl)-N-(3-fluorophenyl)-acetamide hydrochloride [$R_1$=$CH_3$, $R_2$=3-F, $R_3$=$R_4$=H, $R_5$=$CH_3$, $R_6$=$C_7H_{13}$, n=1, m=0, X=Cl]

yield: 44%; melting point: 247-249° C.
$^1$H NMR (300 MHz, DMSO-$d_6$) δ 10.97 (s, 1H, HCl), 9.54 (s, 1H, NH), 7.63-6.86 (m, 4H, ArH), 3.97 (s, 2H, $CH_2$), 3.57 (s, 3H, $NCH_3$), 3.38 (m, 1H, cycloheptyl $C_1$-H), 2.30 (s, 3H, 5-$CH_3$), 2.00-1.43 (m, 12H, cycloheptyl-H).

KHG24642 (2-cycloheptylimino-3,5-dimethyl-1,3-thiazolidine-4-yl)-N-(4-nitrophenyl)-acetamide hydrochloride [$R_1$=$CH_3$, $R_2$=4-$NO_2$, $R_3$=$R_4$=H, $R_5$=$CH_3$, $R_6$=$C_7H_{13}$, n=1, m=1, X=Cl]

yield: 78%; melting point: 255-258° C.
$^1$H NMR (400 MHz, DMSO-$d_6$) δ 11.35 (s, 1H, HCl), 9.49 (s, 1H, NH), 8.26-7.86 (m, 4H, ArH), 4.04 (s, 2H, $CH_2$), 3.55 (s, 3H, $NCH_3$), 3.38 (m, 1H, cycloheptyl $C_1$-H), 2.31 (s, 3H, 5-$CH_3$), 2.00-1.46 (m, 12H, cycloheptyl-H).

KHG24643 (2-cycloheptylimino-3,5-dimethyl-1,3-thiazolidine-4-yl)-N-(4-chlorophenyl)-acetamide hydrochloride [$R_1$=$CH_3$, $R_2$=4-Cl, $R_3$=$R_4$=H, $R_5$=$CH_3$, $R_6$=$C_7H_{13}$, n=1, m=0, X=Cl]

yield: 60%; melting point: 240-242° C.
$^1$H NMR (400 MHz, DMSO-$d_6$) δ 10.59 (s, 1H, HCl), 9.34 (s, 1H, NH), 7.63-7.37 (m, 4H, ArH), 3.91 (s, 2H, $CH_2$), 3.52 (s, 3H, $NCH_3$), 3.38 (m, 1H, cycloheptyl $C_1$-H), 2.30 (s, 3H, 5-$CH_3$), 2.00-1.46 (m, 12H, cycloheptyl-H).

KHG24644 (2-cycloheptylimino-3,5-dimethyl-1,3-thiazolidine-4-yl)-N-(3,5-dichlorophenyl)-acetamide hydrochloride [$R_1$=$CH_3$, $R_2$=3-Cl, $R_3$=5-Cl, =H, $R_5$=$CH_3$, $R_6$=$C_7H_{13}$, n=1, m=0, X=Cl]

yield: 61%; melting point: 248-250° C.
$^1$H NMR (400 MHz, DMSO-$d_6$) δ 11.08 (s, 1H, HCl), 9.42 (s, 1H, NH), 7.70-7.31 (m, 3H, ArH), 3.97 (s, 2H, $CH_2$), 3.53 (s, 3H, $NCH_3$), 3.37 (m, 1H, cycloheptyl $C_1$—H), 2.30 (s, 3H, 5-$CH_3$), 2.00-1.45 (m, 12H, cycloheptyl-H).

KHG24645 (2-cycloheptylimino-3,5-dimethyl-1,3-thiazolidine-4-yl)-N-(2-fluoro-5-nitrophenyl)-acetamide hydrochloride [$R_1$=$CH_3$, $R_2$=2-F, $R_3$=5-$NO_2$, $R_4$=H, $R_5$=$CH_3$, $R_6$=$C_7H_{13}$, n=1, m=0, X=Cl]

yield: 4%; melting point: 248-251° C.
$^1$H NMR (400 MHz, DMSO-$d_6$) δ 10.65 (s, 1H, HCl), 9.39 (s, 1H, NH), 8.99-7.59 (m, 3H, ArH), 4.07 (s, 2H, $CH_2$), 3.53 (s, 3H, $NCH_3$), 3.37 (m, 1H, cycloheptyl $C_1$—H), 2.30 (s, 3H, 5-$CH_3$), 2.00-1.44 (m, 12H, cycloheptyl-H).

KHG24646 (2-cycloheptylimino-3,5-dimethyl-1,3-thiazolidine-4-yl)-N-(3,5-ditrifluoromethylphenyl)-acetamide hydrochloride [$R_1$=$CH_3$, $R_2$=3-$CF_3$, $R_3$=5-$CF_3$, $R_4$=H, $R_5$=$CH_3$, $R_6$=$C_7H_{13}$, n=1, m=0, X=Cl]

yield: 57%; melting point: 217-219° C.
$^1$H NMR (300 MHz, DMSO-$d_6$) δ 11.54 (s, 1H, HCl), 9.46 (s, 1H, NH), 8.32-7.79 (m, 3H, ArH), 4.02 (s, 2H, $CH_2$), 3.56 (s, 3H, $NCH_3$), 3.37 (m, 1H, cycloheptyl $C_1$-H), 2.31 (s, 3H, 5-$CH_3$), 2.00-1.40 (m, 12H, cycloheptyl-H).

KHG24647 (2-cycloheptylimino-3,5-dimethyl-1,3-thiazolidine-4-yl)-N-(4-trifluoromethoxyphenyl)-acetamide hydrochloride [$R_1$=$CH_3$, $R_2$=4-$OCF_3$, $R_3$=$R_4$=H, $R_5$=$CH_3$, $R_6$=$C_7H_{13}$, n=1, m=0, X=Cl]

yield: 49%; melting point 247-271° C.
$^1$H NMR (400 MHz, DMSO-$d_6$) δ 10.64 (s, 1H, HCl), 9.34 (s, 1H, NH), 7.71-7.33 (m, 4H, ArH), 3.92 (s, 2H, $CH_2$), 3.52 (s, 3H, $NCH_3$), 3.38 (m, 1H, cycloheptyl $C_1$-H), 2.30 (s, 3H, 5-$CH_3$), 1.99-1.44 (m, 12H, cycloheptyl-H).

KHG24653 (2-cyclopentylimino-3,5-dimethyl-1,3-thiazolidine-4-yl)-N-phenyl-acetamide hydrochloride [$R_1$=$CH_3$, $R_2$=$R_3$=$R_4$=H, $R_5$=$CH_3$, $R_6$=$C_5H_9$, n=1, m=0, X=Cl]

yield: 50%; melting point 186-188° C.

¹H NMR (300 MHz, DMSO-d₆) δ 10.57 (s, 1H, HCl), 9.48 (s, 1H, NH), 7.62-7.04 (m, 5H, ArH), 3.95 (s, 2H, CH₂), 3.80 (m, 1H, cycloheptyl C₁—H), 3.58 (s, 3H, NCH₃), 2.31 (s, 3H, 5-CH₃), 2.07-1.59 (m, 8H, cycloheptyl-H).

KHG24654 (2-cyclopentylimino-3,5-dimethyl-1,3-thiazolidine-4-yl)-N-(4-methylphenyl)-acetamide hydrochloride [R₁=CH₃, R₂=4-CH₃, R₃=R₄=H, R₅=CH₃, R₆=C₅H₉, n=1, m=0, X=Cl]

yield: 66%; melting point: 228-229° C.

¹H NMR (300 MHz, DMSO-d₆) δ 10.49 (s, 1H, HCl), 9.50 (s, 1H, NH), 7.50-7.09 (m, 4H, ArH), 3.92 (s, 2H, CH₂), 3.77 (m, 1H, cyclopentyl C₁—H), 3.58 (s, 3H, NCH₃), 2.30 (s, 3H, 5-CH₃), 2.24 (s, 3H, Ar—CH₃), 2.07-1.58 (m, 8H, cycloheptyl-H).

KHG24655 (2-cyclopentylimino-3,5-dimethyl-1,3-thiazolidine-4-yl)-N-(3-fluoro)-acetamide hydrochloride [R₁=CH₃, R₂=3-F, R₃=R₄=H, R₅=CH₃, R₆=C₅H₉, n=1, m=0, X=Cl]

yield: 68%; melting point: 213-215° C.

¹H NMR (300 MHz, DMSO-d₆) δ 10.89 (s, 1H, HCl), 9.49 (s, 1H, NH), 7.63-6.88 (m, 4H, ArH), 3.98 (s, 2H, CH₂), 3.78 (m, 1H, cyclopentyl C₁—H), 3.58 (s, 3H, NCH₃), 2.31 (s, 3H, 5-CH₃), 2.07-1.59 (m, 8H, cycloheptyl-H).

KHG24656 (2-cyclopentylimino-3,5-dimethyl-1,3-thiazolidine-4-yl)-N-(4-t-butylphenyl)-acetamide hydrochloride [R₁=CH₃, R₂=4-t-C₄H₉, R₃=R₄=H, R₅=CH₃, R₆=C₅H₉, n=1, m=0, X=Cl]

yield: 57%; melting point: 220-223° C.

¹H NMR (300 MHz, DMSO-d₆) δ 10.42 (s, 1H, HCl), 9.42 (s, 1H, NH), 7.52-7.30 (m, 4H, ArH), 3.91 (s, 2H, CH₂), 3.77 (m, 1H, cyclopentyl C₁—H), 3.56 (s, 3H, NCH₃), 2.30 (s, 3H, 5-CH₃), 2.04-1.58 (m, 8H, cycloheptyl-H).

KHG24657 (2-cyclopentylimino-3,5-dimethyl-1,3-thiazolidine-4-yl)-N-(4-chlorophenyl)-acetamide hydrochloride [R₁=CH₃, R₂=4-Cl, R₃=R₄=H, R₅=CH₃, R₆=C₅H₉, n=1, m=0, X=Cl]

yield: 5%; melting point: 201-203° C.

¹H NMR (300 MHz, DMSO-d₆) δ 10.66 (s, 1H, HCl), 9.39 (s, 1H, NH), 7.64-7.36 (m, 4H, ArH), 3.93 (s, 2H, CH₂), 3.77 (m, 1H, cyclopentyl C₁—H), 3.55 (s, 3H, NCH₃), 2.30 (s, 3H, 5-CH₃), 2.08-1.00 (m, 8H, cycloheptyl-H).

KHG24658 (2-cyclohexylimino-3,5-dimethyl-1,3-thiazolidine-4-yl)-N-(4-nitrophenyl)-acetamide hydrochloride [R₁=CH₃, R₂=4-NO₂, R₃=R₄=H, R₅=CH₃, R₆=C₆H₁₁, n=1, m=0, X=Cl]

yield 27%; melting point: 215-217° C.

¹H NMR (300 MHz, DMSO-d₆) δ 11.20 (s, 1H, HCl), 9.61 (s, 1H, NH), 8.68-7.85 (m, 4H, ArH), 3.94 (s, 2H, CH₂), 3.42 (s, 3H, NCH₃), 3.04 (m, 1H, cyclopentyl C₁—H), 2.23 (s, 3H, 5-CH₃), 1.88-1.13 (m, 8H, cycloheptyl-H).

KHG24659 (2-cyclopentylimino-3,5-dimethyl-1,3-thiazolidine-4-yl)-N-(2-fluorophenyl)-acetamide hydrochloride [R₁=CH₃, R₂=2-F, R₃=R₄=H, R₅=CH₃, R₆=C₅H₉, n=1, m=0, X=Cl]

yield: 47%; melting point: 153-153° C.

¹H NMR (300 MHz, DMSO-d₆) δ 10.18 (s, 1H, HCl), 9.46 (s, 1H, NH), 7.88-7.16 (m, 4H, ArH), 4.00 (s, 2H, CH₂), 3.78 (m, 1H, cyclopentyl C₁—H), 3.57 (s, 3H, NCH₃), 2.31 (s, 3H, 5-CH₃), 2.08-1.59 (m, 8H, cycloheptyl-H).

KHG24660 (2-cycloheptylimino-3-methyl-1,3-thiazolidine-4-yl)-N-(2-fluoro-5-nitrophenyl)-carboxamide hydrobromide [R₁=H, R₂=2-F, R₃=5-NO₂, R₄=H, R₅=CH₃, R₆=C₇H₁₃, n=0, m=0, X=Br]

yield: 48.9%; melting point: 264.8° C.

¹H NMR (300 MHz, DMSO-d₆) δ 11.07 (s, 1H, NH), 9.63 (s, 1H, HBr), 7.89 (s, 1H, vinyl H), 8.66-7.63 (m, 3H, ArH), 3.79 (s, 3H, NCH₃), 3.52 (m, 1H, cycloheptyl-H), 2.03-1.51 (m, 12H, cycloheptyl-H).

KHG24661 (2-cycloheptylimino-3-methyl-1,3-thiazolidine-4-yl)-N-(2-fluoro-5-nitrophenyl)-carboxamide [R₁=H, R₂=2-F, R₃=5-NO₂, R₄=H, R₅=CH₃, R₆=C₇H₁₃, n=0, m=0]

yield 85%; melting point: 151.1° C.

¹H NMR (300 MHz, DMSO-d₆) δ 11.01 (s, 1H, NH), 7.12 (s, 1H, vinyl H), 8.60-7.60 (m, 3H, ArH), 3.59 (s, 3H, NCH₃), 3.50 (m, 1H, cycloheptyl-H), 2.10-1.43 (m, 12H, cycloheptyl-H).

KHG24662 (2-cycloheptylimino-3-methyl-1,3-thiazolidine-4-yl)-N-(4-fluorophenyl)-carboxamide hydrochloride [R₁=H, R₂=4-F, R₃=R₄=H, R₅=CH₃, R₆=C₇H₁₃, n=0, m=0, X=Cl]

yield: 93.4%; melting point: 265.3° C.

¹H NMR (300 MHz, DMSO-d₆) δ 11.14 (s, 1H, HCl), 10.05 (s, 1H, NH), 7.88 (s, 1H, vinyl H), 7.80-7.76 (m, 2H, ArH-3' and ArH-5'), 7.25-7.19 (m, 2H, ArH-2' and ArH-6'), 3.75 (s, 3H, NCH₃), 3.40-3.45 (m, 1H, cycloheptyl-H), 1.44-2.02 (m, 12H, cycloheptyl-H).

KHG24663 (2-cycloheptylimino-3-methyl-1,3-thiazolidine-4-yl)-N-(4-ethylphenyl)-carboxamide hydrobromide [R₁=H, R₂=4-C₂H₅, R₃=R₄=H, R₅=CH₃, R₆=C₇H₁₃, n=0, m=0, X=Br]

yield: 46%; melting point: 278-279° C.

¹H NMR (300 MHz, DMSO-d₆) δ 10.83 (s, 1H, HBr), 9.64 (br. s, 1H, NH), 7.56-7.11 (m, 4H, Ar—), 6.92 (s, 1H, vinyl-H), 3.35 (s, 3H, N—CH₃), 3.32 (br. s, 1H, cycloheptyl-C₁H), 2.58 (q, 2H, J=5.5 Hz, ethyl CH₂), 1.77-1.38 (m, 12H, cycloheptyl-H), 1.24 (t, 3H, J=5.5 Hz, ethyl CH₃).

KHG24664 (2-cycloheptylimino-3-methyl-1,3-thiazolidine-4-yl)-N-(4-ethylphenyl)-carboxamide [R₁=H, R₂=4-C₂H₅, R₃=R₄=H, R₅=CH₃, R₆=C₇H₁₃, n 0, m=0]

yield: 84%; melting point: 194-195° C.

¹H NMR (300 MHz, DMSO-d₆) δ 10.32 (br. s, 1H, NH), 7.57-7.15 (m, 4H, Ar—), 6.83 (s, 1H, vinyl-H), 3.31 (s, 3H, N—CH₃), 3.24 (br. s, 1H, cycloheptyl-C₁H), 2.57 (q, 2H, J=5.5 Hz, ethyl CH₂), 1.73-1.41 (m, 12H, cycloheptyl-H), 1.14 (t, 3H, J=5.5 Hz, ethyl CH₃).

KHG24666 (2-cycloheptylimino-3-methyl-1,3-thiazolidine-4-yl)-N-(3-fluorobenzyl)-carboxamide hydrochloride [R₁=H, R₂=3-F, R₃=R₄=H, R₅=CH₃, R₆=C₇H₁₃, n=0, m=1, X=Cl]

yield: 89.0%; melting point: 226.1° C.

¹H NMR (300 MHz, DMSO-d₆) δ 9.96 (s, 1H, HCl), 9.65 (t, 1H, J=5.86 Hz, NH), 7.74 (s, 1H, vinyl H), 7.41-7.06 (m, 4H, ArH), 4.42 (d, 2H, J=5.88 Hz, CH₂NH), 3.73 (s, 3H, NCH₃), 3.45 (m, 1H, cycloheptyl-H), 2.00-1.42 (m, 12H, cycloheptyl-H).

KHG24667 (2-cycloheptylimino-3-methyl-1,3-thiazolidine-4-yl)-N-(3-fluorobenzyl)-carboxamide [R₁=H, R₂=3-F, R₃=R₄=H, R₅=CH₃, R₆=C₇H₁₃, n=0, m=1]

yield: 67.1%; melting point: 140.1° C.

¹H NMR (300 MHz, DMSO-d₆) δ 9.07 (t, 1H, J=5.97 Hz, NH), 7.41-7.05 (m, 4H, ArH), 6.72 (s, 1H, vinyl H), 4.38 (d, 2H, J=5.94 Hz, CH₂NH), 3.25 (s, 3H, NCH₃), 2.90-2.84 (m, 1H, cycloheptyl-H), 1.71-1.40 (m, 12H, cycloheptyl-H).

KHG24668 (2-cycloheptylimino-3-methyl-1,3-thiazolidine-4-yl)-N-(3-bromobenzyl)-carboxamide hydrobromide [R₁=H, R₂=3-Br, R₃=R₄=H, R₅=CH₃, R₆=C₇H₁₃, n=0, m=1, X=Br]

yield: 58.5%; melting point: 197.3° C.

¹H NMR (300 MHz, DMSO-d₆) δ 9.72 (t, 1H, J=5.86 Hz, NH), 7.71 (s, 1H, vinyl H), 7.53-7.27 (m, 4H, ArH), 4.41 (d, 2H, J=5.83 Hz, CH$_2$NH), 3.71 (s, 3H, NCH$_3$), 3.47-3.40 (m, 1H, cycloheptyl-H), 2.00-1.42 (m, 12H, cycloheptyl-H).

KHG24669 (2-cycloheptylimino-3-methyl-1,3-thiazolidine-4-yl)-N-(3-bromobenzyl)-carboxamide [R$_1$=H, R$_2$=3-Br, R$_3$=R$_4$=H, R$_5$=CH$_3$, R$_6$=C$_7$H$_{13}$, n=0, m=1]

yield: 77.1%; melting point: 133.0° C.

$^1$H NMR (400 MHz, DMSO-d$_6$) δ 9.10 (s, 1H, NH), 7.64-7.27 (m, 4H, ArH), 6.69 (s, 1H, vinyl H), 4.34 (s, 2H, CH$_2$NH), 3.30 (s, 3H, NCH$_3$), 2.78 (m, 1H, cycloheptyl-H), 1.66-1.40 (m, 12H, cycloheptyl-H).

KHG24670 (2-cycloheptylimino-3-methyl-1,3-thiazolidine-4-yl)-N-(2-trifluoromethylbenzyl)-carboxamide hydrobromide [R$_1$=H, R$_2$=2-CF$_3$, R$_3$=R$_4$=H, R$_5$=CH$_3$, R$_6$=C$_7$H$_{13}$, n=0, m=1, X=Br]

yield: 67.9%; melting point: 236.9° C.

$^1$H NMR (300 MHz, CDCl$_3$) δ 9.62-9.56 (m, 2H, NH and HBr), 7.76-7.48 (m, 4H, ArH), 7.71 (s, 1H, vinyl H), 4.60 (d, 2H, J=5.28 Hz, CH$_2$NH), 3.69 (s, 3H, NCH$_3$), 3.46 (br s, 1H, cycloheptyl-H), 2.01-1.49 (m, 12H, cycloheptyl-H).

KHG24671 (2-cycloheptylimino-3-methyl-1,3-thiazolidine-4-yl)-N-(2-trifluoromethylbenzyl)-carboxamide [R$_1$=H, R$_2$=2-CF$_3$, R$_3$=R$_4$=H, R$_5$=CH$_3$, R$_6$=C$_7$H$_{13}$, n=0, m=1]

yield: 79.0%; melting point: 223° C.

$^1$H NMR (300 MHz, CDCl$_3$) δ 7.69-7.39 (m, 4H, ArH), 6.28 (s, 1H, vinyl H), 4.70 (d, 2H, J=6.03 Hz, CH$_2$NH), 3.41 (s, 3H, NCH$_3$), 2.89-2.83 (m, 1H, cycloheptyl-H), 1.79-1.40 (m, 12H, cycloheptyl-H).

KHG24672 (2-cycloheptylimino-3-methyl-1,3-thiazolidine-4-yl)-N-(4-methylphenyl)-carboxamide hydrobromide [R$_1$=H, R$_2$=4-CH$_3$, R$_3$=R$_4$=H, R$_5$=CH$_3$, R$_6$=C$_7$H$_{13}$, n=0, m=0, X=Br]

yield: 60.5%; melting point: 278.9° C.

$^1$H NMR (300 MHz, DMSO-d$_6$) δ 10.74 (s, 1H, NH), 9.57 (s, 1H, HBr), 7.75 (s, 1H, vinyl H), 7.57 (d, 2H, J=8.28 Hz, ArH-2' and ArH-6'), 7.18 (d, 2H, J=8.37 Hz, ArH-3' and ArH-5'), 3.69 (s, 3H, NCH$_3$), 3.48 (m, 1H, cycloheptyl-H), 2.24 (s, 3H, CH$_3$), 2.03-1.41 (m, 12H, cycloheptyl-H).

KHG24673 (2-cycloheptylimino-3-methyl-1,3-thiazolidine-4-yl)-N-(4-methylphenyl)-carboxamide [R$_1$=H, R$_2$=4-CH$_3$, R$_3$=R$_4$=H, R$_5$=CH$_3$, R$_6$=C$_7$H$_{13}$, n=0, m=0]

yield: 78.4%; melting point: 191.1° C.

$^1$H NMR (400 MHz, DMSO-d$_6$) δ 10.30 (s, 1H, NH), 7.54 (d, 2H, J=7.80 Hz, ArH-2' and ArH-6'), 7.12 (d, 2H, J=7.72 Hz, ArH-3' and ArH-5'), 6.71 (s, 1H, vinyl H), 3.25 (s, 3H, NCH$_3$), 2.90-2.86 (m, 1H, cycloheptyl-H), 2.24 (s, 3H, CH$_3$), 1.71-1.40 (m, 12H, cycloheptyl-H).

KHG24674 (2-cycloheptylimino-3-methyl-1,3-thiazolidine-4-yl)-N-(3,5-dichlorophenyl)-carboxamide [R$_1$=H, R$_2$=3-Cl, R$_3$=5-Cl, R$_4$=H, R$_5$=CH$_3$, R$_6$=C$_7$H$_{13}$, n=0, m=0]

yield: 76.6%; melting point: 191.2° C.

$^1$H NMR (300 MHz, DMSO-d$_6$) δ 10.68 (s, 1H, NH), 7.76 (s, 2H, ArH-2' and ArH-6'), 7.34 (s, 1H, ArH-4'), 6.96 (s, 1H, vinyl H), 3.27 (s, 3H, NCH$_3$), 2.90-2.86 (m, 1H, cycloheptyl-H), 1.73-1.41 (m, 12H, cycloheptyl-H).

KHG24675 (2-cycloheptylimino-3-methyl-1,3-thiazolidine-4-yl)-N-(3,5-dichlorophenyl)-carboxamide hydrobromide [R$_1$=H, R$_2$=3-Cl, R$_3$=5-Cl, R$_4$=H, R$_5$=CH$_3$, R$_6$=C$_7$H$_{13}$, n=0, m=0, X=Br]

yield: 83.3%; melting point: 275.2° C.

$^1$H NMR (400 MHz, DMSO-d$_6$) δ 10.97 (s, 1H, NH), 9.60 (s, 1H, HBr), 7.84 (s, 1H, vinyl H), 7.79 (s, 2H, ArH-2' and ArH-6'), 7.39 (s, 1H, ArH-4'), 3.68 (s, 3H, NCH$_3$), 3.50-3.48 (m, 1H, cycloheptyl-H), 2.03-1.24 (m, 12H, cycloheptyl-H).

KHG24676 (2-cycloheptylimino-3-methyl-1,3-thiazolidine-4-yl)-N-(4-chlorophenyl)-carboxamide hydrobromide [R$_1$=H, R$_2$=4-Cl, R$_3$=R$_4$=H, R$_5$=CH$_3$, R$_6$=C$_7$H$_{13}$, n=0, m=0, X=Br]

yield: 71.7%; melting point: 286.5° C.

$^1$H NMR (300 MHz, DMSO-d$_6$) δ 10.95 (s, 1H, NH), 9.61 (s, 1H, HBr), 7.80 (s, 1H, vinyl H), 7.74 (d, 2H, J=8.79 Hz, ArH-2' and ArH-6'), 7.44 (d, 2H, J=8.76 Hz, ArH-3' and ArH-5'), 3.70 (s, 3H, NCH$_3$), 3.50-3.48 (m, 1H, cycloheptyl-H), 2.03-1.41 (m, 12H, cycloheptyl-H).

KHG24677 (2-cycloheptylimino-3-methyl-1,3-thiazolidine-4-yl)-N-(4-chlorophenyl)-carboxamide [R$_1$=H, R$_2$=4-Cl, R$_3$=R$_4$=H, R$_5$=CH$_3$, R$_6$=C$_7$H$_{13}$, n=0, m=0]

yield: 87.2%; melting point: 199.7° C.

$^1$H NMR (400 MHz, DMSO-d$_6$) δ 10.51 (s, 1H, NH), 7.69 (d, 2H, J=7.80 Hz, ArH-2' and ArH-6'), 7.38 (d, 2H, J=7.96 Hz, ArH-3' and ArH-5'), 6.88 (s, 1H, vinyl H), 3.25 (s, 3H, NCH$_3$), 2.88 (m, 1H, cycloheptyl-H), 1.80-1.40 (m, 12H, cycloheptyl-H).

KHG24678 (2-cycloheptylimino-3-methyl-1,3-thiazolidine-4-yl)-N-(4-n-butylphenyl)-carboxamide hydrobromide [R$_1$=H, R$_2$=4-n-C$_4$H$_9$, R$_3$=R$_4$=H, R$_5$=CH$_3$, R$_6$=C$_7$H$_{13}$, n=0, m=0, X=Br]

yield: 64.6%; melting point: 240.8° C.

$^1$H NMR (300 MHz, DMSO-d$_6$) δ 10.76 (s, 1H, NH), 9.60 (s, 1H, HBr), 7.77 (s, 1H, vinyl H), 7.60 (d, 2H, J=8.40 Hz, ArH-2' and ArH-6'), 7.19 (d, 2H, J=8.46 Hz, ArH-3' and ArH-5'), 3.70 (s, 3H, NCH$_3$), 3.50-3.48 (m, 1H, cycloheptyl-H), 2.55 (t, 2H, J=7.58 Hz, CH$_2$CH$_2$CH$_2$CH$_3$), 1.24-2.03 (m, 16H, cycloheptyl-H and CH$_2$CH$_2$CH$_2$CH$_3$), 0.88 (t, 3H, J=7.28 Hz, CH$_2$CH$_2$CH$_2$CH$_3$).

KHG24679 (2-cycloheptylimino-3-methyl-1,3-thiazolidine-4-yl)-N-(4-isopropylphenyl)-carboxamide hydrobromide [R$_1$=H, R$_2$=4-CH(CH$_3$)$_2$, R$_3$=R$_4$=H, R$_5$=CH$_3$, R$_6$=C$_7$H$_{13}$, n=0, m=0, X=Br]

yield: 74.0%; melting point: 282.2° C.

$^1$H NMR (300 MHz, DMSO-d$_6$) δ 10.76 (s, 1H, NH), 9.59 (s, 1H, HBr), 7.77 (s, 1H, vinyl H), 7.61 (d, 2H, J=8.61 Hz, ArH-2' and ArH-6'), 7.39 (d, 2H, J=8.58 Hz, ArH-3' and ArH-5'), 3.71 (s, 3H, NCH$_3$), 3.50-3.48 (m, 1H, cycloheptyl-H), 2.91-2.82 (m, 1H, J=6.86 Hz, CH(CH$_3$)$_2$), 2.04-1.42 (m, 12H, cycloheptyl-H), 1.19 (d, 6H, J=6.88 Hz, CH(CH$_3$)$_2$).

KHG24680 (2-cycloheptylimino-3-methyl-1,3-thiazolidine-4-yl)-N-(4-isopropylphenyl)-carboxamide [R$_1$=H, R$_2$=4-CH(CH$_3$)$_2$, R$_3$=R$_4$=H, R$_5$=CH$_3$, R$_6$=C$_7$H$_{13}$, n=0, m=0]

yield: 69.3%; melting point: 207.6° C.

$^1$H NMR (300 MHz, DMSO-d$_6$) δ 10.33 (s, 1H, NH), 7.57 (d, 2H, J=8.46 Hz, ArH-2' and ArH-6'), 7.20 (d, 2H, J=8.46 Hz, ArH-3' and ArH-5'), 6.83 (s, 1H, vinyl H), 3.27 (s, 3H, NCH$_3$), 2.89-2.80 (m, 2H, J=7.02 Hz, CH(CH$_3$)$_2$ and cycloheptyl-H), 1.74-1.42 (m, 12H, cycloheptyl-H), 1.20 (d, 6H, J=11.15 Hz, CH(CH$_3$)$_2$).

KHG24681 (2-cycloheptylimino-3-methyl-1,3-thiazolidine-4-yl)-N-(4-phenoxyphenyl)-carboxamide hydrobromide [R$_1$=H, R$_2$=4-OC$_6$H$_5$, R$_3$=R$_4$=H, R$_5$=CH$_3$, R$_6$=C$_7$H$_{13}$, n=0, m=0, X=Br]

yield: 69.9%; melting point: 149.5° C.

$^1$H NMR (300 MHz, DMSO-d$_6$) δ 10.86 (s, 1H, NH), 9.58 (s, 1H, HBr), 7.78 (s, 1H, vinyl H), 7.78-6.97 (m, 9H, ArH), 3.71 (s, 3H, NCH$_3$), 3.49 (m, 1H, cycloheptyl-H), 2.04-1.42 (m, 12H, cycloheptyl-H).

KHG24682 (2-cycloheptylimino-3-methyl-1,3-thiazolidine-4-yl)-N-(4-phenoxyphenyl)-carboxamide [R$_1$=H, R$_2$=4-OC$_6$H$_5$, R$_3$=R$_4$=H, R$_5$=CH$_3$, R$_6$=C$_7$H$_{13}$, n=0, m=0]

yield: 75.7%; melting point: 278.6° C.

¹H NMR (300 MHz, DMSO-d₆) δ 10.44 (s, 1H, NH), 7.78-6.97 (m, 9H, ArH), 6.85 (s, 1H, vinyl H), 3.31 (s, 3H, NCH₃), 2.92-2.87 (m, 1H, cycloheptyl-H), 1.73-1.37 (m, 12H, cycloheptyl-H).

KHG24683 (2-cycloheptylimino-3-methyl-1,3-thiazolidine-4-yl)-N-(4-t-butylphenyl)-carboxamide hydrobromide [R₁=H, R₂=4-t-C₄H₉, R₃=R₄=H, R₅=CH₃, R₆=C₇H₁₃, n=0, m=0, X=Br]

yield: 66.7%; melting point: 169.9° C.

¹H NMR (300 MHz, DMSO-d₆) δ 10.76 (s, 1H, NH), 9.59 (s, 1H, HBr), 7.76 (s, 1H, vinyl H), 7.61 (d, 2H, J=8.61 Hz, ArH-2' and ArH-6'), 7.39 (d, 2H, J=8.58 Hz, ArH-3' and ArH-5'), 3.70 (s, 3H, N—CH₃), 3.50-3.47 (m, 1H, cycloheptyl-H), 2.03-1.45 (m, 12H, cycloheptyl-H), 1.26 (s, 9H, C(CH₃)₃).

KHG24684 (2-cycloheptylimino-3-methyl-1,3-thiazolidine-4-yl)-N-(4-t-butylphenyl)-carboxamide [R₁=H, R₂=4-t-C₄H₉, R₃=R₄=H, R₅=CH₃, R₆=C₇H₁₃, n=0, m=0]

yield: 87.5%; melting point: 170.8° C.

¹H NMR (300 MHz, DMSO-d₆) δ 10.34 (s, 1H, NH), 7.58 (d, 2H, J=8.58 Hz, ArH-2' and ArH-6'), 7.34 (d, 2H, J=8.61 Hz, ArH-3' and ArH-5'), 6.82 (s, 1H, vinyl H), 3.27 (s, 3H, NCH₃), 2.90 (m, 1H, cycloheptyl-H), 1.73-1.42 (m, 12H, cycloheptyl-H), 1.26 (s, 9H, C(CH₃)₃).

KHG24685 (2-cycloheptylimino-3-methyl-1,3-thiazolidine-4-yl)-N-(5-chloro-2-fluorophenyl)-carboxamide hydrobromide [R₁=H, R₂=2-F, R₃=5-Cl, R₄=H, R₅=CH₃, R₆=C₇H₁₃, n=0, m=0, X=Br]

yield: 63.5%; melting point: 262.2° C.

¹H NMR (300 MHz, DMSO-d₆) δ 10.85 (s, 1H, NH), 9.61 (s, 1H, HBr), 7.84 (s, 1H, ArH-6'), 7.77 (m, 1H, ArH-3'), 7.41 (m, 1H, ArH-4'), 7.95 (s, 1H, ArH-4'), 7.38 (s, 1H, vinyl H), 3.70 (s, 3H, NCH₃), 3.50 (m, 1H, cycloheptyl-H), 2.03-1.45 (m, 12H, cycloheptyl-H).

KHG24686 (2-cycloheptylimino-3-methyl-1,3-thiazolidine-4-yl)-N-(5-chloro-2-fluorophenyl)-carboxamide [R₁=H, R₂=2-F, R₃=5-Cl, R₄=H, R₅=CH₃, R₆=C₇H₁₃, n=0, m=0]

yield: 77.1%; melting point: 241.2° C.

¹H NMR (300 MHz, DMSO-d₆) δ 10.85 (s, 1H, NH), 7.76-7.73 (m, 1H, ArH-3'), 7.39-7.32 (m, 1H, ArH-4'), 7.30 (s, 1H, ArH-6'), 6.96 (s, 1H, vinyl H), 3.32 (s, 3H, CH₃), 2.90-2.87 (m, 1H, cycloheptyl-H), 1.73-1.41 (m, 12H, cycloheptyl-H).

KHG24687 (2-cycloheptylimino-3-methyl-1,3-thiazolidine-4-yl)-N-(3,5-ditrifluoromethylphenyl)-carboxamide hydrobromide [R₁=H, R₂=3-CF₃, R₃=5-CF₃, R₄=H, R₅=CH₃, R₆=C₇H₁₃, n=0, m=0, X=Br]

yield: 73.7%; melting point: 274.1° C.

¹H NMR (300 MHz, DMSO-d₆) δ 11.40 (s, 1H, NH), 9.66 (s, 1H, HBr), 8.42 (s, 2H, ArH-2' and ArH-6'), 7.95 (m, 1H, ArH-4'), 7.89 (s, 1H, vinyl H), 3.74 (s, 3H, NCH₃), 3.50 (m, 1H, cycloheptyl-H), 2.04-1.45 (m, 12H, cycloheptyl-H).

KHG24688 (2-cycloheptylimino-3-methyl-1,3-thiazolidine-4-yl)-N-(3,5-ditrifluoromethylphenyl)-carboxamide [R₁=H, R₂=3-CF₃, R₃=5-CF₃, R₄=H, R₅=CH₃, R₆=C₇H₁₃, n=0, m=0]

yield: 80.7%; melting point: 193.1° C.

¹H NMR (300 MHz, DMSO-d₆) δ 11.40 (s, 1H, NH), 8.42-7.90 (m, 3H, ArH), 7.85 (s, 1H, vinyl H), 3.67 (s, 3H, NCH₃), 3.40 (m, 1H, cycloheptyl-H), 2.03-0.97 (m, 12H, cycloheptyl-H).

KHG24689 (2-cycloheptylimino-3-methyl-1,3-thiazolidine-4-yl)-N-(4-n-butylphenyl)-carboxamide [R₁=H, R₂=4-n-C₄H₉, R₃=R₄=H, R₅=CH₃, R₆=C₇H₁₃, n=0, m=0]

yield: 69.3%; melting point: 173.3° C.

¹H NMR (300 MHz, DMSO-d₆) δ 10.31 (s, 1H, NH), 7.56 (d, 2H, J=8.40 Hz, ArH-2' and ArH-6'), 7.14 (d, 2H, J=8.40 Hz, ArH-3' and ArH-5'), 6.82 (s, 1H, vinyl H), 3.27 (s, 3H, CH₃), 2.91-2.87 (m, 1H, cycloheptyl-H), 2.55 (t, 2H, J=7.45 Hz, CH₂CH₂CH₂CH₃), 1.74-1.42 (m, 16H, cycloheptyl-H and CH₂CH₂CH₂CH₃), 0.88 (t, 3H, J=7.28 Hz, CH₂CH₂CH₂CH₃).

KHG24775 [2-(1-adamantylimino)-3-(n-butyl)-1,3-thiazolidine-4-yl]-N-(4-chlorophenyl)-acetamide hydrochloride [R₁=H, R₂=4-Cl, R₃=R₄=H, R₅=n-C₄H₉, R₆=1-adamantyl, n=1, m=0, X=Cl]

yield: 72%; melting point: 158° C.

¹H NMR (300 MHz, DMSO-d₆) δ 11.04 (s, 1H, HCl), 8.50 (s, 1H, NH), 7.64-7.35 (d, 4H, J=6.9 Hz, ArH), 7.12 (s, 1H, vinyl-H), 4.27-4.21 (m, 2H, CH₂CH₂CH₂CH₃), 4.00 (s, 2H, CH₂), 2.15-2.07 (m, 15H, adamantyl), 1.58-1.42 (m, 2H, CH₂CH₂CH₂CH₃), 1.31-1.18 (m, 2H, CH₂CH₂CH₂CH₃), 0.79-0.75 (m, 3H, CH₂CH₂CH₂CH₃).

KHG24776 [2-(1-adamantylimino)-3-(n-butyl)-1,3-thiazolidine-4-yl]-N-(4-n-butylphenyl)-acetamide hydrochloride [R₁=H, R₂=4-n-C₄H₉, R₃=R₄=H, R₅=n-C₄H₉, R₆=1-adamantyl, n=1, m=0, X=Cl]

yield: 80%; melting point: 169° C.

¹H NMR (300 MHz, DMSO-d₆) δ 10.64 (s, 1H, HCl), 8.47 (s, 1H, NH), 7.51-7.48 (d, 2H, J=8.4 Hz, ArH), 7.13-7.10 (d, 2H, J=7.8 Hz, ArH), 7.10 (s, 1H, vinyl-H), 4.24-4.19 (m, 2H, N—CH₂CH₂CH₂CH₃), 3.94 (s, 2H, CH₂), 3.09-3.02 (m, 2H, Ar—CH₂CH₂CH₂CH₃), 2.21-1.66 (m, 15H, adamantyl), 1.56-1.44 (m, 2H, N—CH₂CH₂CH₂CH₃), 1.56-1.44 (m, 2H, Ar—CH₂CH₂CH₂CH₃), 1.51-1.21 (m, 2H, N—CH₂CH₂CH₂CH₃), 1.51-1.21 (m, 2H, Ar—CH₂CH₂CH₂CH₃), 0.88-0.84 (m, 3H, N—CH₂CH₂CH₂CH₃), 0.80-0.75 (m, 3H, Ar—CH₂CH₂CH₂CH₃).

KHG24777 [2-(1-adamantylimino)-3-(n-butyl)-1,3-thiazolidine-4-yl]-N-(4-trifluoromethylphenyl)-acetamide hydrochloride [R₁=H, R₂=4-CF₃, R₃=R₄=H, R₅ n-C₄H₉, R₆=1-adamantyl, n=1, m=0, X=Cl]

yield: 71%; melting point: 220° C.

¹H NMR (300 MHz, DMSO-d₆) δ 11.47 (s, 1H, HCl), 8.61 (s, 1H, NH), 7.89-7.66 (d, 4H, J=8.7 Hz, ArH), 7.15 (s, 1H, vinyl-H), 4.34-4.26 (m, 2H, CH₂CH₂CH₂CH₃), 4.08 (s, 2H, CH₂), 2.13-1.66 (m, 15H, adamantyl), 1.57-1.45 (m, 2H, CH₂CH₂CH₂CH₃), 1.33-1.10 (m, 2H, CH₂CH₂CH₂CH₃), 0.78-0.73 (m, 3H, CH₂CH₂CH₂CH₃).

KHG24778 [2-(1-adamantylimino)-3-(n-butyl)-1,3-thiazolidine-4-yl]-N-(3,5-dichlorophenyl)-acetamide hydrochloride [R₁=H, R₂=3-Cl, R₃=5-Cl, R₄=H, R₅=n-C₄H₉, R₆=1-adamantyl, n=1, m=0, X=Cl]

yield: 81%; melting point: 164° C.

¹H NMR (300 MHz, DMSO-d₆) δ 11.50 (s, 1H, HCl), 8.49 (s, 1H, NH), 7.75 (s, 2H, ArH), 7.32 (s, 1H, ArH), 7.16 (s, 1H, vinyl-H), 4.29-4.21 (m, 2H, CH₂CH₂CH₂CH₃), 4.05 (s, 2H, CH₂), 2.17-1.68 (m, 15H, adamantyl), 1.58-1.46 (m, 2H, CH₂CH₂CH₂CH₃), 1.34-1.21 (m, 2H, CH₂CH₂CH₂CH₃), 0.82-0.77 (t, 3H, J=7.2 Hz, CH₂CH₂CH₂CH₃).

KHG24779 [2-(1-adamantylimino)-3-(n-butyl)-1,3-thiazolidine-4-yl]-N-(3,5-difluoromethylphenyl)-acetamide hydrochloride [R₁=H, R₂=3-CF₃, R₃=5-CF₃, R₄=H, R₅=n-C₄H₉, R₆=1-adamantyl, n=1, m=0, X=Cl]

yield: 86%; melting point: 252° C.

¹H NMR (300 MHz, DMSO-d₆) δ 8.51 (s, 1H, NH), 8.36 (s, 2H, ArH), 7.79 (s, 1H, ArH), 7.17 (s, 1H, vinyl-H), 4.32-4.22 (m, 2H, CH₂CH₂CH₂CH₃), 4.09 (s, 2H, CH₂), 2.15-1.66 (m, 15H, adamantyl), 1.58-1.44 (m, 2H, CH₂CH₂CH₂CH₃), 1.33-1.20 (m, 2H, CH₂CH₂CH₂CH₃), 0.77-0.72 (m, 3H, CH₂CH₂CH₂CH₃).

KHG24780 [2-(1-adamantylimino)-3-(n-butyl)-1,3-thiazolidine-4-yl]-N-(4-fluorophenyl)-acetamide hydrochloride [$R_1$=H, $R_2$=4-F, $R_3$H, $R_5$=n-$C_4H_9$, $R_6$=1-adamantyl, n=1, m=0, X=Cl]

yield: 86%; melting point: 163° C.

$^1$H NMR (300 MHz, DMSO-$d_6$) δ 10.91 (s, 1H, HCl), 8.49 (s, 1H, NH), 7.67-7.15 (m, 4H, ArH), 7.12 (s, 1H, vinyl-H), 4.29-4.21 (m, 2H, $CH_2CH_2CH_2CH_3$), 3.97 (s, 2H, $CH_2$), 2.15-1.66 (m, 15H, adamantyl), 1.57-1.45 (m, 2H, $CH_2CH_2CH_2CH_3$), 1.33-1.19 (m, 2H, $CH_2CH_2CH_2CH_3$), 0.80-0.75 (t, 3H, J=7.2 Hz, $CH_2CH_2CH_2CH_3$).

KHG24781 [2-(1-adamantylimino)-3-(n-butyl)-1,3-thiazolidine-4-yl]-N-(4-methylphenyl)-acetamide hydrochloride [$R_1$=H, $R_2$=4-$CH_3$, $R_3$=$R_4$=H, $R_5$=n-$C_4H_9$, $R_6$=1-adamantyl, n=1, m=0, X=Cl]

yield: 79%; melting point: 164° C.

$^1$H NMR (300 MHz, DMSO-$d_6$) δ 10.67 (s, 1H, HCl), 8.50 (s, 1H, NH), 7.50-7.47 (d, 2H, J=8.1 Hz, ArH), 7.11-7.09 (d, 2H, J=8.4 Hz, ArH), 7.11 (s, 1H, vinyl-H), 4.30-4.20 (m, 2H, $CH_2CH_2CH_2CH_3$), 3.95 (s, 2H, $CH_2$), 2.23 (s, 3H, Ar—$CH_3$), 2.07-1.66 (m, 15H, adamantyl), 1.58-1.47 (m, 2H, $CH_2CH_2CH_2CH_3$), 1.32-1.16 (m, 2H, $CH_2CH_2CH_2CH_3$), 0.81-0.76 (m, 3H, $CH_2CH_2CH_2CH_3$).

KHG24782 [2-(1-adamantylimino)-3-(n-butyl)-1,3-thiazolidine-4-yl]-N-(4-ethylphenyl)-acetamide hydrochloride [$R_1$=H, $R_2$=4-$C_2H_5$, $R_3$=$R_4$=H, $R_5$=n-$C_4H_9$, $R_6$=1-adamantyl, n=1, m=0, X=Cl]

yield: 51%; melting point: 156° C.

$^1$H NMR (300 MHz, DMSO-$d_6$) δ 10.68 (s, 1H, HCl), 8.51 (s, 1H, NH), 7.52-7.12 (d, 4H, J=8.7 Hz, ArH), 7.12 (s, 1H, vinyl-H), 4.29-4.21 (m, 2H, $CH_2CH_2CH_2CH_3$), 3.94 (s, 2H, $CH_2$), 2.59-2.46 (m, 2H, $CH_2CH_3$), 2.15-1.66 (m, 15H, adamantyl), 1.58-1.46 (m, 2H, $CH_2CH_2CH_2CH_3$), 1.31-1.17 (m, 2H, $CH_2CH_2CH_2CH_3$), 1.16-1.13 (m, 3H, $CH_2CH_3$), 0.81-0.76 (m, 3H, $CH_2CH_2CH_2CH_3$).

KHG24783 [2-(1-adamantylimino)-3-(n-butyl)-1,3-thiazolidine-4-yl]-N-(4-chloro-2-fluorophenyl)-acetamide hydrochloride [$R_1$=H, $R_2$=2-F, $R_3$=4-$C_1$, $R_4$=H, $R_5$=n-$C_4H_9$, $R_6$=1-adamantyl, n=1, m=0, X=Cl]

yield: 72%; melting point: 161° C.

$^1$H NMR (300 MHz, DMSO-$d_6$) δ 10.51 (s, 1H, HCl), 8.63 (s, 1H, NH), 7.90-7.26 (m, 3H, ArH), 7.12 (s, 1H, vinyl-H), 4.28-4.23 (m, 2H, $CH_2CH_2CH_2CH_3$), 4.05 (s, 2H, $CH_2$), 2.15-1.66 (m, 15H, adamantyl), 1.59-1.47 (m, 2H, $CH_2CH_2CH_2CH_3$), 1.34-1.21 (m, 2H, $CH_2CH_2CH_2CH_3$), 0.85-0.80 (m, 3H, $CH_2CH_2CH_2CH_3$).

KHG24784 [2-(1-adamantylimino)-3-(n-butyl)-1,3-thiazolidine-4-yl]-N-(4-bromophenyl)-acetamide hydrochloride [$R_1$=H, $R_2$=4-Br, $R_3$=H, $R_5$=n-$C_4H_9$, $R_6$=1-adamantyl, n=1, m=0, X=Cl]

yield: 89%; melting point: 172° C.

$^1$H NMR (300 MHz, DMSO-$d_6$) δ 10.87 (s, 1H, HCl), 8.42 (s, 1H, NH), 7.60-7.58 (d, 2H, J=7.2 Hz, ArH), 7.52-7.50 (d, 2H, J=6.9 Hz, ArH), 7.12 (s, 1H, vinyl-H), 4.23-4.18 (m, 2H, $CH_2CH_2CH_2CH_3$), 3.98 (s, 2H, $CH_2$), 2.16-1.68 (m, 15H, adamantyl), 1.58-1.46 (m, 2H, $CH_2CH_2CH_2CH_3$), 1.33-1.20 (m, 2H, $CH_2CH_2CH_2CH_3$), 0.82-0.77 (m, 3H, $CH_2CH_2CH_2CH_3$).

KHG24785 [2-(1-adamantylimino)-3-(n-butyl)-1,3-thiazolidine-4-yl]-N-(5-chloro-2-fluorophenyl)-acetamide hydrochloride [$R_1$=H, $R_2$=2-F, $R_3$=5-$C_1$, $R_4$=H, $R_5$=n-$C_4H_9$, $R_6$=1-adamantyl, n=1, m=0, X=Cl]

yield: 78%; melting point: 156° C.

$^1$H NMR (300 MHz, DMSO-$d_6$) δ 10.54 (s, 1H, HCl), 8.53 (s, 1H, NH), 8.03-7.22 (m, 3H, ArH), 7.13 (s, 1H, vinyl-H), 4.27-4.20 (m, 2H, $CH_2CH_2CH_2CH_3$), 4.06 (s, 2H, $CH_2$), 2.16-1.67 (m, 15H, adamantyl), 1.58-1.49 (m, 2H, $CH_2CH_2CH_2CH_3$), 1.32-1.20 (m, 2H, $CH_2CH_2CH_2CH_3$), 0.86-0.81 (m, 3H, $CH_2CH_2CH_2CH_3$).

KHG24788 [2-(1-adamantylimino)-3-cyclopropyl-1,3-thiazolidine-4-yl]-N-(4-isopropylphenyl)-acetamide hydrochloride [$R_1$=H, $R_2$=4-$CH(CH_3)_2$, $R_3$=$R_4$=H, $R_5$=$C_3H_5$, $R_6$=1-adamantyl, n=1, m=0, X=Cl]

yield: 74%; melting point: 237° C.

$^1$H NMR (300 MHz, DMSO-$d_6$) δ 10.56 (s, 1H, HCl), 8.51 (s, 1H, NH), 7.37-7.16 (d, 4H, J=8.7 Hz, ArH), 7.03 (s, 1H, vinyl-H), 4.15 (s, 2H, $CH_2$), 3.07-2.99 (m, 1H, cyclopropyl-CH), 2.89-2.78 (m, 1H, isopropyl-CH), 2.17-1.68 (m, 15H, adamantyl), 1.28-1.21 (m, 2H, cyclopropyl-$CH_2$), 1.82-1.15 (d, 6H, J=6.9 Hz, isopropyl-$CH_3$), 1.08-1.02 (m, 2H, cyclopropyl-$CH_2$).

KHG24789 [2-(1-adamantylimino)-3-cyclopropyl-1,3-thiazolidine-4-yl]-N-(4-n-butylphenyl)-acetamide hydrochloride [$R_1$=H, $R_2$=4-n-$C_4H_9$, $R_3$=$R_4$=H, $R_5$=$C_3H_5$, $R_6$=1-adamantyl, n=1, m=0, X=Cl]

yield: 87%; melting point: 263° C.

$^1$H NMR (300 MHz, DMSO-$d_6$) δ 10.52 (s, 1H, HCl), 8.49 (s, 1H, NH), 7.51-7.49 (d, 2H, J=8.4 Hz, ArH), 7.14-7.11 (d, 2H, J=8.1 Hz, ArH), 7.03 (s, 1H, vinyl-H), 4.00 (s, 2H, $CH_2$), 3.07-2.98 (m, 1H, cyclopropyl-CH), 2.55-2.50 (m, 1H, $CH_2CH_2CH_2CH_3$), 2.16-1.68 (m, 15H, adamantyl), 1.57-1.46 (m, 2H, $CH_2CH_2CH_2CH_3$), 1.34-1.12 (m, 2H, $CH_2CH_2CH_2CH_3$), 1.34-1.12 (m, 2H, cyclopropyl-$CH_2$), 1.07-1.01 (m, 2H, cyclopropyl-$CH_2$), 0.90-0.87 (t, 3H, J=7.2 Hz, $CH_2CH_2CH_2CH_3$).

KHG24790 [2-(1-adamantylimino)-3-cyclopropyl-1,3-thiazolidine-4-yl]-N-(4-trifluoromethylphenyl)-acetamide hydrochloride [$R_1$=H, $R_2$=4-n-$C_4H_9$, $R_3$=$R_4$=H, $R_5$=$C_3H_5$, $R_6$=1-adamantyl, n=1, m=0, X=Cl]

yield: 79%; melting point: 267° C.

$^1$H NMR (300 MHz, DMSO-$d_6$) δ 11.24 (s, 1H, HCl), 8.54 (s, 1H, NH), 7.88-7.85 (d, 2H, J=8.4 Hz, ArH), 7.70-7.68 (d, 2H, J=8.4 Hz, ArH), 7.06 (s, 1H, vinyl-H), 4.10 (s, 2H, $CH_2$), 3.10-3.01 (m, 1H, cyclopropyl-CH), 2.16-1.68 (m, 15H, adamantyl), 1.30-1.22 (m, 2H, cyclopropyl-$CH_2$), 1.09-1.02 (m, 2H, cyclopropyl-$CH_2$).

KHG24792 [2-(1-adamantylimino)-3-cyclopropyl-1,3-thiazolidine-4-yl]-N-(3,5-ditrifluoromethylphenyl)-acetamide hydrochloride [$R_1$=H, $R_2$=3-$CF_3$, $R_3$=5-$CF_3$, $R_4$=H, $R_5$=$C_3H_5$, $R_6$=1-adamantyl, n=1, m=0, X=Cl]

yield: 89%; melting point: 258° C.

$^1$H NMR (300 MHz, DMSO-$d_6$) δ 8.51 (s, 1H, NH), 8.38 (s, 2H, ArH), 7.79 (s, 1H, ArH), 7.09 (s, 1H, vinyl-H), 4.14 (s, 2H, $CH_2$), 3.11-3.18 (m, 1H, cyclopropyl-CH), 2.17-1.68 (m, 15H, adamantyl), 1.33-1.24 (m, 2H, cyclopropyl-$CH_2$), 1.11-1.05 (m, 2H, cyclopropyl-$CH_2$).

KHG24795 [2-(1-adamantylimino)-3-(n-butyl)-1,3-thiazolidine-4-yl]-N-(4-isopropylphenyl)-acetamide hydrochloride [$R_1$=H, $R_2$=4-$CH(CH_3)_2$, $R_3$=$R_4$=H, $R_5$ n-$C_4H_9$, $R_6$=1-adamantyl, n=1, m=0, X=Cl]

yield: 71%; melting point: 244° C.

$^1$H NMR (300 MHz, DMSO-$d_6$) δ 10.79 (s, 1H, HCl), 8.60 (s, 1H, NH), 7.55-7.52 (d, 2H, J=8.1 Hz, ArH), 7.18-7.16 (d, 2H, J=8.4 Hz, ArH), 7.12 (s, 1H, vinyl-H), 4.31-4.26 (m, 2H, $CH_2CH_2CH_2CH_3$), 3.98 (s, 2H, $CH_2$), 2.87-2.78 (m, 1H, J=6.9 Hz, isopropyl-$C_1$), 2.15-1.67 (m, 15H, adamantyl), 1.59-1.47 (m, 2H, $CH_2CH_2CH_2CH_3$), 1.44-1.22 (m, 2H, $CH_2CH_2CH_2CH_3$), 0.81-0.76 (m, 3H, $CH_2CH_2CH_2CH_3$).

KHG24796 [2-(1-adamantylimino)-3-(n-butyl)-1,3-thiazolidine-4-yl]-N-(4-phenoxyphenyl)-acetamide hydrochloride [$R_1$=H, $R_2$=4-$OC_6H_5$, $R_3$=$R_4$=H, $R_5$=n-$C_4H_9$, $R_6$=1-adamantyl, n=1, m=0, X=Cl]

yield: 89%; melting point: 127° C.

¹H NMR (300 MHz, DMSO-d₆) δ 10.94 (s, 1H, HCl), 8.56 (s, 1H, NH), 7.68-6.94 (m, 9H, ArH), 7.14 (s, 1H, vinyl-H), 4.34-4.24 (m, 2H, CH₂CH₂CH₂CH₃), 4.00 (s, 2H, CH₂), 2.16-1.68 (m, 15H, adamantyl), 1.58-1.47 (m, 2H, CH₂CH₂CH₂CH₃), 1.35-1.22 (m, 2H, CH₂CH₂CH₂CH₃), 0.82-0.78 (m, 3H, CH₂CH₂CH₂CH₃).

KHG24799 [2-(1-adamantylimino)-3-cyclopropyl-1,3-thiazolidine-4-yl]-N-(4-ethylphenyl)-acetamide hydrochloride [R₁=H, R₂=4-n-C₂H₅, R₃=R₄=H, R₅=C₃H₅, R₆=1-adamantyl, n=1, m=0, X=Cl]

yield: 75%; melting point: 266° C.

¹H NMR (300 MHz, DMSO-d₆) δ 10.66 (s, 1H, HCl), 8.53 (s, 1H, NH), 7.49-7.46 (d, 2H, J=8.4 Hz, ArH), 7.09-7.06 (d, 2H, J=8.7 Hz, ArH), 6.98 (s, 1H, vinyl-H), 3.97 (s, 2H, CH₂), 3.05-2.97 (m, 1H, cyclopropyl-CH), 2.52-2.43 (m, 2H, CH₂CH₃), 2.10-1.62 (m, 15H, adamantyl), 1.24-1.16 (m, 2H, cyclopropyl-CH₂), 1.12-1.06 (m, 3H, CH₂CH₃), 1.02-0.96 (m, 2H, cyclopropyl-CH₂).

KHG24800 [2-(1-adamantylimino)-3-cyclopropyl-1,3-thiazolidine-4-yl]-N-(4-phenoxyphenyl)-acetamide hydrochloride [R₁=H, R₂=4-OC₆H₅, R₃=R₄=H, R₅=C₃H₅, R₆=1-adamantyl, n=1, m=0, X=Cl]

yield: 65%; melting point: 263° C.

¹H NMR (300 MHz, DMSO-d₆) δ 10.90 (s, 1H, HCl), 8.61 (s, 1H, NH), 7.39-6.94 (m, 9H, ArH), 7.01 (s, 1H, vinyl-H), 4.05 (s, 2H, CH₂), 3.13-3.05 (m, 1H, cyclopropyl-CH), 2.16-1.68 (m, 15H, adamantyl), 1.32-1.24 (m, 2H, cyclopropyl-CH₂), 1.09-1.02 (m, 2H, cyclopropyl-CH₂).

KHG24801 [2-(1-adamantylimino)-3-cyclopropyl-1,3-thiazolidine-4-yl]-N-(4-chloro-2-fluorophenyl)-acetamide hydrochloride [R₁=H, R₂=2-F, R₃=4-Cl, R₄=H, R₅=C₃H₅, R₆=1-adamantyl, n=1, m=0, X=Cl]

yield: 86%; melting point: 261° C.

¹H NMR (300 MHz, DMSO-d₆) δ 10.59 (s, 1H, HCl), 8.70 (s, 1H, NH), 7.84-7.26 (m, 3H, ArH), 7.05 (s, 1H, vinyl-H), 4.11 (s, 2H, CH₂), 3.14-3.05 (m, 1H, cyclopropyl-CH), 2.15-1.67 (m, 15H, adamantyl), 1.32-1.23 (m, 2H, cyclopropyl-CH₂), 1.09-1.01 (m, 2H, cyclopropyl-CH₂).

KHG24802 [2-(1-adamantylimino)-3-cyclopropyl-1,3-thiazolidine-4-yl]-N-(5-chloro-2-fluorophenyl)-acetamide hydrochloride [R₁=H, R₂=2-F, R₃=5-Cl, R₄=H, R₅=C₃H₅, R₆=1-adamantyl, n=1, m=0, X=Cl]

yield: 77%; melting point: 244° C.

¹H NMR (300 MHz, DMSO-d₆) δ 10.55 (s, 1H, HCl), 8.55 (s, 1H, NH), 8.01-7.23 (m, 3H, ArH), 7.05 (s, 1H, vinyl-H), 4.11 (s, 2H, CH₂), 3.09-3.01 (m, 1H, cyclopropyl-CH), 2.16-1.68 (m, 15H, adamantyl), 1.31-1.23 (m, 2H, cyclopropyl-CH₂), 1.08-1.01 (m, 2H, cyclopropyl-CH₂).

KHG24803 [2-(1-adamantylimino)-3-n-butyl-1,3-thiazolidine-4-yl]-N-(3,4-dioxymethylenephenyl)-acetamide hydrochloride [R₁=H, R₂, R₃₂—OCH₂—O(4-), R₄=H, R₅=n-C₄H₉, R₆=1-adamantyl, n=1, m=0, X=Cl]

yield: 88%; melting point: 220° C.

¹H NMR (300 MHz, DMSO-d₆) δ 10.92 (s, 1H, HCl), 8.60 (s, 1H, NH), 7.35-6.83 (m, 3H, ArH), 7.11 (s, 1H, vinyl-H), 5.98 (s, 2H, OCH₂O), 4.35-4.24 (m, 2H, CH₂CH₂CH₂CH₃), 3.98 (s, 2H, CH₂), 2.15-1.66 (m, 15H, adamantyl), 1.58-1.45 (m, 2H, CH₂CH₂CH₂CH₃), 1.34-1.20 (m, 2H, CH₂CH₂CH₂CH₃), 0.82-0.78 (m, 3H, CH₂CH₂CH₂CH₃).

KHG24804 [2-(1-adamantylimino)-3-cyclopropyl-1,3-thiazolidine-4-yl]-N-(3,4-dioxymethylenephenyl)-acetamide hydrochloride [R₁=H, R₂, R₃=2-OCH₂—O(4-), R₄=H, R₅=C₃H₅, R₆=1-adamantyl, n=1, m=0, X=Cl]

yield: 81%; melting point: 250° C.

¹H NMR (300 MHz, DMSO-d₆) δ 10.77 (s, 1H, HCl), 8.57 (s, 1H, NH), 7.35-6.83 (m, 3H, ArH), 7.05 (s, 1H, vinyl-H), 5.98 (s, 2H, benzodioxol-CH₂), 4.01 (s, 2H, CH₂), 3.11-3.01 (m, 1H, cyclopropyl-CH), 2.15-1.67 (m, 15H, adamantyl), 1.30-1.16 (m, 2H, cyclopropyl-CH₂), 1.08-1.00 (m, 2H, cyclopropyl-CH₂).

KHG24805 [2-(1-adamantylimino)-3-n-propyl-1,3-thiazolidine-4-yl]-N-(3,5-dichlorophenyl)-acetamide hydrochloride [R₁=H, R₂=3-Cl, R₃=5-Cl, R₄=H, R₅=n-C₃H₅, R₆=1-adamantyl, n=1, m=0, X=Cl]

yield: 49.4%; melting point: 153° C.

¹H NMR (300 MHz, DMSO-d₆) δ 11.40 (s, 1H, HCl), 8.47 (s, 1H, NH), 7.73-7.31 (m, 3H, ArH), 7.15 (s, 1H, vinyl-H), 4.20 (m, 2H, CH₂CH₂), 4.03 (s, 2H, CH₂), 2.16-1.63 (m, 15H, adamantyl H), 1.58 (m, 2H, CH₂CH₂CH₃), 0.85 (t, J=7.3 Hz, 3H, CH₃).

KHG24807 [2-(1-adamantylimino)-3-n-propyl-1,3-thiazolidine-4-yl]-N-(4-isopropylphenyl)-acetamide hydrochloride [R₁=H, R₂=4-CH(CH₃)₂, R₃=R₄=H, R₅=n-C₃H₅, R₆=1-adamantyl, n=1, m=0, X=Cl]

yield: 91.8%; melting point: 155° C.

¹H NMR (300 MHz, DMSO-d₆) δ 11.08 (s, 1H, HCl), 8.95 (s, 1H, NH), 7.72-7.01 (m, 4H, ArH), 6.73 (s, 1H, vinyl-H), 4.99 (m, 2H, CH₂CH₂CH₃), 4.18 (s, 2H, CH₂), 2.85 (m, 1H, isopropyl CH), 2.23-1.72 (m, 15H, adamantyl H), 1.66 (m, 2H, CH₂CH₂CH₃), 1.21 (d, J=6.9, 6H, 2× isopropyl CH₃), 0.90 (t, J=7.1 Hz, 3H, CH₃).

KHG24808 [2-(1-adamantylimino)-3-n-propyl-1,3-thiazolidine-4-yl]-N-(4-n-butylphenyl)-acetamide hydrochloride [R₁=H, R₂=4-n-C₄H₉, R₃=R₄=H, R₅=n-C₃H₅, R₆=1-adamantyl, n=1, m=0, X=Cl]

yield: 74.9%; melting point: 213° C.

¹H NMR (300 MHz, DMSO-d₆) δ 10.62 (s, 1H, HCl), 8.49 (s, 1H, NH), 7.51-7.11 (m, 4H, ArH), 7.14 (s, 1H, vinyl-H), 4.22 (m, 2H, CH₂CH₂), 3.95 (s, 2H, CH₂), 2.52 (m, 2H, CH₂CH₂CH₂CH₃), 2.16-1.64 (m, 15H, adamantyl H), 1.61 (m, 2H, CH₂CH₂CH₃), 1.51 (m, 2H, CH₂CH₂CH₂CH₃), 1.26 (m, 2H, CH₂CH₂CH₂CH₃), 0.88 (t, 3H, CH₂CH₂CH₃), 0.84 (m, 3H, CH₂CH₂CH₂CH₃).

KHG24809 [2-(1-adamantylimino)-3-n-propyl-1,3-thiazolidine-4-yl]-N-(4-trifluoromethylphenyl)-acetamide hydrochloride [R₁=H, R₂=4-CF₃, R₃=R₄=H, R₅=n-C₃H₅, R₆=1-adamantyl, n=1, m=0, X=Cl]

yield: 83.7%; melting point: 221° C.

¹H NMR (300 MHz, DMSO-d₆) δ 11.24 (s, 1H, HCl), 8.50 (s, 1H, NH), 7.86-7.68 (m, 4H, ArH), 7.15 (s, 1H, vinyl-H), 4.22 (m, 2H, CH₂CH₂), 4.05 (s, 2H, CH₂), 2.16-1.64 (m, 15H, adamantyl H), 1.59 (m, 2H, CH₂CH₂CH₃), 0.84 (t, J=7.3 Hz, 3H, CH₃).

KHG24811 [2-(1-adamantylimino)-3-n-propyl-1,3-thiazolidine-4-yl]-N-(4-fluorophenyl)-acetamide hydrochloride [R₁=H, R₂=4-F, R₃=R₄=H, R₅=n-C₃H₅, R₆=1-adamantyl, n=1, m=0, X=Cl]

yield: 96.3%; melting point: 138° C.

¹H NMR (300 MHz, CDCl₃) δ 11.25 (s, 1H, HCl), 8.89 (s, 1H, NH), 7.83-6.93 (m, 4H, ArH), 6.73 (s, 1H, vinyl-H), 4.98 (m, 2H, CH₂CH₂), 4.17 (s, 2H, CH₂), 2.23-1.69 (m, 15H, adamantyl H), 1.66 (m, 2H, CH₂CH₂CH₃), 0.89 (t, J=7.3 Hz, 3H, CH₃).

KHG24812 [2-(1-adamantylimino)-3-n-propyl-1,3-thiazolidine-4-yl]-N-(4-bromophenyl)-acetamide hydrochloride [R₁=H, R₂=4-Br, R₃=R₄=H, R₅=n-C₃H₅, R₆=1-adamantyl, n=1, m=0, X=Cl]

yield: 96.4%; melting point: 228° C.

¹H NMR (300 MHz, DMSO-d₆) δ 11.00 (s, 1H, HCl), 8.50 (s, 1H, NH), 7.63-7.49 (m, 4H, ArH), 7.13 (s, 1H, vinyl-H), 4.22 (m, 2H, CH₂CH₂), 4.00 (s, 2H, CH₂), 2.16-1.63 (m, 15H, adamantyl H), 1.58 (m, 2H, CH₂CH₂CH₃), 0.84 (t, J=7.3 Hz, 3H, CH₃).

KHG24813 [2-(1-adamantylimino)-3-n-propyl-1,3-thiazolidine-4-yl]-N-(4-methylphenyl)-acetamide hydrochloride [$R_1$=H, $R_2$=4-$CH_3$, $R_3$=$R_4$=H, $R_5$=n-$C_3H_5$, $R_6$=1-adamantyl, n=1, m=0, X=Cl]

yield: 94.4%; melting point: 239° C.

$^1$H NMR (300 MHz, DMSO-$d_6$) δ 10.66 (s, 1H, HCl), 8.51 (s, 1H, NH), 7.51-7.10 (m, 4H, ArH), 7.12 (s, 1H, vinyl-H), 4.23 (m, 2H, $CH_2CH_2$), 3.96 (s, 2H, $CH_2$), 2.25 (s, 3H, $CH_3$), 2.16-1.63 (m, 15H, adamantyl H), 1.58 (m, 2H, $CH_2CH_2CH_3$), 0.84 (t, J=7.3 Hz, 3H, $CH_2CH_2CH_3$).

KHG24814 [2-(1-adamantylimino)-3-n-propyl-1,3-thiazolidine-4-yl]-N-(4-ethylphenyl)-acetamide hydrochloride [$R_1$=H, $R_2$=4-$C_2H_5$, $R_3$=$R_4$=H, $R_5$=n-$C_3H_5$, $R_6$=1-adamantyl, n=1, m=0, X=Cl]

yield: 86.6%; melting point: 240° C.

$^1$H NMR (300 MHz, CDCl$_3$) δ 11.09 (s, 1H, HCl), 8.97 (s, 1H, NH), 7.73-7.07 (m, 4H, ArH), 6.71 (s, 1H, vinyl-H), 5.00 (m, 2H, $CH_2CH_2CH_3$), 4.19 (s, 2H, $CH_2$), 2.69 (s, 2H, $CH_2CH_3$), 2.24-1.68 (m, 15H, adamantyl H), 1.67 (m, 2H, $CH_2CH_2CH_3$), 1.20 (t, J=7.6 Hz, 3H, $CH_2CH_3$), 0.89 (t, J=7.3 Hz, 3H, $CH_2CH_2CH_3$).

KHG24815 [2-(1-adamantylimino)-3-n-propyl-1,3-thiazolidine-4-yl]-N-(4-phenoxyphenyl)-acetamide hydrochloride [$R_1$=H, $R_2$=4-$OC_6H_5$, $R_3$=$R_4$=H, $R_5$=n-$C_3H_5$, $R_6$=1-adamantyl, n=1, m=0, X=Cl]

yield: 92.1%; melting point: 135° C.

$^1$H NMR (300 MHz, DMSO-$d_6$) δ 10.86 (s, 1H, HCl), 8.54 (s, 1H, NH), 7.66-6.94 (m, 9H, ArH), 7.13 (s, 1H, vinyl-H), 4.24 (m, 2H, $CH_2CH_2$), 3.99 (s, 2H, $CH_2$), 2.16-1.62 (m, 15H, adamantyl H), 1.58 (m, 2H, $CH_2CH_2CH_3$), 0.85 (t, J=7.3 Hz, 3H, $CH_3$).

KHG24816 [2-(1-adamantylimino)-3-n-propyl-1,3-thiazolidine-4-yl]-N-(4-chloro-2-fluorophenyl)-acetamide hydrochloride [$R_1$=H, $R_2$=2-F, $R_3$=4-Cl, $R_4$=H, $R_5$=n-$C_3H_5$, $R_6$=1-adamantyl, n=1, m=0, X=Cl]

yield: 98.4%; melting point: 131° C.

$^1$H NMR (300 MHz, DMSO-$d_6$) δ 10.52 (s, 1H, HCl), 8.64 (s, 1H, NH), 7.90-7.27 (m, 3H, ArH), 7.13 (s, 1H, vinyl-H), 4.24 (m, 2H, $CH_2CH_2$), 4.06 (s, 2H, $CH_2$), 2.16-1.61 (m, 15H, adamantyl H), 1.58 (m, 2H, $CH_2CH_2CH_3$), 0.86 (t, J=7.3 Hz, 3H, $CH_3$).

KHG24817 [2-(1-adamantylimino)-3-n-propyl-1,3-thiazolidine-4-yl]-N-(5-chloro-2-fluorophenyl)-acetamide hydrochloride [$R_1$=H, $R_2$=2-F, $R_3$=5-Cl, $R_4$=H, $R_5$=n-$C_3H_5$, $R_6$=1-adamantyl, n=1, m=0, X=Cl]

yield: 93.6%; melting point: 130° C.

$^1$H NMR (300 MHz, DMSO-$d_6$) δ 10.55 (s, 1H, HCl), 8.57 (s, 1H, NH), 8.04-7.23 (m, 3H, ArH), 7.13 (s, 1H, vinyl-H), 4.22 (m, 2H, $CH_2CH_2$), 4.07 (s, 2H, $CH_2$), 2.16-1.64 (m, 15H, adamantyl H), 1.58 (m, 2H, $CH_2CH_2CH_3$), 0.86 (t, J=7.3 Hz, 3H, $CH_3$).

KHG24818 [2-(1-adamantylimino)-3-n-propyl-1,3-thiazolidine-4-yl]-N-(2-chloro-4-methylphenyl)-acetamide hydrochloride [$R_1$=H, $R_2$=2-Cl, $R_3$=4-$CH_3$, $R_4$=H, $R_5$=n-$C_3H_5$, $R_6$=1-adamantyl, n=1, m=0, X=Cl]

yield: 94.2%; melting point: 201° C.

$^1$H NMR (300 MHz, DMSO-$d_6$) δ 10.09 (s, 1H, HCl), 8.60 (s, 1H, NH), 7.50-7.12 (m, 3H, ArH), 7.12 (s, 1H, vinyl-H), 4.24 (m, 2H, $CH_2CH_2$), 4.02 (s, 2H, $CH_2$), 2.28 (s, 3H, $CH_3$), 2.23-1.62 (m, 15H, adamantyl H), 1.61 (m, 2H, $CH_2CH_2CH_3$), 0.88 (t, J=7.3 Hz, 3H, $CH_2CH_2CH_3$).

KHG24819 [2-(1-adamantylimino)-3-ethyl-1,3-thiazolidine-4-yl]-N-(4-isopropylphenyl)-acetamide hydrochloride [$R_1$=H, $R_2$=4-$CH(CH_3)_2$, $R_3$=$R_4$=H, $R_5$=$C_2H_5$, $R_6$=1-adamantyl, n=1, m=0, X=Cl]

yield: 97.1%; melting point: 158° C.

$^1$H NMR (300 MHz, CDCl$_3$) δ 11.04 (s, 1H, HCl), 8.82 (s, 1H, NH), 7.73-7.10 (m, 4H, ArH), 6.70 (s, 1H, vinyl-H), 5.00 (m, 2H, $CH_2CH_3$), 4.16 (s, 2H, $CH_2$), 2.85 (m, 1H, isopropyl CH), 2.23-1.72 (m, 15H, adamantyl H), 1.21 (m, 6H, 2× isopropyl $CH_3$), 1.20 (m, 3H, $CH_3$).

KHG24820 [2-(1-adamantylimino)-3-ethyl-1,3-thiazolidine-4-yl]-N-(4-n-butylphenyl)-acetamide hydrochloride [$R_1$=H, $R_2$=4-n-$C_4H_9$, $R_3$=$R_4$=H, $R_5$=$C_2H_5$, $R_6$=1-adamantyl, n=1, m=0, X=Cl]

yield: 95.3%; melting point: 141° C.

$^1$H NMR (300 MHz, CDCl$_3$) δ 11.02 (s, 1H, HCl), 8.80 (s, 1H, NH), 7.72-7.04 (m, 4H, ArH), 6.70 (s, 1H, vinyl-H), 4.99 (m, 2H, $CH_2CH_3$), 4.16 (s, 2H, $CH_2$), 2.54 (t, J=7.6 Hz, 2H, $CH_2CH_2CH_2CH_3$), 2.24-1.72 (m, 15H, adamantyl H), 1.55 (m, 2H, $CH_2CH_2CH_2CH_3$), 1.34 (m, 2H, $CH_2CH_2CH_2CH_3$), 1.23 (m, 3H, $CH_2CH_3$), 0.91 (m, 3H, $CH_2CH_2CH_3$).

KHG24821 [2-(1-adamantylimino)-3-ethyl-1,3-thiazolidine-4-yl]-N-(4-trifluoromethylphenyl)-acetamide hydrochloride [$R_1$=H, $R_2$=4-$CF_3$, $R_3$=$R_4$=H, $R_5$=$C_2H_5$, $R_6$=1-adamantyl, n=1, m=0, X=Cl]

yield: 83.2%; melting point: 219° C.

$^1$H NMR (300 MHz, CDCl$_3$) δ 11.47 (s, 1H, HCl), 8.80 (s, 1H, NH), 7.99-7.50 (m, 4H, ArH), 6.72 (s, 1H, vinyl-H), 5.03 (m, 2H, $CH_2CH_3$), 4.21 (s, 2H, $CH_2$), 2.25-1.74 (m, 15H, adamantyl H), 1.22 (t, J=6.9 Hz, 3H, $CH_3$).

KHG24823 [2-(1-adamantylimino)-3-isopropyl-1,3-thiazolidine-4-yl]-N-(4-chlorophenyl)-acetamide hydrochloride [$R_1$=H, $R_2$=4-Cl, $R_3$=$R_4$=H, $R_5$=$CH(CH_3)_2$, $R_6$=1-adamantyl, n=1, m=0, X=Cl]

yield: 93.4%; melting point: 236° C.

$^1$H NMR (300 MHz, CDCl$_3$) δ 11.66 (s, 1H, HCl), 7.87-7.21 (m, 4H, ArH), 7.20 (s, 1H, vinyl-H), 6.71 (br.s, 1H, NH), 5.56 (m, 1H, isopropyl CH), 4.31 (s, 2H, $CH_2$), 2.27-1.71 (m, 15H, adamantyl H), 1.64 (d, J=7.0 Hz, 6H, 2× isopropyl $CH_3$).

KHG24825 [2-(1-adamantylimino)-3-isopropyl-1,3-thiazolidine-4-yl]-N-(4-n-butylphenyl)-acetamide hydrochloride [$R_1$=H, $R_2$=4-n-$C_4H_9$, $R_3$=$R_4$=H, $R_5$=$CH(CH_3)_2$, $R_6$=1-adamantyl, n=1, m=0, X=Cl]

yield: 85.6%; melting point: 178° C.

$^1$H NMR (300 MHz, CDCl$_3$) δ 11.34 (s, 1H, HCl), 7.76-7.06 (m, 4H, ArH), 7.17 (s, 1H, vinyl-H), 6.71 (br.s, 1H, NH), 5.63 (m, 1H, isopropyl CH), 4.31 (s, 2H, $CH_2$), 2.55 (t, J=7.6 Hz, 2H, $CH_2CH_2CH_3$), 2.26-1.69 (m, 15H, adamantyl H), 1.63 (d, J=7.0 Hz, 6H, 2× isopropyl $CH_3$), 1.55 (m, 2H, $CH_2CH_2CH_2CH_3$), 1.30 (m, 2H, $CH_2CH_2CH_2CH_3$), 0.91 (t, J=7.3 Hz, 3H, $CH_2CH_2CH_3$).

KHG24826 [2-(1-adamantylimino)-3-isopropyl-1,3-thiazolidine-4-yl]-N-(4-trifluoromethylphenyl)-acetamide hydrochloride [$R_1$=H, $R_2$=4-$CF_3$, $R_3$=$R_4$=H, $R_5$=$CH(CH_3)_2$, $R_6$=1-adamantyl, n=1, m=0, X=Cl]

yield: 81.8%; melting point: 246° C.

$^1$H NMR (300 MHz, CDCl$_3$) δ 11.90 (s, 1H, HCl), 8.04-7.50 (m, 4H, ArH), 7.23 (s, 1H, vinyl-H), 6.68 (br.s, 1H, NH), 5.56 (m, 1H, isopropyl CH), 4.36 (s, 2H, $CH_2$), 2.28-1.70 (m, 15H, adamantyl H), 1.64 (d, J=7.0 Hz, 6H, 2× isopropyl $CH_3$).

KHG24828 [2-(1-adamantylimino)-3-isopropyl-1,3-thiazolidine-4-yl]-N-(3,5-ditrifluoromethylphenyl)-acetamide hydrochloride [$R_1$=H, $R_2$=3-$CF_3$, $R_3$=5-$CF_3$, $R_4$=H, $R_5$=$CH(CH_3)_2$, $R_6$=1-adamantyl, n=1, m=0, X=Cl]

yield: 69.6%; melting point: 233° C.

$^1$H NMR (300 MHz, CDCl$_3$) δ 12.29 (s, 1H, HCl), 8.43 (s, 2H, ArH), 7.55 (s, 1H, ArH), 7.20 (s, 1H, vinyl-H), 6.80 (br.s, 1H, NH), 5.54 (m, 1H, isopropyl CH), 4.40 (s, 2H, $CH_2$), 2.28-1.75 (m, 15H, adamantyl H), 1.66 (d, J=7.0 Hz, 6H, 2× isopropyl $CH_3$).

KHG24829 [2-(1-adamantylimino)-3-isopropyl-1,3-thiazolidine-4-yl]-N-(4-fluoromethylphenyl)-acetamide hydrochloride [$R_1$=H, $R_2$=4-F, $R_3$=$R_4$=H, $R_5$=CH(CH$_3$)$_2$, $R_6$=1-adamantyl, n=1, m=0, X=Cl]

yield: 89.4%; melting point: 227° C.

$^1$H NMR (300 MHz, CDCl$_3$) δ 11.57 (s, 1H, HCl), 7.87-6.92 (m, 4H, ArH), 7.19 (s, 1H, vinyl-H), 6.85 (br.s, 1H, NH), 5.59 (m, 1H, isopropyl CH), 4.30 (s, 2H, CH$_2$), 2.27-1.70 (m, 15H, adamantyl H), 1.64 (d, J=7.0 Hz, 6H, 2⋋ isopropyl CH$_3$).

KHG24831 [2-(1-adamantylimino)-3-isopropyl-1,3-thiazolidine-4-yl]-N-(4-methylphenyl)-acetamide hydrochloride [$R_1$=H, $R_2$=4-CH$_3$, $R_3$=$R_4$=H, $R_5$=CH(CH$_3$)$_2$, $R_6$=1-adamantyl, n=1, m=0, X=Cl]

yield: 89.9%; melting point: 220° C.

$^1$H NMR (300 MHz, DMSO-d$_6$) δ 10.64 (s, 1H, HCl), 7.95 (br.s, 1H, NH), 7.51-7.10 (m, 4H, ArH), 7.14 (s, 1H, vinyl-H), 4.98 (m, 1H, isopropyl CH), 4.07 (s, 2H, CH$_2$), 2.25 (s, 3H, CH$_3$), 2.16-1.68 (m, 15H, adamantyl H), 1.48 (d, J=6.9 Hz, 6H, 2⋋ isopropyl CH$_3$).

KHG24832 [2-(1-adamantylimino)-3-isopropyl-1,3-thiazolidine-4-yl]-N-(4-ethylphenyl)-acetamide hydrochloride [$R_1$=H, $R_2$=4-C$_2$H$_5$, $R_3$=$R_4$=H, $R_5$=CH(CH$_3$)$_2$, $R_6$=1-adamantyl, n=1, m=0, X=Cl]

yield: 94.7%; melting point: 171° C.

$^1$H NMR (300 MHz, DMSO-d$_6$) δ 10.65 (s, 1H, HCl), 8.91 (br.s, 1H, NH), 7.53-7.14 (m, 4H, ArH), 7.14 (s, 1H, vinyl-H), 4.97 (m, 1H, isopropyl CH), 4.07 (s, 2H, CH$_2$), 2.55 (s, 3H, CH$_2$CH$_3$), 2.16-1.68 (m, 15H, adamantyl H), 1.48 (d, J=6.9 Hz, 6H, 2⋋ isopropyl CH$_3$), 1.15 (t, J=7.5 Hz, 3H, CH$_2$CH$_3$).

KHG24833 [2-(1-adamantylimino)-3-isopropyl-1,3-thiazolidine-4-yl]-N-(4-phenoxyphenyl)-acetamide hydrochloride [$R_1$=H, $R_2$=4-C$_6$H$_5$, $R_3$=$R_4$=H, $R_5$=CH(CH$_3$)$_2$, $R_6$=1-adamantyl, n=1, m=0, X=Cl]

yield: 90.7%; melting point: 164° C.

$^1$H NMR (300 MHz, DMSO-d$_6$) δ 10.73 (s, 1H, HCl), 7.88 (br.s, 1H, NH), 7.64-6.95 (m, 9H, ArH), 7.15 (s, 1H, vinyl-H), 4.96 (m, 1H, isopropyl CH), 4.08 (s, 2H, CH$_2$), 2.17-1.68 (m, 15H, adamantyl H), 1.59 (d, J=7.0 Hz, 6H, 2⋋ isopropyl CH$_3$).

KHG24834 [2-(1-adamantylimino)-3-isopropyl-1,3-thiazolidine-4-yl]-N-(4-chloro-2-fluorophenyl)-acetamide hydrochloride [$R_1$=H, $R_2$=2-F, $R_3$=4-Cl, $R_4$=H, $R_5$=CH(CH$_3$)$_2$, $R_6$=1-adamantyl, n=1, m=0, X=Cl]

yield: 75.9%; melting point: 228° C.

$^1$H NMR (300 MHz, DMSO-d$_6$) δ 10.42 (s, 1H, HCl), 7.98 (br.s, 1H, NH), 7.89-7.27 (m, 3H, ArH), 7.14 (s, 1H, vinyl-H), 4.97 (m, 1H, isopropyl CH), 4.15 (s, 2H, CH$_2$), 2.17-1.68 (m, 15H, adamantyl H), 1.48 (d, J=6.9 Hz, 6H, 2⋋ isopropyl CH$_3$).

KHG24835 [2-(1-adamantylimino)-3-isopropyl-1,3-thiazolidine-4-yl]-N-(5-chloro-2-fluorophenyl)-acetamide hydrochloride [$R_1$=H, $R_2$=2-F, $R_3$=5-Cl, $R_4$=H, $R_5$=CH(CH$_3$)$_2$, $R_6$=1-adamantyl, n=1, m=0, X=Cl]

yield: 98.1%; melting point: 116° C.

$^1$H NMR (300 MHz, DMSO-d$_6$) δ 10.48 (s, 1H, HCl), 8.13 (br.s, 1H, NH), 8.03-7.22 (m, 3H, ArH), 7.15 (s, 1H, vinyl-H), 4.96 (m, 1H, isopropyl CH), 4.17 (s, 2H, CH$_2$), 2.19-1.68 (m, 15H, adamantyl H), 1.48 (d, J=6.9 Hz, 6H, 2⋋ isopropyl CH$_3$).

KHG24836 [2-(1-adamantylimino)-3-isopropyl-1,3-thiazolidine-4-yl]-N-(5-chloro-4-methylphenyl)-acetamide hydrochloride [$R_1$=H, $R_2$=5-Cl, $R_3$=4-CH$_3$, $R_4$=H, $R_5$=CH(CH$_3$)$_2$, $R_6$=1-adamantyl, n=1, m=0, X=Cl]

yield: 93.9%; melting point: 231° C.

$^1$H NMR (300 MHz, DMSO-d$_6$) δ 10.04 (s, 1H, HCl), 8.03 (br.s, 1H, NH), 7.50-7.13 (m, 3H, ArH), 7.15 (s, 1H, vinyl-H), 4.99 (m, 1H, isopropyl CH), 4.13 (s, 2H, CH$_2$), 2.28 (s, 3H, CH$_3$), 2.16-1.68 (m, 15H, adamantyl H), 1.48 (d, J=6.9 Hz, 6H, 2⋋ isopropyl CH$_3$).

KHG24837 [2-(1-adamantylimino)-3-n-propyl-1,3-thiazolidine-4-yl]-N-(3,4-dioxymethylenephenyl)-acetamide hydrochloride [$R_1$=H, $R_2$, $R_3$=3-OCH$_2$—O(4-), $R_4$=H, $R_5$=n-C$_3$H$_7$, $R_6$=1-adamantyl, n=1, m=0, X=Cl]

yield: 83.8%; melting point: 142° C.

$^1$H NMR (300 MHz, DMSO-d$_6$) δ 10.76 (s, 1H, HCl), 8.52 (s, 1H, NH), 7.32-6.85 (m, 3H, ArH), 7.11 (s, 1H, vinyl-H), 5.98 (s, 2H, benzodioxol CH$_2$), 4.22 (m, 2H, CH$_2$CH$_2$CH$_3$), 3.38 (s, 2H, CH$_2$), 2.16-1.62 (m, 15H, adamantyl H), 1.60 (m, 2H, CH$_2$CH$_2$CH$_3$), 0.84 (t, J=7.2 Hz, 3H, CH$_3$).

KHG24838 [2-(1-adamantylimino)-3-isopropyl-1,3-thiazolidine-4-yl]-N-(3,4-dioxymethylenephenyl)-acetamide hydrochloride [$R_1$=H, $R_2$, $R_3$=3-OCH$_2$—O(4-), $R_4$=H, $R_5$=CH(CH$_3$)$_2$, $R_6$=1-adamantyl, n=1, m=0, X=Cl]

yield: 81.4%; melting point: 150° C.

$^1$H NMR (300 MHz, DMSO-d$_6$) δ 10.70 (s, 1H, HCl), 7.92 (br.s, 1H, NH), 7.32-6.85 (m, 3H, ArH), 7.13 (s, 1H, vinyl-H), 5.98 (s, 2H, benzodioxol CH$_2$), 4.94 (m, 1H, isopropyl CH), 4.05 (s, 2H, CH$_2$), 2.16-1.59 (m, 15H, adamantyl H), 1.47 (d, J=6.9 Hz, 6H, 2⋋ isopropyl CH$_3$).

KHG248039 [2-(1-adamantylimino)-3-n-propyl-1,3-thiazolidine-4-yl]-N-(2-fluoro-5-nitrophenyl)-acetamide hydrochloride [$R_1$=H, $R_2$=2-F, $R_3$=4-NO$_2$, $R_4$=H, $R_5$=n-C$_3$H$_7$, $R_6$=1-adamantyl, n=1, m=0, X=Cl]

yield: 86.3%; melting point: 145° C.

$^1$H NMR (300 MHz, DMSO-d$_6$) δ 10.85 (s, 1H, HCl), 8.94-7.58 (m, 3H, ArH), 8.61 (s, 1H, NH), 7.16 (s, 1H, vinyl-H), 4.25 (m, 2H, CH$_2$CH$_2$CH$_3$), 4.13 (s, 2H, CH$_2$), 2.16-1.62 (m, 15H, adamantyl H), 1.60 (m, 2H, CH$_2$CH$_2$CH$_3$), 0.86 (t, J=7.2 Hz, 3H, CH$_3$).

KHG24840 [2-(1-adamantylimino)-3-isopropyl-1,3-thiazolidine-4-yl]-N-(2-fluoro-5-nitrophenyl)-acetamide hydrochloride [$R_1$H, $R_2$=2-F, $R_3$=4-NO$_2$, $R_4$=H, $R_3$=CH(CH$_3$)$_2$, $R_6$=1-adamantyl, n=1, m=0, X=Cl]

yield: 77.9%; melting point: 131° C.

$^1$H NMR (300 MHz, DMSO-d$_6$) δ 10.80 (s, 1H, HCl), 8.94-7.59 (m, 3H, ArH), 8.08 (br.s, 1H, NH), 7.18 (s, 1H, vinyl-H), 4.97 (m, 1H, isopropyl CH), 4.24 (s, 2H, CH$_2$), 2.17-1.59 (m, 15H, adamantyl H), 1.48 (d, J=6.8 Hz, 6H, 2⋋ isopropyl CH$_3$).

KHG24841 [2-(2-adamantylimino)-3-methyl-1,3-thiazolidine-4-yl]-N-(4-n-butylphenyl)-acetamide hydrochloride [$R_1$=H, $R_2$=4-n-C$_4$H$_9$, $R_3$=$R_4$=H, $R_5$=CH$_3$, $R_6$=1-adamantyl, n=1, m=0, X=Cl]

yield: 81%; melting point: 127° C.

$^1$H NMR (300 MHz, DMSO-d$_6$) δ 10.67 (s, 1H, HCl), 8.87 (s, 1H, NH), 7.53-7.50 (d, 2H, J=8.7 Hz, ArH), 7.13-7.10 (d, 2H, J=8.7 Hz, ArH), 7.05 (s, 1H, vinyl-H), 4.00 (s, 2H, CH$_2$), 3.70 (s, 3H, CH$_3$), 3.63-3.53 (m, 1H, admantyl-CH), 2.59-2.53 (m, 2H, CH$_2$CH$_2$CH$_2$CH$_3$), 2.16-1.46 (m, 14H, adamantyl), 1.62-1.42 (m, 2H, CH$_2$CH$_2$CH$_2$CH$_3$), 1.34-1.20 (m, 2H, CH$_2$CH$_2$CH$_2$CH$_3$), 0.90-0.82 (m, 3H, CH$_2$CH$_2$CH$_2$CH$_3$).

KHG24842 [2-(2-adamantylimino)-3-methyl-1,3-thiazolidine-4-yl]-N-(4-fluorophenyl)-acetamide hydrochloride [$R_1$=H, $R_2$=4-F, $R_3$=$R_4$=H, $R_5$=CH$_3$, $R_6$=1-adamantyl, n=1, m=0, X=Cl]

yield: 56%; melting point: 154° C.

$^1$H NMR (300 MHz, DMSO-d$_6$) δ 10.91 (s, 1H, HCl), 8.89-8.87 (d, 1H, NH), 7.68-7.13 (m, 4H, ArH), 7.14 (s, 1H, vinyl-H), 4.03 (s, 2H, CH$_2$), 3.70 (s, 3H, CH$_3$), 3.63-3.57 (m, 1H, admantyl-CH), 2.17-1.55 (m, 14H, 2-adamantyl).

KHG24844 [2-(2-adamantylimino)-3-methyl-1,3-thiazolidine-4-yl]-N-(4-isopropylphenyl)-acetamide hydrochloride [$R_1$=H, $R_2$=4-CH(CH$_3$)$_2$, $R_3$=$R_4$=H, $R_5$=CH$_3$, $R_6$=1-adamantyl, n=1, m=0, X=Cl]

yield: 94%; melting point: 245° C.

$^1$H NMR (300 MHz, DMSO-d$_6$) δ 10.60 (s, 1H, HCl), 8.85-8.84 (d, 1H, NH), 7.53-7.51 (d, 2H, J=8.4 Hz, ArH), 7.20-7.17 (d, 2H, J=8.4 Hz, ArH), 7.13 (s, 1H, vinyl-H), 4.00 (s, 2H, CH$_2$), 3.69 (s, 3H, CH$_3$), 3.64-3.57 (m, 1H, admantyl-CH), 2.89-2.77 (m, 1H, isopropyl-CH), 2.18-1.55 (m, 14H, 2-adamantyl), 1.18-1.64 (d, 6H, J=7.2 Hz, isopropyl-CH$_3$).

KHG24847 [2-(1-adamantylimino)-3-ethyl-1,3-thiazolidine-4-yl]-N-(4-ethylphenyl)-acetamide hydrochloride [$R_1$=H, $R_2$=4-C$_2$H$_5$, $R_3$=$R_4$=H, $R_5$=C$_2$H$_5$, $R_6$=1-adamantyl, n=1, m=0, X=Cl]

yield: 18.9%; melting point: 144-145° C.

$^1$H NMR (300 MHz, DMSO-d$_6$) δ 10.63 (s, 1H, HCl), 8.40 (s, 1H, NH), 7.50 (d, 2H, J=8.4 Hz, ArH), 7.14 (d, 2H, J=8.4 Hz, ArH), 7.11 (s, 1H, vinyl H), 4.32-4.25 (m, 2H, 3-CH$_2$CH$_3$), 3.96 (s, 2H, CH$_2$), 2.55 (m, 2H, CH$_2$CH$_3$), 2.49-1.67 (m, 15H, adamantyl), 1.21-1.12 (m, 6H, 2×CH$_3$).

The novel 2-imino-1,3-thiazoline based compounds according to the present invention have excellent effect of T-type calcium channel inhibition, and thus, it is possible to obtain excellent effect to treat and/or prevent nerve diseases, pain, epilepsy, hypertension, angina pectoris, heart muscle disease, vascular disorder, cancer metastasis, and the like by using the compounds.

What is claimed is:

1. A 2-imino-1,3-thiazoline-based compound represented by Chemical Formula I:

(Chemical Formula I)

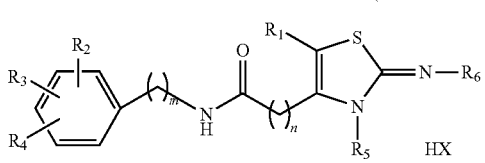

wherein $R_1$ is a hydrogen atom, or a C1-C5 linear or branched alkyl group, $R_2$, $R_3$, and $R_4$ are the same or different from one another, and are independently selected from the group consisting of a hydrogen atom, a halogen atom, a C1-C5 linear or branched alkyl group, a C1-C5 alkyloxy group, a trifluoromethyl group, a trifluoromethoxy group, a phenyloxy group, an amino group, a methanesulfoneamino group, a paratoluenesulfoneamino group, a nitro group, a C1-C5 cyanoalkyl group, a cyano group, a C1-C6 alkoxycarbonyl group, and a C3-C12 cycloalkyl group, $R_5$ is selected from the group consisting of a C1-C5 linear or branched alkyl group, a C3-C6 cycloalkyl group, and a benzyl group, $R_6$ is selected from the group consisting of cyclopentyl, cyclohexyl, cycloheptyl, methyl-cyclohexyl, 1-adamantyl, and 2-adamantyl, n and m are independently 0 or 1, HX is present or absent, and when HX is present, X is a halogen atom.

2. The compound according to claim 1, wherein the $R_5$ is selected from the group consisting of methyl, ethyl, linear or branched propyl, linear or branched butyl, cyclopropyl, cyclohexyl, and benzyl.

3. The compound according to claim 1, wherein the $R_2$, $R_3$, and $R_4$ are the same or different from one another, and are independently selected from the group consisting of a hydrogen atom, a halogen atom, methyl, ethyl, linear or branched propyl, linear or branched butyl, methoxy, trifluoromethyl, trifluoromethoxy, phenyloxy, amino, methanesulfoneamino, paratoluenesulfoneamino, nitro, cyanomethyl, cyano, C1-C6 alkoxycarbonyl, and cyclopentyl.

4. The compound according to claim 1, wherein the $R_1$ is a hydrogen atom or methyl.

5. The compound according to claim 1, wherein the compound is one selected from the group consisting of the compounds shown in the following table:

| Compound code | $R_1$ | n | m | $R_2$, $R_3$, $R_4$ | $R_6$ | $R_8$ | salt(O, HBr, HCl) |
|---|---|---|---|---|---|---|---|
| KHG23210 | H | 1 | 0 | 4-F | CH3 | cy-6 | HCl |
| KHG23354 | H | 1 | 0 | 4-Br | CH3 | cy-6 | HCl |
| KHG23355 | H | 1 | 0 | 4-OPh | CH3 | cy-6 | HCl |
| KHG23356 | H | 1 | 0 | 3-Cl, 5-Cl | CH3 | cy-6 | HCl |
| KHG23360 | H | 1 | 0 | 2-F, 5-NO2 | CH3 | cy-6 | HCl |
| KHG23361 | H | 1 | 0 | 2-F, 4-Cl | CH3 | cy-6 | HCl |
| KHG23362 | H | 1 | 0 | 4-Cl | CH3 | cy-6 | HCl |
| KHG23364 | H | 1 | 0 | 4-isoPr | CH3 | cy-6 | HCl |
| KHG23365 | H | 1 | 0 | 4-n-Bu | CH3 | cy-6 | HCl |
| KHG24070 | H | 1 | 0 | 3-Cl, 4-OCH3 | CH3 | cy-6 | HCl |
| KHG24071 | H | 1 | 0 | 2-Cl, 4-CH3, 5-Cl | CH3 | cy-6 | HCl |
| KHG24072 | H | 1 | 0 | 3-Cl, 4-CH3 | CH3 | cy-6 | HCl |
| KHG24073 | H | 1 | 0 | 4-tBu | CH3 | cy-6 | HCl |
| KHG24074 | H | 1 | 0 | 4-CF3 | CH3 | cy-6 | HCl |
| KHG24075 | H | 1 | 0 | 3-CF3, 5-CF3 | CH3 | cy-6 | HCl |
| KHG24076 | H | 1 | 0 | 3-OCH3 | CH3 | cy-6 | HCl |
| KHG24077 | H | 1 | 0 | 4-CH3 | CH3 | cy-6 | HCl |
| KHG24081 | H | 1 | 0 | 2-F, 4-F | CH3 | cy-6 | HCl |
| KHG24082 | H | 1 | 1 | 2-CH3 | CH3 | cy-6 | HCl |
| KHG24083 | H | 1 | 1 | 2-CF3 | CH3 | cy-6 | HCl |
| KHG24084 | H | 1 | 1 | 3-CF3 | CH3 | cy-6 | HCl |
| KHG24085 | H | 1 | 0 | 3-CO2Et | CH3 | cy-6 | HCl |
| KHG24086 | H | 1 | 1 | 3,4-OCH2O | CH3 | cy-6 | HCl |

-continued

| Compound code | R₁ | n | m | R₂, R₃, R₄ | R₆ | R₈ | salt(O, HBr, HCl) |
|---|---|---|---|---|---|---|---|
| KHG24087 | H | 1 | 0 | 2-F, 5-F | CH3 | cy-6 | HCl |
| KHG24088 | H | 1 | 0 | 3-Cl, 4-Cl | CH3 | cy-6 | HCl |
| KHG24090 | H | 1 | 0 | 3-OCH3, 4-OCH3 | CH3 | cy-6 | HCl |
| KHG24091 | H | 1 | 0 | 3-F, 4-CH3 | CH3 | cy-6 | HCl |
| KHG24092 | H | 1 | 0 | 4-C2H5 | CH3 | cy-5 | HCl |
| KHG24093 | H | 1 | 0 | 4-F | CH3 | cy-5 | HCl |
| KHG24095 | H | 1 | 0 | 2-Cl, 4-F | CH3 | cy-5 | HCl |
| KHG24098 | H | 1 | 0 | 4-Br | CH3 | cy-5 | HCl |
| KHG24099 | H | 1 | 0 | 4-OPh | CH3 | cy-5 | HCl |
| KHG24100 | H | 1 | 0 | 3-Cl, 5-Cl | CH3 | cy-5 | HCl |
| KHG24103 | H | 1 | 0 | 2-F, 5-Cl | CH3 | cy-5 | HCl |
| KHG24104 | H | 1 | 0 | 2-F, 5-NO2 | CH3 | cy-5 | HCl |
| KHG24105 | H | 1 | 0 | 2-F, 4-Cl | CH3 | cy-5 | HCl |
| KHG24106 | H | 1 | 0 | 4-Cl | CH3 | cy-5 | HCl |
| KHG24108 | H | 1 | 0 | 3-NO2 | CH3 | cy-6 | HCl |
| KHG24109 | H | 1 | 0 | 3-F | CH3 | cy-6 | HCl |
| KHG24110 | H | 1 | 0 | 4-isoPr | CH3 | cy-6 | HCl |
| KHG24111 | H | 1 | 0 | 3-CH3, 4-Br | CH3 | cy-6 | HCl |
| KHG24112 | H | 1 | 1 | 4-F | CH3 | cy-6 | HCl |
| KHG24113 | H | 1 | 1 | 4-Cl | CH3 | cy-6 | HCl |
| KHG24115 | H | 1 | 0 | 4-isoPr | CH3 | cy-5 | HCl |
| KHG24116 | H | 1 | 0 | 4-n-Bu | CH3 | cy-5 | HCl |
| KHG24117 | H | 1 | 0 | 4-C2H5 | CH3 | cy-7 | HCl |
| KHG24118 | H | 1 | 0 | 4-F | CH3 | cy-7 | HCl |
| KHG24119 | H | 1 | 0 | 4-OCH3 | CH3 | cy-7 | HCl |
| KHG24120 | H | 1 | 0 | 2-Cl, 4-F | CH3 | cy-7 | HCl |
| KHG24121 | H | 1 | 0 | 4-CH2CN | CH3 | cy-7 | HCl |
| KHG24122 | H | 1 | 0 | 4-Br | CH3 | cy-7 | HCl |
| KHG24123 | H | 1 | 0 | 4-OPh | CH3 | cy-7 | HCl |
| KHG24124 | H | 1 | 0 | 2-Cl, 4-CH3 | CH3 | cy-7 | HCl |
| KHG24125 | H | 1 | 0 | 3-Cl, 5-Cl | CH3 | cy-7 | HCl |
| KHG24126 | H | 1 | 0 | 2-F, 4-CH3 | CH3 | cy-7 | HCl |
| KHG24127 | H | 1 | 0 | 2-F, 4-F | CH3 | cy-7 | HCl |
| KHG24128 | H | 1 | 0 | 2-F, 5-Cl | CH3 | cy-7 | HCl |
| KHG24129 | H | 1 | 0 | 2-F, 5-NO2 | CH3 | cy-7 | HCl |
| KHG24130 | H | 1 | 0 | 2-F, 4-Cl | CH3 | cy-7 | HCl |
| KHG24131 | H | 1 | 0 | 4-Cl | CH3 | cy-7 | HCl |
| KHG24132 | H | 1 | 0 | H | CH3 | cy-7 | HCl |
| KHG24133 | H | 1 | 0 | 4-isoPr | CH3 | cy-7 | HCl |
| KHG24134 | H | 1 | 0 | 4-n-Bu | CH3 | cy-7 | HCl |
| KHG24141 | H | 1 | 0 | 4-OPh | CH3 | cy-3 | HCl |
| KHG24152 | H | 1 | 0 | 4-n-Bu | CH3 | cy-3 | HCl |
| KHG24157 | H | 1 | 1 | 4-Cl | CH3 | cy-5 | HCl |
| KHG24159 | H | 1 | 1 | 4-F | CH3 | cy-7 | HCl |
| KHG24160 | H | 1 | 1 | 4-Cl | CH3 | cy-7 | HCl |
| KHG24161 | H | 1 | 1 | 4-OCH3 | CH3 | cy-7 | HCl |
| KHG24216 | H | 1 | 0 | 3-CF3, 5-CF3 | CH3 | CH2CH2Ph | HCl |
| KHG24218 | H | 1 | 0 | 3-CF3, 5-CF3 | CH3 | CH2-cy-6 | HCl |
| KHG24220 | H | 1 | 0 | 4-isoPr | CH3 | CH2CH2Ph | HCl |
| KHG24222 | H | 1 | 0 | 4-isoPr | CH3 | CH2-cy-6 | HCl |
| KHG24224 | H | 1 | 0 | 4-OPh | CH3 | CH2CH2Ph | HCl |
| KHG24228 | H | 1 | 0 | 4-Cl | CH3 | CH2CH2Ph | HCl |
| KHG24230 | H | 1 | 0 | 4-Cl | CH3 | CH2-cy-6 | HCl |
| KHG24232 | H | 1 | 0 | 2-F, 5-NO2 | CH3 | CH2CH2Ph | HCl |
| KHG24234 | H | 1 | 0 | 2-F, 5-NO2 | CH3 | CH2-cy-6 | HCl |
| KHG24235 | H | 1 | 0 | 4-CH3 | CH3 | 1-Ad | HCl |
| KHG24236 | H | 1 | 0 | 4-CH2CH3 | CH3 | 1-Ad | HCl |
| KHG24237 | H | 1 | 0 | 4-F | CH3 | 1-Ad | HCl |
| KHG24238 | H | 1 | 0 | 4-Cl | CH3 | 1-Ad | HCl |
| KHG24239 | H | 1 | 0 | 4-Br | CH3 | 1-Ad | HCl |
| KHG24240 | H | 1 | 0 | 4-CF3 | CH3 | 1-Ad | HCl |
| KHG24241 | H | 1 | 0 | 3-CF3, 5-CF3 | CH3 | 1-Ad | HCl |
| KHG24242 | H | 1 | 0 | 2-F, 5-Cl | CH3 | 1-Ad | HCl |
| KHG24243 | H | 1 | 0 | 4-isoPr | CH3 | 1-Ad | HCl |
| KHG24244 | H | 1 | 0 | 4-OC6H5 | CH3 | 1-Ad | HCl |
| KHG24261 | H | 1 | 0 | 3-CF3, 5-CF3 | CH2CH3 | cy-6 | HCl |
| KHG24262 | H | 1 | 0 | 4-Cl | n-Bu | cy-6 | HCl |
| KHG24263 | H | 1 | 0 | 4-Br | n-Bu | cy-6 | HCl |
| KHG24266 | H | 1 | 0 | 4-Cl | cy-6 | cy-6 | HCl |
| KHG24267 | H | 1 | 0 | 3-CF3, 5-CF3 | cy-3 | cy-6 | HCl |
| KHG24268 | H | 1 | 0 | 4-CF3 | cy-3 | cy-6 | HCl |
| KHG24270 | H | 1 | 0 | 4-n-Bu | cy-3 | cy-6 | HCl |
| KHG24271 | H | 1 | 0 | 2-F, 5-Cl | cy-3 | cy-6 | HCl |
| KHG24272 | H | 1 | 0 | 4-CH2CH3 | cy-3 | cy-6 | HCl |
| KHG24273 | H | 1 | 0 | 4-Br | cy-3 | cy-6 | HCl |
| KHG24276 | H | 1 | 0 | 4-OPh | CH2CH3 | cy-6 | HCl |
| KHG24277 | H | 1 | 0 | 4-n-Bu | CH2CH3 | cy-6 | HCl |

-continued

| Compound code | R₁ | n | m | R₂, R₃, R₄ | R₆ | R₈ | salt(O, HBr, HCl) |
|---|---|---|---|---|---|---|---|
| KHG24278 | H | 1 | 0 | 2-F, 5-NO2 | CH2CH3 | cy-6 | HCl |
| KHG24279 | H | 1 | 0 | 4-CH3 | CH2CH3 | cy-6 | HCl |
| KHG24280 | H | 1 | 0 | 4-CF3 | CH2CH3 | cy-6 | HCl |
| KHG24281 | H | 1 | 0 | 4-OPh | n-Bu | cy-6 | HCl |
| KHG24282 | H | 1 | 0 | 4-n-Bu | n-Bu | cy-6 | HCl |
| KHG24283 | H | 1 | 0 | 4-isoPr | n-Bu | cy-6 | HCl |
| KHG24284 | H | 1 | 0 | 4-F | n-Bu | cy-6 | HCl |
| KHG24285 | H | 1 | 0 | 4-CH3 | n-Bu | cy-6 | HCl |
| KHG24286 | H | 1 | 0 | 4-CH2CH3 | n-Bu | cy-6 | HCl |
| KHG24287 | H | 1 | 0 | 4-Cl | n-Pr | cy-6 | HCl |
| KHG24288 | H | 1 | 0 | 4-Br | n-Pr | cy-6 | HCl |
| KHG24290 | H | 1 | 0 | 4-OPh | n-Pr | cy-6 | HCl |
| KHG24291 | H | 1 | 0 | 4-n-Bu | n-Pr | cy-6 | HCl |
| KHG24292 | H | 1 | 1 | 4-CH3 | CH2CH3 | cy-6 | HCl |
| KHG24293 | H | 1 | 1 | 4-CH3 | n-Bu | cy-6 | HCl |
| KHG24294 | H | 1 | 0 | 4-isoPr | n-Pr | cy-6 | HCl |
| KHG24295 | H | 1 | 0 | 2-F, 5-NO2 | n-Pr | cy-6 | HCl |
| KHG24296 | H | 1 | 0 | 4-F | n-Pr | cy-6 | HCl |
| KHG24297 | H | 1 | 0 | 4-CH3 | n-Pr | cy-6 | HCl |
| KHG24298 | H | 1 | 0 | 4-CH2CH3 | n-Pr | cy-6 | HCl |
| KHG24299 | H | 1 | 0 | 4-Cl | benzyl | cy-6 | HCl |
| KHG24300 | H | 1 | 0 | 4-Br | benzyl | cy-6 | HCl |
| KHG24303 | H | 1 | 0 | 4-isoPr | benzyl | cy-6 | HCl |
| KHG24305 | H | 1 | 0 | 4-F | benzyl | cy-6 | HCl |
| KHG24306 | H | 1 | 0 | 4-CH2CH3 | benzyl | cy-6 | HCl |
| KHG24307 | H | 1 | 0 | 3-CF3, 5-CF3 | cy-6 | cy-6 | HCl |
| KHG24313 | H | 1 | 0 | 4-CH3 | cy-6 | cy-6 | HCl |
| KHG24315 | H | 1 | 0 | 4-OPh | cy-3 | cy-6 | HCl |
| KHG24336 | H | 0 | 1 | 3-Cl | CH3 | cy-7 | HCl |
| KHG24337 | H | 0 | 1 | 4-Cl | CH3 | cy-7 | HCl |
| KHG24338 | H | 0 | 1 | 3-Cl, 4-Cl | CH3 | cy-7 | HCl |
| KHG24339 | H | 0 | 1 | 4-OCH3 | CH3 | cy-7 | HCl |
| KHG24403 | H | 1 | 0 | 4-F | CH2CH3 | cy-6 | HCl |
| KHG24404 | H | 1 | 0 | 4-CF3 | n-pr | cy-6 | HCl |
| KHG24405 | H | 1 | 0 | 3-Cl, 4-CH3 | n-pr | cy-6 | HCl |
| KHG24406 | H | 1 | 0 | 4-n-Bu | benzyl | cy-6 | HCl |
| KHG24407 | H | 1 | 0 | 4-CF3 | benzyl | cy-6 | HCl |
| KHG24408 | H | 1 | 0 | 2-F, 5-Cl | benzyl | cy-6 | HCl |
| KHG24409 | H | 1 | 0 | 4-n-Bu | CH3 | 1-Ad | HCl |
| KHG24410 | H | 1 | 0 | 3-Cl, 5-Cl | CH3 | 1-Ad | HCl |
| KHG24411 | H | 1 | 0 | 2-F, 4-Cl | CH3 | 1-Ad | HCl |
| KHG24412 | H | 1 | 0 | H | CH3 | 1-Ad | HCl |
| KHG24413 | H | 1 | 0 | 2-Cl, 4-CH3 | CH3 | 1-Ad | HCl |
| KHG24414 | H | 1 | 0 | 3-Cl, 5-Cl | CH2CH3 | cy-6 | HCl |
| KHG24415 | H | 1 | 0 | 3-Cl, 5-Cl | n-pr | cy-6 | HCl |
| KHG24416 | H | 1 | 0 | 3-Cl, 5-Cl | n-Bu | cy-6 | HCl |
| KHG24417 | H | 1 | 0 | 3-Cl, 5-Cl | CH3 | 1-Ad | HCl |
| KHG24418 | H | 1 | 0 | 2-Cl, 4-CH3 | CH3 | 1-Ad | HCl |
| KHG24419 | H | 1 | 0 | 4-OCH3 | CH3 | 1-Ad | HCl |
| KHG24420 | H | 1 | 0 | 2-Cl, 4-CH3 | CH2CH3 | cy-6 | HCl |
| KHG24421 | H | 1 | 0 | 2-Cl, 4-CH3 | n-Bu | cy-6 | HCl |
| KHG24422 | H | 1 | 0 | 3-Cl, 5-Cl | benzyl | cy-6 | HCl |
| KHG24445 | H | 1 | 0 | 4-NO2 | CH3 | cy-7 | HCl |
| KHG24448 | H | 1 | 0 | 4-NHTs | CH3 | cy-7 | HCl |
| KHG24449 | H | 1 | 1 | 4-NHTs | CH3 | cy-7 | HCl |
| KHG24480 | CH3 | 1 | 0 | 4-Cl | CH3 | cy-6 | O |
| KHG24482 | CH3 | 1 | 0 | 4-Br | CH3 | cy-6 | O |
| KHG24483 | CH3 | 1 | 0 | 3-Cl, 5-Cl | CH3 | cy-6 | O |
| KHG24484 | CH3 | 1 | 0 | 2-F, 5-NO2 | CH3 | cy-6 | O |
| KHG24486 | CH3 | 1 | 0 | 4-Br | CH3 | cy-7 | O |
| KHG24516 | CH3 | 1 | 0 | 4-n-Bu | CH3 | cy-7 | HCl |
| KHG24517 | CH3 | 1 | 0 | 4-CH2CH3 | CH3 | cy-7 | HCl |
| KHG24518 | CH3 | 1 | 0 | 4-F | CH3 | cy-7 | HCl |
| KHG24519 | CH3 | 1 | 0 | 4-isoPr | CH3 | cy-7 | HCl |
| KHG24520 | CH3 | 1 | 0 | 4-CF3 | CH3 | cy-7 | HCl |
| KHG24521 | CH3 | 1 | 0 | 4-t-Bu | CH3 | cy-7 | HCl |
| KHG24522 | CH3 | 1 | 0 | 3-CF3, 5-CF3 | CH3 | cy-6 | HCl |
| KHG24523 | CH3 | 1 | 0 | 4-CH2CH3 | CH3 | cy-6 | HCl |
| KHG24524 | CH3 | 1 | 0 | 4-OCF3 | CH3 | cy-6 | HCl |
| KHG24525 | CH3 | 1 | 0 | 4-F | CH3 | cy-6 | HCl |
| KHG24526 | CH3 | 1 | 0 | 4-isoPr | CH3 | cy-6 | HCl |
| KHG24527 | CH3 | 1 | 0 | 4-CF3 | CH3 | cy-6 | HCl |
| KHG24528 | H | 1 | 0 | 3-isoPr | CH3 | cy-6 | HCl |
| KHG24529 | H | 1 | 0 | 3-CF3, 5-CF3 | CH3 | cy-6 | HCl |
| KHG24530 | H | 1 | 0 | 2-Cl, 3-Cl | CH3 | cy-6 | HCl |
| KHG24531 | H | 1 | 0 | 3-Cl, 4-Cl | CH3 | cy-6 | HCl |
| KHG24532 | H | 1 | 0 | 2-Cl, 5-Cl | CH3 | cy-6 | HCl |

-continued

| Compound code | R₁ | n | m | R₂, R₃, R₄ | R₆ | R₈ | salt(O, HBr, HCl) |
|---|---|---|---|---|---|---|---|
| KHG24533 | H | 1 | 0 | 2-Cl, 4-Cl, 5-Cl | CH3 | cy-6 | HCl |
| KHG24534 | H | 1 | 0 | 3-F, 5-F | CH3 | cy-6 | HCl |
| KHG24535 | H | 1 | 0 | 4-CH3 | cy-6 | cy-6 | HCl |
| KHG24547 | H | 1 | 1 | 2-CF3 | cy-6 | cy-6 | HCl |
| KHG24626 | H | 0 | 1 | 2-F, 5-F | CH3 | cy-7 | HCl |
| KHG24627 | H | 0 | 1 | 3-F, 4-F | CH3 | cy-7 | 0 |
| KHG24628 | H | 0 | 1 | 4-CH3 | CH3 | cy-7 | 0 |
| KHG24629 | H | 0 | 1 | 4-CH3 | CH3 | cy-7 | HCl |
| KHG24630 | H | 0 | 1 | 3-CF3, 5-CF3 | CH3 | cy-7 | 0 |
| KHG24632 | H | 0 | 1 | 3-CF3, 5-CF3 | CH3 | cy-7 | HCl |
| KHG24633 | H | 0 | 1 | 2-Br | CH3 | cy-7 | 0 |
| KHG24634 | H | 0 | 1 | 2-Br | CH3 | cy-7 | HCl |
| KHG24636 | CH3 | 1 | 0 | 3-F | CH3 | cy-6 | HCl |
| KHG24638 | CH3 | 1 | 0 | H | CH3 | cy-7 | HCl |
| KHG24639 | CH3 | 1 | 0 | 4-CH3 | CH3 | cy-7 | HCl |
| KHG24640 | CH3 | 1 | 0 | 2-F | CH3 | cy-7 | HCl |
| KHG24641 | CH3 | 1 | 0 | 3-F | CH3 | cy-7 | HCl |
| KHG24642 | CH3 | 1 | 0 | 4-NO2 | CH3 | cy-7 | HCl |
| KHG24643 | CH3 | 1 | 0 | 4-Cl | CH3 | cy-7 | HCl |
| KHG24644 | CH3 | 1 | 0 | 3-Cl, 5-Cl | CH3 | cy-7 | HCl |
| KHG24645 | CH3 | 1 | 0 | 2-F, 5-NO2 | CH3 | cy-7 | HCl |
| KHG24646 | CH3 | 1 | 0 | 3-CF3, 5-CF3 | CH3 | cy-7 | HCl |
| KHG24647 | CH3 | 1 | 0 | 4-OCF3 | CH3 | cy-7 | HCl |
| KHG24656 | CH3 | 1 | 0 | 4-t-Bu | CH3 | cy-5 | HCl |
| KHG24657 | CH3 | 1 | 0 | 4-Cl | CH3 | cy-5 | HCl |
| KHG24666 | H | 0 | 1 | 3-F | CH3 | cy-7 | HCl |
| KHG24667 | H | 0 | 1 | 3-F | CH3 | cy-7 | 0 |
| KHG24668 | H | 0 | 1 | 3-Br | CH3 | cy-7 | HBr |
| KHG24669 | H | 0 | 1 | 3-Br | CH3 | cy-7 | 0 |
| KHG24670 | H | 0 | 1 | 2-CF3 | CH3 | cy-7 | HBr |
| KHG24671 | H | 0 | 1 | 2-CF3 | CH3 | cy-7 | 0 |
| KHG24775 | H | 1 | 0 | 4-Cl | n-Bu | 1-Ad | HCl |
| KHG24776 | H | 1 | 0 | 4-n-Bu | n-Bu | 1-Ad | HCl |
| KHG24777 | H | 1 | 0 | 4-CF3 | n-Bu | 1-Ad | HCl |
| KHG24780 | H | 1 | 0 | 4-F | n-Bu | 1-Ad | HCl |
| KHG24781 | H | 1 | 0 | 4-CH3 | n-Bu | 1-Ad | HCl |
| KHG24782 | H | 1 | 0 | 4-CH2CH3 | n-Bu | 1-Ad | HCl |
| KHG24783 | H | 1 | 0 | 2-F, 4-Cl | n-Bu | 1-Ad | HCl |
| KHG24784 | H | 1 | 0 | 4-Br | n-Bu | 1-Ad | HCl |
| KHG24785 | H | 1 | 0 | 2-F, 5-Cl | n-Bu | 1-Ad | HCl |
| KHG24788 | H | 1 | 0 | 4-isoPr | cy-3 | 1-Ad | HCl |
| KHG24789 | H | 1 | 0 | 4-n-Bu | cy-3 | 1-Ad | HCl |
| KHG24790 | H | 1 | 0 | 4-CF3 | cy-3 | 1-Ad | HCl |
| KHG24792 | H | 1 | 0 | 3-CF3, 5-CF3 | cy-3 | 1-Ad | HCl |
| KHG24795 | H | 1 | 0 | 4-isoPr | n-Bu | 1-Ad | HCl |
| KHG24798 | H | 1 | 0 | 4-CH2CH3 | cy-3 | 1-Ad | HCl |
| KHG24800 | H | 1 | 0 | 4-OPh | cy-3 | 1-Ad | HCl |
| KHG24801 | H | 1 | 0 | 2-F, 4-Cl | cy-3 | 1-Ad | HCl |
| KHG24802 | H | 1 | 0 | 2-F, 5-Cl | cy-3 | 1-Ad | HCl |
| KHG24803 | H | 1 | 0 | 3-OCH2O-4 | n-Bu | 1-Ad | HCl |
| KHG24804 | H | 1 | 0 | 3-OCH2O-4 | cy-3 | 1-Ad | HCl |
| KHG24805 | H | 1 | 0 | 3-Cl, 5-Cl | n-Pr | 1-Ad | HCl |
| KHG24807 | H | 1 | 0 | 4-isoPr | n-Pr | 1-Ad | HCl |
| KHG24808 | H | 1 | 0 | 4-n-Bu | n-Pr | 1-Ad | HCl |
| KHG24809 | H | 1 | 0 | 4-CF3 | n-Pr | 1-Ad | HCl |
| KHG24811 | H | 1 | 0 | 4-F | n-Pr | 1-Ad | HCl |
| KHG24812 | H | 1 | 0 | 4-Br | n-Pr | 1-Ad | HCl |
| KHG24813 | H | 1 | 0 | 4-CH3 | n-Pr | 1-Ad | HCl |
| KHG24814 | H | 1 | 0 | 4-CH2CH3 | n-Pr | 1-Ad | HCl |
| KHG24815 | H | 1 | 0 | 4-OPh | n-Pr | 1-Ad | HCl |
| KHG24816 | H | 1 | 0 | 2-F, 4-Cl | n-Pr | 1-Ad | HCl |
| KHG24817 | H | 1 | 0 | 2-F, 5-Cl | n-Pr | 1-Ad | HCl |
| KHG24818 | H | 1 | 0 | 2-Cl, 4-CH3 | n-Pr | 1-Ad | HCl |
| KHG24819 | H | 1 | 0 | 4-isoPr | CH2CH3 | 1-Ad | HCl |
| KHG24820 | H | 1 | 0 | 4-n-Bu | CH2CH3 | 1-Ad | HCl |
| KHG24821 | H | 1 | 0 | 4-CF3 | CH2CH3 | 1-Ad | HCl |
| KHG24823 | H | 1 | 0 | 4-Cl | isoPr | 1-Ad | HCl |
| KHG24826 | H | 1 | 0 | 4-CF3 | isoPr | 1-Ad | HCl |
| KHG24828 | H | 1 | 0 | 3-CF3, 5-CF3 | isoPr | 1-Ad | HCl |
| KHG24829 | H | 1 | 0 | 4-F | isoPr | 1-Ad | HCl |
| KHG24831 | H | 1 | 0 | 4-CH3 | isoPr | 1-Ad | HCl |
| KHG24832 | H | 1 | 0 | 4-CH2CH3 | isoPr | 1-Ad | HCl |
| KHG24833 | H | 1 | 0 | 4-OPh | isoPr | 1-Ad | HCl |
| KHG24834 | H | 1 | 0 | 2-F, 4-Cl | isoPr | 1-Ad | HCl |
| KHG24835 | H | 1 | 0 | 2-F, 5-Cl | isoPr | 1-Ad | HCl |
| KHG24836 | H | 1 | 0 | 2-Cl, 4-CH3 | isoPr | 1-Ad | HCl |
| KHG24837 | H | 1 | 0 | 3-OCH2O-4 | n-Pr | 1-Ad | HCl |

-continued

| Compound code | $R_1$ | n | m | $R_2, R_3, R_4$ | $R_6$ | $R_8$ | salt(O, HBr, HCl) |
|---|---|---|---|---|---|---|---|
| KHG24838 | H | 1 | 0 | 3-OCH2O-4 | isoPr | 1-Ad | HCl |
| KHG24839 | H | 1 | 0 | 2-F, 5-NO2 | n-Pr | 1-Ad | HCl |
| KHG24840 | H | 1 | 0 | 2-F, 5-NO2 | isoPr | 1-Ad | HCl |
| KHG24842 | H | 1 | 0 | 4-F | CH3 | 2-Ad | HCl |
| KHG24847 | H | 1 | 0 | 4-CH2CH3 | CH2CH3 | 1-Ad | HCl | wherein, cy-5 indicates cyclopentyl, cy-6 indicates cyclohexyl, cy-7 indicates cycloheptyl, Pr indicates propyl, Bu indicates butyl, Ph indicates phenyl, 1-Ad indicates 1-adamantyl, 2-Ad indicates 2-adamantyl, and wherein $R_2$, $R_3$, and $R_4$ represent substituents at the phenyl group, and when the substituent is hydrogen, it is not indicated.

6. A composition for inhibiting T-type calcium channel activity containing the compound of claim 1 as an active ingredient.

7. A composition for treating a disease or symptom selected from the group consisting of pain, epilepsy, hypertension, and angina pectoris, which contains the compound of claim 1 as an active ingredient, wherein the disease or symptom is triggered by over-expression of T-type calcium channel.

8. A composition for food or food additives containing the compound of claim 1.

9. A method of preparing the compound represented by Chemical Formula I, comprising the steps of:

heating/reflowing the compounds represented by Chemical Formulas II and III in a solution of a C1 to C5 alcohol for 5 to 20 hours at 20 to 130° C., to prepare the compound represented by Chemical Formula IV;

adding a basic aqueous solution, heating/reflowing for 30 minutes to 5 hours at 20 to 120° C., and then adjusting the pH to 1 to 4 by adding a hydrogen halide, to prepare the compound represented by Chemical Formula V; and adding the compound represented by Chemical Formula VI and an amide condensation binder to the obtained compound represented by Chemical Formula V, and allowing them to react, to prepare the compound represented by Chemical Formula I:

(Chemical Formula I)

(Chemical Formula II)

(Chemical Formula III)

(Chemical Formula IV)

(Chemical Formula V)

(Chemical Formula VI)

wherein $R_1$ is a hydrogen atom, or a C1-C5 linear or branched alkyl group, $R_2$, $R_3$, and $R_4$ are the same or different from one another, and are independently selected from the group consisting of a hydrogen atom, a halogen atom, a C1C5 linear or branched alkyl group, a C1-C5 alkyloxy group, a trifluoromethyl group, a trifluoromethoxy group, a phenyloxy group, an amino group, a methanesulfoneamino group, a paratoluenesulfoneamino group, a nitro group, a C1-C5 cyanoalkyl group, a cyano group, a C1-C6 alkoxycarbonyl group, and a C3-C12 cycloalkyl group, $R_5$ is selected from the group consisting of a C1-C5 linear or branched alkyl group, a C3-C6 cycloalkyl group, and a benzyl group, $R_6$ is selected from the group consisting of cyclopentyl, cyclohexyl, cycloheptyl, methyl-cyclohexyl, 1-adamantyl, and 2-adamantyl, n and m may be independently 0 or 1, X and Y are the same or different from each other and are independently selected from the group consisting of fluorine, chlorine, bromine, and iodine, and HX is present or absent.

10. A method of preparing the compound represented by Chemical Formula I comprising the step of heating/reflowing the compounds represented by Chemical Formulas VII and VIII in a solution of a C1 to C5 alcohol for 5 to 25 hours at 20 to 130° C., and allowing them to directly react, to prepare the compound represented by Chemical Formula I:

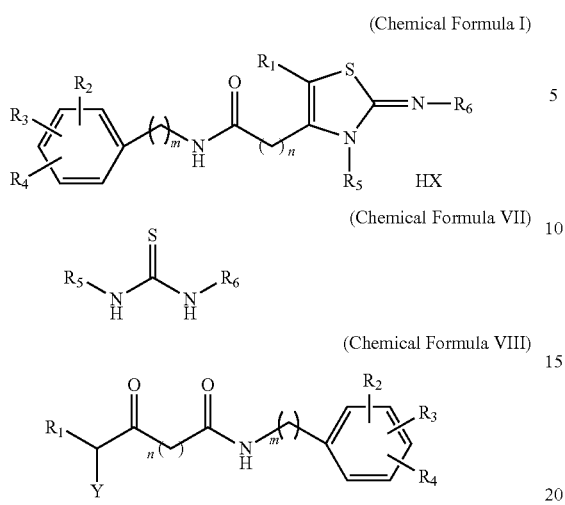

(Chemical Formula I)

(Chemical Formula VII)

(Chemical Formula VIII)

wherein $R_1$ is a hydrogen atom, or a C1-C5 linear or branched alkyl group, $R_2$, $R_3$, and $R_4$ are the same or different from one another, and are independently selected from the group consisting of a hydrogen atom, a halogen atom, a C1-C5 linear or branched alkyl group, a C1-C5 alkyloxy group, a trifluoromethyl group, a trifluoromethoxy group, a phenyloxy group, an amino group, a methanesulfoneamino group, a paratoluenesulfoneamino group, a nitro group, a C1-C5 cyanoalkyl group, a cyano group, a C1-C6 alkoxycarbonyl group, and a C3-C12 cycloalkyl group, $R_5$ is selected from the group consisting of a C1-C5 linear or branched alkyl group, a C3-C6 cycloalkyl group, and a benzyl group, $R_6$ is selected from the group consisting of cyclopentyl, cyclohexyl, cycloheptyl, methyl-cyclohexyl, 1-adamantyl, and 2-adamantyl, n and m are independently 0 or 1, HX is present or absent, and when HX is present, X is a halogen atom.

* * * * *